(12) United States Patent
Yoshida et al.

(10) Patent No.: US 9,327,018 B2
(45) Date of Patent: *May 3, 2016

(54) RECOMBINANT BACULOVIRUS VACCINE

(75) Inventors: Shigeto Yoshida, Tochigi (JP);
Masanori Kawasaki, Osaka (JP);
Makoto Matsumoto, Osaka (JP);
Yoshio Ohba, Osaka (JP); Masahiro Saito, Osaka (JP); Yoshihiro Goto, Osaka (JP); Katsuya Inagaki, Osaka (JP); Masami Mizukoshi, Osaka (JP); Norimitsu Hariguchi, Osaka (JP); Kuniko Hirota, Osaka (JP)

(73) Assignees: EDUCATIONAL FOUNDATION JICHI MEDICAL UNIVERSITY, Tochigi (JP); OTSUKA PHARMACEUTICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/617,825

(22) Filed: Sep. 14, 2012

(65) Prior Publication Data
US 2013/0022637 A1  Jan. 24, 2013

Related U.S. Application Data

(60) Division of application No. 12/192,927, filed on Aug. 15, 2008, which is a continuation-in-part of application No. 12/278,916, filed as application No. PCT/JP2007/052195 on Feb. 8, 2007, now Pat. No. 9,023,365.

(30) Foreign Application Priority Data

Feb. 9, 2006 (JP) .................. 2006-032863
Aug. 7, 2007 (JP) .................. 2007-205785

(51) Int. Cl.
A61K 39/12    (2006.01)
A61P 33/06    (2006.01)
C12N 7/01     (2006.01)
A61K 39/015   (2006.01)
A61K 39/04    (2006.01)
A61K 39/145   (2006.01)
C07K 14/005   (2006.01)
A61K 9/00     (2006.01)
A61K 39/00    (2006.01)

(52) U.S. Cl.
CPC .............. *A61K 39/015* (2013.01); *A61K 39/04* (2013.01); *A61K 39/12* (2013.01); *A61K 39/145* (2013.01); *C07K 14/005* (2013.01); *A61K 9/007* (2013.01); *A61K 9/0043* (2013.01); *A61K 2039/5256* (2013.01); *A61K 2039/5258* (2013.01); *A61K 2039/543* (2013.01); *C07K 2319/00* (2013.01); *C07K 2319/02* (2013.01); *C12N 2710/14143* (2013.01); *C12N 2760/16122* (2013.01); *C12N 2760/16134* (2013.01)

(58) Field of Classification Search
None
See application file for complete search history.

(56) References Cited

U.S. PATENT DOCUMENTS

| | | |
|---|---|---|
| 4,879,236 A | 11/1989 | Smith et al. |
| 5,168,062 A | 12/1992 | Stinski |
| 5,169,784 A | 12/1992 | Summers et al. |
| 5,385,839 A | 1/1995 | Stinski |
| 5,753,220 A | 5/1998 | Suzuki et al. |
| 5,762,939 A | 6/1998 | Smith et al. |
| 5,770,400 A | 6/1998 | Miyazaki et al. |
| 5,811,260 A | 9/1998 | Miyazaki et al. |
| 5,858,368 A | 1/1999 | Smith et al. |
| 5,976,552 A | 11/1999 | Volvovitz |
| 6,103,526 A | 8/2000 | Smith et al. |
| 6,183,993 B1 | 2/2001 | Boyce et al. |
| 6,190,887 B1 | 2/2001 | Boyce et al. |
| 6,245,532 B1 | 6/2001 | Smith et al. |
| 6,338,953 B1 | 1/2002 | Boyce et al. |
| 6,485,729 B1 | 11/2002 | Smith et al. |
| 6,589,783 B2 | 7/2003 | Novy et al. |
| 6,607,912 B2 | 8/2003 | Blissard et al. |

(Continued)

FOREIGN PATENT DOCUMENTS

| | | |
|---|---|---|
| JP | 3366328 B2 | 1/2002 |
| JP | 2002-253263 A | 9/2002 |

(Continued)

OTHER PUBLICATIONS

Yoshida et al. Virology 316, 2003 vol. 316, pp. 161-170.*

(Continued)

*Primary Examiner* — Shanon A Foley
*Assistant Examiner* — Myron Hill
(74) *Attorney, Agent, or Firm* — Sughrue Mion, PLLC

(57) ABSTRACT

The present invention provides a novel transfer vector and a recombinant baculovirus; methods for the production thereof; pharmaceuticals containing the recombinant baculovirus as an active ingredient, which are useful as preventive or therapeutic drugs for infectious diseases such as malaria and influenza; and methods for preventing and treating infectious diseases such as malaria and influenza. More specifically, the invention provides a recombinant transfer vector capable of expressing a foreign gene fused to a virus gene under the control of a dual promoter; a recombinant baculovirus; methods for the production thereof; pharmaceuticals containing the recombinant baculovirus as an active ingredient; and methods for preventing and treating infectious diseases such as malaria and influenza comprising administrating the recombinant baculovirus to patients.

4 Claims, 20 Drawing Sheets

(56) References Cited

U.S. PATENT DOCUMENTS

| | | | |
|---|---|---|---|
| 6,716,823 | B1 | 4/2004 | Tang et al. |
| 6,793,926 | B1 | 9/2004 | Rasty et al. |
| 6,858,205 | B2 | 2/2005 | Blissard et al. |
| 6,951,649 | B2 | 10/2005 | Smith et al. |
| 7,722,889 | B2 * | 5/2010 | Duffy et al. ............. 424/268.1 |
| 2002/0071848 | A1 | 6/2002 | Smith et al. |
| 2003/0045492 | A1 | 3/2003 | Tang et al. |
| 2003/0104580 | A1 | 6/2003 | Inaba et al. |
| 2003/0125278 | A1 | 7/2003 | Tang et al. |
| 2004/0009153 | A1 | 1/2004 | Blissard et al. |
| 2004/0009936 | A1 | 1/2004 | Tang et al. |
| 2004/0071733 | A1 | 4/2004 | Takaku et al. |
| 2005/0009184 | A1 | 1/2005 | Maitland |
| 2005/0019928 | A1 | 1/2005 | Rasty et al. |
| 2005/0064557 | A1 | 3/2005 | Inaba et al. |
| 2005/0208066 | A1 | 9/2005 | Chao et al. |
| 2005/0208661 | A1 | 9/2005 | Matsuura |
| 2006/0183231 | A1 | 8/2006 | Pachuk et al. |
| 2007/0042977 | A1 | 2/2007 | Erti |
| 2010/0233202 | A1 | 9/2010 | Yoshida et al. |
| 2011/0159034 | A1 | 6/2011 | Mcmichael et al. |

FOREIGN PATENT DOCUMENTS

| | | | |
|---|---|---|---|
| JP | 2003-284557 | A | 10/2003 |
| JP | 2005-15346 | A | 1/2005 |
| JP | 2006-180865 | A | 7/2006 |
| JP | 2007-23044 | A | 2/2007 |
| TW | 200804597 | A | 1/2008 |
| WO | 95/26982 | A2 | 10/1995 |
| WO | 96/33738 | A1 | 10/1996 |
| WO | 96/37624 | A1 | 11/1996 |
| WO | 98/11243 | A3 | 3/1998 |
| WO | 98/46262 | A1 | 10/1998 |
| WO | 98/55640 | A1 | 12/1998 |
| WO | 99/08713 | A1 | 2/1999 |
| WO | 99/09193 | A1 | 2/1999 |
| WO | 00/66179 | A1 | 11/2000 |
| WO | 00/73480 | A1 | 12/2000 |
| WO | 02/14527 | A2 | 2/2002 |
| WO | 02/062381 | A1 | 8/2002 |
| WO | 03/016450 | A1 | 2/2003 |
| WO | 03/020322 | A1 | 3/2003 |
| WO | 03/070920 | A1 | 8/2003 |
| WO | 2004/029259 | A1 | 4/2004 |
| WO | 2004/041852 | A2 | 5/2004 |
| WO | 2005/040388 | A2 | 5/2005 |
| WO | 2006/056753 | A2 | 6/2006 |
| WO | 2007/027860 | A2 | 3/2007 |
| WO | 2007037265 | A1 | 4/2007 |

OTHER PUBLICATIONS

Tani et al. Virology 2001 vol. 279, pp. 343-353.*
Pieroni et al. Human Gene Therapy 2001 vol. 12, pp. 871-881.*
Abe et al. "Baculovirus Induces an Innate Immune Response and Confers Protection from Lethal Influenza Virus Infection in Mince", Journal of Immunology, 2003 vol. 171, pp. 1133-1139.
Andrea Facciabene, et al., "Baculovirus Vectors Elicit Antigen-Specific Immune Responses in Mice", Journal of Virology, vol. 78, No. 16, 2004, pp. 8663-8672.
Bingke Bai et al., "Vaccination of mice with recombinant baculovirus expressing spike or nucleocapsid protein of SARS-like coronavirus generates humoral and cellular immune responses", Molecular Immunology 45 (2008) pp. 868-875.
Boublik, Y. et al., "Eukaryotic Virus Display: Engineering the Major Surface Glycoprotein of the Autographa californica Nuclear Polyhedrosis Virus (AcNPV) for the Presentation of Foreign Proteins on the Virus Surface", Biotechnology, vol. 13, pp. 1079-1084, 1995.
Caton, Andrew J., The Antigenic Structure of the Influenza Virus A/PR/8/34 Hemagglutinin (H1 Subtype), Cell, vol. 31, (1982), pp. 417-427.
Christian Hofmann et al., "Efficient gene transfer into human hepatocytes by baculovirus vectors", Proc. Natl. Acad. Sci. USA, vol. 92, pp. 10099-10103, 1995.
David R. O'Reilly, et al., "Baculovirus Expression Vectors", A Laboratory Manual, pp. 41-46; Oxford University Press, 1994.
Dung-Fang Lee et al., "A Baculovirus Superinfection System: Efficient Vehicle for Gene Transfer into *Drosophila* S2 Cells", Journal of Virology, vol. 74, No. 24, pp. 11873-11880, 2000.
European Search Report dated Jul. 18, 2011 for European Patent Application No. 10193968.4.
European Search Report dated Jul. 22, 2011 issue in corresponding Application No. 1193966.8.
European Search Report dated Oct. 29, 2009, corresponding to European Application No. EP 07 70 8219.
Frederick M. Boyce et al., "Baculovirus-mediated gene transfer into mammalian cells", Proc. Natl. Acad. Sci. USA, vol. 93, pp. 2348-2352, 1996.
Gardner, Malcolm J., "Genome sequence of the human malaria parasite Plasmodium falciparum", Nature, (2002), vol. 419, No. 6906, pp. 498-511.
Hideki Tani et al., "Characterization of Cell-Surface Determinants Important for Baculovirus infection", Virology 279, pp. 343-353 (2001).
J.P. Condreay et al., "Transient and stable gene expression in mammalian cells transduced with a recombinant baculovirus vector", Proc. Natl. Acad. Sci. USA, vol. 96, pp. 127-132, 1999.
J.T. Mangor et al., "A GP64-Null Baculovirus Pseudotyped with Vesicular Stomatitis Virus G Protein", Journal of Virology, vol. 75, No. 6, pp. 2544-2556, 2001.
K. Kojima et al., "Tandem repetition of baculovirus ie1 promoter results in upregulation of transcription", Arch Virol (2001) 146: pp. 1407-1414.
K. M. Lima, et al, "Single dose of a vaccine based on DNA encoding mycobacterial hsp65 protein plus TDM-loaded PLGA microspheres protects mice against a virulent strain of *Mycobacterium tuberculosis*", Gene Therapy, Macmillan Press Ltd., vol. 10, No. 8, pp. 678-685, 2003.
Kaba, Stephen A., "Novel baculovirus-derived p67 subunit vaccines efficacious against East Coast fever in Cattle" Vaccine 23, (2005), pp. 2791-2800.
Kazumi Arai, et al., "Vaccine efficacy for a novel recombinant baculovirus virion expressing the Plasmodium berghei merozoite surface protein 119kDa fragment on its surface", Kokusai Hoken Iryo, 2006 Nen, vol. 21, special extra Issue, p. 163, Endai Bango P2-05.
Kuie-Chun Wang et al., "Baculovirus as a Highly Efficient Gene Delivery Vector for the Expression of Hepatitis Delta Virus Antigens in Mammalian Cells", Biotechnology and Bioengineering, vol. 89 No. 4, pp. 464-473, 2005.
L. Ikonomou et al., "Insect cell culture for industrial production of recombinant proteins", Appl. Microbiol Biotechnol., 62,pp. 1-20, (2003).
John J. Davis et al., "Oncolysis and Suppression of Tumor Growth by a GFP-Expressing Oncolytic Adenovirus Controlled by an hTERT and CMV Hybrid Promoter", Cancer Gene Ther., vol. 13, No. 7, pp. 720-723, 2006.
Liqun Lu et. al., "Baculovirus surface-displayed hemagglutinin of H5N1 influenza virus sustains its authentic cleavage, hemagglutination activity, and antigenicity", BBRC. 358 (2007), pp. 404-409.
Luisa Pieroni et al., In Vivo Gene Transfer in Mouse Skeletal Muscle Mediated by Baculovirus Vectors, Human Gene Therapy 12: pp. 871-881 (2001).

Makoto Matsumoto, "Atarashii Vaccine Kaihatsu no Tameno Zen Rinsho Jikken ni Tsuite, Asia Chiiki tono Kenkyu Network no Katsuyo ni yoru Tazai Taisei Kekkaku no Seigyo ni Kansuru Kenkyu", Heisei 17 Nendo Sokatsu Bntan Kenkyu Hokokusho, 2006 Nen, 3 Gatsu, pp. 112-115.

Mann et al., "Optimisation of a lipiid based oral delivery system containing A/Panama influenza haemagglutinin", Vaccine, 2004, vol. 22, pp. 2425-2429.

Office Action dated Aug. 15, 2011 for U.S. Appl. No. 12/278,916.

R. Grabherr et al., "Developments in the use of baculoviruses for the surface display of complex eukaryotic proteins", Trends in Biotechnology, vol. 19, No. 6, pp. 231-236, 2001.

(56) References Cited

OTHER PUBLICATIONS

Safdar, Amar, et al., "Dose-Related Safety and Immunogenicity of Baculovirus-Expressed Trivalent Infuenza Vaccine: A Double-Blind, Controlled Trial in Adult Patents with Non-Hodgkin B Cell Lymphona", The Journal of Infectous Deseases, (2006) 194:1394-7.

Strauss, R., et al., "Baculovirus-based Vaccination Vectors Allow for Efficient Induction of Immune Responses Against Plasmodium falciparum Circumsporozoite Protein", Molecular Therapy, vol. 15, No. 1, pp. 193-202, 2007.

Tami, Cecilia, et al., "Immunological properties of FMDV-gP64 fusion proteins expressed on SFP cell and baculovirus surfaces" Vaccine, 23, (2004) pp. 840-845.

Ying Li et al., "Neuronal gene transfer by baculovirus-derived vectors accommodating a neuronespecific promoter", Exp. Physiol., vol. 90, No. 1, pp. 39-44, (2004).

Yoshida, S. et al., "Baculovirus virions displaying Plasmodium berghei circums porozoite protein 21 protect mice against malaria sporozoite infection", Virology, vol. 316, pp. 161 to 170, 2003.

Yu-Chen Hu, "Baculovirus Vectors for Gene Therapy", Advances in Virus Research, vol. 68pp. 287, 296, & 298, (2006).

* cited by examiner

Fig. 16

Detected by gp64 Monoclonal Antibody (AcV5)

1: AcNPV-WT
2: AcNPV-CAP-PfCSP
3: AcNPV-CAP-HA1/Anhui
4: AcNPV-CAP-HA1/Vietnam

Fig. 17 (A)

Detected by Anti-PfCSP Monoclonal Antibody (2A10)

1: AcNPV-CAP-PfCSP
2: AcNPV-CAP-PfCSP/272
3: AcNPV-CAP-PfCSP/467

Detected by H5N1/Vietnam Rabbit Polyclonal Antibody (IT-003-005)

1: AcNPV-WT (Cell Lysate)
2: AcNPV-CAP-HA1/Anhui (Cell Lysate)
3: AcNPV-CAP-HA1/Vietnam (Cell Lysate)
4: AcNPV-WT (Virion)
5: AcNPV-CAP-HA1/Vietnam (Virion)
6: Purified H5N1/Anhui Antigen (IT-003-0053p)

| No. | Virus Name | Mammalian Cell Promoter | Viral Promoter | Antigen ORF | ORF size (a.a.) | Fusion Protein | ORF size (a.a.) | Antigen + Membran protein (a.a.) | Total ORF size (a.a.) |
|---|---|---|---|---|---|---|---|---|---|
| 1 | CAP-HA1/Anhui | CAG | Polyhedrin | Anhui (17-345) | 329 | gp64 (21-512) | 492 | 821 | 847 |
| 2 | CAP-HA1/Anhui/272 | CAG | Polyhedrin | Anhui (17-345) | 329 | gp64 (272-512) | 241 | 570 | 596 |
| 3 | CAP-HA1/Anhui/467 | CAG | Polyhedrin | Anhui (17-345) | 329 | gp64 (467-512) | 48 | 375 | 401 |
| 4 | CAP-HA1/Vietnam | CAG | Polyhedrin | Vietnam (17-346) | 330 | gp64 (21-512) | 492 | 822 | 848 |
| 5 | CAP-HA1/Vietnam/51 | CAG | Polyhedrin | Vietnam (17-346) | 330 | gp64 (51-512) | 462 | 792 | 818 |
| 6 | CAP-HA1/Vietnam/101 | CAG | Polyhedrin | Vietnam (17-346) | 330 | gp64 (101-512) | 412 | 742 | 768 |
| 7 | CAP-HA1/Vietnam/154 | CAG | Polyhedrin | Vietnam (17-346) | 330 | gp64 (154-512) | 359 | 689 | 715 |
| 8 | CAP-HA1/Vietnam/201 | CAG | Polyhedrin | Vietnam (17-346) | 330 | gp64 (201-512) | 312 | 642 | 668 |
| 9 | CAP-HA1/Vietnam/272 | CAG | Polyhedrin | Vietnam (17-346) | 330 | gp64 (272-512) | 241 | 571 | 597 |
| 10 | CAP-HA/Vietnam/467 | CAG | Polyhedrin | Vietnam (17-346) | 330 | gp64 (467-512) | 46 | 376 | 402 |
| 11 | CAP-AH/345 | CAG | Polyhedrin | Anhui_GD (1-345) | 345 | gp64 (21-512) | 492 | 837 | 863 |
| 12 | CAP-AH/345/467 | CAG | Polyhedrin | Anhui_GD (1-345) | 345 | gp64 (467-512) | 46 | 391 | 417 |
| 13 | CAP-AH/410 | CAG | Polyhedrin | Anhui_GD (17-410) | 394 | gp64 (21-512) | 492 | 886 | 912 |
| 14 | CAP-AH/410/467 | CAG | Polyhedrin | Anhui_GD (17-410) | 394 | gp64 (467-512) | 46 | 440 | 466 |
| 15 | CAP-AH/473 | CAG | Polyhedrin | Anhui_GD (17-473) | 457 | gp64 (21-512) | 492 | 949 | 975 |
| 16 | CAP-AH/473/467 | CAG | Polyhedrin | Anhui_GD (17-473) | 457 | gp64 (467-512) | 46 | 503 | 529 |
| 17 | CAP-AH/520 | CAG | Polyhedrin | Anhui_GD (17-520) | 504 | gp64 (21-512) | 492 | 996 | 1022 |
| 18 | CAP-AH/520/467 | CAG | Polyhedrin | Anhui_GD (17-520) | 504 | gp64 (467-512) | 46 | 550 | 576 |
| 19 | CAP-VN/346 | CAG | Polyhedrin | Vietnam_GD (17-346) | 330 | gp64 (21-512) | 492 | 822 | 848 |
| 20 | CAP-VN/346/467 | CAG | Polyhedrin | Vietnam_GD (17-346) | 330 | gp64 (467-512) | 46 | 376 | 402 |
| 21 | CAP-VN/410 | CAG | Polyhedrin | Vietnam_GD (17-410) | 394 | gp64 (21-512) | 492 | 886 | 912 |
| 22 | CAP-VN/410/467 | CAG | Polyhedrin | Vietnam_GD (17-410) | 394 | gp64 (467-512) | 46 | 440 | 466 |
| 23 | CAP-VN/473 | CAG | Polyhedrin | Vietnam_GD (17-473) | 457 | gp64 (21-512) | 492 | 949 | 975 |
| 24 | CAP-VN/473/467 | CAG | Polyhedrin | Vietnam_GD (17-473) | 457 | gp64 (467-512) | 46 | 503 | 529 |
| 25 | CAP-VN/520 | CAG | Polyhedrin | Vietnam_GD (17-520) | 504 | gp64 (21-512) | 492 | 996 | 1022 |
| 26 | CAP-VN/520/467 | CAG | Polyhedrin | Vietnam_GD (17-520) | 504 | gp64 (467-512) | 46 | 550 | 576 |
| 27 | CAP-PfCSP | CAG | Polyhedrin | PfCSP(19-373) | 355 | gp64 (21-512) | 492 | 847 | 873 |
| 28 | CAP-PfCSP/272 | CAG | Polyhedrin | PfCSP(19-373) | 356 | gp64 (272-512) | 241 | 596 | 622 |
| 29 | CAP-PfCSP/467 | CAG | Polyhedrin | PfCSP(19-373) | 355 | gp64 (467-512) | 46 | 401 | 427 |
| 30 | CAP-PfCSP(A361E) | CAG | Polyhedrin | PfCSP(19-373)/A361E | 355 | gp64 (21-512) | 492 | 847 | 873 |
| 31 | CAP-PfCSP(A361E)/272 | CAG | Polyhedrin | PfCSP(19-373)/A361E | 355 | gp64 (272-512) | 241 | 596 | 622 |
| 32 | CAP-PfCSP(A361E)/467 | CAG | Polyhedrin | PfCSP(19-373)/A361E | 355 | gp64 (467-512) | 46 | 401 | 427 |
| 33 | CAP-PfCSP-76 | CAG | Polyhedrin | PfCSP(76-373) | 298 | gp64 (21-512) | 492 | 790 | 816 |
| 34 | CAP-PfCSP-76/467 | CAG | Polyhedrin | PfCSP(76-373) | 298 | gp64 (467-512) | 46 | 344 | 370 |
| 35 | CAP-PfCSP+209 | CAG | Polyhedrin | PfCSP+(209-373) | 165 | gp64 (21-512) | 492 | 657 | 683 |
| 36 | CAP-PfCSP+209/467 | CAG | Polyhedrin | PfCSP+(209-373) | 165 | gp64 (467-512) | 46 | 211 | 237 |
| 37 | CAP-PfCSP+76/209 | CAG | Polyhedrin | PfCSP+(76-128 + 209-373) | 218 | gp64 (21-512) | 492 | 710 | 736 |
| 38 | CAP-PfCSP+76/209/467 | CAG | Polyhedrin | PfCSP+(76-128 + 209-373) | 218 | gp64 (467-512) | 46 | 264 | 290 |
| 39 | CAP-CO/full | CAG | Polyhedrin | PfCSP_GD(1-397) | 397 | gp64 (21-512) | 492 | 889 | 915 |
| 40 | CAP-CO/full/467 | CAG | Polyhedrin | PfCSP_GD(1-397) | 397 | gp64 (467-512) | 46 | 443 | 469 |
| 41 | CAP-CO/19 | CAG | Polyhedrin | PfCSP_GD(19-373) | 355 | gp64 (21-512) | 492 | 847 | 873 |
| 42 | CAP-CO/19/467 | CAG | Polyhedrin | PfCSP_GD(19-373) | 355 | gp64 (467-512) | 46 | 401 | 427 |
| 43 | CAP-CO/76 | CAG | Polyhedrin | PfCSP_GD(76-373) | 298 | gp64 (21-512) | 492 | 790 | 816 |
| 44 | CAP-CO/76/467 | CAG | Polyhedrin | PfCSP_GD(76-373) | 298 | gp64 (467-512) | 46 | 344 | 370 |
| 45 | CAP-CO/205 | CAG | Polyhedrin | PfCSP_GD(205-373) | 169 | gp64 (21-512) | 492 | 661 | 687 |
| 46 | CAP-CO/205/467 | CAG | Polyhedrin | PfCSP_GD(205-373) | 169 | gp64 (467-512) | 46 | 215 | 241 |
| 47 | CA39-HA1/Anhui | CAG | vp39p | Vietnam (17-346) | 330 | gp64 (21-512) | 492 | 822 | 848 |
| 48 | CA64-HA1/Anhui | CAG | gp64p | Vietnam (17-346) | 330 | gp64 (21-512) | 492 | 822 | 848 |
| 49 | CA39-PfCSP(A361E) | CAG | vp39p | PfCSP(19-373)/A361E | 355 | gp64 (21-512) | 492 | 847 | 873 |
| 50 | CA64-PfCSP(A361E) | CAG | gp64p | PfCSP(19-373)/A361E | 355 | gp64 (21-512) | 492 | 847 | 873 |
| 51 | CAP-CO/full/VSV | CAG | Polyhedrin | PfCSP_GD(1-397) | 397 | VSV-G (458-549) | 92 | 489 | 515 |
| 52 | CAP-CO/19/VSV | CAG | Polyhedrin | PfCSP_GD(19-373) | 355 | VSV-G (458-549) | 92 | 447 | 473 |
| 53 | CAP-CO/76/VSV | CAG | Polyhedrin | PfCSP_GD(76-373) | 298 | VSV-G (458-549) | 92 | 390 | 416 |
| 54 | CAP-CO/205/VSV | CAG | Polyhedrin | PfCSP_GD(205-373) | 169 | VSV-G (458-549) | 92 | 261 | 287 |
| 55 | Dual-Pfs25-PfCSP-gp64 | CMV | Polyhedrin | Pfs25 (23-171) + PfCSP(19-373) | 504 | gp64 (21-512) | 492 | 996 | 1099 |
| 56 | Dual-PfMSP1-PfCSP-gp64 | CMV | Polyhedrin | PfMSP1(1587-1682) + PfCSP(19-373) | 451 | gp64 (21-512) | 492 | 943 | 1024 |

RECOMBINANT BACULOVIRUS VACCINE

CROSS REFERENCE TO RELATED APPLICATIONS

This is a Divisional application of U.S. application Ser. No. 12/192,927 filed on Aug. 15, 2008, which is a Continuation-in-Part of U.S. application Ser. No. 12/278,916 filed on Aug. 8, 2008 now U.S. Pat. No. 9,023,365 (national phase entry of the International application No. PCT/JP2007/052195) claiming priority of the Japanese Application No. 2006-032863 and on the International Patent Application filed on Aug. 6, 2008 claiming priority of the Japanese Application No. 2007-205785; entire contents of which are incorporated by reference herein.

TECHNICAL FIELD

The present invention provides a novel transfer vector, a recombinant baculovirus obtained by homologous recombination of the transfer vector and a baculovirus DNA and methods for production thereof.

The present invention also relates to pharmaceuticals (e.g., vaccines, preventive or therapeutic drugs for infectious diseases such as malaria and influenza) comprising the recombinant baculovirus as an active ingredient.

BACKGROUND ART

Baculovirus has been used as a vector in methods of industrially producing a desired protein using insect cells. In recent years, it has been found that baculovirus can introduce a foreign gene not only into insect cells but also into mammalian cells, and the possibility of their use as a vector for introducing a therapeutic gene has been found. In Patent document 1, a recombinant baculovirus expression vector having multiple independent promoters composed of a DNA region comprising a gene encoding a viral non-structural protein in the promoter derived from an early gene from the baculovirus and a DNA region comprising a gene encoding a viral structural protein in the promoter derived from a late gene has been disclosed.

In Patent document 2, the method in which a non-mammalian DNA virus comprising a promoter controlled so that an exogenous gene is expressed from a vector in which the desired exogenous genes have been linked to the multiple independent promoters is introduced into a cell and the exogenous gene is expressed in the mammalian cell has been disclosed.

Furthermore, in Patent document 3, the method of producing the protein by gene recombination technology using the baculovirus has been disclosed, and the method of producing the protein by expressing a fusion gene obtained by linking a gp64 gene of the baculovirus to a gene encoding the desired protein, producing the desired protein in a form in which the desired protein has been fused to viral particles, collecting the viral particles fused with the desired protein, and cleaving the desired protein from the viral particles to collect the desired protein has been disclosed.

In Patent document 4, for a baculovirus expression system, a recombinant baculovirus expression vector having multiple independent promoters comprising a first nucleic acid sequence encoding a detection marker linked in the form capable of functioning to a first promoter which is active in a host cell and is inactive in a non-acceptable cell, and a second nucleic acid sequence comprising a foreign nucleic acid sequence linked in the form capable of functioning to a second promoter which is active in the non-acceptable cell has been disclosed.

In patent document 5, it has been disclosed that an influenza virus hemagglutinin (HA) antigen-expressing recombinant baculovirus vector linked to a CAG promoter derived from chicken β actin is useful as a vaccine formulation because the vector has a preventive effect on infection with influenza virus.

In Patent document 6, the method of producing a baculovirus vector comprising a co-transfection step in which a plasmid in which genes encoding proteins expressible on the cell surface have been linked to the baculovirus promoter and the promoter derived from the mammalian cell, respectively, and a plasmid in which genes encoding proteins expressible on the cell surface have been linked to two baculovirus promoters, respectively are co-transfected in the insect cell has been disclosed.

And in patent document 7, a study on an anti-influenza virus activity on the infection with influenza virus using the recombinant baculovirus in which cDNA from influenza virus HA has been incorporated in the CAG promoter has been disclosed, and it has been disclosed that not only the recombinant baculovirus but also a wild type baculovirus has the activity.

This way, in recent years, various recombinant baculoviruses have been developed, and pharmaceutical development for mammals using them has been studied utilizing the recombinant baculovirus as the active ingredient.

In the related art, a recombinant baculovirus vector having a novel structure, and the development of a pharmaceutical formulation, particularly a vaccine formulation using the recombinant baculovirus as the active ingredient, which is effective for infectious diseases such as malaria and influenza, or diseases such as cancer have been desired.

Patent document 1: Japanese Patent No. 3366328, Multiple promoter baculovirus expression system and defect particle products.
Patent document 2: WO98/011243, Non-mammalian DNA virus having modified coating protein.
Patent document 3: JP No. 2002-235236-A, Methods of producing proteins
Patent document 4: JP No. 2003-284557-A, novel baculovirus-transfecting vector and recombinant baculovirus for expression of foreign gene.
Patent document 5: WO02/062381, Baculovirus vector vaccine.
Patent document 6: WO04/029259, Baculovirus vector, method of producing baculovirus vector and method of introducing gene.
Patent document 7: JP No. 2005-15346-A, Baculovirus-containing anti-viral agent.

DISCLOSURE OF INVENTION

Problems to be Solved by the Invention

An object of the present invention is to provide a novel recombinant transfer vector, a recombinant baculovirus obtained by homologous recombination of the recombinant transfer vector and a baculovirus DNA, and methods for production thereof. Another object of the present invention is to provide a pharmaceutical preparation, particularly a vaccine formulation containing the recombinant baculovirus as an active ingredient

Means for Solving the Problems

The present inventors have found a transfer vector having a novel structure capable of expressing a protein having a desired immunogenicity, or a fusion protein of a partial protein or the protein having the immunogenicity with cytokine in insect cells and vertebrate (particularly mammal, bird and fish) cells other than insect cells, and a recombinant baculovirus obtained by homologous recombination of the transfer vector and a baculovirus DNA. By providing the recombinant baculovirus, the pharmaceutical having the recombinant baculovirus as the active ingredient having effective preventive and/or therapeutic effects on infectious diseases was extensively studied. As a result, the present inventors have newly found that the recombinant baculovirus has the effect as the desired pharmaceutical.

And, according to the present invention, the recombinant transfer vector having the novel structure, the recombinant baculovirus obtained by homologous recombination of the transfer vector and the baculovirus DNA and the methods for production thereof were confirmed, and it was confirmed that the recombinant baculovirus itself was useful as the pharmaceutical capable of expressing the protein having the desired immunogenicity in the target cells and was useful as the preventive pharmaceutical for the infectious diseases such as malaria and influenza, and here the present invention was completed.

The present invention provides the invention shown in the following [1] to [51]

[1] A method of producing a transfer vector comprising a structure in which a dual promoter and a fusion gene are incorporated, characterized in that the fusion gene comprising at least one gene encoding a protein capable of being a component of a viral particle and at least one immunogenic foreign gene are linked downstream of the dual promoter linking one vertebrate promoter and another baculovirus promoter.

[2] The method according to [1], wherein the vertebrate promoter is a mammalian promoter.

[3] The method according to [1], characterized in that the gene encoding at least one protein capable of being the component of the viral particle is any of a baculovirus gp64 gene, a Vesicular stomatitis virus glycoprotein gene, a type I human immunodeficiency virus glycoprotein gene, a human respiratory syncytial virus membrane glycoprotein gene, a type A influenza virus hemagglutinin protein gene, a type B influenza virus hemagglutinin protein gene, a herpes simplex virus glycoprotein gene and a murine hepatitis virus S protein gene.

[4] The method according to [1], wherein the vertebrate promoter is selected from any of a cytomegalovirus promoter, an SV40 promoter, a retrovirus promoter, a metallothionein promoter, a heat shock protein promoter, a CAG promoter, an elongation factor 1α promoter, an actin promoter, a ubiquitin promoter, an albumin promoter and an MHC class II promoter.

[5] The method according to [1], wherein the baculovirus promoter is selected from a polyhedrin promoter, a p10 promoter, an IE1 promoter, an IE2 promoter, a p35 promoter, a p39 promoter, and a gp64 promoter.

[6] The method according to [1], wherein the immunogenic foreign gene is selected from any of a malaria antigen, an influenza antigen, an *M. tuberculosis* antigen, a SARS virus antigen, a West Nile fever virus antigen, a dengue fever virus antigen, an HIV antigen, an HCV antigen, a *leishmania* antigen, a *trypanosoma* antigen, a *leucocytozoon* antigen alone, or a fusion antigen of at least one selected from these antigen gene group with a cytokine.

[7] The method according to [1], wherein the transfer vector is any of pDual-Hsp65-gp64, pDual-PbCSP-gp64, pDual-H1N1/HA1-64, pDual-PbTRAMP-gp64, pDual-PbAMA1D123-gp64, pDual-PbMSP129-64, pDual-PfCSP-64, pDual-PfAMA1-gp64, pDual-Pfs25-gp64, pDual-H5N1/HA1-gp64, pDual-SARS/S-gp64, pCP-H1N1/HA1-gp64, pCAP-H1N1/HA1-gp64, pCU-H1N1/HA1-gp64, pDual-H1N1/NP-gp64, pDual-H1N1/M2-gp64, pDual-H1N1/NAe-gp64, pDual-M2e-gp64, pCP-HA1/NC99-gp64, pCP-H1N1/HA0-gp64, pCP-H1N1/HA2-gp64, pCP-H1N1/HA1-vp39 and pCP-H1N1/NP-vp39, pCAP-PfCSP, pCAP-PfCSP/272, pCAP-PfCSP/467, pCAP-PfCSP(A361E), pCAP-PfCSP(A361E)/272, pCAP-PfCSP(A361E)/467, pCAP-PfCSP-76, pCAP-PfCSP-76/467, pCAP-PfCSP+209, pCAP-PfCSP+209/467, pCAP-PfCSP+76/209, pCAP-PfCSP+76/209/467, pCAP-HA1/Anhui, pCAP-HA1/Anhui/272, pCAP-HA1/Anhui/467, pCAP-HA1/Vietnam, pCAP-HA1/Vietnam/51, pCAP-HA1/Vietnam/101, pCAP-HA1/Vietnam/154, pCAP-HA1/Vietnam/201, pCAP-HA1/Vietnam/272, pCAP-HA1/Vietnam/467, pCAP-AH/345, pCAP-AH/345/467, pCAP-AH/410, pCAP-AH/410/467, pCAP-AH/473, pCAP-AH/473/467, pCAP-AH/520, pCAP-AH/520/467, pCAP-VN/346, pCAP-VN/346/467, pCAP-VN/410, pCAP-VN/410/467, pCAP-VN/473, pCAP-VN/473/467, pCAP-VN/520, pCAP-VN/520/467, pCAP-CO/full, pCAP-CO/full/467, pCAP-CO/19, pCAP-CO/19/467, pCAP-CO/76, pCAP-CO/76/467, pCAP-CO/205, pCAP-CO/205/467, pCA39-HA1/Anhui, pCA64-HA1/Anhui, pCA39-PfCSP(A361E), pCA64-PfCSP(A361E), pCAP-CO/full/VSV, pCAP-CO/19/VSV, pCAP-CO/76/VSV, pCAP-CO/205/VSV, pDual-Pfs25-PfCSP-gp64, and pDual-PfMSP1-PfCSP-gp64.

[8] A method of producing a recombinant baculovirus comprising the steps of producing a transfer vector comprising a structure in which a dual promoter and a fusion gene are incorporated, characterized in that the fusion gene comprising at least one gene encoding a protein capable of being a component of a viral particle and at least one immunogenic foreign gene are linked downstream of the dual promoter linking one vertebrate promoter and another baculovirus promoter; co-transfecting the transfer vector and a baculovirus DNA into a host cell of an insect; and separating the recombinant baculovirus.

[9] The method according to [8], characterized in that the gene encoding at least one protein capable of being the component of the viral particle is any of a baculovirus gp64 gene, a Vesicular stomatitis virus glycoprotein gene, a type I human immunodeficiency virus glycoprotein gene, a human respiratory syncytial virus membrane glycoprotein gene, a type A influenza virus hemagglutinin protein gene, a type B influenza virus hemagglutinin protein gene, a herpes simplex virus glycoprotein gene and a murine hepatitis virus S protein gene.

[10] The method according to [9], wherein the vertebrate promoter is selected from any of a cytomegalovirus promoter, an SV40 promoter, a retrovirus promoter, a metallothionein promoter, a heat shock protein promoter, a CAG promoter, an elongation factor 1α promoter, an actin promoter, a ubiquitin promoter, an albumin promoter and an MHC class II promoter.

[11] The method according to [8], wherein the baculovirus promoter is selected from a polyhedrin promoter, a p10 promoter, an IE1 promoter, a p35 promoter, a p39 promoter, and a gp64 promoter.

[12] The method according to [8], wherein the immunogenic foreign gene is selected from any of a malaria antigen, an influenza antigen, an *M. tuberculosis* antigen, a SARS virus antigen, a West Nile fever virus antigen, a dengue fever virus antigen, an HIV antigen, an HCV antigen, a *leishmania* antigen, *trypanosoma* antigen, a *leucocytozoon* antigen alone, or a fusion antigen of one selected from these antigen gene group with a cytokine.

[13] The method according to [8], wherein the recombinant baculovirus is any of AcNPV-Dual-Hsp65, AcNPV-Dual-PbCSP, AcNPV-Dual-H1N1/HA1, AcNPV-Dual-Pb-TRAMP, AcNPV-Dual-PbAMA1D123, AcNPV-Dual-PbMSP129, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39 and AcNPV-CP-H1N1/NP-vp39, AcNPV-CAP-PfCSP, AcNPV-CAP-PfCSP/272, AcNPV-CAP-PfCSP/467, AcNPV-CAP-PfCSP(A361E), AcNPV-CAP-PfCSP(A361E)/272, AcNPV-CAP-PfCSP(A361E)/467, AcNPV-CAP-PfCSP-76, AcNPV-CAP-PfCSP-76/467, AcNPV-CAP-PfCSP+209, AcNPV-CAP-PfCSP+209/467, AcNPV-CAP-PfCSP+76/209, AcNPV-CAP-PfCSP+76/209/467, AcNPV-CAP-HA1/Anhui, AcNPV-CAP-HA1/Anhui/272, AcNPV-CAP-HA1/Anhui/467, AcNPV-CAP-HA1/Vietnam, AcNPV-CAP-HA1/Vietnam/51, AcNPV-CAP-HA1/Vietnam/101, AcNPV-CAP-HA1/Vietnam/154, AcNPV-CAP-HA1/Vietnam/201, AcNPV-CAP-HA1/Vietnam/272, AcNPV-CAP-HA1/Vietnam/467, AcNPV-CAP-AH/345, AcNPV-CAP-AH/345/467, AcNPV-CAP-AH/410, AcNPV-CAP-AH/410/467, AcNPV-CAP-AH/473, AcNPV-CAP-AH/473/467, AcNPV-CAP-AH/520, AcNPV-CAP-AH/520/467, AcNPV-CAP-VN/346, AcNPV-CAP-VN/346/467, AcNPV-CAP-VN/410, AcNPV-CAP-VN/410/467, AcNPV-CAP-VN/473, AcNPV-CAP-VN/473/467, AcNPV-CAP-VN/520, AcNPV-CAP-VN/520/467, AcNPV-CAP-CO/full, AcNPV-CAP-CO/full/467, AcNPV-CAP-CO/19, AcNPV-CAP-CO/19/467, AcNPV-CAP-CO/76, AcNPV-CAP-CO/76/467, AcNPV-CAP-CO/205, AcNPV-CAP-CO/205/467, AcNPV-CA39-HA1/Anhui, AcNPV-CA64-HA1/Anhui, AcNPV-CA39-PfCSP(A361E), AcNPV-CA64-PfCSP(A361E), AcNPV-CAP-CO/full/VSV, AcNPV-CAP-CO/19/VSV, AcNPV-CAP-CO/76/VSV, AcNPV-CAP-CO/205/VSV, AcNPV-Dual-Pfs25-PfCSP-gp64, and AcNPV-Dual-PfMSP1-PfCSP-gp64.

[14] A transfer vector comprising a structure in which a fusion gene comprising at least one gene encoding a protein capable of being a component of a viral particle and at least one immunogenic foreign gene were linked downstream of the dual promoter linking one vertebrate promoter and another baculovirus promoter is incorporated.

[15] The transfer vector according to [14], characterized in that the gene encoding at least one protein capable of being the component of the viral particle is any of a baculovirus gp64 gene, a Vesicular stomatitis virus glycoprotein gene, a type I human immunodeficiency virus glycoprotein gene, a human respiratory syncytial virus membrane glycoprotein gene, a type A influenza virus hemagglutinin protein gene, a type B influenza virus hemagglutinin protein gene, a herpes simplex virus glycoprotein gene and a murine hepatitis virus S protein gene.

[16] The transfer vector according to [14], wherein the vertebrate promoter is selected from any of a cytomegalovirus promoter, an SV40 promoter, a retrovirus promoter, a metallothionein promoter, a heat shock protein promoter, a CAG promoter, an elongation factor 1α promoter, an actin promoter, a ubiquitin promoter, an albumin promoter and an MHC class II promoter.

[17] The transfer vector according to [14], wherein the baculovirus promoter is selected from a polyhedrin promoter, a p10 promoter, an IE1 promoter, an IE2 promoter, a p35 promoter, a p39 promoter, and a gp64 promoter.

[18] The transfer vector according to [14], wherein the immunogenic foreign gene is selected from any of a malaria antigen, an influenza antigen, an *M. tuberculosis* antigen, a SARS virus antigen, a West Nile fever virus antigen, a dengue fever virus antigen, an HIV antigen, an HCV antigen, a *leishmania* antigen, a *trypanosoma* antigen, a *leucocytozoon* antigen alone, or a fusion antigen of one selected from these antigen gene group with a cytokine.

[19] The transfer vector according to [14], which is any of pDual-Hsp65-gp64, pDual-PbCSP-gp64, pDual-H1N1/HA1-gp64, pDual-PbTRAMP-gp64, pDual-PbAMA1D123-gp64, pDual-PbMSP129, pDual-PfCSP-gp64, pDual-PfAMA1-gp64, pDual-Pfs25-gp64, pDual-H5N1/HA1-gp64, pDual-SARS/S-gp64, pCP-H1N1/HA1-gp64, pCAP-H1N1/HA1-gp64, pCU-H1N1/HA1-gp64, pDual-H1N1/NP-gp64, pDual-H1N1/M2-gp64, pDual-H1N1/NAe-gp64, pDual-M2e-gp64, pCP-HA1/NC99-gp64, pCP-H1N1/HA0-gp64, pCP-H1N1/HA2-gp64, pCP-H1N1/HA1-vp39 and pCP-H1N1/NP-vp39, pCAP-PfCSP, pCAP-PfCSP/272, pCAP-PfCSP/467, pCAP-PfCSP(A361E), pCAP-PfCSP(A361E)/272, pCAP-PfCSP(A361E)/467, pCAP-PfCSP-76, pCAP-PfCSP-76/467, pCAP-PfCSP+209, pCAP-PfCSP+209/467, pCAP-PfCSP+76/209, pCAP-PfCSP+76/209/467, pCAP-HA1/Anhui, pCAP-HA1/Anhui/272, pCAP-HA1/Anhui/467, pCAP-HA1/Vietnam, pCAP-HA1/Vietnam/51, pCAP-HA1/Vietnam/101, pCAP-HA1/Vietnam/154, pCAP-HA1/Vietnam/201, pCAP-HA1/Vietnam/272, pCAP-HA1/Vietnam/467, pCAP-AH/345, pCAP-AH/345/467, pCAP-AH/410, pCAP-AH/410/467, pCAP-AH/473, pCAP-AH/473/467, pCAP-AH/520, pCAP-AH/520/467, pCAP-VN/346, pCAP-VN/346/467, pCAP-VN/410, pCAP-VN/410/467, pCAP-VN/473, pCAP-VN/473/467, pCAP-VN/520, pCAP-VN/520/467, pCAP-CO/full, pCAP-CO/full/467, pCAP-CO/19, pCAP-CO/19/467, pCAP-CO/76, pCAP-CO/76/467, pCAP-CO/205, pCAP-CO/205/467, pCA39-HA1/Anhui, pCA64-HA1/Anhui, pCA39-PfCSP(A361E), pCA64-PfCSP(A361E), pCAP-CO/full/VSV, pCAP-CO/19/VSV, pCAP-CO/76/VSV, pCAP-CO/205/VSV, pDual-Pfs25-PfCSP-gp64, and pDual-PfMSP1-PfCSP-gp64.

[20] A recombinant baculovirus produced by the method of producing the recombinant baculovirus according to any of [8] to [13].

[21] The recombinant baculovirus according to [20] which is any of AcNPV-Dual-Hsp65, AcNPV-Dual-PbCSP, AcNPV-Dual-H1N1/HA1, AcNPV-Dual-PbTRAMP, AcNPV-Dual-PbAMA1D123, AcNPV-Dual-PbMSP129, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39 and AcNPV-CP-H1N1/NP-vp39, AcNPV-CAP-PfCSP, AcNPV-CAP-PfCSP/272, AcNPV-CAP-PfCSP/467, AcNPV-CAP-PfCSP(A361E), AcNPV-CAP-PfCSP(A361E)/272, AcNPV-CAP-PfCSP(A361E)/467, AcNPV-CAP-PfCSP-76, AcNPV-CAP-PfCSP-76/467, AcNPV-CAP-PfCSP+209, AcNPV-CAP-PfCSP+209/467, AcNPV-CAP-PfCSP+76/209, AcNPV-CAP-PfCSP+76/209/467, AcNPV-CAP-HA1/Anhui, AcNPV-CAP-HA1/Anhui/272, AcNPV-CAP-HA1/Anhui/467, AcNPV-CAP-HA1/Vietnam, AcNPV-CAP-HA1/Vietnam/51, AcNPV-CAP-HA1/Vietnam/101, AcNPV-CAP-HA1/Vietnam/154, AcNPV-CAP-HA1/Vietnam/201, AcNPV-CAP-HA1/Vietnam/272, AcNPV-CAP-HA1/Vietnam/467, AcNPV-CAP-AH/345, AcNPV-CAP-AH/345/467, AcNPV-CAP-AH/410, AcNPV-CAP-AH/410/467, AcNPV-CAP-AH/473, AcNPV-CAP-AH/473/467, AcNPV-CAP-AH/520, AcNPV-CAP-AH/520/467, AcNPV-CAP-VN/346, AcNPV-CAP-VN/346/467, AcNPV-CAP-VN/410, AcNPV-CAP-VN/410/467, AcNPV-CAP-VN/473, AcNPV-CAP-VN/473/467, AcNPV-CAP-VN/520, AcNPV-CAP-VN/520/467, AcNPV-CAP-CO/full, AcNPV-CAP-CO/full/467, AcNPV-CAP-CO/19, AcNPV-CAP-CO/19/467, AcNPV-CAP-CO/76, AcNPV-CAP-CO/76/467, AcNPV-CAP-CO/205, AcNPV-CAP-CO/205/467, AcNPV-CA39-HA1/Anhui, AcNPV-CA64-HA1/Anhui, AcNPV-CA39-PfCSP(A361E), AcNPV-CA64-PfCSP(A361E), AcNPV-CAP-CO/full/VSV, AcNPV-CAP-CO/19/VSV, AcNPV-CAP-CO/76/VSV, AcNPV-CAP-CO/205/VSV, AcNPV-Dual-Pfs25-PfCSP-gp64, and AcNPV-Dual-PfMSP1-PfCSP-gp64.

[22] A pharmaceutical composition comprising the recombinant baculovirus according to [20] or [21].

[23] The pharmaceutical composition according to [22], comprising any of AcNPV-Dual-H1N1/HA1, AcNPV-H1N1/HA1, AcNPV-CAP-H1N1/HA1, AcNPV-Dual-PfCSP, AcNPV-Dual-PfAMA1, AcNPV-Dual-Pfs25, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39 and AcNPV-CP-H1N1/NP-vp39.

[24] A pharmaceutical composition comprising the recombinant baculovirus according to claim [20] or [21], wherein the composition is administered intramuscularly, intranasally or by inhalation.

[25] A vaccine comprising any of AcNPV-Dual-H1N1/HA1, AcNPV-H1N1/HA1, AcNPV-CAP-H1N1/HA1, AcNPV-Dual-PfCSP, AcNPV-Dual-PfAMA1, AcNPV-Dual-Pfs25, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39 and AcNPV-CP-H1N1/NP-vp39 as an active ingredient.

[26] A vaccine comprising any one of AcNPV-CAP-PfCSP, AcNPV-CAP-PfCSP/272, AcNPV-CAP-PfCSP/467, AcNPV-CAP-PfCSP(A361E), AcNPV-CAP-PfCSP(A361E)/272, AcNPV-CAP-PfCSP(A361E)/467, AcNPV-CAP-PfCSP-76, AcNPV-CAP-PfCSP-76/467, AcNPV-CAP-PfCSP+209, AcNPV-CAP-PfCSP+209/467, AcNPV-CAP-PfCSP+76/209, AcNPV-CAP-PfCSP+76/209/467, AcNPV-CAP-HA1/Anhui, AcNPV-CAP-HA1/Anhui/272, AcNPV-CAP-HA1/Anhui/467, AcNPV-CAP-HA1/Vietnam, AcNPV-CAP-HA1/Vietnam/51, AcNPV-CAP-HA1/Vietnam/101, AcNPV-CAP-HA1/Vietnam/154, AcNPV-CAP-HA1/Vietnam/201, AcNPV-CAP-HA1/Vietnam/272, AcNPV-CAP-HA1/Vietnam/467, AcNPV-CAP-AH/345, AcNPV-CAP-AH/345/467, AcNPV-CAP-AH/410, AcNPV-CAP-AH/410/467, AcNPV-CAP-AH/473, AcNPV-CAP-AH/473/467, AcNPV-CAP-AH/520, AcNPV-CAP-AH/520/467, AcNPV-CAP-VN/346, AcNPV-CAP-VN/346/467, AcNPV-CAP-VN/410, AcNPV-CAP-VN/410/467, AcNPV-CAP-VN/473, AcNPV-CAP-VN/473/467, AcNPV-CAP-VN/520, AcNPV-CAP-VN/520/467, AcNPV-CAP-CO/full, AcNPV-CAP-CO/full/467, AcNPV-CAP-CO/19, AcNPV-CAP-CO/19/467, AcNPV-CAP-CO/76, AcNPV-CAP-CO/76/467, AcNPV-CAP-CO/205, AcNPV-CAP-CO/205/467, AcNPV-CA39-HA1/Anhui, AcNPV-CA64-HA1/Anhui, AcNPV-CA39-PfCSP(A361E), AcNPV-CA64-PfCSP(A361E), AcNPV-CAP-CO/full/VSV, AcNPV-CAP-CO/19/VSV, AcNPV-CAP-CO/76/VSV, AcNPV-CAP-CO/205/VSV, AcNPV-Dual-Pfs25-PfCSP-64, and AcNPV-Dual-PfMSP1-PfCSP-gp64.

[27] The vaccine according to [25] or [26], wherein the vaccine is administered intramuscularly, intranasally or by inhalation.

[28] A therapeutic or preventive agent for influenza virus infection, comprising AcNPV-Dual-H1N1/HA1, AcNPV-H1N1/HA1, AcNPV-CAP-H1N1/HA1, AcNPV-Dual-PfCSP, AcNPV-Dual-PfAMA1, AcNPV-Dual-Pfs25, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39, AcNPV-CP-H1N1/NP-vp39 as an active ingredient.

[29] A therapeutic or preventive agent for influenza virus infection, comprising as an active ingredient any one of AcNPV-CAP-HA1/Anhui, AcNPV-CAP-HA1/Anhui/272, AcNPV-CAP-HA1/Anhui/467, AcNPV-CAP-HA1/Vietnam, AcNPV-CAP-HA1/Vietnam/51, AcNPV-CAP-HA1/Vietnam/101, AcNPV-CAP-HA1/Vietnam/154, AcNPV-CAP-HA1/Vietnam/201, AcNPV-CAP-HA1/Vietnam/272, AcNPV-CAP-HA1/Vietnam/467, AcNPV-CAP-AH/345, AcNPV-CAP-AH/345/467, AcNPV-CAP-AH/410, AcNPV-CAP-AH/410/467, AcNPV-CAP-AH/473, AcNPV-CAP-AH/473/467, AcNPV-CAP-AH/520, AcNPV-CAP-AH/520/467, AcNPV-CAP-VN/346, AcNPV-CAP-VN/346/467, AcNPV-CAP-VN/410, AcNPV-CAP-VN/410/467, AcNPV-CAP-VN/473, AcNPV-CAP-VN/473/467, AcNPV-CAP-VN/520, AcNPV-CAP-VN/520/467, AcNPV-CA39-HA1/Anhui, and AcNPV-CA64-HA1/Anhui.

[30] The therapeutic or preventive agent for influenza virus infection according to [28] or [29], wherein the agent is administered intramuscularly, intranasally or by inhalation.

[31] A vaccine for influenza virus infection, comprising any of AcNPV-Dual-H1N1/HA1, AcNPV-H1N1/HA1, AcNPV-CAP-H1N1/HA1, AcNPV-Dual-PfCSP, AcNPV-Dual-PfAMA1, AcNPV-Dual-Pfs25, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39 and AcNPV-CP-H1N1/NP-vp39 as an active ingredient.

[32] A vaccine against influenza virus infection, comprising as an active ingredient any one of AcNPV-CAP-HA1/Anhui, AcNPV-CAP-HA1/Anhui/272, AcNPV-CAP-HA1/Anhui/467, AcNPV-CAP-HA1/Vietnam, AcNPV-CAP-HA1/Vietnam/51, AcNPV-CAP-HA1/Vietnam/101, AcNPV-CAP-HA1/Vietnam/154, AcNPV-CAP-HA1/Vietnam/201, AcNPV-CAP-HA1/Vietnam/272, AcNPV-CAP-HA1/Vietnam/467, AcNPV-CAP-AH/345, AcNPV-CAP-AH/345/467, AcNPV-CAP-AH/410, AcNPV-CAP-AH/410/467, AcNPV-CAP-AH/473, AcNPV-CAP-AH/473/467, AcNPV-CAP-AH/520, AcNPV-CAP-AH/520/467, AcNPV-CAP-VN/346, AcNPV-CAP-VN/346/467, AcNPV-CAP-VN/410, AcNPV-CAP-VN/410/467, AcNPV-CAP-VN/473, AcNPV-CAP-VN/473/467, AcNPV-CAP-VN/520, AcNPV-CAP-VN/520/467, AcNPV-CA39-HA1/Anhui, and AcNPV-CA64-HA1/Anhui.

[33] The vaccine for influenza virus infection according to [31] or [32], wherein the agent is administered intramuscularly, intranasally or by inhalation.

[34] A therapeutic or preventive agent for human malaria infection, comprising as an active ingredient any one of AcNPV-CAP-PfCSP, AcNPV-CAP-PfCSP/272, AcNPV-CAP-PfCSP/467, AcNPV-CAP-PfCSP(A361E), AcNPV-CAP-PfCSP(A361E)/272, AcNPV-CAP-PfCSP(A361E)/

467, AcNPV-CAP-PfCSP-76, AcNPV-CAP-PfCSP-76/467, AcNPV-CAP-PfCSP+209, AcNPV-CAP-PfCSP+209/467, AcNPV-CAP-PfCSP+76/209, AcNPV-CAP-PfCSP+76/209/467, AcNPV-CAP-CO/full, AcNPV-CAP-CO/full/467, AcNPV-CAP-CO/19, AcNPV-CAP-CO/19/467, AcNPV-CAP-CO/76, AcNPV-CAP-CO/76/467, AcNPV-CAP-CO/205, AcNPV-CAP-CO/205/467, AcNPV-CA39-PfCSP(A361E), AcNPV-CA64-PfCSP(A361E), AcNPV-CAP-CO/full/VSV, AcNPV-CAP-CO/19/VSV, AcNPV-CAP-CO/76/VSV, AcNPV-CAP-CO/205/VSV, AcNPV-Dual-Pfs25-PfCSP-64, and AcNPV-Dual-PfMSP1-PfCSP-gp64.

[35] A therapeutic or preventive agent for human malaria infection according to [34], which is administered by the intramuscular, respiratory, or nasal route.

[36] A therapeutic or preventive agent for human malaria infection, comprising as an active ingredient any one of AcNPV-CAP-PfCSP, AcNPV-CAP-PfCSP/272, AcNPV-CAP-PfCSP/467, AcNPV-CAP-PfCSP(A361E), AcNPV-CAP-PfCSP(A361E)/272, AcNPV-CAP-PfCSP(A361E)/467, AcNPV-CAP-PfCSP-76, AcNPV-CAP-PfCSP-76/467, AcNPV-CAP-PfCSP+209, AcNPV-CAP-PfCSP+209/467, AcNPV-CAP-PfCSP+76/209, AcNPV-CAP-PfCSP+76/209/467, AcNPV-CAP-CO/full, AcNPV-CAP-CO/full/467, AcNPV-CAP-CO/19, AcNPV-CAP-CO/19/467, AcNPV-CAP-CO/76, AcNPV-CAP-CO/76/467, AcNPV-CAP-CO/205, AcNPV-CAP-CO/205/467, AcNPV-CA39-PfCSP(A361E), AcNPV-CA64-PfCSP(A361E), AcNPV-CAP-CO/full/VSV, AcNPV-CAP-CO/19/VSV, AcNPV-CAP-CO/76/VSV, AcNPV-CAP-CO/205/VSV, AcNPV-Dual-Pfs25-PfCSP-64, and AcNPV-Dual-PfMSP1-PfCSP-gp64.

[37] A therapeutic or preventive agent for human malaria infection according to [36], which is administered by the intramuscular, respiratory, or nasal route.

[38] A method for producing an immunopotential action in a mammal, comprising administrating a recombinant baculovirus produced by the method according to any of [8] to [13] as an active ingredient to the mammal.

[39] The method according to [38], wherein the recombinant baculovirus is any of AcNPV-Dual-Hsp65, AcNPV-Dual-PbCSP, AcNPV-Dual-H1N1/HA1, AcNPV-Dual-Pb-TRAMP, AcNPV-Dual-PbAMA1D123, AcNPV-Dual-PbMSP129, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39 and AcNPV-CP-H1N1/NP-vp39, AcNPV-CAP-PfCSP, AcNPV-CAP-PfCSP/272, AcNPV-CAP-PfCSP/467, AcNPV-CAP-PfCSP(A361E), AcNPV-CAP-PfCSP(A361E)/272, AcNPV-CAP-PfCSP(A361E)/467, AcNPV-CAP-PfCSP-76, AcNPV-CAP-PfCSP-76/467, AcNPV-CAP-PfCSP+209, AcNPV-CAP-PfCSP+209/467, AcNPV-CAP-PfCSP+76/209, AcNPV-CAP-PfCSP+76/209/467, AcNPV-CAP-HA1/Anhui, AcNPV-CAP-HA1/Anhui/272, AcNPV-CAP-HA1/Anhui/467, AcNPV-CAP-HA1/Vietnam, AcNPV-CAP-HA1/Vietnam/51, AcNPV-CAP-HA1/Vietnam/101, AcNPV-CAP-HA1/Vietnam/154, AcNPV-CAP-HA1/Vietnam/201, AcNPV-CAP-HA1/Vietnam/272, AcNPV-CAP-HA1/Vietnam/467, AcNPV-CAP-AH/345, AcNPV-CAP-AH/345/467, AcNPV-CAP-AH/410, AcNPV-CAP-AH/410/467, AcNPV-CAP-AH/473, AcNPV-CAP-AH/473/467, AcNPV-CAP-AH/520, AcNPV-CAP-AH/520/467, AcNPV-CAP-VN/346, AcNPV-CAP-VN/346/467, AcNPV-CAP-VN/410, AcNPV-CAP-VN/410/467, AcNPV-CAP-VN/473, AcNPV-CAP-VN/473/467, AcNPV-CAP-VN/520, AcNPV-CAP-VN/520/467, AcNPV-CAP-CO/full, AcNPV-CAP-CO/full/467, AcNPV-CAP-CO/19, AcNPV-CAP-CO/19/467, AcNPV-CAP-CO/76, AcNPV-CAP-CO/76/467, AcNPV-CAP-CO/205, AcNPV-CAP-CO/205/467, AcNPV-CA39-HA1/Anhui, AcNPV-CA64-HA1/Anhui, AcNPV-CA39-PfCSP(A361E), AcNPV-CA64-PfCSP(A361E), AcNPV-CAP-CO/full/VSV, AcNPV-CAP-CO/19/VSV, AcNPV-CAP-CO/76/VSV, AcNPV-CAP-CO/205/VSV, AcNPV-Dual-Pfs25-PfCSP-64, and AcNPV-Dual-PfMSP1-PfCSP-gp64.

[40] The method according to [38] or [39], wherein the composition is administered intramuscularly, intranasally or by inhalation.

[41] A method for preventing or treating a virus infection in mammals, comprising administrating a recombinant baculovirus produced by the method according to any of [8] to [13] as an active ingredient to the mammal.

[42] The method according to [41], wherein the recombinant baculovirus is any of AcNPV-Dual-Hsp65, AcNPV-Dual-PbCSP, AcNPV-Dual-H1N1/HA1, AcNPV-Dual-Pb-TRAMP, AcNPV-Dual-PbAMA1D123, AcNPV-Dual-PbMSP129, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39 and AcNPV-CP-H1N1/NP-vp39.

[43] The method according to [41] or [42], wherein the composition is administered intramuscularly, intranasally or by inhalation.

[44] A method of preventing malaria or influenza infection or of treating malaria or influenza, comprising administering to a subject an effective amount of the recombinant baculovirus of [21], the composition for infectious diseases of claim [22] or [23], or the vaccine of [25], [26], [27], [31], [32] or [33].

[45] A method according to [44], wherein the recombinant baculovirus, composition, or vaccine is administered to the subject as a liposomal formulation.

[46] A method according to [44], wherein the recombinant baculovirus, composition, or vaccine is administered to the subject by the intramuscular, respiratory, or nasal route.

[47] A method according to [45], wherein the recombinant baculovirus, composition, or vaccine is administered to the subject by the intramuscular, respiratory, or nasal route.

[48] A method of immunostimulation comprising administering to a subject an effective amount of the recombinant baculovirus of [21], the composition for infectious diseases of claim [22] or [23], or the vaccine of [25], [26], [27], [31], [32] or [33].

[49] A method according to [48], wherein the recombinant baculovirus, composition, or vaccine is administered to the subject as a liposomal formulation.

[50] A method according to [48], wherein the recombinant baculovirus, composition, or vaccine is administered to the subject by the intramuscular, respiratory, or nasal route.

[51] A method according to [49], wherein the recombinant baculovirus, composition, or vaccine is administered to the subject by the intramuscular, respiratory, or nasal route.

Effect of the Invention

According to the present invention, a novel recombinant transfer vector, a recombinant baculovirus obtained by homologous recombination of the recombinant transfer vector and a baculovirus DNA, and methods for production thereof are provided. Pharmaceuticals comprising the recombinant baculovirus of the present invention as an active ingredient are useful as the therapeutic or preventive drugs for the infectious diseases such as malaria, influenza, tuberculosis and hepatitis, cancers and autoimmune diseases, or as cellular medicine and vaccine formulations.

BRIEF DESCRIPTION OF THE DRAWINGS

FIG. 16 shows the test results of the expression of vaccine antigens from recombinant baculoviruses of the present invention in insect cells in Example 14.

FIG. 17 (B) shows a Western blotting analysis showing the expression of H5N1/HA1 gene in viral particles of recombinant baculoviruses produced from recombinant transfer vectors.

FIG. 20 shows the transfer vectors of the present invention.

BEST MODES FOR CARRYING OUT THE INVENTION

Figure 1:
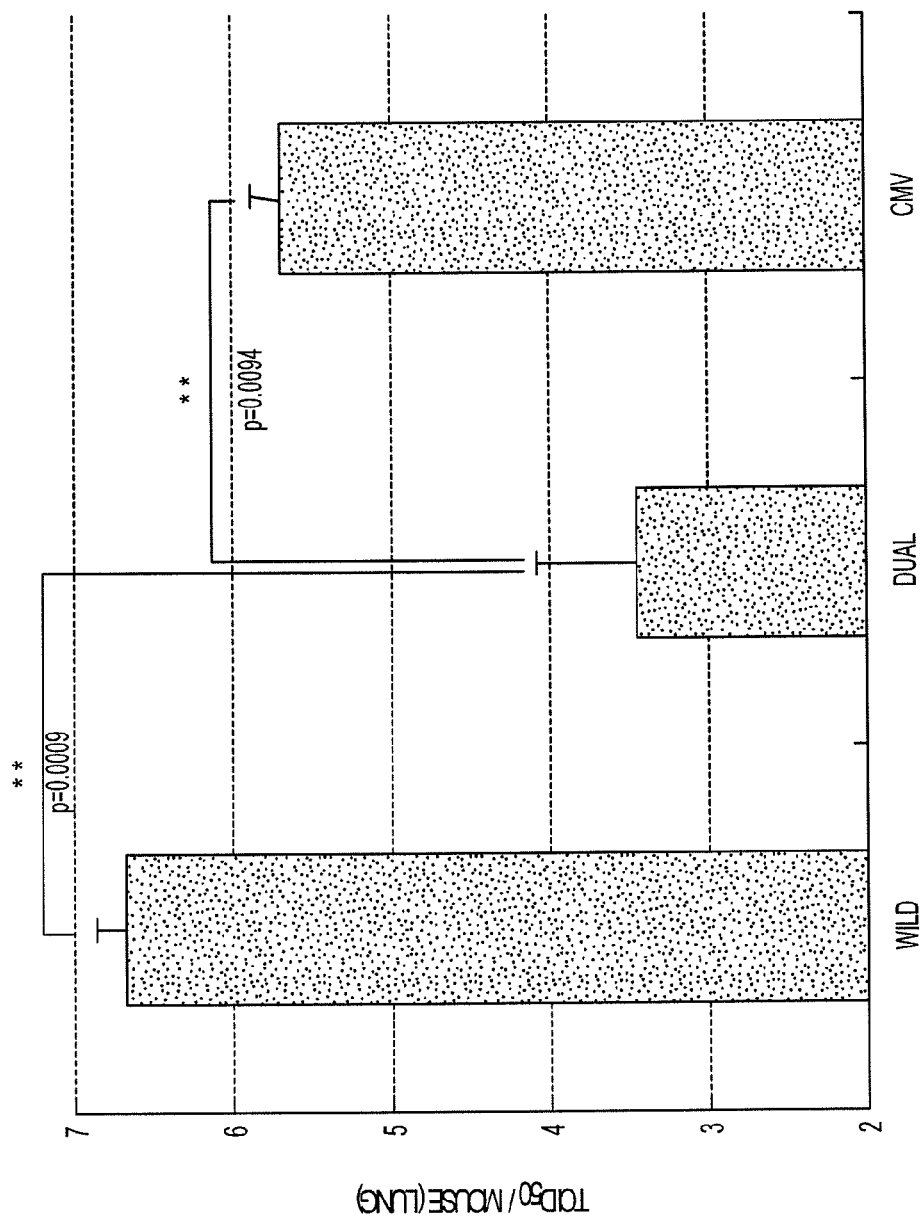
FIG. 1 is a view showing preventive effect (virus infectivity titer) of recombinant baculovirus AcNPV-Dual-H1N1/HA1 on infection with influenza virus.

The abbreviations used for the amino acids, peptides, base sequences, and nucleic acids in the present specification are based on the abbreviations specified in the IUPAC-IUB Communication on Biochemical Nomenclature, Eur. J. Biochem., 138: (1984) and "Guideline for Preparing Specifications Including Base Sequences and Amino Acid Sequences" (Patent Office), and those commonly used in this technical field.

A DNA molecule herein encompasses not only double strand DNA but also single strand DNA including sense chains and antisense chains which compose them. The length of DNA is not limited to a length thereof. Therefore, the polynucleotide (DNA molecule) encoding the immunogenic foreign gene of the present invention includes the double strand DNA including genomic DNA and the single strand DNA (sense chain) including cDNA and the single strand DNA (antisense chain) having the sequence complementary to the sense chain and synthetic DNA fragments thereof unless otherwise mentioned.

The polynucleotide or the DNA molecule herein is not limited in the functional region, and can include at least one of an expression suppression region, a coding region, a leader sequence, an exon and an intron.

Further, examples of the polynucleotide include RNA and DNA. The polypeptide containing a specific amino acid sequence and the polynucleotide containing a specific DNA sequence include fragments, homologs, derivatives, and mutants of the polynucleotide.

The mutants of the polynucleotide, e.g., mutant DNA include naturally occurring allelic mutants, not naturally occurring mutants and mutants having deletion, substitution, addition and insertion. But, these mutants encode the polypeptide having substantially the same function as the function of the polypeptide encoded by the polynucleotide before the mutation.

In the present invention, the transfer vector refers to a plasmid for producing the recombinant baculovirus, comprising the structure in which a fusion gene linking at least one gene encoding a protein capable of being a component of a viral particle and at least one immunogenic foreign gene are incorporated as a fusion gene downstream of a dual promoter comprising a vertebrate promoter (mammalian promoter, bird promoter, fish promoter) and a baculovirus promoter which are connected.

In one of the preferable embodiment of the invention, it is preferable that the immunogenic foreign gene is located downstream of the dual promoter and upstream of the gene encoding the protein capable of being the component of the viral particle.

The recombinant baculovirus of the present invention is used as the active ingredient of the pharmaceuticals or vaccines for vertebrates. As the vertebrates, mammals including human beings, e.g., horses, swines, sheeps, goats, monkeys, mice, dogs and cats, birds such as chickens, quails, gooses, dabblers, pigeons, turkeys, pintados and parrots, and fishes such as yellow tails, adult yellowtails, sea breams, amberjacks, scads, striped jacks, striped pigfish, salmons, blueback salmons, carps, crucian carps, rainbow trouts, brook trouts and amago trouts can be exemplified.

In one embodiment, the present invention provides the transfer vector comprising the novel structure in which the fusion gene comprising the gene encoding a viral membrane protein that can be expressed in an insect cell and one immunogenic foreign gene are incorporated as a fusion gene under the control of the dual promoter comprising a vertebrate promoter and a baculovirus promoter which are connected. By co-transfecting this transfer vector together with a baculovirus DNA into an insect cell to induce a homologous recombination, it is possible to obtain the recombinant baculovirus comprising the fusion gene incorporated under the control of the baculovirus promoter, which can express in an insect cell and can produce a fusion protein capable of being the component of the budded viral particle.

In the present invention, when the recombinant baculovirus is administered to a vertebrate, the fusion protein of the protein capable of being the component of the budded viral particle and the immunogenic protein probably functions as a component vaccine. When the recombinant baculovirus administered to a vertebrate invades a vertebrate cell, a fusion antigen with the target immunogenic foreign antigen encoded by the viral genome is produced in the viral genome, and functions as a DNA vaccine.

Therefore, in the case of the mammal, by administering the recombinant baculovirus of the present invention to the mammal, the fusion protein of the protein capable of being the component of the viral particle and the immunogenic protein is presented as antigen and is produced in the cell of the mammal. The fusion protein is thought to function as the preventive or therapeutic agent for infections with virus, protozoa and bacteria due to its immunopotential or immunostimulation action.

The baculovirus DNA to be co-transfected with the transfer vector may be any of a wild type, a mutant and a recombinant baculovirus DNA. Host cells to be co-transfected include, for example, cells from the insect such as *Spodoptera frugiperda*.

In the present invention, a immunogenic foreign gene is a gene encoding an amino acid sequence of an antigenic protein which can be used as an immunogen of immunotherapy including vaccine therapy for prevention and treatment of infectious diseases, such as malaria, influenza and tuberculosis, autoimmune disease and cancers. Examples of the antigen protein include malaria antigen, influenza virus antigen and *M. tuberculosis* antigen is referred to as the immunogenic foreign gene.

Here, the "foreign" gene means a gene introduced from outside, including a gene that is originally present in the cell when introduced from outside.

In the present invention, the gene encoding the amino acid sequence of the protein which is the above immunogen is not particularly limited as the gene encoding the amino acid sequence of the antigenic protein as long as the gene is the gene encoding the amino acid sequence of the antigenic protein having the immunogenicity against a substance which causes the diseases such as infectious diseases, cancers and autoimmune diseases. Examples of these genes encoding the amino acid sequence of the antigenic protein having the immunogenicity include the followings.

As the gene encoding the amino acid sequence of the malaria antigen, for example, the genes encoding the amino acid sequences of the proteins such as a surface antigen CSP (Circumsporozoite Protein) of sporozoite surface of malaria parasite, MSP1 (merozoite surface protein 1) of a membrane protein of metrozoite surface, a malaria S antigen secreted from erythrocytes infected with malaria, PfEMP1 protein present in knob of the erythrocytes infected with malaria, SERA protein, TRAMP protein and AMA1 protein are exemplified.

As the gene encoding the amino acid sequence of the influenza virus antigen, the genes encoding the amino acid sequences of the proteins such as HA antigen (hemagglutinin antigen), NA antigen (neuraminidase antigen), M2 antigen (matrix protein antigen) and NP antigen (nucleoprotein antigen) can be exemplified.

As the gene encoding the amino acid sequence of the antigenic protein for tuberculosis, the genes encoding the amino acid sequences of the proteins such as HSP65 (65-kDa heat shock protein), α-antigen (Antigen85A, Antigen85B, Antigen85C), Mtb72f, MDP-1, ESAT-6, MPB51m, Mtb8.8, Mtb9.9, Mtb32, Mtb39 and Mtb11.

With respect to vertebrate genes, as the mammalian genes, the genes encoding the amino acid sequences of the antigenic proteins of the infectious diseases in human beings, cattle, horses, swines, sheeps, monkeys, mice, dogs and cats can be exemplified. As the bird genes, the antigen genes (e.g., bird influenza S antigen) of the infectious diseases in chickens, dabblers, pigeons, turkeys, pintados and parrots can be exemplified. As the fish genes, the antigen genes of the infectious diseases in yellow tails, adult yellowtails, sea breams, amberjacks, scads, striped jacks, striped pigfish, salmons, blueback salmons, carps, crucian carps, rainbow trouts, brook trouts and amago trouts are included.

Pathogen genes whose association with the infectious diseases in the above mammals, birds and fishes has been reported are easily available from the institutions where public data such as GenBank registering the pathogen genes have been stored.

In the present invention, for the immunogenic foreign genes, in addition to the above immune antigens present outside the human body, for example, cytokine genes present inside the human body, e.g., an IL-12 gene, an IL-6 gene, an IL-6 receptor gene, an IL-2 gene, an IL-18 gene, an IFN-γ gene and an M-CSF gene, or fusion genes obtained by fusing a given antigen having the immunogenicity with the above antigenic protein using gene recombination technology are also addressed as the immunogenic foreign genes in the present invention as long as they are introduced from the outside.

In the present invention, it is possible to provide the transfer vector having these immunogenic foreign genes and the recombinant baculovirus obtained by homologous recombination thereof, as well as provide a pharmaceutical composition comprising the recombinant baculovirus having the immunogenic foreign gene as the active ingredient and the vaccine formulation composed of the pharmaceutical composition.

The baculovirus used for the present invention is an insect pathogen virus is in a group of DNA viruses (Baculoviridae) having a cyclic double strand DNA as a gene which causes infection in an insect and is one group (Baculoviridae) of DNA viruses having a cyclic double strand DNA as the gene. Among them, one group of the viruses referred to as a nuclear polyhedrosis virus (NPV) makes an inclusion body referred to as a polyhedron in a nucleus in an infected cell in the late phase of the infection. Even if the foreign gene to be expressed is inserted in place of a polyhedron gene, the virus infects, grows and produces the desired foreign gene product in a large amount with no problem. Thus, this has been practically applied to the production of the desired protein in recent years.

As the baculovirus used for the present invention, *Autographa Californica* Nuclear Polyhedorosis Virus: AcNPV, *Bombyx mori* Nuclear Polyhedorosis Virus: BmNPV, *Orgyia pseudotsugata* Nuclear Polyhedorosis Virus: OpNPV and *Lymantria disper* Nuclear Polyhedorosis Virus LdNPV can be exemplified.

The baculovirus DNA may be any DNA which can perform the homologous recombination with the transfer vector of the present invention. Specifically, the viral gene of the baculovirus DNA which can perform the homologous recombination with the transfer vector of the present invention is 130 kbp which is huge, and the immunogenic foreign gene of 15 kbp or more can be inserted. The baculovirus gene itself is scarcely expressed in the vertebrate cells. Thus, there is almost no need to consider its cytotoxicity, and thus, it is thought that no harmful immune response is induced.

(1) Transfer Vector and Production of Transfer Vector of the Present Invention
Production of Immunogenic Foreign Gene DNA The immunogenic foreign gene DNA capable of being fused to the viral gene, which is one of the components of the baculovirus transfer vector can be easily produced and acquired by synthesizing based on nucleic acid sequence information of the polynucleotide encoding the amino acid sequence of the antigenic protein having the objective immunogenicity disclosed herein, or directly synthesizing (chemical DNA synthesis method) the DNA corresponding to the nucleic acid sequence of a coding region of the immunogenic foreign gene based on the nucleic acid sequence information of the immunogenic foreign gene. General gene engineering techniques can be applied to this production (e.g., see Molecular Cloning 2d Ed, Cold Spring Harbor Lab. Press (1989); Zoku Seikagaku Jikken Kouza, "Idenshi Kenkyuho I, II, III" edited by the Japanese Biochemistry Society, 1986).

As the synthesis methods of the DNA, chemical synthesis means such as phosphate triester method and phosphate amidite method (J. Am. Chem. Soc., 89, 4801 (1967); ibid., 91, 3350 (1969); Science, 150, 178 (1968); Tetrahedron Lett., 22, 1859 (1981); ibid., 24, 245 (1983)) and combination methods thereof can be exemplified. More specifically, the DNA can also be chemically synthesized by a phosphoramidite method or the triester method, and can be synthesized using a commercially available automatic oligonucleotide synthesizer. A double strand fragment can be obtained by synthesizing a complementary chain and annealing the complementary chain with a chemically synthesized single strand under an appropriate condition or adding the complementary chain with appropriate primer sequences to the chemically synthesized single strand using a DNA polymerase.

As specific one aspect of the immunogenic foreign gene DNA produced in the present invention, DNA composed of the DNA sequence encoding the amino acid sequence of the *M. tuberculosis* antigen protein, the DNA sequence encoding the amino acid sequence of the malaria antigen protein or the DNA sequence encoding the amino acid sequence of the influenza virus antigen protein can be exemplified.

The DNA utilized in the present invention is not limited to a full length DNA sequence of a DNA sequence encoding the amino acid sequence of a polypeptide of antigenic protein having immunogenicity, and may be a DNA sequence encoding a partial sequence as long as the protein of the amino acid sequence encoded by the DNA sequence has immunogenicity.

The DNA utilized in the present invention may be a DNA sequence obtained by fusing a DNA sequence encoding the amino acid sequence of an antigenic protein having antigenicity to a cytokine gene present inside of human body, e.g., IL-12 gene, IL-1 gene, IL-6 gene, IL-6 receptor gene, IL-2 gene, IL-18 gene, IFN-α gene, IFN-β gene, IFN-γ gene, TNF gene, TGF-β gene, GM-CSF gene and M-CSF gene.

The fused DNA sequence is not limited to a full length of the coding region of a DNA sequence encoding an amino acid sequence of the polypeptide of an antigenic protein having antigenicity and a DNA sequence of a cytokine gene, and may be a partial DNA sequence.

The DNA of the immunogenic foreign gene used for the present invention is not limited to a DNA molecule having such a particular DNA sequence, and can also have a DNA sequence obtained by combining and selecting an optional codon for each amino acid residue. The choice of a codon can be performed in accordance with standard methods. At that time, for example, it is possible to consider a usage frequency of a codon in the host utilized. (Nucleic Acids Res., 9, 43 (1981)).

The method of producing the DNA of immunogenic foreign gene used for the present invention by gene engineering techniques can be more specifically performed by preparing cDNA library from an appropriate origin which expresses the DNA of the immunogenic foreign gene in accordance with standard methods and selecting a desired clone from the library using an appropriate probe or an antibody against an expressed product which is inherent for the immunogenic foreign gene (see Proc. Natl. Acad. Sci., USA., 78, 6613 (1981); Science, 222, 778 (1983)).

In the above, as the origin of the genomic DNA, various cells, tissues and cultured cells derived therefrom which express the DNA of the immunogenic foreign gene can be exemplified. In particular, it is preferable to use an extract of an erythrocytes infected with malaria parasites, an extract of a cells infected with influenza virus or an extract of *M. tuberculosis* as origin. The extraction and separation of total DNA and RNA from the origin, the separation and purification of mRNA and the acquisition and cloning of cDNA can be performed in accordance with standard methods.

The production of the DNA of the immunogenic foreign gene can also be performed by extracting mRNA of each immunogen, then adding poly A to RNA, collecting the poly A-added RNA, producing cDNA using a reverse transcriptase, adding restriction enzyme sites to both ends of the cDNA and using a phage library prepared by incorporating the cDNA into a phage, in addition to obtaining using cDNA library of each immunogen obtained by the extraction, separation and purification of mRNA from immunogenic tissue or cell using the extract as origin.

The method of screening the DNA of the immunogenic foreign gene from the cDNA library is not particularly limited, and can be performed in accordance with ordinary methods. As a specific method, for example, a method of selecting a corresponding cDNA clone by immunological screening using a specific antibody (e.g., anti-malaria antibody, anti-influenza virus antibody, anti-*M. tuberculosis* antibody) against the protein produced by the cDNA; a plaque hybridization method using a probe selectively binding to the objective DNA sequence; a colony hybridization method; and the combinations thereof can be exemplified.

As a probe used in hybridization methods, DNA fragments chemically synthesized based on the information for the DNA sequence of the immunogenic foreign gene are common. The immunogenic foreign gene already acquired and the DNA sequences of fragments thereof can be advantageously utilized as the above probe. Furthermore, a sense primer and an antisense primer designed based on the DNA sequence information of the immunogenic foreign gene can also be used as the probe for the above screening.

The DNA (nucleotides) used as the probe is the partial DNA (nucleotides) corresponding to the DNA sequence of the immunogenic foreign gene, and has at least 15 consecutive DNA, preferably at least 20 consecutive DNA and more preferably at least 30 consecutive DNA. A positive clone itself for producing the above DNA can also be used as the probe.

When the DNA of the immunogenic foreign gene is acquired, a DNA/RNA amplification method by PCR (Science, 230, 1350 (1985)) can be utilized suitably. In particular, when a full length cDNA is hardly obtained from the library, RACE method [Rapid amplification of cDNA ends; Jikken Igaku 12(6), 35 (1994)], in particular, 5'-RACE method [M. A. Frohman, et al., Proc. Natl. Acad. Sci., USA., 8, 8998 (1988)] is suitably employed.

A primer used for PCR can be designed based on the DNA sequence information of the immunogenic foreign gene, and synthesized in accordance with standard methods. As this primer, as shown in Examples described later, DNA portions (SP6 promoter primer and T7 terminator primer) added to both ends of the vector plasmid in which the DNA of the immunogenic foreign gene is incorporated in can also be used.

The isolation/purification of the DNA/RNA fragment amplified by PCR can be performed in accordance with standard methods, e.g., gel electrophoresis.

For the DNA of the immunogenic foreign gene obtained as the above or various DNA fragments, their DNA sequences can be determined in accordance with standard methods, e.g., dideoxy method (Proc. Natl. Acad. Sci., USA., 74, 5463 (1977)) or Maxam-Gilbert method (Methods in Enzymology, 65, 499 (1980)), or simply using a commercially available sequencing kit.

Any gene can be used as a gene encoding an amino acids of a protein capable of being the component of a viral particle, as long as it is the gene encoding a protein that can be expressed as the protein capable of being the component of the viral particle in an insect cell and as a fusion protein by fusing the immunogenic foreign gene in the objective cell.

As the gene encoding the amino acids of the protein capable of being the component of the viral particle, for example, the genes of a gp64 protein (GenBank Accession No. L22858), a Vesicular stomatitis virus glycoprotein (GenBank Accession No. M21416), a herpes simplex virus glycoprotein (KOS; GenBank Accession No. K01760), a type I human immunodeficiency virus gp120 (GenBank Accession No. U47783), a human respiratory syncytial virus membrane glycoprotein (GenBank Accession No. M86651), a type A influenza virus hemagglutinin protein (GenBank Accession No. U38242), or the gene of envelop proteins of viruses closely related to the baculovirus can be exemplified. In the present invention, the gp64 gene shown in Examples described later can be preferably exemplified.

The DNA of the gene encoding the amino acids of the protein capable of being the component of the viral particle can be easily produced and acquired by synthesizing based on the nucleic acid sequence information of the polynucleotide encoding the amino acid sequence of the polypeptide of the gene encoding the amino acids of the objective protein capable of being the component of the viral particle, or by directly synthesizing the DNA corresponding to the nucleotide sequence encoding the amino acid sequence based on the amino acid sequence information of the gene encoding the amino acids of the protein capable of being the component of the viral particle (chemical DNA synthesis) as is the case with the production of the DNA of the immunogenic foreign gene.

A DNA sequence corresponding to a nucleic acid sequence encoding amino acids of a protein capable of being a component of a viral particle is not limited to a full length of a coding region, and may be a DNA composed of a partial DNA sequence.

As is the case with the production of the DNA molecule of the immunogenic foreign gene, the DNA of the gene encoding the amino acids of the protein capable of being the component of the viral particle can be produced by general gene engineering techniques (e.g., see Molecular Cloning 2d Ed, Cold Spring Harbor Lab. Press(1989); Zoku Seikagaku Jikken Kouza, "Idenshi Kenkyuho I, II, III" edited by the Japanese Biochemistry Society, 1986).

In the present invention, a commercially available vector plasmid in which a part of the promoter which controls the expression of the immunogenic foreign gene described later is previously incorporated and the gene (portion) encoding the amino acids of the protein capable of being the component of the viral particle is previously introduced can also be used.

Vertebrate Promoters

As the vertebrate promoter (capable of functioning in vertebrates) which is one of the components of the transfer vector used for the present invention, the promoters such as mammalian promoters, bird promoters and fish promoters can be exemplified.

Mammalian Promoters

As a mammalian promoter (capable of functioning in mammals) which is one of the components of the transfer vector used for the present invention, a cytomegalovirus promoter, an SV40 promoter, a retrovirus promoter, a metallothionein promoter, a heat shock protein promoter, a CAG promoter, an elongation factor 1α promoter, an actin promoter, a ubiquitin promoter, an albumin promoter and an MHC class II promoter can be exemplified.

Bird Promoters

As bird promoters, a β actin promoter, a heat shock protein promoter, an elongation factor promoter, a ubiquitin promoter and an albumin promoter can be exemplified.

Fish Promoters

As fish promoters, an actin promoter, a heat shock protein promoter and an elongation factor promoter can be exemplified.

Baculovirus Promoters

As a baculovirus promoter which is one of the components of the baculovirus transfer vector used for the present invention, a polyhedrin promoter, a p10 promoter, an IE1 promoter, a p35 promoter, a p39 promoter, and a gp64 promoter can be exemplified.

Production of Recombinant Transfer Vector

The present invention relates to a novel transfer vector having a structure that can express the desired immunogenic foreign gene as antigenic protein in both an insect cell and a vertebrate cell, particularly a mammalian cell. In the present invention, the structure of the novel transfer vector is characterized in that the DNA sequence encoding the amino acid sequence of the desired immunogenic protein and the DNA sequence encoding the amino acid sequence of the protein capable of being the component of the viral particle are incorporated downstream of the dual promoter comprising a vertebrate promoter, particularly a mammalian promoter, and a baculovirus promoter, which are connected. DNA regions comprising the DNA sequences of two promoters; one is a vertebrate promoter, particularly a mammalian promoter and another is a baculovirus promoter. These two promoters may be directly linked, or an intervening DNA sequence may be present between the DNA sequences of the two promoters. However, in the latter case, each promoter needs to have activities in an insect cell and a vertebrate cell, particularly in a mammalian cell. In the promoter region, either the vertebrate promoter, particularly the mammalian promoter or the baculovirus promoter can be placed in the closer region to the gene to be expressed. In Examples described later, the baculovirus is placed in closer region to the gene to be expressed than the mammalian promoter.

In the said structure, the DNA sequence of the fusion gene of a gene encoding a protein capable of being a component of viral particles and a desired immunogenic foreign gene may be such that these two genes are directly linked to each other, or an intervening DNA sequence is present between the genes. In the latter case, however, it is necessary not to cause a frameshift of the downstream gene and the upstream gene. Preferably, the antigen-presenting domain of the protein of a foreign gene having the desired immunogenicity is fused to a protein capable of being a component of viral particles. Therefore, the protein of a foreign gene having the desired immunogenicity should not be cut off from the protein capable of being a component of viral particles, but should be used in a fused form.

A fusion gene comprising these two genes may be formed in advance and this may be incorporated in the vector. Alternatively, one gene may be incorporated in the vector in advance, and subsequently the other gene may be incorporated in the vector to form the fusion gene in the vector.

To produce such a transfer vector, commercially available expression vectors having essential components of the transfer vector of the present invention, i.e., a promoter region containing a vertebrate promoter, particularly a mammalian promoter, and a baculovirus promoter, and a gene region encoding the amino acid sequence of a protein capable of being a component of viral particles, may be used. The required components can be inserted by cleaving such a commercially available expression vector arbitrarily with restriction enzymes and incorporating other promoter to insert a fused DNA sequence of a foreign gene having the desired immunogenicity and a gene encoding the amino acid sequence of a protein capable of being a component of viral particles into the cloning region of the vector, or by inserting a foreign gene having the desired immunogenicity into the N terminus side of the DNA region of a gene encoding the amino acid sequence of a protein capable of being a component of viral particles, which is previously incorporated in a plasmid.

For the detection of the protein, a His-tag or an HVS-tag may be added upstream of a polyA tail at a C terminus side of the DNA sequence fusing the desired immunogenic foreign gene to the gene encoding the amino acid sequence of the protein capable of being the component of the viral particle. Alternatively, for the expression, the purification or the detection of the recombinant fusion protein, the DNA sequence encoding a FLAG sequence composed of 8 amino acids may be inserted as a peptide tag between the promoter region and the region in which the desired immunogenic foreign gene is fused to the gene encoding the amino acid sequence of the protein capable of being the component of the viral particle. In the present invention, the plasmid vector having the structure that can express the desired immunogenic foreign protein as antigenic protein in both an insect cell and a vertebrate cell, particularly a mammalian cell, may be produced by using a commercially available plasmid that has a part of the structure. The amino acid sequence of the peptide may intervene for cleaving the fusion protein with the enzyme in a vertebrate cell. In the transfer vector of the present invention, an enhancer for increasing a transcription activity in a vertebrate cell, particularly the mammalian cell, may be placed upstream of the two promoters, or the DNA sequence encoding the amino acid sequence of a signal peptide for facilitating extracellular secretion of the expressed protein in hosts may be bound to the gene to be fused and expressed. A vertebrate terminator region, e.g., a rabbit β globulin terminator which is effective in the vertebrate cell may be placed for terminating the transcription downstream the gene to be fused and expressed.

As the above, the transfer vector capable of expressing the fusion gene of the immunogenic foreign gene capable of expressing the desired immunogenicity in the baculovirus particle and the gene encoding the amino acid sequence of the protein capable of being the component of the viral particle can be produced.

Specific examples of the transfer vector and the method for production thereof according to the present invention are as shown in the Examples described later. More specifically, as transfer vectors having a structure; in which a vertebrate promoter (particularly as a mammalian promoter) such as a cytomegalovirus (CMV) promoter, a CAG promoter modified from CMV promoter and a ubiquitin (UBB) promoter fused CMV enhancer, and a baculovirus promoter such as a polyhedrin (polh) promoter, vp39 promoter and gp64 promoter are linked, and the DNA sequence, in which foreign genes such as influenza virus antigen gene, malaria antigen gene and M. tuberculosis antigen gene and a gene encoding the amino acid sequence of the protein capable of the component of the viral particle such as gp64 antigen gene are fused, is inserted: pDual-Hsp65-gp64, pDual-PbCSP-gp64, pDual-H1N1/HA1-gp64, pDual-PbTRAMP-gp64, pDual-PbAMA1D123-gp64, pDual-PbMSP129-gp64, pDual- PfCSP-gp64, pDual-PfAMA1-gp64, pDual-Pfs25-gp64, pDual-H5N1/HA1-gp64 and pDual-SARS/S-gp64, pCP-H1N1/HA1-gp64, pCAP-H1N1/HA1-gp64, pCU-H1N1/HA1-gp64, pDual-H1N1/NP-gp64, pDual-H1N1/M2-gp64, pDual-H1N1/NAe-gp64, pDual-M2e-gp64, pCP-HA1/NC99-gp64, pCP-H1N1/HA0-gp64, pCP-H1N1/HA2-gp64, pCP-H1N1/HA1-vp39, pCP-H1N1/NP-vp39, pCAP-PfCSP, pCAP-PfCSP/272, pCAP-PfCSP/467, pCAP-PfCSP (A361E), pCAP-PfCSP(A361E)/272, pCAP-PfCSP(A361E)/467, pCAP-PfCSP-76, pCAP-PfCSP-76/467, pCAP-PfCSP+209, pCAP-PfCSP+209/467, pCAP-PfCSP+76/209, pCAP-PfCSP+76/209/467, pCAP-HA1/Anhui, pCAP-HA1/Anhui/272, pCAP-HA1/Anhui/467, pCAP-HA1/Vietnam, pCAP-HA1/Vietnam/51, pCAP-HA1/Vietnam/101, pCAP-HA1/Vietnam/154, pCAP-HA1/Vietnam/201, pCAP-HA1/Vietnam/272, pCAP-HA1/Vietnam/467, pCAP-AH/345, pCAP-AH/345/467, pCAP-AH/410, pCAP-AH/410/467, pCAP-AH/473, pCAP-AH/473/467, pCAP-AH/520, pCAP-AH/520/467, pCAP-VN/346, pCAP-VN/346/467, pCAP-VN/410, pCAP-VN/410/467, pCAP-VN/473, pCAP-VN/473/467, pCAP-VN/520, pCAP-VN/520/467, pCAP-CO/full, pCAP-CO/full/467, pCAP-CO/19, pCAP-CO/19/467, pCAP-CO/76, pCAP-CO/76/467, pCAP-CO/205, pCAP-CO/205/467, pCA39-HA1/Anhui, pCA64-HA1/Anhui, pCA39-PfCSP(A361E), pCA64-PfCSP(A361E), pCAP-CO/full/VSV, pCAP-CO/19/VSV, pCAP-CO/76/VSV, pCAP-CO/205/VSV, pDual-Pfs25-PfCSP-gp64, and pDual-PfMSP1-PfCSP-gp64 can be exemplified.

(2) Production of Recombinant Baculovirus

The present invention provides a method of producing a recombinant baculovirus comprising a step of producing a transfer vector having a structure in which a fusion gene containing at least one gene encoding a protein capable of being a component of the viral particle and at least one immunogenic foreign gene is incorporated downstream of a dual promoter comprising two linked promoters, i.e., a vertebrate promoter and a baculovirus promoter; and a step of co-transfecting the transfer vector and a baculovirus DNA into a host cell and isolating the recombinant baculovirus.

In the above method of producing the recombinant baculovirus, methods of introducing the desired recombinant DNA (transfer vector) into the host and methods of transforming therewith are not particularly limited, and various methods which are well known and commonly used can be employed. Such methods can be performed in accordance with the ordinary gene recombination technology (e.g., Science, 224, 1431 (1984); Biochem. Biophys. Res. Comm., 130, 692 (1985); Proc. Natl. Acad. Sci. USA, 80, 5990 (1983). The recombinant DNA (transfer vector) can be expressed and produced with reference to Ohno et al., "Tanpaku Jikken Protocol 1 Functional analysis, Saibo Kogaku Bessatu Jikken Protocol Series, 1997, Shujunsha". For general techniques of handling of the insect cells, gene recombination and co-transfection, the same techniques as in the well-known methods of making recombinant virus in insect cells can be used (Zenji Matsuura, Proteins, Nucleic acids and Enzymes, 37:211-222, 1992; Zenji Matsuura, Saibo 33(2):30-34, 2001).

The resulting recombinant baculovirus can be cultured in accordance with the standard methods. By culturing, a fusion product (expressed product) in which the DNA of the immunogenic foreign gene and the DNA encoding the amino acid sequence of the protein capable of being the component of the viral particle of the present invention are fused designed as desired is expressed, produced (accumulated) or secreted inside, outside the cells or on the cell membrane.

As a medium used for the culture, various media commonly used can be appropriately selected and used depending on the host cells employed, and the culture can be performed under the condition suitable for growth of the host cells.

More specifically, the method of producing the recombinant baculovirus comprises the step of preparing the baculovirus DNA for performing the homologous recombination with the transfer vector produced above and the step of co-transfecting the transfer vector and the baculovirus DNA in the insect cells such as Sf-9 cells, Sf-21 cells derived from *Spodoptera frugiperda*, Tn5 cells (High Five cells supplied from Invitrogen) derived from *Trichoplusia ni* as the host cells.

The baculovirus DNA produced above for performing the homologous recombination with the transfer vector may be any of the wild type, the mutant or the recombinant baculovirus DNA.

A baculovirus DNA can enhance a probability of homologous recombination as long as it has the DNA structure homologous to the DNA derived from the baculovirus DNA located upstream of the dual promoters used for the transfer vector so as to produce the homologous recombination with the transfer vector of the present invention, except for the DNA derived from a baculovirus which sandwiches a fusion gene in which DNA in the dual promoter region, the immunogenic foreign gene and the gene encoding the protein capable of being the component of the viral particle are fused.

To induce the homologous recombination, it is better that the transfer vector and the baculovirus DNA is mixed at a weight ratio of about 1:1 to 10:1.

After introducing into the insect cell simultaneously by the step of co-transfection and culturing the cell, plaques of the virus are made from the culture supernatant, then suspended in the medium, subsequently the virus is eluted from the agar by vortex to yield a solution comprising the recombinant virus.

In the above, the commercially available baculovirus DNA may be used, and for example, it is possible to use BacVector-1000 DNA and BacVector-2000 DNA (supplied from Novagen) in which the polyhedrin gene is removed from AcNPV.

The co-transfection of the transfer vector and the baculovirus DNA obtained above in the insect cell for the homologous recombination can be performed using the commercially available vector transfection kit described above (BacVector Transfection Kits supplied from Novagen) in accordance with instructions attached to the vector transfection kit. As the above, the transfer vector produced above can be co-transfected together with the baculovirus DNA in the insect cell such as Sf-9 cell to yield the recombinant baculovirus.

In the present invention, in accordance with the above method of producing the recombinant baculovirus, the transfer vectors such as pDual-Hsp65-gp64, pDual-PbCSP-gp64, pDual-H1N1/HA1-gp64, pDual-PbTRAMP-gp64, pDual-PbAMA1D123-gp64, pDual-PbMSP129-gp64, pDual-PfCSP-gp64, pDual-PfAMA1-gp64, pDual-Pfs25-gp64, pDual-H5N1/HA1-gp64, pDual-SARS/S-gp64, pCP-H1N1/HA1-gp64, pCAP-H1N1/HA1-gp64, pCU-H1N1/HA1-gp64, pDual-H1N1/NP-64, pDual-H1N1/M2-gp64, pDual-H1N1/NAe-gp64, pDual-M2e-gp64, pCP-HA1/NC99-gp64, pCP-H1N1/HA0-gp64, pCP-H1N1/HA2-gp64, pCP-H1N1/HA1-vp39, pCP-H1N1/NP-vp39, pCAP-PfCSP, pCAP-PfCSP/272, pCAP-PfCSP/467, pCAP-PfCSP(A361E), pCAP-PfCSP(A361E)/272, pCAP-PfCSP(A361E)/467, pCAP-PfCSP-76, pCAP-PfCSP-76/467, pCAP-PfCSP+209, pCAP-PfCSP+209/467, pCAP-PfCSP+76/209, pCAP-PfCSP+76/209/467, pCAP-HA1/Anhui, pCAP-HA1/Anhui/272, pCAP-HA1/Anhui/467, pCAP-HA1/Vietnam, pCAP-HA1/Vietnam/51, pCAP-HA1/Vietnam/101, pCAP-HA1/

Vietnam/154, pCAP-HA1/Vietnam/201, pCAP-HA1/Vietnam/272, pCAP-HA1/Vietnam/467, pCAP-AH/345, pCAP-AH/345/467, pCAP-AH/410, pCAP-AH/410/467, pCAP-AH/473, pCAP-AH/473/467, pCAP-AH/520, pCAP-AH/520/467, pCAP-VN/346, pCAP-VN/346/467, pCAP-VN/410, pCAP-VN/410/467, pCAP-VN/473, pCAP-VN/473/467, pCAP-VN/520, pCAP-VN/520/467, pCAP-CO/full, pCAP-CO/full/467, pCAP-CO/19, pCAP-CO/19/467, pCAP-CO/76, pCAP-CO/76/467, pCAP-CO/205, pCAP-CO/205/467, pCA39-HA1/Anhui, pCA64-HA1/Anhui, pCA39-PfCSP(A361E), pCA64-PfCSP(A361E), pCAP-CO/full/VSV, pCAP-CO/19/VSV, pCAP-CO/76/VSV, pCAP-CO/205/VSV, pDual-Pfs25-PfCSP-gp64, and pDual-PfMSP1-PfCSP-gp64, and the baculovirus DNA were used and co-transfected in the Sf-9 insect cell to yield the recombinant baculoviruses such as AcNPV-Dual-Hsp65, AcNPV-Dual-PbCSP, AcNPV-Dual-H1N1/HA1, AcNPV-Dual-Pb-TRAMP, AcNPV-Dual-PbAMA1D123, AcNPV-Dual-PbMSP129, AcNPV-Dual-PfCSP, AcNPV-Dual-PfAMA1, AcNPV-Dual-Pfs25, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39, AcNPV-CP-H1N1/NP-vp39, AcNPV-CAP-PfCSP, AcNPV-CAP-PfCSP/272, AcNPV-CAP-PfCSP/467, AcNPV-CAP-PfCSP(A361E), AcNPV-CAP-PfCSP(A361E)/272, AcNPV-CAP-PfCSP(A361E)/467, AcNPV-CAP-PfCSP-76, AcNPV-CAP-PfCSP-76/467, AcNPV-CAP-PfCSP+209, AcNPV-CAP-PfCSP+209/467, AcNPV-CAP-PfCSP+76/209, AcNPV-CAP-PfCSP+76/209/467, AcNPV-CAP-HA1/Anhui, AcNPV-CAP-HA1/Anhui/272, AcNPV-CAP-HA1/Anhui/467, AcNPV-CAP-HA1/Vietnam, AcNPV-CAP-HA1/Vietnam/51, AcNPV-CAP-HA1/Vietnam/101, AcNPV-CAP-HA1/Vietnam/154, AcNPV-CAP-HA1/Vietnam/201, AcNPV-CAP-HA1/Vietnam/272, AcNPV-CAP-HA1/Vietnam/467, AcNPV-CAP-AH/345, AcNPV-CAP-AH/345/467, AcNPV-CAP-AH/410, AcNPV-CAP-AH/410/467, AcNPV-CAP-AH/473, AcNPV-CAP-AH/473/467, AcNPV-CAP-AH/520, AcNPV-CAP-AH/520/467, AcNPV-CAP-VN/346, AcNPV-CAP-VN/346/467, AcNPV-CAP-VN/410, AcNPV-CAP-VN/410/467, AcNPV-CAP-VN/473, AcNPV-CAP-VN/473/467, AcNPV-CAP-VN/520, AcNPV-CAP-VN/520/467, AcNPV-CAP-CO/full, AcNPV-CAP-CO/full/467, AcNPV-CAP-CO/19, AcNPV-CAP-CO/19/467, AcNPV-CAP-CO/76, AcNPV-CAP-CO/76/467, AcNPV-CAP-CO/205, AcNPV-CAP-CO/205/467, AcNPV-CA39-HA1/Anhui, AcNPV-CA64-HA1/Anhui, AcNPV-CA39-PfCSP(A361E), AcNPV-CA64-PfCSP(A361E), AcNPV-CAP-CO/full/VSV, AcNPV-CAP-CO/19/VSV, AcNPV-CAP-CO/76/VSV, AcNPV-CAP-00/205/VSV, AcNPV-Dual-Pfs25-PfCSP-64, and AcNPV-Dual-PfMSP1-PfCSP-gp64.

Also, the recombinant baculoviruses such as AcNPV-Dual-H5N1/HA1 and AcNPV-Dual-SARS/S can be obtained.

In addition to the above method of producing the recombinant baculovirus, as the other method of producing the recombinant baculovirus, it is possible to use the method of inserting the foreign gene efficiently in *Escherichia coli* by utilizing a transposon for a phagemid (bacmid) in which the entire baculovirus genome is incorporated. According to the method, the recombinant baculovirus can be easily produced and collected by only extracting the bacmid bearing the viral gene from microbial cells and transfecting it in the insect cell.

The purification of the recombinant baculovirus of the present invention obtained by the above method of producing the recombinant baculovirus can be performed using the virus purification method known publicly.

For the purification of the recombinant baculovirus, for example, 0.5 to 1.0 mL of a stock virus (usually $1 \times 10^{7-8}$ pfu/mL) obtained by the above method of producing the recombinant baculovirus is inoculated to the insect cells ($1 \times 10^7$ cells/10 cm dish) such as Sf-9 cells, the culture supernatant is collected several days (4 days) after the infection, and a virus pellet obtained by centrifugation is suspended in buffer such as PBS. The resulting suspension is applied on sucrose gradient of 10 to 60%, which is then centrifuged (25,000 rpm, 60 minutes, 4° C.) to collect a virus band. The collected virus is further suspended in PBS, subsequently centrifuged (same condition as the above), and the resulting purified recombinant virus pellet is stored in the buffer such as PBS at 4° C.

An infectivity titer of the above resulting purified recombinant virus can be measured by plaque assay (Fields VIROLOGY 4th Edition p29-32 2001; BACULOVIRUS EXPRESSION VECTORS: A LABORATORY MANUAL, Oxford University Press, 1994) using the insect cells such as Sf-9 cells.

In the recombinant virus exemplified in the present invention, the N terminus of the baculovirus protein gp64 is exposed outside the particle and its C terminus is exposed inside the particle. Thus, if the protein encoded by the desired immunogenic foreign gene is fused to the N terminus of gp64, its entirety is exposed outside the viral protein particle as the component of the viral particle in an insect cell, and thus the antigen is more easily presented, which is suitable for the object of the vaccine formulation of the present invention.

(3) Pharmaceutical Composition of the Present Invention (Pharmaceutical Comprising Recombinant Baculovirus of the Present Invention as Active Ingredient)

The recombinant baculovirus of the present invention which is the active ingredient in the pharmaceutical composition of the present invention can be obtained by the gene engineering techniques shown in the above (2).

It is important that the pharmaceutical composition of the present invention contain as the active ingredient the recombinant baculovirus obtained by homologous recombination of the baculovirus DNA and the transfer vector constructed, and that the transfer vector is constructed so that the fusion gene of the immunogenic foreign gene and the gene encoding the amino acid sequence of the protein capable of being the component of the viral particle can be expressed in the insect cells and the vertebrate cells, particularly cells from mammals including human being.

In particular, the present invention provides the pharmaceutical composition comprising any of the particular recombinant baculovirus, such as AcNPV-Dual-H1N1/HA1, AcNPV-Dual-Hsp65, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39, AcNPV-CP-H1N1/NP-vp39, AcNPV-CAP-PfCSP, AcNPV-CAP-PfCSP/272, AcNPV-CAP-PfCSP/467, AcNPV-CAP-PfCSP(A361E), AcNPV-CAP-PfCSP(A361E)/272, AcNPV-CAP-PfCSP(A361E)/467, AcNPV-CAP-PfCSP-76, AcNPV-CAP-PfCSP-76/467, AcNPV-CAP-PfCSP+209, AcNPV-CAP-PfCSP+209/467, AcNPV-CAP-PfCSP+76/209, AcNPV-CAP-PfCSP+76/209/467, AcNPV-CAP-HA1/Anhui, AcNPV-CAP-HA1/Anhui/272, AcNPV-CAP-HA1/Anhui/467, AcNPV-CAP-HA1/Vietnam, AcNPV-CAP-HA1/Vietnam/51, AcNPV-CAP-HA1/Vietnam/101, AcNPV-CAP-HA1/Vietnam/154, AcNPV-CAP-HA1/Vietnam/201, AcNPV-CAP-HA1/Vietnam/272, AcNPV-CAP-HA1/Vietnam/467, AcNPV-CAP-AH/345, AcNPV-CAP-AH/345/467, AcNPV-CAP-AH/410, AcNPV-CAP-AH/410/467, AcNPV-CAP-AH/473, AcNPV-CAP-AH/473/467, AcNPV-CAP-AH/520, AcNPV-CAP-AH/520/467, AcNPV-CAP-VN/346, AcNPV-CAP-VN/346/467, AcNPV-CAP-VN/410, AcNPV-CAP-VN/410/467, AcNPV-CAP-VN/473, AcNPV-CAP-VN/473/467, AcNPV-CAP-VN/520, AcNPV-CAP-VN/520/467, AcNPV-CAP-CO/full, AcNPV-CAP-CO/full/467, AcNPV-CAP-CO/19, AcNPV-CAP-CO/19/467, AcNPV-CAP-CO/76, AcNPV-CAP-CO/76/467, AcNPV-CAP-CO/205, AcNPV-CAP-CO/205/467, AcNPV-CA39-HA1/Anhui, AcNPV-CA64-HA1/Anhui, AcNPV-CA39-PfCSP(A361E), AcNPV-CA64-PfCSP(A361E), AcNPV-CAP-CO/full/VSV, AcNPV-CAP-CO/19/VSV, AcNPV-CAP-CO/76/VSV, AcNPV-CAP-CO/205/VSV, AcNPV-Dual-Pfs25-PfCSP-gp64, or AcNPV-Dual-PfMSP1-PfCSP-gp64 as active ingredient.

The recombinant baculovirus of the present invention, such as AcNPV-Dual-H1N1/HA1, AcNPV-Dual-Hsp65, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39, AcNPV-CP-H1N1/NP-vp39, AcNPV-CAP-PfCSP, AcNPV-CAP-PfCSP/272, AcNPV-CAP-PfCSP/467, AcNPV-CAP-PfCSP(A361E), AcNPV-CAP-PfCSP(A361E)/272, AcNPV-CAP-PfCSP(A361E)/467, AcNPV-CAP-PfCSP-76, AcNPV-CAP-PfCSP-76/467, AcNPV-CAP-PfCSP+209, AcNPV-CAP-PfCSP+209/467, AcNPV-CAP-PfCSP+76/209, AcNPV-CAP-PfCSP+76/209/467, AcNPV-CAP-HA1/Anhui, AcNPV-CAP-HA1/Anhui/272, AcNPV-CAP-HA1/Anhui/467, AcNPV-CAP-HA1/Vietnam, AcNPV-CAP-HA1/Vietnam/51, AcNPV-CAP-HA1/Vietnam/101, AcNPV-CAP-HA1/Vietnam/154, AcNPV-CAP-HA1/Vietnam/201, AcNPV-CAP-HA1/Vietnam/272, AcNPV-CAP-HA1/Vietnam/467, AcNPV-CAP-AH/345, AcNPV-CAP-AH/345/467, AcNPV-CAP-AH/410, AcNPV-CAP-AH/410/467, AcNPV-CAP-AH/473, AcNPV-CAP-AH/473/467, AcNPV-CAP-AH/520, AcNPV-CAP-AH/520/467, AcNPV-CAP-VN/346, AcNPV-CAP-VN/346/467, AcNPV-CAP-VN/410, AcNPV-CAP-VN/410/467, AcNPV-CAP-VN/473, AcNPV-CAP-VN/473/467, AcNPV-CAP-VN/520, AcNPV-CAP-VN/520/467, AcNPV-CAP-CO/full, AcNPV-CAP-CO/full/467, AcNPV-CAP-CO/19, AcNPV-CAP-CO/19/467, AcNPV-CAP-CO/76, AcNPV-CAP-CO/76/467, AcNPV-CAP-CO/205, AcNPV-CAP-CO/205/467, AcNPV-CA39-HA1/Anhui, AcNPV-CA64-HA1/Anhui, AcNPV-CA39-PfCSP(A361E), AcNPV-CA64-PfCSP(A361E), AcNPV-CAP-CO/full/VSV, AcNPV-CAP-CO/19/VSV, AcNPV-CAP-CO/76/VSV, AcNPV-CAP-CO/205/VSV, AcNPV-Dual-Pfs25-PfCSP-64, and AcNPV-Dual-PfMSP1-PfCSP-gp64 which is the active ingredient in the pharmaceutical composition of the present invention has the actions which enhances an infection-preventing effect on the infectious antigen and reduces the infectivity titer, and this action or activity can be utilized to treat diseases associated with the infection of target cells or tissues. Such target cells affected by the infection include, for example blood cells, and other target cells include hepatic cells, renal cells, brain cells, lung cells, epithelial cells and muscular cells. The tissues comprising these cells include lung, liver, kidney, arterial and venous veins, stomach, intestine, urethra, skin and muscle.

The pharmaceutical composition enhances infection-preventing effects against infectious antigens, for example, malaria antigens such as sporozoite surface antigens (CSP and TRAP) of malaria parasites, merozoite surface membrane protein MSP1, malaria S antigen secreted from erythrocytes infected with malaria, PfEMP1 protein present in the knobs of erythrocytes infected with malaria, SERA protein, TRAMP protein, AMA1 protein, and Pfs25 known as a transmission-blocking antigen; and influenza antigens such as HA antigen, NA antigen, M2 antigen, and NP antigen, and reduces the infectivity titer (e.g., viral infectivity titer), thereby increasing the survival period and survival rate of mammals including humans, compared to the group not administered the pharmaceutical composition of the present invention. Therefore, the pharmaceutical composition is particularly useful as a preventive or therapeutic agent for malaria and influenza virus infections.

The pharmaceutical composition of the present invention is useful as the preventive or therapeutic agent for infectious diseases caused by the pathogen and their complications, e.g., viral diseases caused by influenza virus, papilloma virus, herpes virus, AIDS virus, hepatitis C virus, SARS virus, west Nile fever virus and dengue fever virus, parasite diseases caused by malaria, trypanosome and *leishmania* parasites, and bacterial diseases caused by bacteria, such as dysentery, enteric fever, cholera, pneumococcus, MRSA, VRE, *Neisseria gonorrhoeae* and *Chlamydia*, syphilis and tuberculosis by utilizing the actions to enhance the infection-preventing effect on the infectious antigen and reduce the infectivity titer.

By using the immunogenic foreign gene for the vertebrate other than the human being in the transfer vector for obtaining the recombinant baculovirus which is the active ingredient in the pharmaceutical composition of the present invention, it is possible to utilize the pharmaceutical composition of the present invention for procedures of the diseases associated with the infection of the target cells and the tissue as chicken influenza vaccine, bovine trypanosome vaccine and Japanese trout cold water disease vaccine by utilizing its actions to enhance the infection-preventing effect on the infectious antigen and reduce the infectivity titer.

The pharmaceutical composition of the present invention can be prepared as the composition comprising the pharmaceutically effective amount of the recombinant baculovirus and a pharmaceutically acceptable carrier.

For the infection-preventing effect of the recombinant baculovirus of the present invention in the vertebrate, particularly, the mammals including the human being or the mammalian cells, for example, the pharmaceutical composition produced by the recombinant baculovirus of the present invention and the composition capable of being added for pharmaceutical administration is administered intramuscularly, intranasally or by inhalation in the vertebrate, particularly, the mammal including the human being, which is subsequently immunized with the pharmaceutical composition comprising the recombinant baculovirus of the present invention as the active ingredient multiple times. The pharmaceutical composition of the invention is administered particularly by inhalation.

The preventive effect on the infection can be evaluated by comparing the survival rate of vertebrates administered with the recombinant baculovirus with those not administered therewith in a certain period of time after multiple immunization with the inventive pharmaceutical composition and a subsequent infection with a target pathogen.

(4) Vaccine of the Present Invention

The recombinant baculovirus, such as AcNPV-Dual-H1N1/HA1, AcNPV-Dual-Hsp65, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39, AcNPV-CP-H1N1/NP-vp39, AcNPV-CAP-PfCSP, AcNPV-CAP-PfCSP/272, AcNPV-CAP-PfCSP/467, AcNPV-CAP-PfCSP(A361E), AcNPV-CAP-PfCSP(A361E)/272, AcNPV-CAP-PfCSP(A361E)/467, AcNPV-CAP-PfCSP-76, AcNPV-CAP-PfCSP-76/467, AcNPV-CAP-PfCSP+209, AcNPV-CAP-PfCSP+209/467, AcNPV-CAP-PfCSP+76/209, AcNPV-CAP-PfCSP+76/209/467, AcNPV-CAP-HA1/Anhui, AcNPV-CAP-HA1/Anhui/272, AcNPV-CAP-HA1/Anhui/467, AcNPV-CAP-HA1/Vietnam, AcNPV-CAP-HA1/Vietnam/51, AcNPV-CAP-HA1/Vietnam/101, AcNPV-CAP-HA1/Vietnam/154, AcNPV-CAP-HA1/Vietnam/201, AcNPV-CAP-HA1/Vietnam/272, AcNPV-CAP-HA1/Vietnam/467, AcNPV-CAP-AH/345, AcNPV-CAP-AH/345/467, AcNPV-CAP-AH/410, AcNPV-CAP-AH/410/467, AcNPV-CAP-AH/473, AcNPV-CAP-AH/473/467, AcNPV-CAP-AH/520, AcNPV-CAP-AH/520/467, AcNPV-CAP-VN/346, AcNPV-CAP-VN/346/467, AcNPV-CAP-VN/410, AcNPV-CAP-VN/410/467, AcNPV-CAP-VN/473, AcNPV-CAP-VN/473/467, AcNPV-CAP-VN/520, AcNPV-CAP-VN/520/467, AcNPV-CAP-CO/full, AcNPV-CAP-CO/full/467, AcNPV-CAP-CO/19, AcNPV-CAP-CO/19/467, AcNPV-CAP-CO/76, AcNPV-CAP-CO/76/467, AcNPV-CAP-CO/205, AcNPV-CAP-CO/205/467, AcNPV-CA39-HA1/Anhui, AcNPV-CA64-HA1/Anhui, AcNPV-CA39-PfCSP(A361E), AcNPV-CA64-PfCSP(A361E), AcNPV-CAP-CO/full/VSV, AcNPV-CAP-CO/19/VSV, AcNPV-CAP-CO/76/VSV, AcNPV-CAP-CO/205/VSV, AcNPV-Dual-Pfs25-PfCSP-64, or AcNPV-Dual-PfMSP1-PfCSP-gp64 which is the active ingredient of the pharmaceutical composition of the present invention is purified as the viral particle budded from the insect cell, comprising an expressed product of the fusion DNA sequence fusing the gene encoding the amino acid sequence of the protein capable of being the component of the viral particle to the immunogenic foreign gene of the present invention having the desired immunogenicity to enhance the preventive effect on the infection with the pathogen and exhibit the action to reduce the infectivity titer. Then, it is thought that the foreign antigen protein which became the component of the viral particle facilitates acquired immunity (humoral immunity and cellular immunity) by administering the pharmaceutical composition in the form of the viral particle to the vertebrate, particularly, the mammals including the human being, and further the antigenic protein which is the expressed product of the fusion DNA sequence further facilitates the acquired immunity (humoral immunity and cellular immunity) in the vertebrate cells, particularly, the cells in the mammals including the human being. Thus, the recombinant baculovirus of the present invention is useful as the vaccine.

In particular, the present invention provides the vaccine comprising any of the particular recombinant baculovirus such as AcNPV-Dual-H1N1/HA1, AcNPV-Dual-Hsp65, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39, AcNPV-CP-H1N1/NP-vp39, AcNPV-CAP-PfCSP, AcNPV-CAP-PfCSP/272, AcNPV-CAP-PfCSP/467, AcNPV-CAP-PfCSP(A361E), AcNPV-CAP-PfCSP(A361E)/272, AcNPV-CAP-PfCSP(A361E)/467, AcNPV-CAP-PfCSP-76, AcNPV-CAP-PfCSP-76/467, AcNPV-CAP-PfCSP+209, AcNPV-CAP-PfCSP+209/467, AcNPV-CAP-PfCSP+76/209, AcNPV-CAP-PfCSP+76/209/467, AcNPV-CAP-HA1/Anhui, AcNPV-CAP-HA1/Anhui/272, AcNPV-CAP-HA1/Anhui/467, AcNPV-CAP-HA1/Vietnam, AcNPV-CAP-HA1/Vietnam/51, AcNPV-CAP-HA1/Vietnam/101, AcNPV-CAP-HA1/Vietnam/154, AcNPV-CAP-HA1/Vietnam/201, AcNPV-CAP-HA1/Vietnam/272, AcNPV-CAP-HA1/Vietnam/467, AcNPV-CAP-AH/345, AcNPV-CAP-AH/345/467, AcNPV-CAP-AH/410, AcNPV-CAP-AH/410/467, AcNPV-CAP-AH/473, AcNPV-CAP-AH/473/467, AcNPV-CAP-AH/520, AcNPV-CAP-AH/520/467, AcNPV-CAP-VN/346, AcNPV-CAP-VN/346/467, AcNPV-CAP-VN/410, AcNPV-CAP-VN/410/467, AcNPV-CAP-VN/473, AcNPV-CAP-VN/473/467, AcNPV-CAP-VN/520, AcNPV-CAP-VN/520/467, AcNPV-CAP-CO/full, AcNPV-CAP-CO/full/467, AcNPV-CAP-CO/19, AcNPV-CAP-CO/19/467, AcNPV-CAP-CO/76, AcNPV-CAP-CO/76/467, AcNPV-CAP-CO/205, AcNPV-CAP-CO/205/467, AcNPV-CA39-HA1/Anhui, AcNPV-CA64-HA1/Anhui, AcNPV-CA39-PfCSP(A361E), AcNPV-CA64-PfCSP(A361E), AcNPV-CAP-CO/full/VSV, AcNPV-CAP-CO/19/VSV, AcNPV-CAP-CO/76/VSV, AcNPV-CAP-CO/205/VSV, AcNPV-Dual-Pfs25-PfCSP-64, or AcNPV-Dual-PfMSP1-PfCSP-gp64 as the active ingredient.

As in the pharmaceutical composition of the above (3), the vaccine enhances infection-preventing effects against infectious antigens such as malaria antigens such as sporozoite surface antigens (CSP and TRAP) of the malaria parasite, merozoite surface membrane protein MSP1, malaria S antigen secreted from erythrocytes infected with malaria, PfEMP1 protein present in the knobs of erythrocytes infected with malaria, SERA protein, TRAMP protein, and AMA1 protein; and influenza antigens such as influenza virus HA antigen, influenza virus NA antigen, influenza virus M2 antigen, and influenza virus NP antigen; the vaccine also reduces the infectivity titer (e.g., the viral infectivity titer), thereby increasing the survival period and survival rate of mammals, including humans, compared with the group not administered with the pharmaceutical composition of the present invention. Thus, the vaccine is particularly useful as a preventive or therapeutic agent for malaria and influenza virus infection.

The vaccine of the present invention is useful as the preventive or therapeutic agent for infectious diseases caused by the pathogen and their complications, e.g., the viral diseases caused by influenza virus, papilloma virus, herpes virus, AIDS virus, hepatitis C virus, SARS virus, west Nile fever virus and dengue fever virus, the parasite diseases caused by malaria, trypanosome and *leishmania* parasites, and bacterial diseases caused by bacteria of dysentery, enteric fever, cholera, pneumococcus, MRSA, VRE, *Neisseria gonorrhoeae* and *Chlamydia*, syphilis and tuberculosis, by utilizing the actions to enhance the infection-preventing effect on the infectious antigen and reduce the infectivity titer.

By using the immunogenic foreign gene for the vertebrate other than the human being in the transfer vector for obtaining the recombinant baculovirus which is the active ingredient in the vaccine of the present invention, it is possible to utilize the pharmaceutical composition of the present invention for procedures of the diseases associated with the infection of the target cells and the tissue as chicken influenza vaccine, bovine trypanosome vaccine and Japanese trout cold water disease vaccine by utilizing its actions to enhance the infection-preventing effect on the infectious antigen and reduce the infectivity titer.

The recombinant baculovirus, such as AcNPV-Dual-H1N1/HA1, AcNPV-Dual-Hsp65, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39, AcNPV-CP-H1N1/NP-vp39, AcNPV-CAP-PfCSP, AcNPV-CAP-PfCSP/272, AcNPV-CAP-PfCSP/467, AcNPV-CAP-PfCSP(A361E), AcNPV-CAP-PfCSP(A361E)/272, AcNPV-CAP-PfCSP(A361E)/467, AcNPV-CAP-PfCSP-76, AcNPV-CAP-PfCSP-76/467, AcNPV-CAP-PfCSP+209, AcNPV-CAP-PfCSP+209/467, AcNPV-CAP-PfCSP+76/209, AcNPV-CAP-PfCSP+76/209/467, AcNPV-CAP-HA1/Anhui, AcNPV-CAP-HA1/Anhui/272, AcNPV-CAP-HA1/Anhui/467, AcNPV-CAP-HA1/Vietnam, AcNPV-CAP-HA1/Vietnam/51, AcNPV-CAP-HA1/Vietnam/101, AcNPV-CAP-HA1/Vietnam/154, AcNPV-CAP-HA1/Vietnam/201, AcNPV-CAP-HA1/Vietnam/272, AcNPV-CAP-HA1/Vietnam/467, AcNPV-CAP-AH/345, AcNPV-CAP-AH/345/467, AcNPV-CAP-AH/410, AcNPV-CAP-AH/410/467, AcNPV-CAP-AH/473, AcNPV-CAP-AH/473/467, AcNPV-CAP-AH/520, AcNPV-CAP-AH/520/467, AcNPV-CAP-VN/346, AcNPV-CAP-VN/346/467, AcNPV-CAP-VN/410, AcNPV-CAP-VN/410/467, AcNPV-CAP-VN/473, AcNPV-CAP-VN/473/467, AcNPV-CAP-VN/520, AcNPV-CAP-VN/520/467, AcNPV-CAP-CO/full, AcNPV-CAP-CO/full/467, AcNPV-CAP-CO/19, AcNPV-CAP-CO/19/467, AcNPV-CAP-CO/76, AcNPV-CAP-CO/76/467, AcNPV-CAP-CO/205, AcNPV-CAP-CO/205/467, AcNPV-CA39-HA1/Anhui, AcNPV-CA64-HA1/Anhui, AcNPV-CA39-PfCSP(A361E), AcNPV-CA64-PfCSP(A361E), AcNPV-CAP-CO/full/VSV, AcNPV-CAP-CO/19/VSV, AcNPV-CAP-CO/76/VSV, AcNPV-CAP-CO/205/VSV, AcNPV-Dual-Pfs25-PfCSP-64, or AcNPV-Dual-PfMSP1-PfCSP-gp64 of the present invention, which is the active ingredient in the vaccine of the present invention, can enhance infection-preventing effects on the infectious antigen and reduces the infectivity titer, and this action or activity can be utilized for procedures of the diseases associated with the infection of the target cells or tissues. Such target cells affected by the infection include, for example blood cells, and other target cells include hepatic cells, renal cells, brain cells, lung cells, epithelial cells and muscular cells. The tissues comprising these cells include lung, liver, kidney, arterial and venous veins, stomach, intestine, urethra, skin and muscle.

The vaccine of the present invention as the pharmaceutical composition in the above (3) can be prepared as the composition comprising the pharmaceutically effective amount of the recombinant baculovirus (any one of AcNPV-Dual-H1N1/HA1, AcNPV-Dual-Hsp65, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39, AcNPV-CP-H1N1/NP-vp39, AcNPV-CAP-PfCSP, AcNPV-CAP-PfCSP/272, AcNPV-CAP-PfCSP/467, AcNPV-CAP-PfCSP(A361E), AcNPV-CAP-PfCSP(A361E)/272, AcNPV-CAP-PfCSP(A361E)/467, AcNPV-CAP-PfCSP-76, AcNPV-CAP-PfCSP-76/467, AcNPV-CAP-PfCSP+209, AcNPV-CAP-PfCSP+209/467, AcNPV-CAP-PfCSP+76/209, AcNPV-CAP-PfCSP+76/209/467, AcNPV-CAP-HA1/Anhui, AcNPV-CAP-HA1/Anhui/272, AcNPV-CAP-HA1/Anhui/467, AcNPV-CAP-HA1/Vietnam, AcNPV-CAP-HA1/Vietnam/51, AcNPV-CAP-HA1/Vietnam/101, AcNPV-CAP-HA1/Vietnam/154, AcNPV-CAP-HA1/Vietnam/201, AcNPV-CAP-HA1/Vietnam/272, AcNPV-CAP-HA1/Vietnam/467, AcNPV-CAP-AH/345, AcNPV-CAP-AH/345/467, AcNPV-CAP-AH/410, AcNPV-CAP-AH/410/467, AcNPV-CAP-AH/473, AcNPV-CAP-AH/473/467, AcNPV-CAP-AH/520, AcNPV-CAP-AH/520/467, AcNPV-CAP-VN/346, AcNPV-CAP-VN/346/467, AcNPV-CAP-VN/410, AcNPV-CAP-VN/410/467, AcNPV-CAP-VN/473, AcNPV-CAP-VN/473/467, AcNPV-CAP-VN/520, AcNPV-CAP-VN/520/467, AcNPV-CAP-CO/full, AcNPV-CAP-CO/full/467, AcNPV-CAP-CO/19, AcNPV-CAP-CO/19/467, AcNPV-CAP-CO/76, AcNPV-CAP-CO/76/467, AcNPV-CAP-CO/205, AcNPV-CAP-CO/205/467, AcNPV-CA39-HA1/Anhui, AcNPV-CA64-HA1/Anhui, AcNPV-CA39-PfCSP(A361E), AcNPV-CA64-PfCSP(A361E), AcNPV-CAP-CO/full/VSV, AcNPV-CAP-CO/19/VSV, AcNPV-CAP-CO/76/VSV, AcNPV-CAP-CO/205/VSV, AcNPV-Dual-Pfs25-PfCSP-gp64, and AcNPV-Dual-PfMSP1-PfCSP-gp64) and the pharmaceutically acceptable carrier.

The vaccine can be prepared into a pharmaceutical composition form utilizing the acceptable as the pharmaceutical as with the pharmaceutical composition in the above (3) in accordance with the standard methods. The carrier can include, for example, physiologically acceptable solutions such as sterile saline and sterile buffered saline.

The vaccine (hereinafter, the formulation is the same as in the pharmaceutical composition) can be prepared as a liposome formulation comprising the recombinant baculovirus (any one of AcNPV-Dual-H1N1/HA1, AcNPV-Dual-Hsp65, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39, AcNPV-CP-H1N1/NP-vp39, AcNPV-CAP-PfCSP, AcNPV-CAP-PfCSP/272, AcNPV-CAP-PfCSP/467, AcNPV-CAP-PfCSP(A361E), AcNPV-CAP-PfCSP(A361E)/272, AcNPV-CAP-PfCSP(A361E)/467, AcNPV-CAP-PfCSP-76, AcNPV-CAP-PfCSP-76/467, AcNPV-CAP-PfCSP+209, AcNPV-CAP-PfCSP+209/467, AcNPV-CAP-PfCSP+76/209, AcNPV-CAP-PfCSP+76/209/467, AcNPV-CAP-HA1/Anhui, AcNPV-CAP-HA1/Anhui/272, AcNPV-CAP-HA1/Anhui/467, AcNPV-CAP-HA1/Vietnam, AcNPV-CAP-HA1/Vietnam/51, AcNPV-CAP-HA1/Vietnam/101, AcNPV-CAP-HA1/Vietnam/154, AcNPV-CAP-HA1/Vietnam/201, AcNPV-CAP-HA1/Vietnam/272, AcNPV-CAP-HA1/Vietnam/467, AcNPV-CAP-AH/345, AcNPV-CAP-AH/345/467, AcNPV-CAP-AH/410, AcNPV-CAP-AH/410/467, AcNPV-CAP-AH/473, AcNPV-CAP-AH/473/467, AcNPV-CAP-AH/520, AcNPV-CAP-AH/520/467, AcNPV-CAP-VN/346, AcNPV-CAP-VN/346/467, AcNPV-CAP-VN/410, AcNPV-CAP-VN/410/467, AcNPV-CAP-VN/473, AcNPV-CAP-VN/473/467, AcNPV-CAP-VN/520, AcNPV-CAP-VN/520/467, AcNPV-CAP-CO/full, AcNPV-CAP-CO/full/467, AcNPV-CAP-CO/19, AcNPV-CAP-CO/19/467, AcNPV-CAP-CO/76, AcNPV-CAP-CO/76/467, AcNPV-CAP-CO/205, AcNPV-CAP-CO/205/467, AcNPV-CA39-HA1/Anhui, AcNPV-CA64-HA1/Anhui, AcNPV-CA39-PfCSP(A361E), AcNPV-CA64-PfCSP(A361E), AcNPV-CAP-CO/full/VSV, AcNPV-CAP-CO/19/VSV, AcNPV- CAP-CO/76/VSV, AcNPV-CAP-00/205/VSV, AcNPV-Dual-Pfs25-PfCSP-64, and AcNPV-Dual-PfMSP1-PfCSP-gp64) as the active ingredient, and can be combined with an adjuvant. Specific examples of the vaccine (pharmaceutical composition) of the present invention can include the liposome formulation. The liposome formulation can be one in which the recombinant baculovirus of the present invention is retained in the liposome using acidic phospholipid as a membrane component or using neutral phospholipid and acidic phospholipid as the membrane component.

The neutral phospholipid and acidic phospholipid used as the membrane component are not particularly limited, and various lipids commonly used for the liposome formulation can be used alone or in mixture of two or more.

A liposome membrane is formed in accordance with the standard methods using the acidic phospholipid alone or combining the neutral phospholipid and the acidic phospholipid. In the case of combining the neutral phospholipid, the rate of the acidic phospholipid to be combined may be about 0.1 to 100 mol %, preferably 1 to 90 mol % and more preferably about 10 to 50 mol % in the liposome membrane components.

To prepare the liposome, for example, cholesterol or the like can be added. This can control the fluidity of phospholipids and facilitates the liposome preparation. In general, the cholesterol is preferably added in an equivalent amount or less, and preferably in a 0.5-fold amount to an equivalent amount by weight, to the phospholipid.

For the rate of the active ingredient and the acidic phospholipid in the liposome formulation, the rate of the acidic phospholipid is about 0.5 to 100 equivalents, preferably about 1 to 60 equivalents and more preferably about 1.5 to 20 equivalents relative to the active ingredient.

The amount of the recombinant baculovirus of the present invention which is the active ingredient to be used can be several mol % to several tens mol %, preferably about 5 to 10 mol % and typically around 5 mol %.

The production, concentration and particle diameter control of the above liposome formulation can be performed in accordance with the standard methods. Various additives described above can also be combined with the liposome formulation if desired. Fatty acid (e.g., behenic acid, stearic acid, palmitic acid, myristic acid, oleic acid), alkyl group, cholesteryl group and the like can also be bound thereto and used. The production of the liposome formulation prepared by binding them can also be performed in accordance with the standard methods (see Long Circulating Liposomes: old drugs, New therapeutics., M. C. Woodle, G. Storm, Eds: Springer-Verlag Berlin(1998)).

The vaccine (pharmaceutical composition) of the present invention can be preferably used as a vaccine composition. When it is used, it is preferable for enhancing an anti-infection (anti-malaria or anti-influenza) effect to be combined with the adjuvant in pharmaceutically effective amount.

As the adjuvant, any ones commonly used for this type of vaccine can be used without limitation. As examples thereof, Freund's complete adjuvant, muramyl dipeptide, aluminium hydroxide, BCG, IL-12, N-acetylmuramine-L-alanyl-D-isoglutamine, thymosin α1 and QS-21 can be exemplified. The amount of the adjuvant to be combined can be appropriately determined depending on softening, erythema of skin, fever, headache and muscular pain which are likely expressed as a part of the immune response in the human beings or the animal after the administration thereof. The vaccine (pharmaceutical composition) of the present invention can be combined with other publicly known pharmaceutical articles such as immune response-facilitating peptide and antibacterial agents (synthetic antibacterial agents).

Optional drugs and additives can be further contained in the vaccine (pharmaceutical composition). As examples thereof, the drug such as calcium ion which aids intracellular uptake of the recombinant baculovirus of the present invention can be exemplified. The drugs and additives, e.g., the liposome, and for example, fluorocarbon emulsifier, cochleate, tubule, golden particles, biodegradable microsphere and cationic polymers which make the transfection easy can be used.

The amount of the active ingredient contained in the vaccine (pharmaceutical composition) (formulation) of the present invention is not particularly limited and can be selected from the wide range as long as it is the pharmaceutically effective amount. The dosage of the vaccine (pharmaceutical composition) is not particularly limited, and can be appropriately selected from the wide range depending on the desired therapeutic effect, the administration method (administration route), the therapeutic period, age and gender of the patient, and other conditions.

When the recombinant baculovirus as an active ingredient of the vaccine (pharmaceutical composition) of the present invention is administered to a human, the recombinant baculovirus is administered in an amount corresponding to $10^2$ to $10^{14}$ PFU, preferably $10^5$ to $10^{12}$ PFU, and more preferably $10^6$ to $10^{10}$ PFU per patient, calculated as the PFU of the recombinant virus.

The dosage of the recombinant baculovirus (any one of AcNPV-Dual-H1N1/HA1, AcNPV-Dual-Hsp65, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39, AcNPV-CP-H1N1/NP-vp39, AcNPV-CAP-PfCSP, AcNPV-CAP-PfCSP/272, AcNPV-CAP-PfCSP/467, AcNPV-CAP-PfCSP(A361E), AcNPV-CAP-PfCSP(A361E)/272, AcNPV-CAP-PfCSP(A361E)/467, AcNPV-CAP-PfCSP-76, AcNPV-CAP-PfCSP-76/467, AcNPV-CAP-PfCSP+209, AcNPV-CAP-PfCSP+209/467, AcNPV-CAP-PfCSP+76/209, AcNPV-CAP-PfCSP+76/209/467, AcNPV-CAP-HA1/Anhui, AcNPV-CAP-HA1/Anhui/272, AcNPV-CAP-HA1/Anhui/467, AcNPV-CAP-HA1/Vietnam, AcNPV-CAP-HA1/Vietnam/51, AcNPV-CAP-HA1/Vietnam/101, AcNPV-CAP-HA1/Vietnam/154, AcNPV-CAP-HA1/Vietnam/201, AcNPV-CAP-HA1/Vietnam/272, AcNPV-CAP-HA1/Vietnam/467, AcNPV-CAP-AH/345, AcNPV-CAP-AH/345/467, AcNPV-CAP-AH/410, AcNPV-CAP-AH/410/467, AcNPV-CAP-AH/473, AcNPV-CAP-AH/473/467, AcNPV-CAP-AH/520, AcNPV-CAP-AH/520/467, AcNPV-CAP-VN/346, AcNPV-CAP-VN/346/467, AcNPV-CAP-VN/410, AcNPV-CAP-VN/410/467, AcNPV-CAP-VN/473, AcNPV-CAP-VN/473/467, AcNPV-CAP-VN/520, AcNPV-CAP-VN/520/467, AcNPV-CAP-CO/full, AcNPV-CAP-CO/full/467, AcNPV-CAP-CO/19, AcNPV-CAP-CO/19/467, AcNPV-CAP-CO/76, AcNPV-CAP-CO/76/467, AcNPV-CAP-CO/205, AcNPV-CAP-CO/205/467, AcNPV-CA39-HA1/Anhui, AcNPV-CA64-HA1/Anhui, AcNPV-CA39-PfCSP(A361E), AcNPV-CA64-PfCSP(A361E), AcNPV-CAP-CO/full/VSV, AcNPV-CAP-CO/19/VSV, AcNPV-CAP-CO/76/VSV, AcNPV-CAP-CO/205/VSV, AcNPV-Dual-Pfs25-PfCSP-64, and AcNPV-Dual-PfMSP1-PfCSP-gp64) which is the active ingredient of the vaccine (pharmaceutical composition) of the present invention is selected from the very wide range as the amount of expressible DNA introduced into the vaccine host or the amount of transcribed RNA. Their amounts also depend on strength of transcription and translation promoters used for the transfer vector.

The vaccine (pharmaceutical composition) of the present invention is administered by directly injecting a recombinant baculovirus suspension in which the vector is suspended in PBS (phosphate buffered saline) or saline into a local site (e.g., in lung tissue, in liver, in muscle and in brain), inhaling through nose or airway, or administering in blood vessel (e.g., intra-arterial, intravenous, and in portal vein). The vaccine of the invention is preferably administered by inhalation.

It is preferable that the vaccine (pharmaceutical composition) of the present invention is administered not once but once to multiple times by observing the state after the initial administration and administering the additional vaccine(s). This makes it possible to enhance the desired effect. It is possible to additionally immunize with the pharmaceutical composition composed of the recombinant baculovirus (any one of AcNPV-Dual-H1N1/HA1, AcNPV-Dual-Hsp65, AcNPV-Dual-PfCSP, AcNPV-Dual-PfAMA1, AcNPV-Dual-Pfs25, AcNPV-Dual-H5N1/HA1, AcNPV-Dual-SARS/S, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39, AcNPV-CP-H1N1/NP-vp39, AcNPV-CAP-PfCSP, AcNPV-CAP-PfCSP/272, AcNPV-CAP-PfCSP/467, AcNPV-CAP-PfCSP (A361E), AcNPV-CAP-PfCSP(A361E)/272, AcNPV-CAP-PfCSP(A361E)/467, AcNPV-CAP-PfCSP-76, AcNPV-CAP-PfCSP-76/467, AcNPV-CAP-PfCSP+209, AcNPV-CAP-PfCSP+209/467, AcNPV-CAP-PfCSP+76/209, AcNPV-CAP-PfCSP+76/209/467, AcNPV-CAP-HA1/Anhui, AcNPV-CAP-HA1/Anhui/272, AcNPV-CAP-HA1/Anhui/467, AcNPV-CAP-HA1/Vietnam, AcNPV-CAP-HA1/Vietnam/51, AcNPV-CAP-HA1/Vietnam/101, AcNPV-CAP-HA1/Vietnam/154, AcNPV-CAP-HA1/Vietnam/201, AcNPV-CAP-HA1/Vietnam/272, AcNPV-CAP-HA1/Vietnam/467, AcNPV-CAP-AH/345, AcNPV-CAP-AH/345/467, AcNPV-CAP-AH/410, AcNPV-CAP-AH/410/467, AcNPV-CAP-AH/473, AcNPV-CAP-AH/473/467, AcNPV-CAP-AH/520, AcNPV-CAP-AH/520/467, AcNPV-CAP-VN/346, AcNPV-CAP-VN/346/467, AcNPV-CAP-VN/410, AcNPV-CAP-VN/410/467, AcNPV-CAP-VN/473, AcNPV-CAP-VN/473/467, AcNPV-CAP-VN/520, AcNPV-CAP-VN/520/467, AcNPV-CAP-CO/full, AcNPV-CAP-CO/full/467, AcNPV-CAP-CO/19, AcNPV-CAP-CO/19/467, AcNPV-CAP-CO/76, AcNPV-CAP-CO/76/467, AcNPV-CAP-CO/205, AcNPV-CAP-CO/205/467, AcNPV-CA39-HA1/Anhui, AcNPV-CA64-HA1/Anhui, AcNPV-CA39-PfCSP(A361E), AcNPV-CA64-PfCSP(A361E), AcNPV-CAP-CO/full/VSV, AcNPV-CAP-CO/19/VSV, AcNPV-CAP-CO/76/VSV, AcNPV-CAP-CO/205/VSV, AcNPV-Dual-Pfs25-PfCSP-64, and AcNPV-Dual-PfMSP1-PfCSP-gp64) of the present invention after administering the vaccine (pharmaceutical composition). The combination of the above various drugs to be combined also has the possibility to enhance the therapeutic effect by the administration of the vaccine (pharmaceutical composition).

In one embodiment of the vaccine (pharmaceutical composition) of the present invention, the recombinant baculovirus which is one of the active ingredient of the vaccine (pharmaceutical composition) of the present invention can be formulated by mixing the recombinant baculovirus obtained by homologous recombination of the transfer vector in which the fusion gene obtained by fusing the desired immunogenic foreign gene and the gene encoding the protein capable of being the component of the viral particle is introduced with the baculovirus DNA in the form capable of injecting a unit dose (solution, suspension or emulsion) with the pharmaceutically acceptable carrier (i.e., non-toxic for the vertebrates including the human beings in the dosage and concentration to be administered, and compatible with other ingredients in the formulation). For example, the formulation preferably contains no antioxidant and no other compounds publicly known to be harmful for the recombinant baculovirus.

The carrier appropriately contains the additives in small amounts, such as substances which augment an isotonic property and a chemical stability. Such substances are non-toxic for the mammals including the human beings in the dosage and concentration to be administered, and can include buffers such as phosphoric acid, citric acid, succinic acid, acetic acid and other organic acids or salts thereof, antioxidants such as ascorbic acid, low molecular weight (e.g., less than about 10 residues) polypeptides (e.g., polyarginine or tripeptide) proteins (e.g., serum albumin, gelatin, or immunoglobulin), amino acids (e.g., glycine, glutamic acid, aspartic acid or arginine), monosaccharides, disaccharides and other carbohydrates (including cellulose or derivatives thereof, glucose, mannose, or dextrin), chelating agents (e.g., EDTA), sugar alcohols (e.g., mannitol or sorbitol), counterions (e.g., sodium), and/or nonionic surfactants (e.g., polysorbate, poloxamer).

The pharmaceutical vaccine (composition) comprising the recombinant baculovirus can be stored representatively in a unit or multiple dose container, e.g., a sealed ampoule or a vial as an aqueous solution or a lyophilized product.

(5) Method of Preventing Virus Infection

The present invention further provides a method of preventing or treating infectious diseases caused by the pathogen and their complications, e.g., viral diseases caused by influenza virus, papilloma virus, herpes virus, AIDS virus, hepatitis C virus, SARS virus, west Nile fever virus and dengue fever virus, parasite diseases caused by malaria, trypanosome and *leishmania* parasites, and bacterial diseases caused by bacteria, such as dysentery, enteric fever, cholera, pneumococcus, MRSA, VRE, *Neisseria gonorrhoeae* and *Chlamydia*, syphilis and tuberculosis. The present method comprises administering an effective amount of the recombinant baculovirus, vaccine, formulation, and pharmaceutical composition of the invention to a subject. The present invention further provides a method of immunostimulation comprising administering an effective amount of the recombinant baculovirus, vaccine, formulation, and pharmaceutical composition of the invention to a subject. Examples of the subjects include those that may be infected with malaria parasites or influenza viruses, such as humans and other animals (such as mammals, birds, reptiles, fish, and amphibians), and those infected with malaria parasites or influenza viruses. The influenza virus with which the subject is infected is preferably an influenza A virus, and more preferably an influenza A subtype H1 virus, or an influenza A subtype H3 virus. Examples of malaria parasites include *Plasmodium falciparum, Plasmodium vivax, Plasmodium malariae*, and *Plasmodium ovale*.

The recombinant baculovirus of the present invention is formed alone or together with a pharmaceutically acceptable carrier into a vaccine, formulation, or pharmaceutical composition, and administered to the subject.

The administration route may be, for example, any administration route mentioned above. The pharmaceutically acceptable carrier for use in the present invention can be suitably selected from carriers commonly used in this technical field, according to the form of the pharmaceutical composition to be produced.

For example, when the pharmacological composition is formed into an aqueous solution, purified water (sterile water) or a physiological buffer solution can be used as the carrier.

When the pharmaceutical composition is formed into other appropriate solutions, organic esters capable of being injected, such as glycol, glycerol and olive oil, can be used as the carrier. The composition may contain stabilizers, excipients and the like commonly used in this technical field, and particularly in the field of vaccine formulations.

The amount of recombinant baculovirus in the vaccine, formulation, or pharmaceutical composition of the present invention is not particularly limited, and can be suitably selected from a wide range. In general, the amount of recombinant baculovirus in the composition is preferably about 0.0002 to about 0.2 (w/v %), and more preferably 0.001 to 0.1 (w/v %). The administration method of the recombinant baculovirus, vaccine, formulation, or pharmaceutical composition of the invention is not particularly limited, and can be suitably selected according to the dosage form, the patient's age, gender and other conditions, the severity of the disease, etc. A preferable dosage form thereof is a form for parenteral administration, such as injections, drops, nasal drops, and inhalants. When the composition is formed into an injection or drops, the injection can be intravenously administered as mixed with a replacement fluid such as a glucose solution or an amino acid solution as required, or can be administered intramuscularly, intracutaneously, subcutaneously or intraperitoneally.

The daily dosage of the recombinant baculovirus, vaccine, formulation, or pharmaceutical composition of the present invention may vary depending on the subject's condition, body weight, age, gender, etc., and therefore cannot be completely specified. However, the dosage is usually such that the recombinant baculovirus is administered in an amount of 0.001 to 100 mg per kg of body weight per day. The vaccine, formulation, or composition of the invention can be administered in one or more administrations per day.

When the recombinant baculovirus as an active ingredient of the vaccine (formulation or pharmaceutical composition) of the present invention is administered, the recombinant baculovirus is administered in an amount corresponding to $10^2$ to $10^{14}$ PFU, preferably $10^5$ to $10^{12}$ PFU, and more preferably $10^6$ to $10^{10}$ PFU per patient, calculated as the PFU of the recombinant virus.

The vaccine (composition) of the present invention is administered according to Good Medical Practice, considering the clinical condition (for example, the condition to be prevented or treated) of each patient, the delivery site of the vaccine (composition) containing the recombinant baculovirus, the target tissue, the administration method, the dosage regimen, and other factors publicly known to those skilled in the art. Therefore, the proper dosage of the vaccine (composition) herein is determined in consideration of the above.

EXAMPLES

The present invention will be described below in more detail with reference to Examples. These Examples are exemplifications only and do not limit the present invention.

Example 1

Transfer Vector Plasmid and Method for Production Thereof of the Present Invention (1) Construction of Transfer Vector Plasmid pTriEx-Hsp65-gp64 of the Present Invention
(1.1) Construction of Plasmid pBACsurf-CSP
A plasmid pcDNA-CS87 was made by obtaining a NheI-NotI fragment comprising the sequence fusing genomic DNA from *Plasmodium berghei* ANKA strain, a signal sequence of murine Igk secretion and a FLAG sequence in accordance with Yoshida et al's method (Yoshida, S., et al., B.B.R.C., 271, 107-115 (2000) and inserting the NheI-NotI fragment in a NheI-NotI site of pcDNA3.1 (supplied from Invitrogen).

A blood sample was collected from a BALB/c mouse infected with malaria parasite *P. berghei* ANKA, and *P. berghei* genomic DNA was extracted using QIAamp DNA Midi Kit (supplied from Qiagen). Subsequently, the *P. berghei* ANKA genomic DNA was amplified by PCR using a primer pbCSP1: 5'-GGAGG<u>GCTAGC</u> *ATGGAGACAGA-CACACTCCTGCTATGGGTACTGCTGCTCTG GGTTC-CAGGTTCCACTGGTGACGCGGATCCACTGCAG* <u>GACTACAAGGACGTAGACAAGGGATATG</u>
GACAAAATAAAGCATCCAAGCCC-3' (SEQ ID NO: 1) (a NheI site newly made is represented by an underline, the signal sequence of murine Igk secretion is represented by Italic and the FLAG sequence is represented by a double underline) and PbCSP-R1: GGAGG<u>GCGGCCGC</u>ATCCCGGGTTTTCTTATTTGAACCTTTT-CGTTTTCTAACTCTTATACCAGAA CC-3' (SEQ ID NO: 2) (a NotI site newly made is represented by the underline). The PCR was performed using PfuDNA polymerase (supplied from Stratagene) by 30 cycles (denaturing at 94° C. for 30 seconds, annealing at 55° C. for one minute and extending at 72° C. for 2 minutes). The PCR product does not have glycosyl phosphatidyl inositol (GPI) anchor and encodes PbCSP fused to the signal sequence of murine Igk secretion in place of its original signal sequence.

The PCR product was purified, cleaved with restriction enzymes NheI/NotI, which was then inserted in the NheI/NotI sites of pcDNA3.1 (supplied from Invitrogen), and a resulting plasmid was designed as pcDNA-CS87. The pcDNA-CS87 plasmid contains a CMV promoter, the signal sequence of murine Igk secretion, a protein (corresponding to 21 to 299 amino acids) encoded by the PbCSP gene, a poly A signal derived from a bovine growth hormone gene and a poly A sequence.

A gene fragment encoding an amino acid sequence at positions 21 to 306 of a peptide from PbCSP was obtained by cleaving the pcDNA-CS87 with the restriction enzymes PstI and SmaI, the DNA fragment was inserted in the PstI and SmaI sites of pBACsurf (supplied from Novagen), and the constructed plasmid was designed as pBACsurf-CSP.
(1.2) Construction of Plasmid pBACsurf-Hsp65
An Hsp65 gene was obtained by extracting genomic DNA from *M. tuberculosis* H37Rv strain using QIAamp DNA Midi Kit (supplied from Qiagen) and cloning by PCR. That is, the genomic DNA extracted from *M. tuberculosis* H37Rv strain was amplified by PCR using a primer, phsp65-F1: 5'-AATAATAGATCT AATGGCCAAGACAATTGCGTACGACGAAGA-3 (SEQ ID NO: 3) (a BglII site is represented by the underline) and phsp65-R1: AATCCAATGCGGCCGC GGGAATTCGATTCCTGCAGGTCAGAAATCCATGCCACCCATGTCGCC-3 (SEQ ID NO: 4) (the NotI site is represented by the underline).

The PCR product was purified, cleaved with the restriction enzymes BglII/NotI, ligated to the BamHI/NotI sites in pcDNA3.1 (supplied from Invitrogen), and the resulting plasmid was designated as pcDNA-hsp65.

The pcDNA-hsp65 plasmid is a construct in which the signal sequence of murine Igk secretion was fused to the hsp65 gene.

The PCR was performed with pcDNA-hsp65 as a template using the primer phsp65-F2: 5-CACC CCTGCAGGACTACAAGGACGACGATGACAAG GAATTCATGGCCAAGAC AATTGCGTACGACGAA-GAGGCC-3' (SEQ ID NO: 5) (Sse8387I, EcoRI sites are represented by underlines, and the FLAG sequence is represented by Italic), and phsp65-R2: (5'-CCCGGGCGAAATCCATGCCACCCATGTCGCCGCCA-CC-3' (SEQ ID NO: 6) (a Cfr9I site is represented by the underline). The resulting Hsp65 gene DNA fragment (about 1660 bp) was cloned into pENTR/D-TOPO (supplied from Invitrogen), subsequently cleaved with Sse8387I/Cfr9I, which was then inserted in the PstI/Cfr9I sites of pBACsurf-CSP (Yoshida et al. Virology 316: 161-70, 2003) obtained above.

The plasmid constructed as the above was designed as pBACsurf-Hsp65.

(1.3) Construction of Plasmid pENTR-gp64

The PCR was performed with pBACgus-1 (supplied from Novagen) as the template using the primer pPolh-F2: 5'-CACCCGGACCGGATAATTAAAATGAT AACCATCTCGCAAATAAATAAG-3' (SEQ ID NO: 7) (a RsrII site is represented by the underline), and pgp64-R2: 5'-GGTACCATATTGTCTATTACGGTTTCTAATCATAC-3' (SEQ ID NO: 8) (a KpnI site is represented by the underline). The resulting gp64 gene DNA fragment (about 1700 bp) was inserted in pENTR/D-TOPO to construct the plasmid pENTR-gp64.

The plasmid constructed as the above was designated as pENTR-gp64.

(1.4) Construction of Transfer Vector pDual-Hsp65-gp64 of the Present Invention pDual-Hsp65-gp64 was cleaved with PstI/Cfr9I, and the hsp65 gene DNA fragment (about 1660 bp) was inserted in the PstI/Cfr9I sites of pENTR-gp64 to construct the plasmid pENTR-Hsp65-gp64.

Furthermore, pENTR-hsp65-gp64 was cleaved with RsrII/KpnI, and a DNA fragment (about 3360 bp) composed of a polyhedrin promoter and the hsp65gp64 gene was inserted in RsrII/KpnI of TriEx-3 (supplied from Novagen) to construct the transfer vector plasmid pDual-Hsp65-gp64 in which the expression was controlled by the desired dual promoters.

(2) Construction of Transfer Vector pDual-PbCSP-gp64 of the Present Invention

The plasmid pBACsurf-CSP obtained in (1.1.1) was cleaved with PstI/Cfr9I, and a PbCSP gene DNA fragment (about 890 bp) was inserted in the PstI/Cfr9I sites of pDual-Hsp65-gp64 to construct the plasmid pDual-PbCSP-gp64.

(3) Construction of Transfer Vector pDual-H1N1/HA1-gp64 of the Present Invention RNA was extracted from a culture supernatant of MDCK cells infected with influenza virus PR8/34 strain using QIAamp MiniElute Virus Spin Kit (QIAGEN), and amplified by RT-PCR using the primer HA-f: 5'-CCTGCAGGTATGAAGGCAAACCTACTGGTC-3' (SEQ ID NO: 9) (a SbfI site is represented by the underline) and HA-r: 5'-GCCCGGGCGATGCATATTCTGCA-3 (SEQ ID NO: 10) (a SbfI site is represented by the underline). The resulting influenza virus HA gene fragment with full length of 1700 bp was cloned into pCR-Blunt II-TOPO (supplied from Invitrogen).

The resulting plasmid was designed as pCR-Blunt-HA. The PCR was performed with the pCR-Blunt-HA as the template using the primer pHA-F1: 5'-CACC GAATTCGACACAATATGTATAGGCTACCATGCG-3' (SEQ ID NO: 11) (an EcoRI site is represented by the underline) and pHA-R1: 5'-CCCGGGCACCTCTGGATTGGATGGACGGAATG-3' (SEQ ID NO: 12) (a Cfr9I site is represented by the underline). The resulting H1N1/HA1 gene DNA fragment (about 1000 bp) was cloned into pENTR/D-TOPO (supplied from Invitrogen), subsequently cleaved with EcoRI/Cfr9I, which was then inserted in the EcoRI/Cfr9I sites of pDual-Hsp65-gp64 to construct the plasmid pDual-H1N1/HA1-64.

(4) Construct of Transfer Vector pDual-PbTRAMP-gp64 of the Present Invention

The blood sample was collected from a BALB/c mouse infected with malaria parasite *P. berghei* ANKA, and *P. berghei* genomic DNA was extracted using QIAamp DNA Midi Kit (supplied from Qiagen).

A PbTRAMP gene was cloned by PCR with this genomic DNA as the template according to the following method. That is, the PCR was performed using the primer pTRAMP-F1: 5'-CACC GAATTCAAAATTGATACGAAAAAAAATGAAG-3' (SEQ ID NO: 13) (the EcoRI site is represented by the underline) and pTRAMP-R1: CCCGGG CTTTTAATTTTGAG-GAGTCTTTATTTTC-3' (SEQ ID NO: 14) (the Cfr9I site is represented by the underline). The resulting PbTRAMP DNA fragment (about 800 bp) was cloned into pENTR/D-TOPO (supplied from Invitrogen), subsequently cleaved with EcoRI/Cfr9I, which was then inserted in the EcoRI/Cfr9I sites of pBACsurf-Hsp65. The constructed plasmid was designated as pBACsurf-PbTRAMP.

Subsequently, the pBACsurf-PbTRAMP was cleaved with EcoRI/Cfr9I, and a PbTRAMP gene DNA fragment (about 860 bp) was inserted in the EcoRI/Cfr9I sites of pDual-Hsp65-gp64 to construct the plasmid pDual-PbTRAMP-gp64.

(5) Construction of Transfer Vector pDual-PbAMA1D123-gp64 of the Present Invention The blood sample was collected from the BALB/c mouse infected with malaria parasite *P. berghei* ANKA, and the *P. berghei* genomic DNA was extracted using QIAamp DNA Midi Kit (supplied from Qiagen).

A PbAMA1 gene domain 123 (D123) gene was cloned by PCR with this genomic DNA as the template according to the following method. That is, the PCR was performed using the primer pAMA-F1: 5'-CACCGAATTC AATCCATGG-GAAAAGTATACGGAAAAATAT-3' (SEQ ID NO: 15) (the EcoRI site is represented by the underline) and pAMA-R1: 5'-CCCGGGCTTCTCTGGTTTGATGGGCTTTCATATGCA-C-3' (SEQ ID NO: 16) (the Cfr9I site is represented by the underline). The resulting PbAMA1D123 DNA fragment (about 1280 bp) was cloned into pENTR/D-TOPO (supplied from Invitrogen), subsequently cleaved with EcoRI/Cfr9I, which was then inserted in the EcoRI/Cfr9I sites of pBAC-surf-Hsp65. The constructed plasmid was designated as pBACsurf-PbAMA1D123.

Subsequently, the pBACsurf-PbAMA1D123 was cleaved with EcoRI/Cfr9I, and the PbAMA1D123 gene DNA fragment (about 1280 bp) was inserted in the EcoRI/Cfr9I sites of pDual-Hsp65-gp64 obtained in the above (1.4) to construct the plasmid pDual-PbAMA1D123-gp64.

(6) Construction of Transfer Vector pDual-PbMSP119-gp64 of the Present Invention The blood sample was collected from the BALB/c mouse infected with malaria parasite *P. berghei* ANKA, and the *P. berghei* genomic DNA was extracted using QIAamp DNA Midi Kit (supplied from Qiagen).

A PbMSP119 gene was cloned by PCR with this genomic DNA as the template according to the following method. That is, the PCR was performed using the primer pMsp1-F1: 5'-CACCCTGCAGGACTACAAGGACGACGATG ACAAGCACATAGCCTCAATAGCTTTAAATAACTTAA ATAAATCTGG-3' (SEQ ID NO: 17) (the PstI site is represented by the underline) and pMsp1-R1: 5'-CCCGGGTTCCCATAAAGCTGGAAGAGCTACAGAAT-ACACC-3' (SEQ ID NO: 18) (the Cfr9I site is represented by the underline). The resulting PbMSP119 DNA fragment (about 450 bp) was cloned into pENTR/D-TOPO (supplied from Invitrogen), subsequently was cleaved with PstI/Cfr9I, which was then inserted in the PstI/Cfr9I sites of pBACsurf-Hsp65. The constructed plasmid was designated as pBACsurf-PbMSP119.

Subsequently, the pBACsurf-PbMSP119 was cleaved with PstI/Cfr9I, and the PbMSP-119 gene DNA fragment (about 450 bp) was inserted in the PstI/Cfr9I sites of pDual-Hsp65-gp64 to construct the plasmid pDual-PbMSP-1,9-gp64.

(7) Construction of Transfer Vector pDual-PfCSP-gp64 of the Present Invention

The genomic DNA of falciparum malaria parasite, *P. falciparum* was extracted from human erythrocytes infected with *P. falciparum* 3D7 strain using QIAamp DNA Midi Kit (QIAGEN). A PfCSP gene was cloned by PCR with this genomic DNA as the template according to the following method. That is, the PCR was performed using the primer pPfCSP-F1: 5'-CACCGAATTCTTATTCCAGGAATAC-CAGTGCTATGGAAGT-3' (SEQ ID NO: 19) (the EcoRI site is represented by the underline) and pPfCSP-R1: 5'-CCCGGGCTTTTTCCATTTTACAAATTTTTTTTC-3' (SEQ ID NO: 20) (the Cfr9I site is represented by the underline). The resulting PfCSP DNA fragment (about 1100 bp) was cloned into pENTR/D-TOPO (supplied from Invitrogen), subsequently cleaved with EcoRI/Cfr9I, which was then inserted in the EcoRI/Cfr9I sites of pDual-PbAMA1D123-gp64. The constructed plasmid was designated as pDual-PfCSP-gp64.

(8) Construction of Transfer Vector pDual-PfAMA1-gp64 of the Present Invention

The genomic DNA of falciparum malaria parasite, *P. falciparum* was extracted from human erythrocytes infected with *P. falciparum* 3D7 strain using QIAamp DNA Midi Kit (QIAGEN). The PfAMA1 gene was cloned by PCR with this genomic DNA as the template according to the following method. That is, the PCR was performed using the primer pPfAMA1-F1: 5'-CACCCTGCAG GACTACAAGGAC-GACGATGACAAGCAGAATTATTGGGAACATCCATAT CAAAATAGTGATGTG-3' (SEQ ID NO: 21) (the PstI site is represented by the underline, the FLAG sequence represented by Italic) and pPfAMA1-R1: 5'-CCCGGGCTTTCATTTTATCATAAGTTGGTTTATG-3' (SEQ ID NO: 22) (the Cfr9I site is represented by the underline). The resulting PfAMA1 DNA fragment (about 3500 bp) was cloned into pENTR/D-TOPO (supplied from Invitrogen), subsequently cleaved with PstI/Cfr9I, which was then inserted in the PstI/Cfr9I sites of PbAMA1D123-gp64. The constructed plasmid was designated as pDual-PfAMA1-gp64.

(9) Construction of Transfer Vector pDual-Pfs25-gp64 of the Present Invention

The genomic DNA of falciparum malaria parasite, *P. falciparum* was extracted from human erythrocytes infected with *P. falciparum* 3D7 strain using QIAamp DNA Midi Kit (QIAGEN). The Pfs25 gene was cloned by PCR with this genomic DNA as the template according to the following method. That is, the PCR was performed using the primer pPfs25-F1: 5'-CACCGAATTCAAAGTTACCGTGG ATACTGTATGCAAAAGAGGA-3' (SEQ ID NO: 23) (the EcoRI site is represented by the underline) and pPfs25-R1: 5'-CCCGGGCAGTACATATAGAGCTTTCATTATCTAT-3' (SEQ ID NO: 24) (the Cfr9I site is represented by the underline). The resulting Pfs25 DNA fragment (about 530 bp) was cloned into pENTR/D-TOPO (supplied from Invitrogen), subsequently cleaved with EcoRI/Cfr9I, which was then inserted in the EcoRI/Cfr9I sites of PbAMA1D123-gp64. The constructed plasmid was designated as pDual-Pfs25-gp64.

(10) Construction of Transfer Vector pDual-H5N1/HA1-gp64 of the Present Invention An HA1 gene is synthesized from bird influenza virus H5N1, and inserted in the EcoRI/Cfr9I sites of pDual-Hsp65-gp64 to construct the plasmid pDual-H5N1/HA1-gp64.

(11) Construction of Transfer Vector pDual-SARS/S-gp64 of the Present Invention

An S gene of SARS virus is synthesized and inserted in the EcoRI/Cfr9I sites of pDual-Hsp65-gp64 to construct the plasmid pDual-SARS/S-gp64.

(12) Construction of Transfer Vector pCP-H1N1/HA1-gp64 of the Present Invention

The PCR was performed with pCR-Blunt-HA as the template using Polh-f RsrII (5'-GGGCGGACCGGATAATTAAAATGATAACCATCTCG-3': SEQ ID NO: 25) (the RsrII site is represented by the underline) and GP64-r DraIII (5'-GGGCACTTAGTGATATTGTCTATTACGGTTTCTAATC-3': SEQ ID NO: 26) (the DraIII site is represented by the underline). A resulting DNA fragment of 2700 bp was linked to a vector obtained by digesting pDual-H1N1/HA1-gp64 with the restriction enzymes RsrII and DraIII to construct pCP-H1N1/HA1-gp64.

(13) Construction of Transfer Vector pCAP-H1N1/HA1-gp64 of the Present Invention HA1 obtained by cleaving pCP-H1N1/HA1-gp64 with the restriction enzymes RsrII and DraIII and a gp64 gene fragment were inserted in the vector obtained by cleaving pTriEx-1.1 (supplied from Novagen) with the restriction enzymes RsrII and DraIII to construct a plasmid pCAP-H1N1/HA1-gp64.

(14) Construction of Transfer Vector pCU-H1N1/HA1-gp64 of the Present Invention

The PCR was performed with pTriEx3.1 as the template using CMVenh-f FseI (5'-GGGGGCCGGCCCTAGTTATTAATAGTAATCAATTAC-3': SEQ ID NO: 27) (the FseI site is represented by the underline) and CMVenh-r KpnI (5'-GGGGGTACCCATGGTAATAGCGATG ACTAATACG-3': SEQ ID NO: 28) (the KpnI site is represented by the underline) to amplify a CMV enhancer region. In addition, the PCR was performed with human genomic DNA as the template using UBBp-f KpnI (5'-GGGGGTACCTCGAGGAAGGTTTCTTCAACTC-3': SEQ ID NO: 29) (the KpnI site is represented by the underline) and UBBp-r RsrII (5'-GGGCGGTCCGGACCTAGTTTAAAAGTAAAACATAAG-3': SEQ ID NO: 30) (the RsrII site is represented by the underline) to amplify an UBB promoter region. Resulting two fragments were linked to the vector obtained by digesting pCP-H1N1/HA1-gp64 with the restriction enzymes FseI and RsrII to construct pCU-H1N1/HA1-gp64.

(15) Construction of Transfer Vector pDual-H1N1/NP-gp64 of the Present Invention The RT-PCR was performed with genomic RNA from influenza virus PR8/34 strain as the template using NP-f EcoRI (5'-ACGGAATTCCATTCAATTCAAACTGGA-3': SEQ ID NO: 31 (the EcoRI site is represented by the underline) and NP-r Cfr9I (5'-GATCCCGGGCCTTGTCAATGCTGAATGGCAA-3': SEQ ID NO: 32) (the Cfr9I site is represented by the underline). A resulting fragment was digested with the restriction enzymes EcoRI and Cfr9I, and inserted in pCP-H1N1/HA1-gp64 digested with the restriction enzymes EcoRI and Cfr9I to make pDual-H1N1/NAe-gp64.

(16) Construction of Transfer Vector pDual-H1N1/M2-gp64 of the Present Invention The RT-PCR was performed with genomic RNA from influenza virus PR8/34 strain as the template using M2-f EcoRI (5'-CGGAATTCATGAGTCTTCTAACCGAGG-3': SEQ ID NO: 33) (the EcoRI site is represented by the underline) and M2-r Cfr9I (5'-GAT CCCGGGCCTCCAGCTCTATGCTGAC-3': SEQ ID NO: 34) (the Cfr9I site is represented by the underline). A resulting fragment was digested with the restriction enzymes EcoRI and Cfr9I, and inserted in pCP-H1N1/HA1-gp64 digested with the restriction enzymes EcoRI and Cfr9I to make pDual-H1N1/M2-gp64.

(17) Construction of Transfer Vector pDual-H1N1/NAe-gp64 of the Present Invention The RT-PCR was performed with genomic RNA from influenza virus PR8/34 strain as the template using NAe-f EcoRI (5'-ACGGAATTCCATTCAATTCAAACTGGA-3': SEQ ID NO: 35) (the EcoRI site is represented by the underline) and NAe-r Cfr9I (5'-GAT CCCGGGCCTTGTCAATGCTGAATGGCAA-3': SEQ ID NO: 36) (the Cfr9I site is represented by the underline). A resulting fragment was digested with the restriction enzymes EcoRI and Cfr9I, and inserted in pCP-H1N1/HA1-gp64 digested with the restriction enzymes EcoRI and Cfr9I to make pDual-H1N1/NAe-gp64.

(18) Construction of Transfer Vector pDual-M2e-gp64 of the Present Invention

The PCR was performed with pDual-H1N1/M2-gp64 as the template using M2-f EcoRI (5'-CG GAATTCATGAGTCTTCTAACCGAGG-3': SEQ ID NO: 37) (the EcoRI site is represented by the underline) and M2e-r Cfr9I (5'-GATCCCGGGCATCACTTGAACCGTTGCA-3': SEQ ID NO: 38) (the Cfr9I site is represented by the underline). A resulting fragment was digested with the restriction enzymes EcoRI and Cfr9I, and inserted in pCP-H1N1/HA1-gp64 digested with the restriction enzymes EcoRI and Cfr9I to make pDual-M2e-gp64.

(19) Construction of Transfer Vector pCP-HA1/NC99-gp64 of the Present Invention

RNA was extracted from a frozen stock of influenza virus NewCaledonia99/20 (NC99) using QIAamp MiniElute Virus Spin Kit (QIAGEN), and the RT-PCR was performed using HA1-f EcoRI(5'-GAT GAATTCGACACAATATGTATAGGCTACC-3': SEQ ID NO:39) (the EcoRI site is represented by the underline) and HA1-r CFr9I (NC99) (5'-GAT CCCGGGCTCTGGATTGAATGGATGGGATG-3': SEQ ID NO:40) (the Cfr9I site is represented by the underline) to amplify an HA1 gene fragment. A resulting fragment and pCP-H1N1/HA1-gp64 were treated with the restriction enzymes EcoRI and Cfr9I to newly insert the HA1 gene fragment derived from NC99 in an HA1 introduction region of pCP-H1N1/HA1-gp64. A resulting plasmid was designated as pCP-HA1/NC99-64.

(20) Construction of Transfer Vector pCP-H1N1/HA0-gp64 of the Present Invention

The PCR was performed with pCR-Blunt-HA as the template using HA0-f EcoRI (5'-GGG GAATTCATGAAGGCAAACCTACTGG-3': SEQ ID NO: 41) (the EcoRI site is represented by the underline) and HA2-r Cfr9I (5'-GATCCCGGGCGATGCATATTCTGCA-3': SEQ ID NO: 42) (the Cfr9I site is represented by the underline) to amplify the full length HA gene. A resulting fragment and pCP-H1N1/HA1-gp64 were treated with the restriction enzymes EcoRI and Cfr9I to newly insert the HA0 gene fragment in the HA1 introduction region of pCP-H1N1/HA1-gp64. A resulting plasmid was designated as pCP-H1N1/HA0-gp64.

(21) Construction of Transfer Vector pCP-H1N1/HA2-gp64 of the Present Invention

The PCR was performed with pCR-Blunt-HA as the template using HA2-f EcoRI (5'-GAT GAATTCATATTTGGAGCCATTGCCG-3': SEQ ID NO: 43) (the EcoRI site is represented by the underline) and HA2-r Cfr9I (5'-GATCCCGGGCGATGCATATTCTGCA-3': SEQ ID NO: 44) (the Cfr9I site is represented by the underline) to amplify the full length HA gene. A resulting fragment and pCP-H1N1/HA1-gp64 were treated with the restriction enzymes EcoRI and Cfr9I to newly insert the HA2 gene fragment in the HA1 introduction region of pCP-H1N1/HA1-gp64. A resulting plasmid was designated as pCP-H1N1/HA2-gp64.

(22) Construction of Transfer Vector pCP-H1N1/HA1-vp39 of the Present Invention

The PCR was performed with baculovirus DNA attached to BacVector-2000 Transfection Kit (Novagen) as the template using vp39-f (5'-CTT ACTAGTATGGACTACAAGGACGACGATGACAAG GAATTCGG CGGCGGCGGCTCGGCGCTAGTGC-CCGTGGGT-3': SEQ ID NO: 45) (the SpeI site is represented by the underline and the EcoRI site is represented by the double underline) and vp39-r (5'-CTT CACTTAGTGATGGTGATGATGGTGGTGCCCGGG GCTTTAAAGCTTGACGGCTATTCCTCCACC-3': SEQ ID NO: 46) (the DraIII site is represented by the underline and the SmaI is represented by the double underline) to amplify a vp39 gene region. An amplified fragment and pDual-H1N1/HA1-gp64 were cleaved with the restriction enzymes SpeI and DraIII, and ligated one another to construct pDual-vp39. Furthermore, the PCR was performed with pDual-H1N1/HA1-gp64 as the template using Polh-S1 (5' GCTAACCAT-GTTCATGCC-3': SEQ ID NO: 47) and HA1-r EcoRI (5'-GGGGAATTCACCTCTGGATTGGAT GGAC-3': SEQ ID NO: 48) (the EcoRI site is represented by the underline). A resulting fragment was digested with EcoRI to prepare the HA1 gene. A resulting fragment was inserted in pDual-vp39 digested with EcoRI to construct pCP-H1N1/HA1-vp39.

(23) Construction of Transfer Vector pCP-H1N1/NP-vp39 of the Present Invention

The PCR was performed with pDual-H1N1/NP-gp64 as the template using NP-f 5 EcoRI (5'-ACG GAATTCATGGCGTCCCAAGGCACC-3': SEQ ID NO: 49) (the EcoRI site is represented by the underline) and NP-r EcoRI (5'-ACG GAATTCATTGTCGTACTCCTCTGCATTG-3': SEQ ID NO: 50) (the EcoRI site is represented by the underline). A resulting fragment was digested with EcoRI. A resulting fragment was inserted in pDual-vp39 digested with EcoRI to construct pCP1-H1N1/NP-vp39.

Reference Example 1

Construction of pBACgus-CMV-PbCSP (1.1) Construction of pcDNA-GL3 (luc)

pGL3-Enhancer (Promega) was cleaved with the restriction enzymes HindIII/XbaI, a luciferase gene DNA fragment (about 1690 bp) was ligated to the HindIII/XbaI sites of pcDNA3.1 (supplied from Invitrogen), and the resulting plasmid was designated as pcDNA-GL3(luc).

(1.2) Construct of pBACgus-CMV-IgHsp65 pcDNA-hsp65 obtained in the above Example 1 (1.2) was cleaved with the restriction enzymes BamHI/NotI, and inserted in the BamHI/NotI sites to produce pcDNA-Ighsp65. The resulting plasmid was designated as pcDNA-IgHsp65.

Subsequently, the pcDNA-IgHsp65 was cleaved with BglII/SphI, and a gene cassette (about 2850 bp) composed of the CMV promoter, the Hsp65 gene carrying the murine Igk signal sequence, and the poly A signal derived from the bovine growth hormone was inserted in the BglII/SphI sites of pBACgus-1 (Novagen). The constructed plasmid was designated as pBACgus-CMV-Hsp65.

(1.3) Construction of pBACgus-CMV-GL3

The plasmid pcDNA-GL3(luc) obtained above was cleaved with the restriction enzymes NheI/XbaI, the luciferase gene DNA fragment (about 1690 bp) was inserted in the NheI/XbaI sites of the plasmid pBACgus-CMV-Hsp65, and the resulting plasmid was designated as pBACgus-CMV-GL3.

(1.4) Construction of pBACgus-CMV-PbCSP

A gene fragment encoding the amino acid sequence corresponding to positions 21 to 306 of the PbCSP peptide was yielded by cleaving the plasmid pBACsurf-CSP with the restriction enzymes PstI and SmaI, the DNA fragment (about 858 bp) was inserted in the PstI and SmaI sites of pBACgus-CMV-GL3 obtained above, and the resulting plasmid was designated as pBACgus-CMV-PbCSP.

(1.5) Construction of pBACgus-CMV-HA-full pCR-Blunt-HA was cleaved with BamHI/Sse83871, and an HA gene DNA fragment (about 1750 bp) was inserted in the BamHI/PstI site of pBluescript II (KS-) to construct the plasmid pBluescript-HA.

Furthermore, the pBluescript-HA was cleaved with HindIII/XbaI, and an HA gene DNA fragment (about 1800 bp) was inserted in the HindIII/XbaI sites of pBACgus-CMV-GL3 obtained in (1.3) to construct the plasmid pBACgus-CMV-HA-full.

Example 1-2

(1) Construction of Transfer Vector Plasmids pCAP-PfCSP, pCAP-PfCSP/272, and pCAP-PfCSP/467 of the Present Invention (1.1) Construction of Plasmid pBACsurf-Hsp65

An Hsp65 gene was obtained by extracting genomic DNA from M. tuberculosis H37Rv strain using a QIAamp DNA Midi Kit (Qiagen), and cloning by PCR. More specifically, the genomic DNA extracted from the M. tuberculosis H37Rv strain was amplified by PCR using primers phsp65-F1 (5'-AATAAT<u>AGATCT</u>AATGGCCAAGACAATTGCGTAC-GACGAAGA-3' (SEQ ID NO: 3); the BglII site is underlined) and phsp65-R1 (5'-AATCCAAT<u>GCGGCCGC</u>GGGAATTCGAT TCCTGCAGGTCA-GAAATCCATGCCACCCATGTCGCC-3' (SEQ ID NO: 4); the NotI site is underlined). The PCR product was purified, cleaved with restriction enzymes BglII and NotI, ligated to pcDNA3.1(+) (from Invitrogen) digested with BamHI and NotI. The resulting plasmid was designated pcDNA-hsp65. PCR was performed with pcDNA-hsp65 as a template using primers phsp65-F2 (5'-CACC <u>CCTGCAGG</u>ACTACAAGGACGACGATGACAA <u>GGAATTC</u>ATGGCCAAGAC AATTGCGTACGACGAA-GAGGCC-3' (SEQ ID NO: 5); the Sse8387I and EcoRI sites are underlined, and the FLAG sequence is italicized), and phsp65-R2 (5'-<u>CCCGGG</u>CGAAATCCATGCCA CCCAT-GTCGCCGCCACC-3' (SEQ ID NO: 6); the Cfr9I site is underlined). The resulting Hsp65 gene DNA fragment was cloned into pENTR/D-TOPO (from Invitrogen), then cleaved with Sse83871/Cfr9I and inserted into the PstI/Cfr9I site of pBACsurf-CSP (Yoshida et al., Virology 316: 161-70, 2003). The plasmid thus constructed was designed pBACsurf-Hsp65.

(1.2) Construction of Plasmid pENTR-gp64

PCR was performed with pBACsurf-1 (from Novagen) as a template using primers pPolh-F2 (5'-CACC <u>CGGACCGG</u>ATAATTAAAATGATAACCATCTCGCAA-ATAAATAAG-3' (SEQ ID NO: 7); the RsrII site is underlined), and pgp64-R2 (5'-<u>GGTACC</u>ATATTGTCTATTACGGTTTCTAATCATAC-3' (SEQ ID NO: 8); the KpnI site is underlined). The resulting gp64 gene DNA fragment was inserted into pENTR/D-TOPO to construct a plasmid pENTR-gp64. The plasmid thus constructed was designated pENTR-gp64.

(1.3) Construction of Transfer Vector pDual-Hsp65-gp64 of the Present Invention pBACsurf-Hsp65 was cleaved with PstI/Cfr9I, and the hsp65 gene DNA fragment was inserted into the PstI/Cfr9I site of pENTR-gp64 to construct a plasmid pENTR-Hsp65-gp64. The pENTR-Hsp65-gp64 was cleaved with RsrII/KpnI, and a DNA fragment consisting of a polyhedrin promoter and hsp65-gp64 gene was inserted into pTriEx-3.1 (Novagen) cleaved with RsrII and KpnI to construct a transfer vector plasmid pDual-Hsp65-gp64 enabling the expression of a fusion protein of Hsp65 antigen and gp64 protein in mammalian and insect cells under the control of the desired dual promoter consisting of CMA promoter and polyhedrin promoter.

(1.4) Construction of Transfer Vector pDual-H1N1/HA1-gp64 of the Present Invention RNA was extracted from a culture supernatant of MDCK cells infected with influenza virus PR/8/34 strain using a QIAamp MinElute Virus Spin Kit (from Qiagen), and amplified by RT-PCR using primers HA-f (5'-<u>CCTGCAGG</u>TATGAAGGCAAACCTACTGGTC-3' (SEQ ID NO: 9); the SbfI site is underlined) and HA-r (5'-G<u>CCCGGG</u>CGATGCATATTCTGCA-3' (SEQ ID NO: 10); the SbfI site is underlined). The resulting influenza virus HA gene fragment was cloned into pCR-Blunt II-TOPO (from Invitrogen). The resulting plasmid was designated as pCR-Blunt-HA. PCR was performed with the pCR-Blunt-HA as a template using primers pHA-F1 (5'-CACC <u>GAATTC</u>GACACAATATGTATAGGCTACCATGCG-3' (SEQ ID NO: 11); the EcoRI site is underlined) and pHA-R1 (5'-<u>CCCGGG</u>CACCTCTGGATTGGATGGACGGAATG-3' (SEQ ID NO: 12); the Cfr9I site is underlined). The resulting H1N1/HA1 gene DNA fragment was cloned into pENTR/D-TOPO, then cleaved with EcoRI/Cfr9I and inserted into the EcoRI/Cfr9I site of pDual-Hsp65-gp64 to construct a plasmid pDual-H1N1/HA1-gp64.

(1.5) Construction of Plasmid pBACsurf-HA1 pDual-H1N1/HA1-gp64 was cleaved with EcoRI/CfrI, and the DNA fragment of H1N1/HA1 gene was inserted into pBACsurf-Hsp65 digested with EcoRI and CfrI to construct a plasmid pBACsurf-HA1.

(1.6) Construction of Plasmid pCP-H1N1/HA1-64

PCR was performed with pBACsurf-HA1 as a template using Polh-f RsrII (5'-GGG <u>CGGACCGG</u>ATAATTAAAATGATAACCATCTCG-3' (SEQ ID NO: 25); the RsrII site is underlined) and GP64-r DraIII (5'-GGG<u>CACTTAGTGA</u>TATTGT CTATTACG-GTTTCTAATC-3' (SEQ ID NO: 26); the DraIII site is underlined). The resulting DNA fragment was inserted into pDual-H1N1/HA1-gp64 digested with RsrII and DraIII to yield pCP-H1N1/HA1-gp64.

(1.7) Construction of Plasmid pCAP-H1N1/HA1-gp64 pCP-H1N1/HA1-gp64 was cleaved with restriction enzymes RsrII and DraIII to prepare HA1 and gp64 gene fragments. The fragments were inserted into a vector prepared by digesting pTriEx-1.1 (from Novagen) with restriction enzymes RsrII and DraIII to yield a transfer vector plasmid pCAP-H1N1/HA1-gp64 enabling the expression of a fusion protein of HA1 antigen and gp64 protein in mammalian and insect cells under the control of the desired dual promoter consisting of CAG promoter and polyhedrin promoter.

(1.8) Construction of Plasmid pCAP-H1N1/NP-64

RT-PCR was performed with genomic RNA of influenza virus PR/8/34 strain as a template using NP-f EcoRI (5'-ACG GAATTCCATTCAATTCAAACTGGA-3' (SEQ ID NO: 31); the EcoRI site is underlined) and NP-r Cfr9I (5'-GAT CCCGGGCCTTGTCAATGCTGAATGGCAA-3' (SEQ ID NO: 32); the Cfr9I site is underlined). The obtained fragments were digested with restriction enzymes EcoRI and Cfr9I, and inserted into pCAP-H1N1/HA1-gp64 digested with restriction enzymes EcoRI and Cfr9I to yield pCAP-H1N1/NP-gp64.

(1.9) Construction of Plasmids pCAP-H1N1/NP/272 and pCAP-H1N1/NP/467

PCR was performed using gp64 (272)-f (5'-GACTC-CCCGGGTCGAGCACCGAGTCAAGAAG-3' (SEQ ID NO: 51); the XmaI site is underlined), gp64 (467)-f (5'-GACTCCCCGGGACATCACTTCCATGGCTGAA-3' (SEQ ID NO: 52); the XmaI site is underlined), and GP64-r DraIII (5'-GGG CACTTAGTGATATTGTCTATTACGGTTTCTAATC-3' (SEQ ID NO: 26); the DraIII site is underlined) of pCAP-H1N1/HA1-gp64. The obtained fragments were digested with restriction enzymes XmaI and DraIII, and inserted into pCAP-H1N1/NP-gp64 digested with XmaI and DraIII to yield pCAP-H1N1/NP/272 and pCAP-H1N1/NP/467.

(1.10) Construct of Transfer Vectors pCAP-PfCSP, cCAP-PfCSP/272 and pCAP-PfCSP/467 of the Present Invention

*P. falciparum* genomic DNA was extracted from human erythrocytes infected with *Plasmodium falciparum* 3D7 strain using a QIAamp DNA Midi Kit (from Qiagen). A PfCSP gene was cloned by PCR with this genomic DNA as a template according to the following method. The PCR was performed using primers PfCSP-f (19) (5'-GACT CTGCAGTTATTCCAGGAATACCAGTGCTATGGAAG-3' (SEQ ID NO: 53); the PstI site is underlined) and PfCSP-r (373) (5'-CGAT CCCGGGCTTTTTCCATTTTACAAATTTTTTTTTCAAT-ATC-3' (SEQ ID NO: 54); the XmaI site is underlined). The resulting DNA fragment was inserted into pCAP-H1N1/NP-gp64, pCAP-H1N1/NP/272, and pCAP-H1N1/NP/467, each digested with PstI and XmaI. The constructed plasmids were designated pCAP-PfCSP, pCAP-PfCSP/272, and pCAP-PfCSP/467.

The GenBank accession number of the amino acid sequence of the *Plasmodium falciparum* 3D7 circumporozoite (CS) protein is XP_001351122.

(2) Construction of Transfer Vector pDual-Pfs25-PfCSP-gp64 of the Present Invention (2.1) Construction of Plasmid pDual-PbAMA1D123-gp64

A blood sample was collected from a BALB/c mouse infected with malaria parasite *P. berghei* ANKA strain, and *P. berghei* genomic DNA was extracted using a QIAamp DNA Midi Kit (Qiagen). A PbAMA1 gene domain 123 (D123) was cloned by PCR with this genomic DNA as a template according to the following method. PCR was performed using primers pAMA-F1 (5'-CACCGAATTC AATCCATGG-GAAAAGTATACGGAAAAATAT-3' (SEQ ID NO: 15); the EcoRI site is underlined) and pAMA1-R1 (5'-CCCGGGCTTCTCTGGTTTGATGGGCTTTCATATGCA-C-3' (SEQ ID NO: 16); the Cfr9I site is underlined). The resulting PbAMA1D123 DNA fragment was cloned into pENTR/D-TOPO, then cleaved with EcoRI/Cfr9I and inserted into pBACsurf-Hsp65 digested with EcoRI and Cfr9I. The constructed plasmid was designated pBACsurf-PbAMA1D123.

Subsequently, the pBACsurf-PbAMA1D123 was cleaved with EcoRI/Cfr9I, and the PbAMA1D123 gene DNA fragment was inserted into pDual-Hsp65-gp64 digested with EcoRI and Cfr9I to yield a plasmid pDual-PbAMA1D123-gp64.

(2.2) Construction of Plasmid pDual-PfCSP-gp64

A PfCSP gene was cloned by PCR with *P. falciparum* genomic DNA as a template according to the following method. The PCR was performed using primers pPfCSP-F1 (5'-CACCGAATTCTTATTCCAGGAATACCAGT GCTATGGAAGT-3' (SEQ ID NO: 19); the EcoRI site is underlined) and pPfCSP-R1 (5'-CCCGGGCTTTTTCCATTTTACAAA TTTTTTTTTC-3' (SEQ ID NO: 20); the Cfr9I site is underlined). The resulting PfCSP DNA fragment was cloned into pENTR/D-TOPO, then cleaved with EcoRI/Cfr9I and inserted into pDual-PbAMA1D123-gp64 digested with EcoRI and Cfr9I. The constructed plasmid was designated pDual-PfCSP-gp64.

(2.3) Construction of Transfer Vector pDual-Pfs25-PfCSP-gp64 of the Present Invention A Pfs25 gene was cloned by PCR with *P. falciparum* genomic DNA as a template according to the following method. The PCR was performed using primers pPfs25-F1 (5'-CACCGAATTCAAAGTTACCGTGGATACTGTA TGCAAAAGAGGA-3' (SEQ ID NO: 23); the EcoRI site is underlined) and pPfs25-R2 (5'-CAATTGAGATCCGCCGC-CACCGCCACCAGTACATATA-GAGCTTTCATTATCTATTATAAATCCAT C-3' (SEQ ID NO: 55); the MunI site is underlined). The resulting Pfs25 DNA fragment was cloned into pENTR/D-TOPO, then cleaved with EcoRI/MunI, and inserted into pDual-PfCSP-gp64 digested with EcoRI. The constructed plasmid was designated pDual-Pfs25-PfCSP-gp64.

(3) Construction of Transfer Plasmid pDual-PfMSP1-PfCSP-gp64 of the Present Invention A PfMSP1 gene was cloned by PCR with *P. falciparum* genomic DNA as a template according to the following method. The PCR was performed using primers pPfMSP119-F1 (5'-CACCGAATTCAACATTTCACAACAC CAAT-GCGTAAAAAAAC-3': (SEQ ID NO: 56); the EcoRI site is underlined) and pPfMSP119-R2 (5'-CAATTGAGATCCGCCGCCACCGCCACCGTTAGAGG-AACTGCAGAAAATACCATCGAAAAGTGGA-3' (SEQ ID NO: 57); the MunI site is underlined). The resulting PfMSP119 DNA fragment was cloned into pENTR/D-TOPO, then cleaved with EcoRI and MunI, and inserted into pDual-PbCSP-gp64 digested with EcoRI. The constructed plasmid was designated pDual-PfMSP1-PfCSP-gp64.

(4) Construction of the Transfer Vector Plasmids pCAP-PfCSP (A361E), pCAP-PfCSP(A361E)/272, and pCAP-PfCSP(A361E)/467 of the Present Invention PCR was performed with pCAP-PfCSP using PfCSP-f (19) (5'-GACTCTGCAGTTATTCCAGGAATACCAGT GCTATGGAAG-3': (SEQ ID NO: 53); the PstI site is underlined) and PfCSP-r (373 A361E) (5'-CGAT CCCGGGCTTTTTCCATTTTACAAATTTTTTTTCAAT ATCATTTTC-3': (SEQ ID NO: 58); the XmaI site is underlined). The obtained DNA fragment was cleaved with PstI and XmaI, and inserted into pCAP-H1N1/NP-gp64, pCAP-H1N1/NP/272, and pCAP-H1N1/NP/467, each digested with PstI and XmaI. The constructed plasmids were designated pCAP-PfCSP (A361E), pCAP-PfCSP (A361E)/272, and pCAP-PfCSP (A361E)/467.

(5) Construction of Transfer Plasmids pCAP-PfCSP-76 and pCAP-PfCSP-76/467 of the Present Invention PCR was performed with pCAP-PfCSP (A361E) using PfCSP-f (76) (5'-GACT CTGCAGGATGATGGAAATAACGAAGACAACG-3': (SEQ ID NO: 59); the PstI site is underlined) and PfCSP-r (373 A361E) (5'-CGATCCCGGGCTTTTTCCATTTT ACAAATTTTTTTTCAATATCATTTTC-3': (SEQ ID NO: 58); the XmaI site is underlined). The resulting DNA fragment was cleaved with PstI and XmaI, and then inserted into pCAP-H1N1/NP-gp64 and pCAP-H1N1/NP/467, each cleaved with PstI and XmaI. The constructed plasmids were designated pCAP-PfCSP-76 and pCAP-PfCSP-76/467.

(6) Construction of Transfer Plasmids pCAP-PfCSP+209 and pCAP-PfCSP+209/467

An artificial gene sequence (PfCSP+: SEQ ID NO: 60) was prepared from the amino acid sequence of PfCSP of *P. falciparum* 3D7 strain (in which, however, the A at the 361-position was replaced by E) using codons frequently used in Sf9 and human cells. Using the obtained artificial gene sequence as a template, PCR was performed using PfCSP-f (+209) (5'-GACTCTGCAGAACGCTAATCC AAACGCTAATCCCAACGCTAATCCCAATGCC-3' (SEQ ID NO: 61); the PstI site is underlined) and PfCSP-r(+A361E) (5'-CGAT CCCGGGCTTTTTCCATTTTGCAAATTTTTTT-3' (SEQ ID NO: 62); the XmaI site is underlined). The resulting DNA fragments were cleaved with PstI and XmaII, and then inserted into pCAP-H1N1/NP-gp64 and pCAP-H1N1/NP/467 digested with PstI and XmaII. The constructed plasmids were designated pCAP-PfCSP+209 and pCAP-PfCSP+209/467.

(7) Construction of Transfer Plasmids pCAP-PfCSP+76/209 and pCAP-PfCSP+76/209/467 of the Present Invention Using the artificial gene sequence (PfCSP+: SEQ ID NO: 60) as a template, PCR was performed using PfCSP-f(+76) (5'-GACT CTGCAGGACGACGGCAACAACGAAGACAACG-3' (SEQ ID NO: 63); the PstI site is underlined), PfCSP-r(+128) (5'-CGTTAGGATCCACATTTGGGTTGGCATTTGGG-3' (SEQ ID NO: 64); the BamHI site is underlined), PfCSP-f (+209) BamHI (5'-GACT GGATCCAACGCTAATCCAAACGCTAATCCC-3': (SEQ ID NO: 65); the BamH I site is underlined), and PfCSP-r(+A361E) (5'-CGAT CCCGGGCTTTTTCCATTTTGCAAATTTTTTT-3' (SEQ ID NO: 62); the XmaI site is underlined) from the obtained artificial gene sequence. The resulting DNA fragments were cleaved with PstI/BamHI and BamHI/XmaI, respectively, and then inserted into pCAP-H1N1/NP-gp64 and pCAP-H1N1/NP/467, each digested with PstI and XmaI. The constructed plasmids were designated pCAP-PfCSP+76/209 and pCAP-PfCSP+76/209/467.

(8) Construction of Transfer Plasmids pCAP-HA1/Anhui, pCAP-HA1/Anhui/272, and pCAP-HA1/Anhui/467

An artificial gene sequence (SEQ ID NO: 66) was prepared from the amino acid sequence of the hemagglutinin region of influenza virus H5N1/Anhui/1/05 using codons frequently used in Sf9 and human cells. Using the obtained artificial gene sequence as a template, PCR was performed using AH-F1 (5'-CAGTCTGCAGGACCAGATTTGCATC-3': (SEQ ID NO: 67); the PstI site is underlined) and AH-R4 (5'-CAGT CCCGGGCTCTCTTGCGCCTGC-3': (SEQ ID NO: 68); the XmaI site is underlined). The obtained DNA fragment was cleaved with PstI and XmaI, and then inserted into pCAP-H1N1/NP-gp64, pCAP-H1N1/NP/272 and pCAP-H1N1/NP/467, each digested with PstI and XmaI. The constructed plasmids were designated pCAP-HA1/Anhui, pCAP-HA1/Anhui/272, and pCAP-HA1/Anhui/467.

The GenBank accession number of the amino acid sequence of the hemagglutinin of influenza virus A/H5N1/Anhui/1/05 is ABD28180.

(9) Construction of Transfer Vector Plasmids pCAP-HA1/Vietnam, pCAP-HA1/Vietnam/51, pCAP-HA1/Vietnam/101, pCAP-HA1/Vietnam/154, pCAP-HA1/Vietnam/201, pCAP-HA1/Vietnam/272, and pCAP-HA1/Vietnam/467 of the Present Invention An artificial gene sequence (SEQ ID NO: 69) was prepared from the amino acid sequence of the HA1 region of the hemagglutinin of influenza virus H5N1/Vietnam/1203/4 using codons frequently used in Sf9 and human cells. Using the obtained artificial gene sequence as a template, PCR was performed using VN-F1 (5'-CAGT CTGCAGGACCAGATCTGTATC-3': (SEQ ID NO: 70); the PstI site is underlined), and VN-R4 (5'-CAGT CCCGGGCTCTCTTCTTCCTGC-3': (SEQ ID NO: 71); the XmaI site is underlined). The obtained DNA fragment was cleaved with PstI and XmaI, and inserted into pCAP-H1N1/NP-gp64, pCAP-H1N1/NP/272 and pCAP-H1N1/NP/467, each digested with PstI and XmaI. The constructed plasmids were designated pCAP-HA1/Vietnam, pCAP-HA1/Vietnam/272, and pCAP-HA1/Vietnam/467.

Further, using pCAP-HA1/Vietnam as a template, PCR was performed using primers gp64(51)-f (5'-GACTC CCGGGTGGAAATCACCATCGTGGAGACG-3': (SEQ ID NO: 72); the XmaI site is underlined), or gp64(101)-f (5'-GACTC CCGGGATTTGCTTATGTGGAGCATCAGG-3': (SEQ ID NO: 73); the XmaI site is underlined), or gp64(154)-f (5'-GACTC CCGGGCGCACCACACGTGCAACAAATCG-3': (SEQ ID NO: 74); the XmaI site is underlined), or gp64(201)-f (5'-GACTC CCGGGACACTGTGCTTCATCGAGACGGC-3': (SEQ ID NO: 75); the XmaI site is underlined), and GP64-r DraIII (5'-GGG CACTTAGTGATATTGTCTATTACGGTTTCTAATC-3' (SEQ ID NO: 26); the DraIII site is underlined). The obtained DNA fragments were cleaved with XmaI and DraIII, and inserted into pCAP-HA1/Vietnam digested with XmaI and DraIII. The constructed plasmids were designated pCAP-HA1/Vietnam/51, pCAP-HA1/Vietnam/101, pCAP-HA1/Vietnam/154, and pCAP-HA1/Vietnam/201.

The GenBank accession number of the amino acid sequence of the hemagglutinin of influenza virus A/H5N1/Vietnam/1203/2004 is AAW80717.

(10) Construction of Transfer Vector Plasmids pCAP-AH/345, pCAP-AH/345/467, pCAP-AH/410, pCAP-AH/410/467, pCAP-AH/473, pCAP-AH/473/467, pCAP-AH/520, pCAP-AH/520/467 of the Present Invention An artificial gene sequence (SEQ ID NO: 76) was prepared from the amino acid sequence of the HA region of the hemagglutinin of influenza virus A/H5N1/Anhui/1/05 by codon optimization using Gene Designer available from DNA2.0, Inc. Using this artificial sequence as a template, PCR was performed using AH17-F (5'-GACT CTGCAGGATCAGATCTGTATTGGGTACC-3': (SEQ ID NO: 77); the PstI site is underlined, and AH345-R (5'-CGAT CCCGGGCTCTCTTTCTCCTCCGCTCGC-3': (SEQ ID NO: 78); the XmaI site is underlined), or AH410-R (5'-CGAT CCCGGGCGGCCTCGAACTGGGTGTTCATT-3': (SEQ ID NO: 79); the XmaI site is underlined), or AH473-R (5'-CGATCCCGGGCGTCTCTGAGTTGAAGGCGCAC-3': (SEQ ID NO: 80); the XmaI site is underlined, or AH520-R (5'-CGAT CCCGGGCACCACTAATTTCCTCTCGCTTC-3': (SEQ ID NO: 81); the XmaI site is underlined). The obtained DNA fragment was cleaved with PstI and XmaI, and inserted into pCAP-HA1/Anhui or pCAP-HA1/Anhui/467 digested with PstI and XmaI. The constructed plasmids were designated pCAP-AH/345, pCAP-AH/345/467, pCAP-AH/410, pCAP-AH/410/467, pCAP-AH/473, pCAP-AH/473/467, pCAP-AH/520, and pCAP-AH/520/467.

(11) Construction of Transfer Vector Plasmids pCAP-VN/346, pCAP-VN/346/467, pCAP-VN/410, pCAP-VN/410/467, pCAP-VN/473, pCAP-VN/473/467, pCAP-VN/520, and pCAP-VN/520/467 of the Present Invention An artificial gene sequence (SEQ ID NO: 82) was prepared from the amino acid sequence of the HA region of the hemagglutinin of influenza virus A/H5N1/Vietnam/1203/2004 by codon optimization using Gene Designer available from DNA2.0, Inc. Using this artificial sequence as a template, PCR was performed using primer VN17-F (5'-GACT CTGCAGGATCAGATCTGTATCGGATATC-3': (SEQ ID NO: 83); the PstI site is underlined), and VN346-R (5'-CGAT CCCGGGCCCGCTTTTTCCTCCTCCGTTCG-3': (SEQ ID NO: 84); the XmaI site is underlined), or VN410-R (5'-CGATCCCGGGCCTCAAACTGCGTATTCATTTTG-3': (SEQ ID NO: 85); the XmaI site is underlined), or VN473-R (5'-CGAT CCCGGGCTCTAAGCTGGAGCCTGACTTTGTC-3': (SEQ ID NO: 86); the XmaI site is underlined), or VN520-R (5'-CGAT CCCGGGCACTAATCTCCTCTCTTTTAAGTC-3': (SEQ ID NO: 87); the XmaI site is underlined). The obtained DNA fragment was cleaved with PstI and XmaI, and inserted into pCAP-HA1/Anhui or pCAP-HA1/Anhui/467 digested with PstI and XmaI. The constructed plasmids were designated pCAP-VN/346, pCAP-VN/346/467, pCAP-VN/410, pCAP-VN/410/467, pCAP-VN/473, pCAP-VN/473/467, pCAP-VN/520, and pCAP-VN/520/467.

(12) Construction of Transfer Vector Plasmids pCAP-CO/full, pCAP-CO/full/467, pCAP-CO/19, pCAP-CO/19/467, pCAP-CO/76, pCAP-CO/76/467, pCAP-CO/205, and pCAP-CO/205/467 of the Present Invention An artificial gene sequence (SEQ ID NO: 88) was prepared from the amino acid sequence of the CSP of *Plasmodium falciparum* 3D7 strain by codon optimization using Gene Designer available from DNA2.0, Inc. Using this artificial sequence as a template, PCR was performed using a pair of primers consisting of PfCSP_opt-f (5'-GACT CTGCAGATGATGCGAAAATTGGCCATACTG-3': (SEQ ID NO: 89); the PstI site is underlined) and PfCSP_opt-r (397) (5'-CGATCCCGGGCATTGAGGAACAGAAA GGAAAGAACCATG-3': (SEQ ID NO: 90); the XmaI site is underlined); PfCSP_opt-f (19) (5'-GACT CTGCAGCTGTTTCAGGAATACCAGTGCTATGG-3': (SEQ ID NO: 91); (the PstI site is underlined) and PfCSP_opt-r (373) (5'-CGATCCCGGGCCTTCT CCATCTTA-CAAATTTTCTTTTCAATATCATTAGC-3': (SEQ ID NO: 92); the XmaI site is underlined); PfCSP_opt-f (76) (5'-GACTCTGCAGGACGACGGAAATAATGAGG ACAACG-3': (SEQ ID NO: 93); the PstI site is underlined) and PfCSP_opt-r (373) (5'-CGAT CCCGGGCCTTCTCCATCTTACAAATTTTCTTTTCAA-TATCATTAGC-3': (SEQ ID NO: 92); the XmaI site is underlined); and PfCSP_opt-f (205) (5'-GACT CTGCAGAATGCAAACCCAAATGCCAATCCAAACGC-3': (SEQ ID NO: 94); the PstI site is underlined) and PfCSP_opt-r (373) (5'-CGATCCCGGG CCTTCTCCATCTTA-CAAATTTTCTTTTCAATATCATTAGC-3': (SEQ ID NO: 92); the XmaI site is underlined). The obtained DNA fragments were cleaved with PstI and XmaI, and inserted into pCAP-HA1/Anhui or pCAP-HA1/Anhui/467 digested with PstI and XmaI. The constructed plasmids were designated pCAP-CO/full, pCAP-CO/full/467, pCAP-CO/19, pCAP-CO/19/467, pCAP-CO/76, pCAP-CO/76/467, pCAP-CO/205, and pCAP-CO/205/467.

(13) Construction of Transfer Vector Plasmids pCA64-HA1/Anhui and pCA64-PfCSP (A361E) of the Present Invention Using the Triple Cut DNA of BacVector-2000 DNA (from Novagen), PCR was performed using gp64-p-f (5'-GACT CGGACCGGCCAGATAAAAATAATCTTATCAATTAAG-3': (SEQ ID NO: 95); the RsrII site is underlined) and gp64-p-r (5'-CGATACTAGTAGCACTGAGGCTTCT TATATAC-CCG-3': (SEQ ID NO: 96); the SpeI site is underlined). The obtained DNA fragment was cleaved with RsrII and SpeI, and inserted into pCAP-HA1/Anhui or pCAP-PfCSP (A361E) digested with RsrII and SpeI to construct transfer vector plasmids pCA64-HA1/Anhui and pCA64-PfCSP (A361E) enabling the expression of a fusion protein of HA1 antigen or PfCSP antigen and gp64 protein in mammalian and insect cells under the control of the desired dual promoter consisting of CAG promoter and gp64 promoter.

(14) Construction of Transfer Vector Plasmids pCA39-HA1/Anhui and pCA39-PfCSP (A361E) of the Present Invention Using the Triple Cut DNA of BacVector-2000 DNA (from Novagen), PCR was performed using vp39-p-f (5'-GACT CGGACCGCGTCGTACAAATCGAAATATTGTTGTG-3': (SEQ ID NO: 97); the RsrII site is underlined) and vp39-p-r (5'-CGAT ACTAGTGTGATTGAGAAAGAAATCTCTTATTC-3': (SEQ ID NO: 98); the SpeI site is underlined). The obtained DNA fragment was cleaved with RsrII and SpeI, and inserted into pCAP-HA1/Anhui or pCAP-PfCSP (A361E) digested with RsrII and SpeI to construct transfer vector plasmids pCA39-HA1/Anhui and pCA39-PfCSP (A361E) enabling the expression of a fusion protein of HA1 antigen or PfCSP antigen and gp64 protein in mammalian and insect cells under the control of the desired dual promoter consisting of CAG promoter and vp39 promoter.

(15) pCAP-CO/full/VSV, pCAP-CO/19/VSV, pCAP-CO/76/VSV, and pCAP-00/205/VSV of the Present Invention Using pVSV-G (from Clonetech) as a template, PCR was performed using VSV-G-f (5'-GACTC CCCGGGCGTTCGAACATCCTCACATTCAAG-3' (SEQ ID NO: 99); the XmaI site is underlined), VSV-G-r (5'-GACT CACTTAGTGCTTTCCAAGTCGGTTCATCTC-3': (SEQ ID NO: 100); the DraIII site is underlined). The obtained DNA fragment was inserted into pCAP-CO/full, pCAP-CO/19, pCAP-CO/76, and pCAP-CO/205, each digested with XmaI and DraIII. The constructed plasmids were designated pCAP-CO/full/VSV, pCAP-CO/19/VSV, pCAP-CO/76/VSV, and pCAP-CO/205/VSV.

Example 2

Recombinant Baculovirus and Method for Production Thereof of the Present Invention (1) The recombinant baculovirus was made using the kit (BacVector-2000 Transfection Kit supplied from Novagen) for making the recombinant baculovirus, by co-transfecting BacVector-2000 DNA with each of the transfer vectors: pDual-Hsp65-gp64, pDual-PbCSP-gp64, pDual-H1N1/HA1-gp64, pDual-PbTRAMP-gp64, pDual-PbAMA1D123-gp64, pDual-PbMSP-119-gp64, pDual-PfCSP-gp64, pDual-PfAMA1-gp64, pDual-Pfs25-gp64, pCP-H1N1/HA1-gp64, pCAP-H1N1/HA1-gp64, pCU-H1N1/HA1-gp64, pDual-H1N1/NP-gp64, pDual-H1N1/M2-gp64, pDual-H1N1/NAe-gp64, pDual-M2e-gp64, pCP-HA1/NC99-gp64, pCP-H1N1/HA0-gp64, pCP-H1N1/HA2-gp64, pCP-H1N1/HA1-vp39, pCP-H1N1/NP-vp39 constructed in the above Example 1, and the plasmids, pBACgus-CMV-PbCSP and pBACgus-CMV-HA-full obtained in Reference Example 1 into Sf-9 cells.

The recombinant baculoviruses made were designated as AcNPV-Dual-Hsp65, AcNPV-Dual-PbCSP, AcNPV-Dual-H1N1/HA1, AcNPV-Dual-PbTRAMP, AcNPV-Dual-PbAMA1D123, AcNPV-Dual-PbMSP-119, AcNPV-CMV-PbCSP, AcNPV-CMV-HA-full, AcNPV-H1N1/HA1, AcNPV-CAP-H1N1/HA1, AcNPV-CU-H1N1/HA1, AcNPV-Dual-H1N1/NP, AcNPV-Dual-H1N1/M2, AcNPV-Dual-H1N1/NAe, AcNPV-Dual-M2e, AcNPV-CP-HA1/NC99, AcNPV-CP-H1N1/HA0, AcNPV-CP-H1N1/HA2, AcNPV-CP-H1N1/HA1-vp39 and AcNPV-CP-H1N1/NP-vp39, respectively.

The Sf-9 cells were cultured so as to become $2\times10^7$ cells per 150 mm plate for culture (sumilon supplied from Akita Sumitomo Bakelite Co., Ltd.), and each baculovirus described above was infected at an infection multiplicity of about 5. After 5 to 6 days, the medium was centrifuged at 10,000×g at 4° C. for 25 minutes to collect a supernatant, which was further centrifuged using a Beckman ultracentrifuge (SW28 swing rotor) at 25,000 rpm at 4° C. for 90 minutes to yield viral particles.

(2) The recombinant baculovirus can be made using the kit (BacVector-2000 Transfection Kit supplied from Novagen) for making the recombinant baculovirus, by co-transfecting BacVector-2000 DNA with each of the transfer vectors: pDual-H5N1/HA1-gp64 and pDual-SARS/S-gp64 constructed in the above Example 1 into the Sf-9 cells. The recombinant baculoviruses to be made is designated as AcNPV-H5N1/HA1 and AcNPV-Dual-SARS/S, respectively.

The Sf-9 cells were cultured so as to become $2\times10^7$ cells per 150 mm plate for culture (sumilon supplied from Akita Sumitomo Bakelite Co., Ltd.), and each baculovirus described above was infected at an infection multiplicity of about 5. After 5 to 6 days, the medium can be centrifuged at 10,000×g at 4° C. for 25 minutes to collect the supernatant, which can be further centrifuged using the Beckman ultracentrifuge (SW28 swing rotor) at 25,000 rpm at 4° C. for 90 minutes to yield viral particles.

Example 2-2

(1) Recombinant baculoviruses were produced using a kit for producing recombinant baculoviruses (BacVector-2000 Transfection Kit from Novagen) by co-transfecting BacVector-2000 DNA with each of the following transfer vectors constructed in Example 1: pCAP-PfCSP, pCAP-PfCSP/272, pCAP-PfCSP/467, pCAP-PfCSP(A361E), pCAP-PfCSP(A361E)/272, pCAP-PfCSP(A361E)/467, pCAP-PfCSP-76, pCAP-PfCSP-76/467, pCAP-PfCSP+209, pCAP-PfCSP+209/467, pCAP-PfCSP+76/209, pCAP-PfCSP+76/209/467, pCAP-HA1/Anhui, pCAP-HA1/Anhui/272, pCAP-HA1/Anhui/467, pCAP-HA1/Vietnam, pCAP-HA1/Vietnam/51, pCAP-HA1/Vietnam/101, pCAP-HA1/Vietnam/154, pCAP-HA1/Vietnam/201, pCAP-HA1/Vietnam/272, pCAP-HA1/Vietnam/467, pCAP-AH/345, pCAP-AH/345/467, pCAP-AH/410, pCAP-AH/410/467, pCAP-AH/473, pCAP-AH/473/467, pCAP-AH/520, pCAP-AH/520/467, pCAP-VN/346, pCAP-VN/346/467, pCAP-VN/410, pCAP-VN/410/467, pCAP-VN/473, pCAP-VN/473/467, pCAP-VN/520, pCAP-VN/520/467, pCAP-CO/full, pCAP-CO/full/467, pCAP-CO/19, pCAP-CO/19/467, pCAP-CO/76, pCAP-CO/76/467, pCAP-CO/205, pCAP-CO/205/467, pCA39-HA1/Anhui, pCA64-HA1/Anhui, pCA39-PfCSP(A361E), pCA64-PfCSP(A361E), pCAP-CO/full/VSV, pCAP-CO/19/VSV, pCAP-CO/76/VSV, pCAP-CO/205/VSV, pDual-Pfs25-PfCSP-gp64, pDual-PfMSP1-PfCSP-gp64 into Sf9 cells. The resulting recombinant baculoviruses were designated AcNPV-CAP-PfCSP, AcNPV-CAP-PfCSP/272, AcNPV-CAP-PfCSP/467, AcNPV-CAP-PfCSP(A361E), AcNPV-CAP-PfCSP(A361E)/272, AcNPV-CAP-PfCSP(A361E)/467, AcNPV-CAP-PfCSP-76, AcNPV-CAP-PfCSP-76/467, AcNPV-CAP-PfCSP+209, AcNPV-CAP-PfCSP+209/467, AcNPV-CAP-PfCSP+76/209, AcNPV-CAP-PfCSP+76/209/467, AcNPV-CAP-HA1/Anhui, AcNPV-CAP-HA1/Anhui/272, AcNPV-CAP-HA1/Anhui/467, AcNPV-CAP-HA1/Vietnam, AcNPV-CAP-HA1/Vietnam/51, AcNPV-CAP-HA1/Vietnam/101, AcNPV-CAP-HA1/Vietnam/154, AcNPV-CAP-HA1/Vietnam/201, AcNPV-CAP-HA1/Vietnam/272, AcNPV-CAP-HA1/Vietnam/467, AcNPV-CAP-AH/345, AcNPV-CAP-AH/345/467, AcNPV-CAP-AH/410, AcNPV-CAP-AH/410/467, AcNPV-CAP-AH/473, AcNPV-CAP-AH/473/467, AcNPV-CAP-AH/520, AcNPV-CAP-AH/520/467, AcNPV-CAP-VN/346, AcNPV-CAP-VN/346/467, AcNPV-CAP-VN/410, AcNPV-CAP-VN/410/467, AcNPV-CAP-VN/473, AcNPV-CAP-VN/473/467, AcNPV-CAP-VN/520, AcNPV-CAP-VN/520/467, AcNPV-CAP-CO/full, AcNPV-CAP-CO/full/467, AcNPV-CAP-CO/19, AcNPV-CAP-CO/19/467, AcNPV-CAP-CO/76, AcNPV-CAP-CO/76/467, AcNPV-CAP-CO/205, AcNPV-CAP-CO/205/467, AcNPV-CA39-HA1/Anhui, AcNPV-CA64-HA1/Anhui, AcNPV-CA39-PfCSP(A361E), AcNPV-CA64-PfCSP(A361E), AcNPV-CAP-CO/full/VSV, AcNPV-CAP-CO/19/VSV, AcNPV-CAP-CO/76/VSV, AcNPV-CAP-00/205/VSV, AcNPV-Dual-Pfs25-PfCSP-64, and AcNPV-Dual-PfMSP1-PfCSP-gp64.

Example 3

Pharmacological Effect Test of Recombinant Baculovirus of the Present Invention (Pharmacological Effect Test as Malaria Vaccine)
(Malaria Infection Prevention Test)
3. Experimental Methods
3.1 Vaccine Inoculation A recombinant virus solution for vaccine was inoculated to BALB/c female mice three times at three week intervals. In the case of injection into thigh muscle, the amount was 0.2 mL/body, and the virus solution was prepared so that the virus amount was $5 \times 10^6$ pfu/body.

3.2 Infection of Mice with Malaria

The mice in each group were anaesthetized with a anesthesia solution for mice, 3 weeks after the third vaccine inoculation, and infected with malaria by making *Anopheles stephensi* SDA 500 strain infected with *Plasmodium berghei* ANKA 2.34 clone bite the mice.

3.3 Calculation of Mouse Survival Rate in Each Group

After the infection with malaria, death cases in each group were counted, and the survival rate of the mice in each group was calculated.

3.4 For the Malaria Infection Prevention Effect of the Pharmaceutical Composition of the Present Invention as the Vaccine, the Results of the Pharmacological Effect Test are Shown in Table 1. The Survival Rate in Each Group was Shown in Right Columns in Table 1.

As shown in Table 1, all of the mice in which the erythrocytes infected with malaria in peripheral blood had been identified were died within 38 days after the infection. Among the recombinant virus in which the antigen (CSP) gene in the sporozoite phase had been inserted, in the group (group No. 4) in which the recombinant baculovirus (Example 1 (2)) containing the transfer vector: AcNPV-Dual-PbCSP) obtained in Example 2 had been inoculated intramuscularly, 100% of the infection prevention effect was observed.

In the wild type baculovirus (group No. 2), no difference from the control group (group No. 1) was observed. In the group (group No. 3) in which the recombinant baculovirus obtained in Example 2 using the mammal promoter (AcNPV-CMV-PbCSP, including the vector in Reference Example 1) had been included, the slightly higher survival rate was observed compared with the control group, suggesting the probability that the effect by the virus inoculation appeared although it was weak.

TABLE 1

Survival rates of mice in each group

| Group No. | Survival/cases | Survival rate (%) |
| --- | --- | --- |
| 1 None | 5/20 | 25 |
| 2 AcNPV-WT | 6/20 | 30 |
| 3 AcNPV-CMV-PbCSP | 5/10 | 50 |
| 4 AcNPV-Dual-PbCSP | 10/10 | 100 |

Example 4

Pharmacological Effect Test of Recombinant Baculovirus of the Present Invention (Pharmacological Effect Test as Influenza Virus Vaccine)
(Influenza Virus Infection Prevention Test)
4. Experimental Methods
4.1 Vaccine A virus solution for vaccine was inoculated twice at 2 week intervals. The vaccine virus was injected at $10^{6.5}$ PFU per mouse in thigh muscle using a syringe with 26G for insulin injection.

4.2 Preparation of Virus Solution for Challenge

On a current day of the infection with influenza virus, a stored virus solution of the influenza virus A/PR/8/34 strain was naturally thawed at room temperature. The thawed stored virus solution was diluted to 1000 $TCID_{50}$/0.05 mL for lower respiratory tract infection and 1000 $TCID_{50}$/0.005 mL for upper respiratory tract infection using Dulbecco's Phosphate Buffer Saline: (D-PBS) containing 10% sterile BSA: bovine serum albumin to make the virus solution for challenge.

4.3 Intranasal Inoculation of Virus Solution

Two weeks after the second vaccine inoculation, the mice were anesthetized by intramuscularly administering 0.05 mL of the anesthesia solution for mice. The influenza virus solution made in 4.2 was inoculated in the nose of the mice at 0.005 mL for the upper respiratory tract infection or 0.05 mL for the lower respiratory tract infection.

4.4. Sampling of Lung

Three days after the virus inoculation, 0.1 mL per mouse of the anesthesia solution for mice was intramuscularly administered to 4 mice in each group, and euthanized by bleeding from aorta abdominalis under the anesthesia. Subsequently, the mice were anatomized, and the lung was sterilely removed.

4.5 Records of Survival Rate of the Mice after the Inoculation of Influenza Virus Until 11 days after the inoculation of influenza virus, the survival rate of the mice was confirmed and recorded once a day.

4.6 Preparation of Lung Homogenate and Dilution Solution

A lung homogenate was made by adding 3 mL of 0.1% BSA, 10 mM HEPES, Minimum Essential Medium (MEM, GIBCO) containing antibiotics and homogenizing using a polytron homogenizer. The lung homogenate was dispensed in cryotubes and stored in an ultralow temperature freezer.

A series of dilution of 10 times or $10^{0.5}$ times was made using the MEM medium to which the above antibiotics and trypsin (SIGMA, T-4549, 2 mg/mL) had been added.

4.7 Preparation of Medium for Cell Growth

The medium for cell growth (MEM+10% FBS) was prepared by adding 50 mL of fetal bovine serum: FBS to 500 ml of MEM, and stored in a refrigerator until use.

4.8 Culture of MDCK (Madin-Darby Canine Kidney) Derived from Canine Kidney

The frozen and stored MDCK cells were rapidly thawed in warmed water, then suspended in 10 mL of the medium for cell growth, and the supernatant was removed by centrifugation (1000 rpm, 5 minutes, 4° C.). A cell pellet collected by centrifugation was suspended in the medium for cell growth. The cells were seeded in a culture flask, and cultured in an incubator with 5% $CO_2$ at 37° C. After the start of the culture, morphology and growth of the cells were observed under a microscope, just before the MDCK cells became confluent, the cells were washed with D-PBS (−), the treatment with trypsin was given to the cells to disperse, and the cells were suspended in the medium for cell growth. The cell suspension was seeded in the culture flask, and the fresh medium for cell growth was added to make cell passage.

4.9 Preparation of Medium for Viral Growth (Maintenance Medium)

The medium in which BSA at 0.1% had been added to 500 mL of MEM (10 mM HEPES buffer was added) was rendered the medium for virus growth (MEM+0.1% BSA), and was stored in the refrigerator after the preparation until use. The antibiotics was added in use.

4.10 Measurement of Viral Infectivity Titer (Cytopathic Effect, CPE Method)

Just before the MDCK cells in the culture flask became confluent, the treatment with trypsin was given to the cells to disperse the cells, the number of the cells was counted, and a suspension of MDCK cells at $6 \times 10^5$ cells/mL was prepared using the maintenance medium. This was dispensed by 0.05 mL in each well of a 96-well plate, and cultured overnight in the $CO_2$ incubator with 5% $CO_2$ at 37° C.

On the subsequent day, it was confirmed that the cells adhered, and each lung homogenate dilution made previously was dispensed by 0.05 mL in each well for 6 wells in the 96-well plate, which was then cultured in the $CO_2$ incubator with 5% $CO_2$ at 37° C. for 3 days.

On the 3rd day of the culture, it was confirmed that the cells in the well are denatured, then a 30% formalin-containing crystal violet solution was dispensed by 0.05 mL in each well in the 96-well plate to fix and stain the cells, and the infectivity titer of the virus in the lung was calculated by Reed-Munch method.

4.11 Effects of Each Vaccine Group on Infectivity Titer of Virus in vivo in the Mouse The infectivity titers in the murine lung homogenates in the control group (inoculated with AcNPV) and the test groups (inoculated with the recombinant baculovirus [including the transfer vector: AcNPV-Dual-H1N1/HA1 obtained in Example 1(3)] and the recombinant baculovirus [containing the vector: AcNPV-CMV-H1N1/HA full obtained in Reference Example 1]) were compared. Each viral infectivity titer was converted into logarithm. The therapeutic effect among the groups was analyzed by Tukey test (Release 8.1, SAS Institute Japan Ltd) considering its multiplicity.

The results are shown in FIG. 1.

Figure 2:
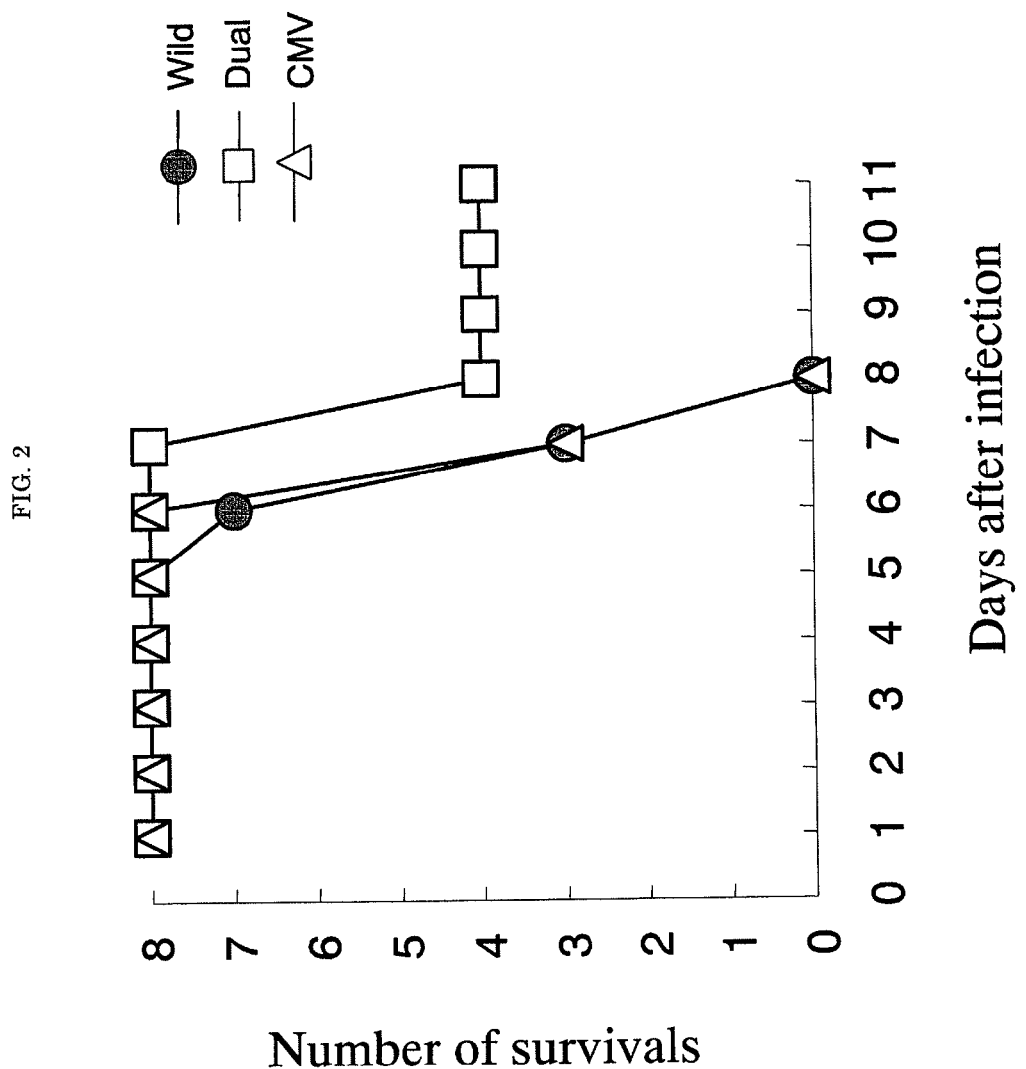
FIG. 2 is a view showing the preventive effect (survival period) of the recombinant baculovirus AcNPV-Dual-H1N1/HA1 on infection with influenza virus.

Effect of Each Vaccine on Survival Period after the Infection with Influenza Virus The survival periods in the control group (inoculated with AcNPV) and the vaccine groups (inoculated with AcNPV-Dual-H1N1/HA1 or AcNPV-CMV-H1N1/HA full) were compared using log rank test, and the results are shown in FIG. 2.

Statistical analysis was performed using SAS system (SAS Institute Japan, R.8.1). A significant level was 5%.

4.12 Infectivity Titer of Virus in Lung

In the group in which AcNPV-Dual-H1N1/HA1 had been inoculated intramuscularly, the infectivity titer of the virus in lung on the day 6 after the infection was significantly inhibited (p=0.0009) compared with the control group (inoculated with AcNPV). Meanwhile, in the group in which AcNPV-Dual-H1N1/HA1 had been inoculated intramuscularly, the infectivity titer of the virus in lung on the day 6 after the infection was significantly inhibited (p=0.0094) compared with the group in which AcNPV-CMV-H1N1/HA full had been inoculated.

4.13 Survival Period

In the group in which AcNPV-Dual-H1N1/HA1 had been inoculated intramuscularly, the survival period was significantly prolonged (p=0.0031) compared with the control group (inoculated with AcNPV). Meanwhile, the survival period in the group in which AcNPV-CMV-H1N1/HA full had been inoculated was not significantly different (p=0.7851) from that in the control group (inoculated with AcNPV). The survival period in the group in which AcNPV-Dual-H1N1/HA1 had been inoculated intramuscularly was significantly prolonged (p=0.0031) compared with the group in which AcNPV-CMV-H1N1/HA full had been inoculated.

In this evaluation system, the mouse causes influenza virus pneumonia and dies. Thus, it can be speculated that growth of the virus in lung was inhibited to reduce the death of mouse from the pneumonia by inoculating AcNPV-Dual-H1N1/HA1 intramuscularly.

Example 5

Expression Test of Vaccine Antigen from Recombinant Baculovirus of the Present Invention in Insect Cells The Sf-9 cells were cultured at $3 \times 10^6$ cells per well in a 12-well plate, and baculovirus particles of AcNPV-Dual-PbCSP, AcNPV-Dual-HSP65 or AcNPV-Dual-H1N1/HA1 obtained in Example 2 or the wild type baculovirus, AcNPV-WT as the control were infected at infection multiplicity of about 5. After 3 to 4 days, the culture supernatant was removed, the plate was rinsed three times with PBS, and then 0.2 mL per well of Leamuli solution (Tris-hydrochloride pH 6.8, 2% SDS, 10% glycerol, 0.1% bromophenol blue) containing 2% 2-mercaptoethanol was added to completely lyse the cells. The sample was boiled at 95° C. for 5 minutes, and electrophoresed on SDS-PAGE. After the electrophoresis, the protein was transferred onto a PVDF membrane (Immobilon-P supplied from Millipore) and blocking was performed by immersing the membrane in block ace (supplied from Dai Nippon Pharmaceutical Co., Ltd.) at 4° C. for 12 hours. Western blotting was performed by the following procedure. The membrane to which the proteins from the Sf-9 cells infected with each baculovirus had been transferred was incubated with a mouse anti-FLAG monoclonal antibody (supplied from Sigma) as the primary antibody, and then incubated with a biotin-labeled goat anti-mouse IgG (H+ L) antibody as the second antibody (supplied from Vector). Further, an avidin labeled alkaline phosphatase (supplied from GIBCO-BRL) was added and a color was developed with NBT/BCIP (supplied from GIBCO-BRL) to detect bands of the protein.

Figure 3:
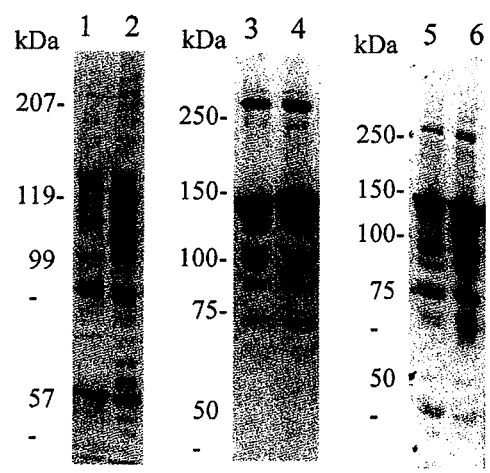
FIG. 3 is views showing Western blotting analysis of expression of a fusion product in infected insect cell by recombinant baculovirus the influenza virus HA gene (H1N1/HA1), the *M. tuberculosis* Hsp65 gene (Hsp65) or the malaria parasite CSP gene (PbCSP) produced from the transfer vector.
Lane 1: AcNPV-WT
Lane 2: AcNPV-Dual-H1N1/HA1
Lane 3: AcNPV-WT
Lane 4: AcNPV-Dual-Hsp65
Lane 5: AcNPV-WT
Lane 6: AcNPV-Dual-PbCSP.

The results are shown in FIG. 3.

FIG. 3 shows Western blotting analysis showing the expression of the fusion antigen of the influenza virus HA gene, the M. tuberculosis Hsp65 gene and the malaria parasite CSP gene from the recombinant transfer vector in the recombinant baculovirus in the insect cells. In the figure, the lane 1 shows the bands from the wild type baculovirus (AcNPV-WT), the lane 2 shows bands from the recombinant baculovirus (AcNPV-Dual-H1N1/HA1) in which the influenza virus HA gene was inserted under the dual promoters of the present invention, the lane 3 shows the bands from the wild type baculovirus (AcNPV-WT), the lane 4 shows the bands from the recombinant baculovirus (AcNPV-Dual-Hsp65) in which the M. tuberculosis Hsp65 gene was inserted under the dual promoters of the present invention, the lane 5 shows the bands from the wild type baculovirus (AcNPV-WT), and the lane 6 shows the bands from the recombinant baculovirus (AcNPV-Dual-PbCSP) in which the malaria parasite CSP gene was inserted under the dual promoters of the present invention.

As shown in the lanes 2, 4 and 6 in the figure, the band corresponding to the expressed fusion product of the immunogenic foreign antigen gene and the gp64 gene is observed in the recombinant baculovirus in which each antigen gene and the gp64 gene were fused and expressed under the dual promoters of the present invention.

From this, it has been identified that the immunogenic foreign antigen gene and the gp64 gene can be fused and expressed in the insect cells.

Example 6

Expression Test of Vaccine Antigen from Recombinant Baculovirus of the Present Invention in Mammal HepG2 cells were infected with AcNPV-Dual-Hsp65, or AcNPV-WT as the control at an infection multiplicity of about 1. After 24 hours, the culture supernatant was removed, the plate was rinsed three times with PBS, and then an acetone ethanol solution (7:3) cooled at −20° C. was added to fix the cells at −20° C. for 5 minutes. The blocking was performed at room temperature by adding 5% normal goat serum (supplied from Sigma). Subsequently, a mouse anti-Hsp65 antibody (Yoshida et al., Vaccine 2005) as the primary antibody and then the FITC-labeled goat anti-mouse IgG (H+L) were added and incubated. The reacted cells were detected under a fluorescence microscope.

HepG2 cells were also cultured $1 \times 10^7$ cells per 100 mm plate for cell culture, and infected with the baculovirus particles, AcNPV-Dual-H1N1/HA1 or AcNPV-CMV-H1N1/HA full or AcNPV-WT as the control at an infection multiplicity of about 5. After 2 hours, the culture supernatant was removed, the plate was rinsed three times with PBS, and then the cells were cultured in the medium not containing methionine and cysteine (medium in which 10% FBS dialyzed against PBS was added to Dulbecco's Modified Eagle medium (Invitrogen)) for 3 hours. An isotope-labeled methionine and cysteine solution (TRANS35S-LABEL MP Biomedicals, Inc.) was added at a final concentration 5 µCi/mL. After 12 hours, the culture supernatant was removed, the plate was rinsed three times with PBS, and then the cells were lysed with 0.5 mL of RIPA buffer (1% Sodium deoxycholate, 1% Triton X-100, 0.1% SDS, 10 mM Tris-HCl[pH 7.5]) to make a sample. The sample was added to Protein A-Sepharose CL-4B (Pharmacia) carrier to which the serum from the mouse infected with influenza virus had been absorbed in advance, and incubated on ice for 2 hours. The carrier was washed 5 times with RIPA buffer, Leamuli solution containing 2% 2-mercaptoethanol was added, the sample was boiled at 95° C. for 5 minutes, and electrophoresed on 6% SDS-PAGE. After the electrophoresis, the gel was dried, and the protein reacted with the antibody was detected by autoradiography.

Figure 4:
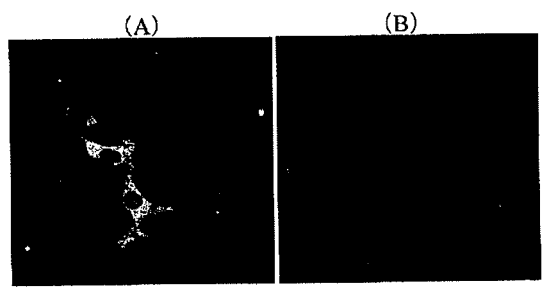
FIG. 4 is a view of fluorescence labeled staining where recombinant baculovirus produced from recombinant transfer vector in vertebrate cells has expressed a fusion product of tuberculosis HSP65 gene and the gp64 gene.
(A): HepG2 cells transduced with AcNPV-Dual-Hsp65;
(B): HepG2 cells transduced with AcNPV-WT.
Figure 5:
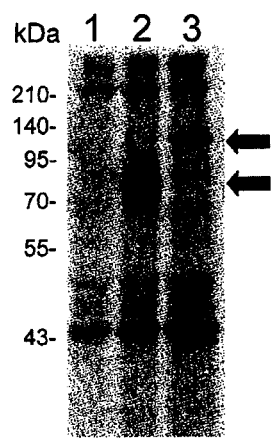
FIG. 5 is a view identifying by immunoprecipitation that the recombinant baculovirus produced from the recombinant transfer vector in the mammalian animal cells has expressed a fusion protein encoded by an influenza virus HA antigen gene and the gp64 gene. Immunoprecipitation of HepG2 cells introduced with recombinant baculoviruses. HepG2 cells were transduced with AcNPV-WT (lane 1), AcNPV-CMV-HA full (lane 2) or AcNPV-Dual-HA1N (lane 3). At 3 h after transduction, cells were radiolabeled with [$^{35}$S]methionine for 12 h. Cell lysates were immunoprecipitated with serum from mice infected with H1N1 influenza virus.

The results are shown in FIGS. 4 and 5.

FIG. 4 (A) shows the cells stained with the fluorescence labeled antibody showing the expression of the *M. tuberculosis* Hsp65 gene in the recombinant baculovirus in HepG2 cells.

FIG. 4 (B) shows the case in which the wild type baculovirus was added to HepG2 cells.

As is evident from (A) in the figure, it is found that the recombinant baculovirus using the transfer vector with the dual promoters of the present invention can express the objective antigen in the mammalian cells.

This suggests that when administered to the mammal including human beings, the recombinant baculovirus produced from the recombinant transfer vector of the present invention invades into the mammalian cells, the mammalian promoter is operated, and the objective foreign antigen gene and the gp64 gene are fused in the mammalian cells to induce the acquired immunity.

FIG. 5 shows immunoprecipitation analysis of the expression of the fusion antigen in the recombinant baculovirus in which the influenza virus HA antigen gene was incorporated under the dual promoters in the mammalian cells. In the figure, the lane 1 shows the wild type baculovirus (AcNPV-WT), the lane 2 shows the recombinant baculovirus (AcNPV-CMV-H1N1/HA full) in which the influenza virus HA antigen gene was incorporated under the CMV promoter, and the lane 3 shows the recombinant baculovirus (AcNPV-Dual-H1N1/HA1) in which the influenza virus HA antigen gene was incorporated to fuse with the gp64 gene and express under the dual promoter.

In the recombinant baculovirus (AcNPV-CMV-H1N1/HA full) in which the influenza virus HA antigen gene was incorporated under the CMV promoter and the recombinant baculovirus (AcNPV-Dual-H1N1/HA1) in which the influenza virus HA antigen gene was incorporated to fuse with the gp64 gene and express under the dual promoters, it is evident that the protein which specifically reacts with the serum infected with influenza virus, i.e., the protein including the HA antigen was newly synthesized in HepG2 cells.

From this, it is thought that the recombinant baculovirus of the present invention expresses the antigen protein encoded by the desired immunogenic foreign antigen gene even in the mammalian cells, and that when the recombinant virus is administered to the mammals including human beings, with the expression of the fusion antigen in human cells, the acquired immunity specific for the antigen can be induced.

Example 7

Identification Test of Fusion Antigen in Vaccine Antigen Presented on Viral Particle (Virion) of Recombinant Baculovirus of the Present Invention To 0.005 mL of each virus concentration solution of the baculovirus particles, AcNPV-WT, AcNPV-CMV-PbCSP, AcNPV-PbCSPsurf or AcNPV-Dual-PbCSP collected by ultracentrifuge, 0.005 mL of Leamuli solution (2×) was added, which was then boiled at 95° C. for 5 minutes, and electrophoresed on 6% SDS-PAGE. After the electrophoresis, the proteins were transferred onto the PVDF membrane (Immobilon-P supplied from Millipore) and blocking was performed by immersing the membrane in block ace (supplied from Dai Nippon Pharmaceutical Co., Ltd.) at 4° C. for 12 hours. The Western blotting was performed by the following procedure. The membrane to which the viral particle proteins had been transferred was incubated with the mouse anti-FLAG monoclonal antibody (supplied from Sigma) as the primary antibody, and then incubated with the biotin-labeled goat anti-mouse IgG (H+L) antibody as the second antibody (supplied from Vector). Further, avidin-labeled alkaline phosphatase (supplied from GIBCO-BRL) was added and the color was developed with NBT/BCIP (supplied from GIBCO-BRL) to detect bands of the protein.

Figure 6:
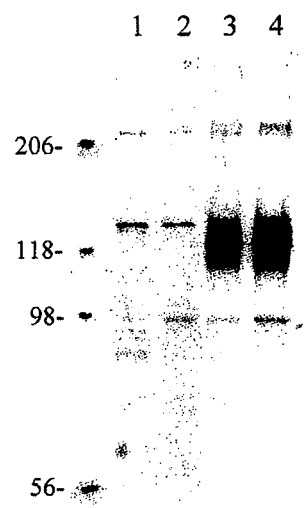
FIG. 6 is a view of Western blotting analysis showing fusion expression of a malaria parasite CSP gene and the gp64 gene in viral particles of the recombinant baculovirus produced from the recombinant transfer vector in insect cells.
Lane 1: AcNPV-WT
Lane 2: AcNPV-CMV-PbCSP
Lane 3: AcNPV-PbCSPsurf
Lane 4: AcNPV-Dual-PbCSP.

The results are shown in FIG. 6.

FIG. 6 shows the Western blotting analysis showing the expression of the malaria CSP gene (PbCSP) in the viral particles of the recombinant baculovirus made from the recombinant transfer vector. In the figure, the lane 1 shows the wild type baculovirus, the lane 2 shows the recombinant baculovirus made from the transfer vector in which the PbCSP antigen gene was inserted under the control of the mammalian promoter, the lane 3 shows the recombinant baculovirus made from the transfer vector in which the PbCSP antigen gene was inserted to fuse with the gp64 gene and express under the control of the baculovirus polyhedrin promoter, and the lane 4 shows the recombinant baculovirus made from the transfer vector in which the PbCSP antigen gene was inserted to fuse with the gp64 gene and express under the control of the dual promoters. The baculoviruses were electrophoresed and the expression product of the fused PbCSP gene and gp64 gene was identified.

As shown in the lanes 3 and 4, for AcNPV-PbCSPsurf and AcNPV-Dual-PbCSP, the strong band which indicated the presence of the fusion antigen was identified in the recombinant viral particles.

This way, from Example 7, it is found that in the recombinant baculovirus produced from the recombinant transfer vector of the present invention, the expression product of the fused gp64 gene to the desired immunogenic foreign gene can be present in the recombinant viral particles.

Example 8

Sustained Gene Expression by Exchange of Promoter

1) Sustained Gene Expression by Exchange of Promoter

In order to identify whether the recombinant virus sustains the antigen expression in cultured cells, HeLa cells were infected with AcNPV-CP-H1N1/HA1, AcNPV-CAP-H1N1/HA1 or AcNPV-CU-H1N1/HA1, and the antigen expression was identified. The cells were seeded in a 24-well plate at $1.0 \times 10^4$ cells/well, and then infected with the virus at MOI=10, 20, 100, which was adhered for one hour. Subsequently the virus was removed from a cell culture supernatant, and the cells were cultured in an incubator. The cells were collected with time, and RNA was extracted. RT-PCR was performed with the extracted RNA as the template using the primer HA1_F01 (5'-GAGCTGAGGGAGCAATTGAG-3' (sequence: SEQ ID NO: 101) and the primer HA1_R01 (5'-GGGTGATGAATACCCCACAG-3' (sequence: SEQ ID NO:102). The amplified DNA was analyzed on electrophoresis.

As a result, the expression was identified in all three types, confirming that the CMV promoter can be converted to another eukaryotic promoter with respect to the recombinant baculovirus of the present invention.

Figure 7:
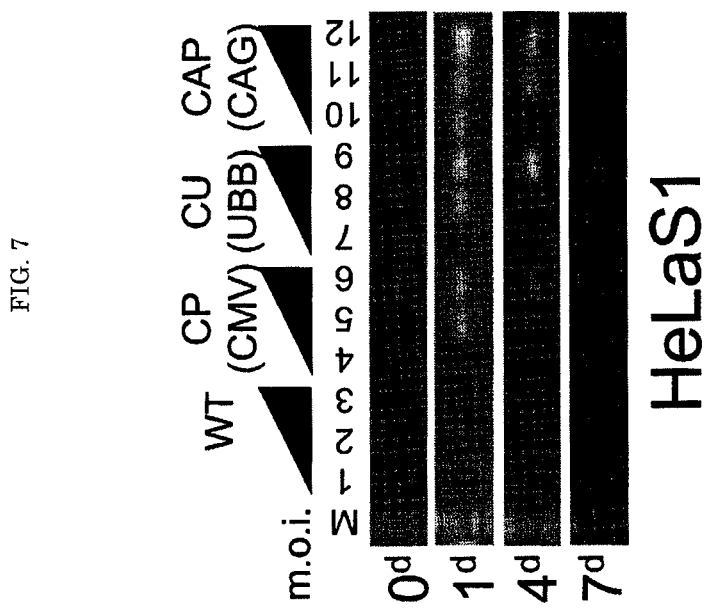
FIG. 7 is a view showing results of RT-PCT identifying that an HA1 antigen recombinant baculovirus obtained by exchanging a vertebrate promoter has expressed a fusion product of HA1 and gp64 in HeLa cells.

FIG. 7 shows the results of detecting the gene expression in HeLa cells by RT-PCR. M represents DNA markers for electrophoresis. Samples are as follows:
1. RNA from cells infected with wild type virus at MOI=10;
2. RNA from cells infected with wild type virus at MOI=20;
3. RNA from cells infected with wild type virus at MOI=100;
4. RNA from cells infected with AcNPV-CP-H1N1/HA1 at MOI=10;
5. RNA from cells infected with AcNPV-CP-H1N1/HA1 at MOI=20;
6. RNA from cells infected with AcNPV-CP-H1N1/HA1 at MOI=100;
7. RNA from cells infected with AcNPV-CU-H1N1/HA1 at MOI=10;
8. RNA from cells infected with AcNPV-CU-H1N1/HA1 at MOI=20;
9. RNA from cells infected with AcNPV-CU-H1N1/HA1 at MOI=100;
10. RNA from cells infected with AcNPV-CAP-H1N1/HA1 at MOI=10;
11. RNA from cells infected with AcNPV-CAP-H1N1/HA1 at MOI=20; and
12. RNA from cells infected with AcNPV-CAP-H1N1/HA1 at MOI=100. The sample was collected with time 0 hour, one day, 4 days and 7 days after the infection, was amplified by RT-PCR, and amplified DNA was electrophoresed.

Example 9

Antibody Titer and Cellular Immunity Induced by PbCSP Antigen Recombinant Virus 1. Vaccine Inoculation A solution of the recombinant virus for vaccination was inoculated to BALB/c female mice three times at three week intervals. An inoculated dose was prepared at 0.2 mL/body corresponding to $1 \times 10^8$ pfu/body of a virus amount for intramuscular injection at a thigh muscle. The wild type virus (AcNPV-WT), AcNPV-PbCSPsurf (Yoshida et al. Virology 316: 161-70, 2003) or AcNPV-Dual-PbCSP was injected as the vaccine.

2. Anatomy of Mice

The mouse was euthanized three weeks after the last immunization, and serum and spleen were removed from the mouse. The serum was used for measuring the specific antibody titer and the spleen was used for ELISPOT assay.

3. Measurement of Antibody Titers

The antibody titer was measured by ELISA using a plate on which a PbCSP recombinant protein forcibly expressed in *Escherichia coli* and purified/recovered had been immobilized. The ELISA was performed according to the standard methods. As a result, although no increase of the antibody titer was identified in groups in which no virus had been inoculated or the wild type virus had been inoculated, the increase of the specific antibody titer could be identified in the group in which AcNPV-PbCSPsurf had been inoculated and the group in which AcNPV-Dual-PbCSP had been inoculated.

Figure 8:
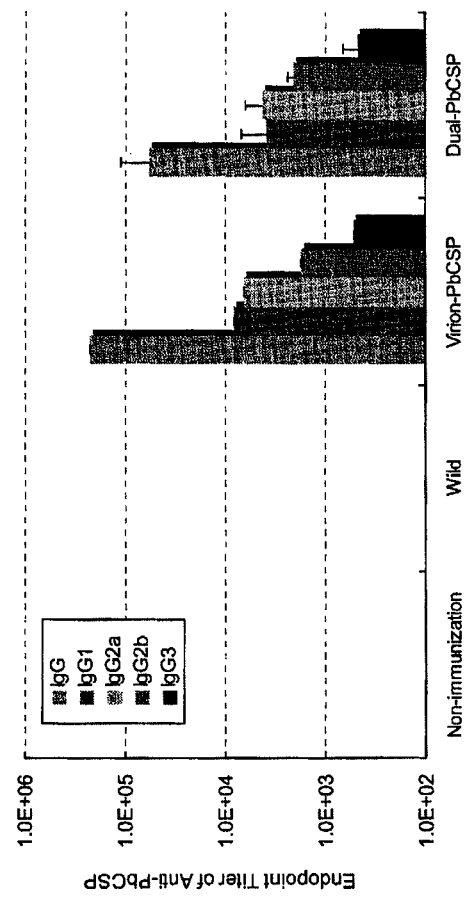
FIG. 8 is a view showing production of IgG antibody specific for a PbCSP antigen in sera from mice inoculated with the recombinant baculovirus.

In FIG. 8, IgG antibody titers specific for PbCSP in the non-inoculation group, the wild type virus inoculation group, the AcNPV-PbCSPsurf inoculation group and the AcNPV-Dual-PbCSP inoculation group are shown.

4. Evaluation of Cellular Immunity Using ELISPOT Assay

ELISPOT assay was performed using spleen cells from immunized mice. The spleen cells from the mouse were prepared and an appropriate number of the cells were added to MultiScreen-IP (Millipore). A peptide (amino acid sequence: SYIPSAEKI SEQ ID NO: 103) known as a CD 8 epitope of PbCSP was added thereto, which was then cultured overnight. Subsequently the reaction was performed using ELISPOT Mouse IFN-γ ELISPOT Set (BD Sciences), and a color was developed using AEC substrate set (BD Sciences). The cell number which had responded specifically for the antigen was identified by measuring colored spots. As a result, no antigen specific cell could be identified in the group in which no virus, the wild type virus or AcNPV-PbCSPsurf had been inoculated, but about 350 reacted cells per $10^6$ spleen cells were identified in the group in which AcNPV-Dual-PbCSP had been inoculated. This has demonstrated that AcNPV-Dual-PbCSP can more significantly induce the cellular immunity than AcNPV-PbCSPsurf.

Figure 9:
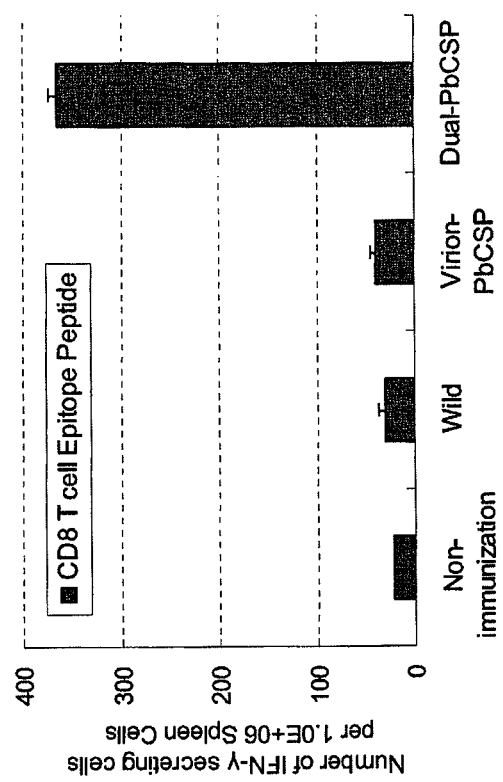
FIG. 9 is a view showing numbers of IFN-producing cells reactive to a CTL epitope of PbCSP in spleen cells from mice inoculated with the recombinant baculovirus.

In FIG. 9, the numbers of IFN-γ-producing cells specific for the CTL epitope of PbCSP in the non-inoculation group, the wild type virus inoculation group, the AcNPV-PbCSPsurf inoculation group and the AcNPV-Dual-PbCSP inoculation group are shown.

Example 10

Test for Confirming Anti-virus Effects of Vaccine Comprising a Recombinant Baculovirus as an Active Ingredient (Test for Confirming Effects of M2e Recombinant Baculovirus)

The M2e recombinant baculovirus (AcNPV-Dual-M2e) in an amount of $3.4 \times 10^8$ PFU per mouse was inoculated in thigh muscle twice at two week interval. The mice were infected with influenza virus A/PR8/34 by inoculating 0.005 mL of solution containing 1000 $TCID_{50}$ of the virus intranasally two weeks after the final vaccine inoculation. On 6 days after the infection, the mice were euthanized, the lung was removed, and the amount of virus in the lung was detected using MDCK cells. As a result, no influenza virus could be detected in all mice inoculated with AcNPV-Dual-M2e. At the same time, this was the same effect as in the group in which the HA1 recombinant baculovirus vaccine (AcNPV-Dual-H1N1/HA1) (1.0×10⁷ PFU per mouse) had been inoculated in the thigh muscle.

Figure 10:
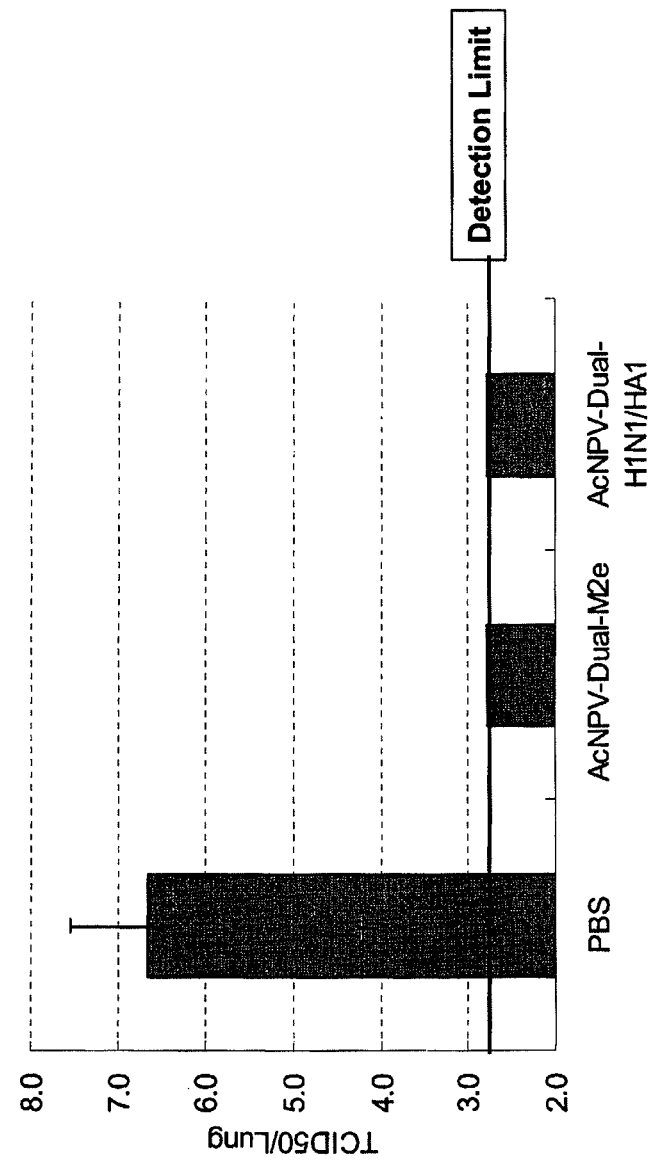
FIG. 10 is a view showing preventive effects (virus infectivity titer) by the recombinant baculovirus AcNPV-Dual-M2e on infection with influenza virus.
Figure 11:
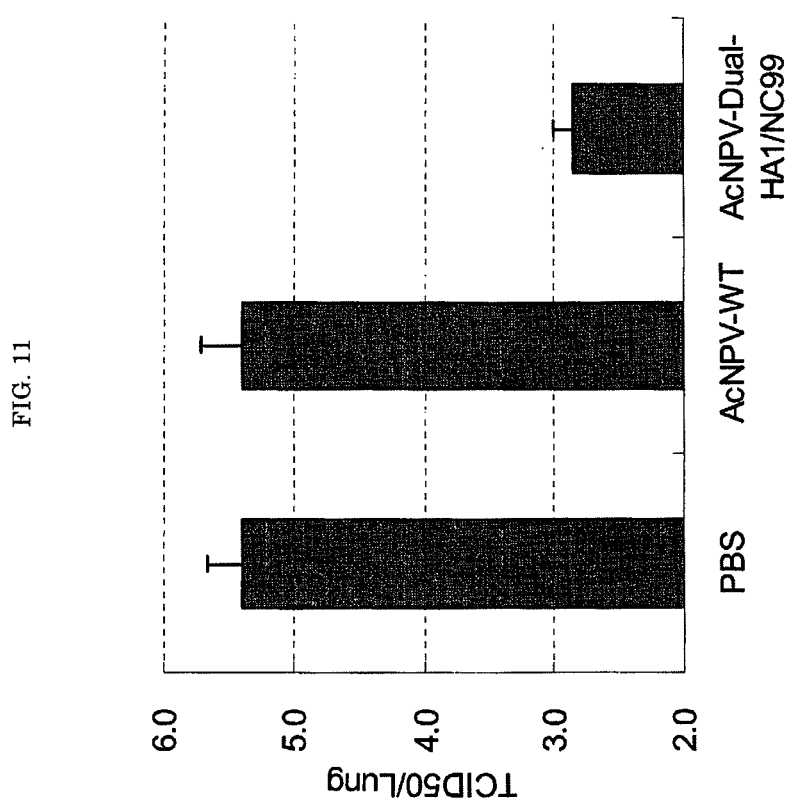
FIG. 11 is a view showing preventive effects (virus infectivity titer) by recombinant baculovirus AcNPV-Dual-HA1/NC99 on infection with influenza virus.
Figure 12:
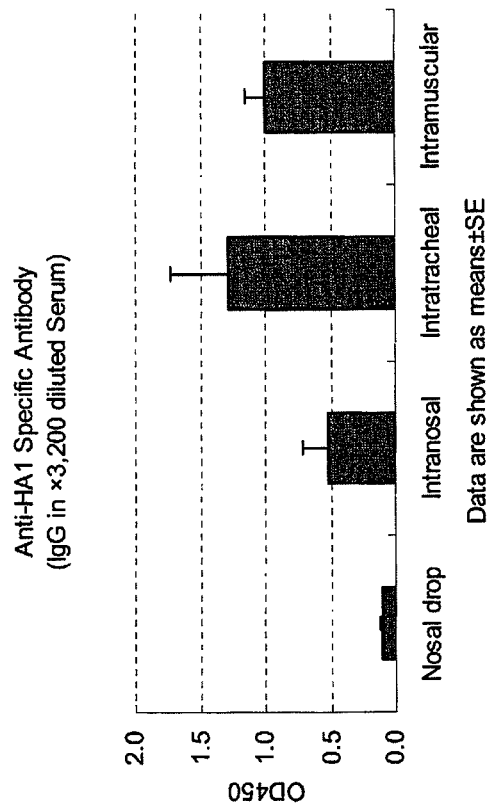
FIG. 12 is a view showing the production of IgG antibody specific for influenza virus in blood, induced by the recombinant baculovirus AcNPV-Dual-H1N1/HA1 administered via different four routes.
Figure 13:
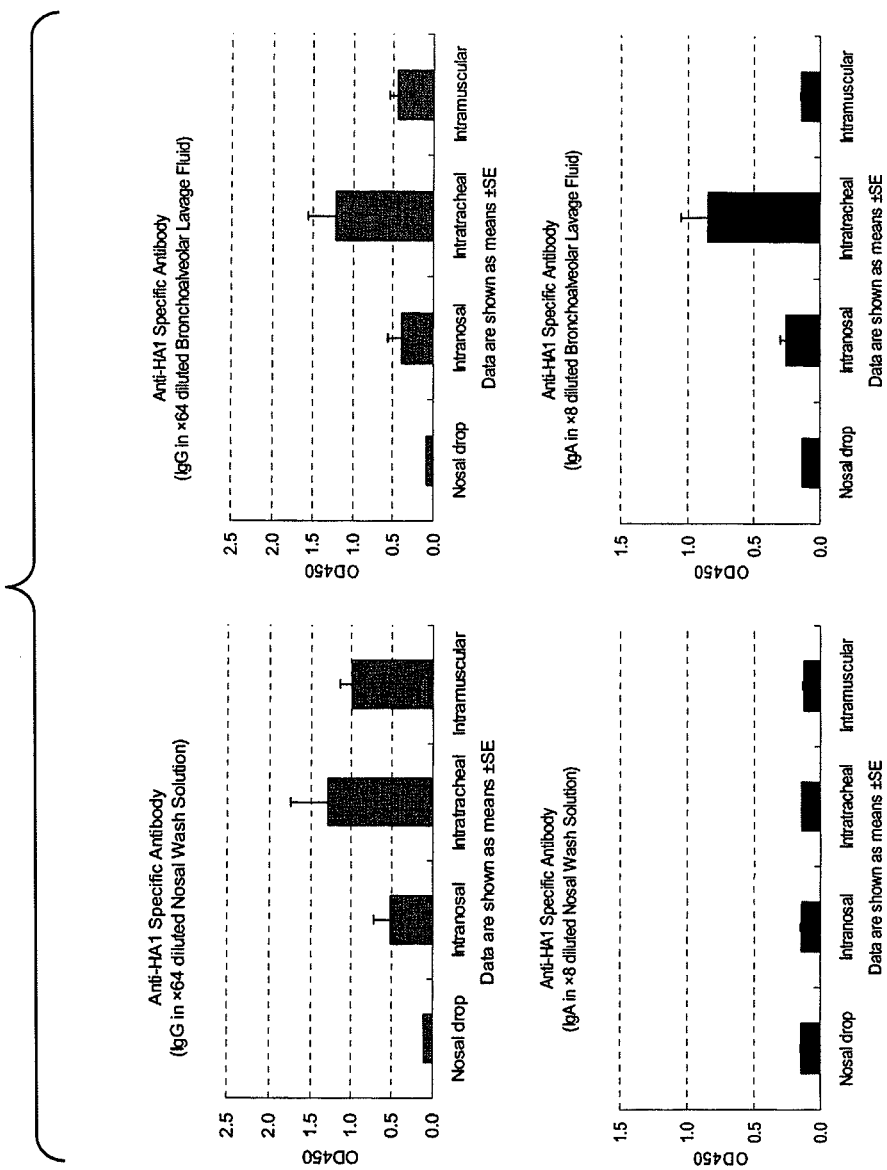
FIG. 13 is a view showing the production of IgG antibody and IgA antibody specific for influenza virus in nasal wash and alveolar wash, induced by the recombinant baculovirus AcNPV-Dual-H1N1/HA1 administered via different four routes.
Figure 14:
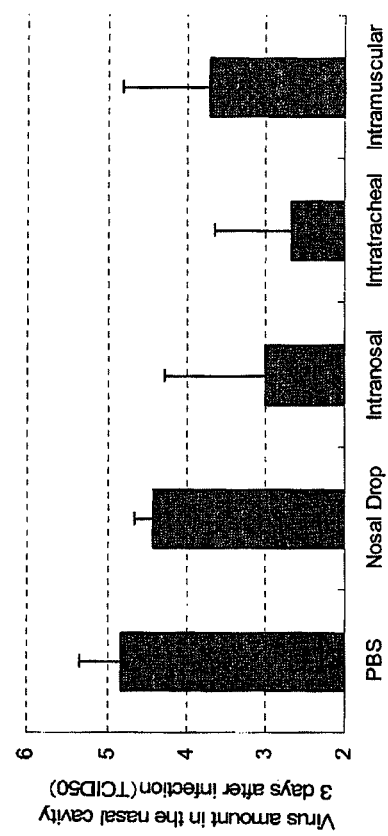
FIG. 14 is a view showing the preventive effects (virus infectivity titer) on influenza virus in nasal cavity by the recombinant baculovirus AcNPV-Dual-H1N1/HA1 administered via different four routes.
Figure 15:
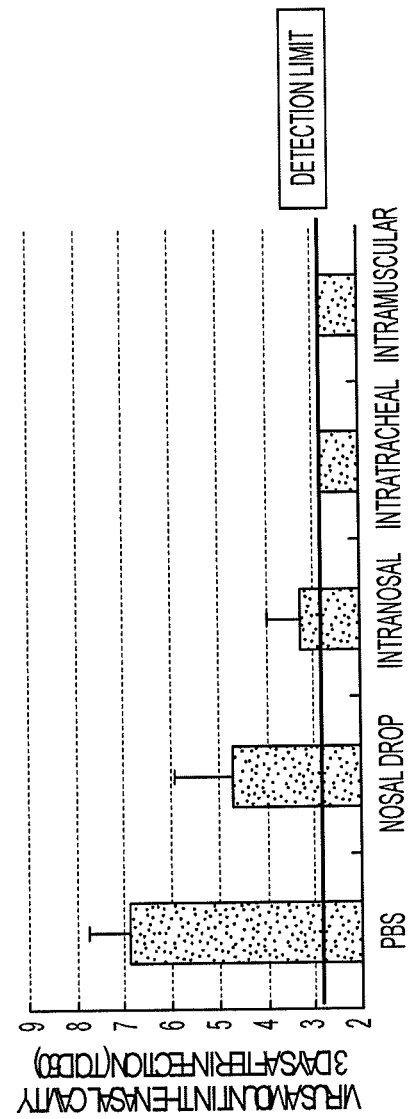
FIG. 15 is a view showing the preventive effects (virus infectivity titer) on intrapulmonary influenza virus by the recombinant baculovirus AcNPV-Dual-H1N1/HA1 administered via different four routes.
Figure 17:
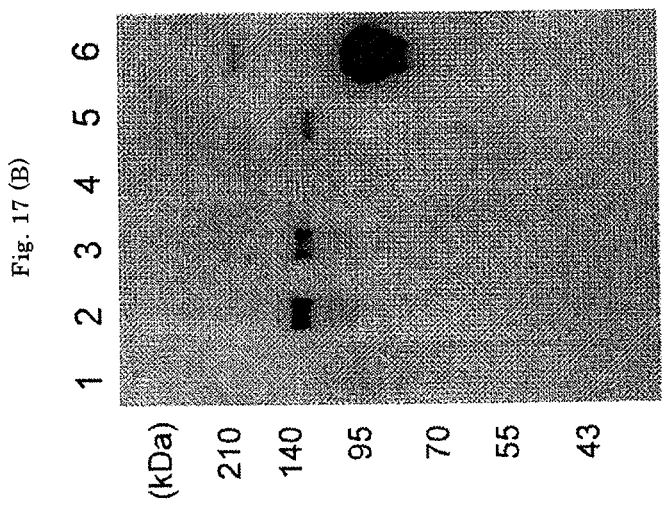
FIG. 17 (A) shows a Western blotting analysis showing the expression of the CSP gene (PfCSP) of human malaria in viral particles of recombinant baculoviruses produced from recombinant transfer vectors.
Figure 18:
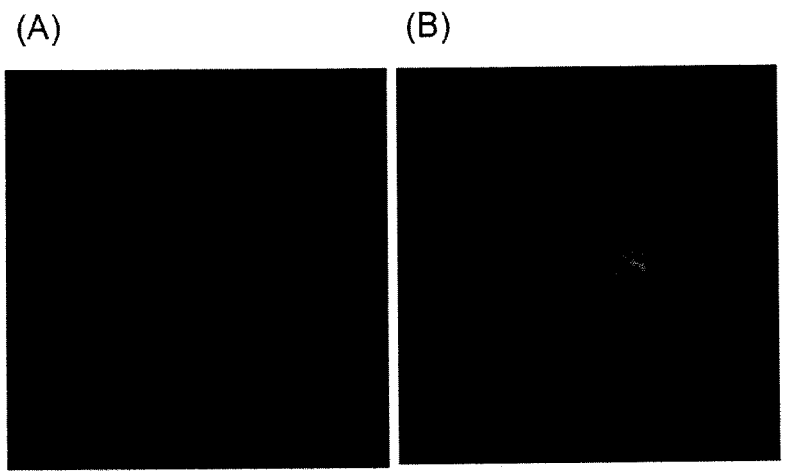
FIG. 18 shows HepG2 cells stained with a fluorescence-labeled antibody, which indicates that an antigen is expressed by a recombinant baculovirus containing a fusion gene of PfMSP1 gene and PfCSP gene in the HepG2 cells. The results of FIG. 18 (A) confirmed that a PfCSP antigen is expressed. The results of FIG. 18 (B) confirmed that a PfMSP-1$_{19}$ antigen is expressed.
Figure 19A:
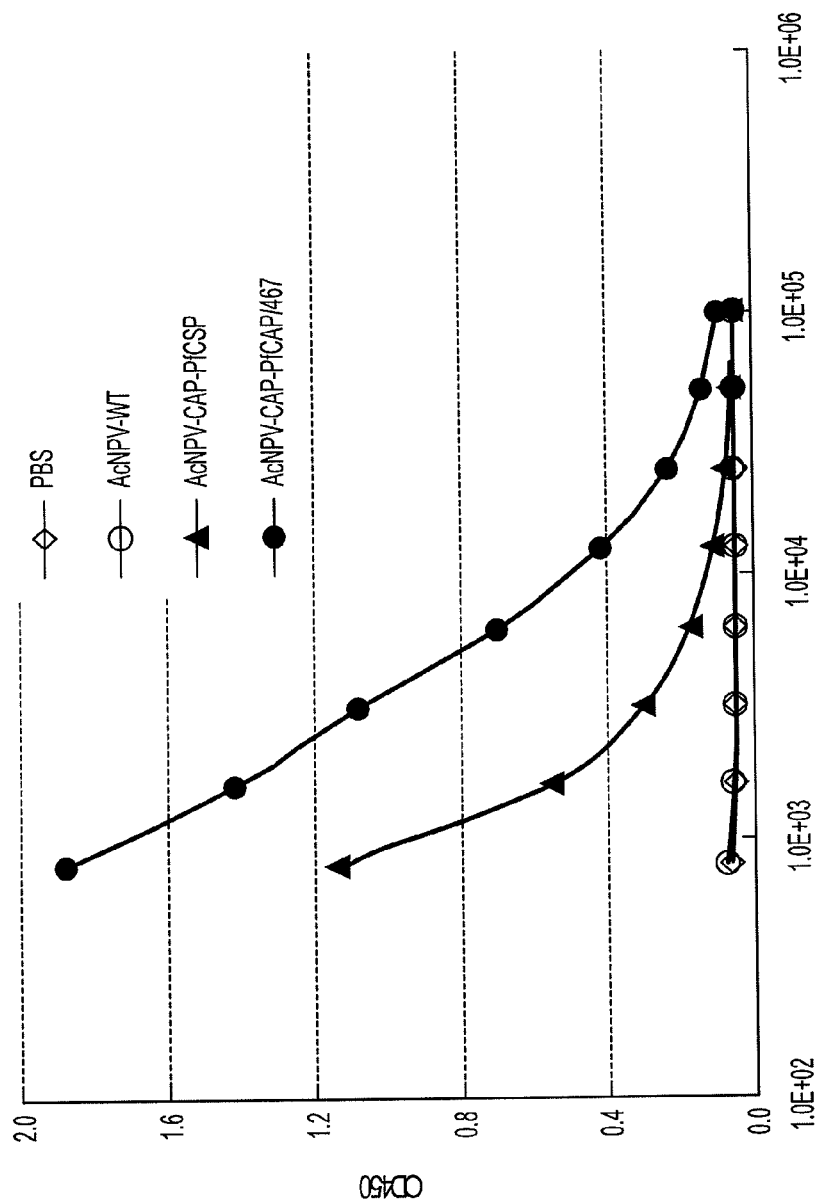
FIG. 19 shows the results of measurement of antibody titers obtained in Example 17.
Figure 19B:
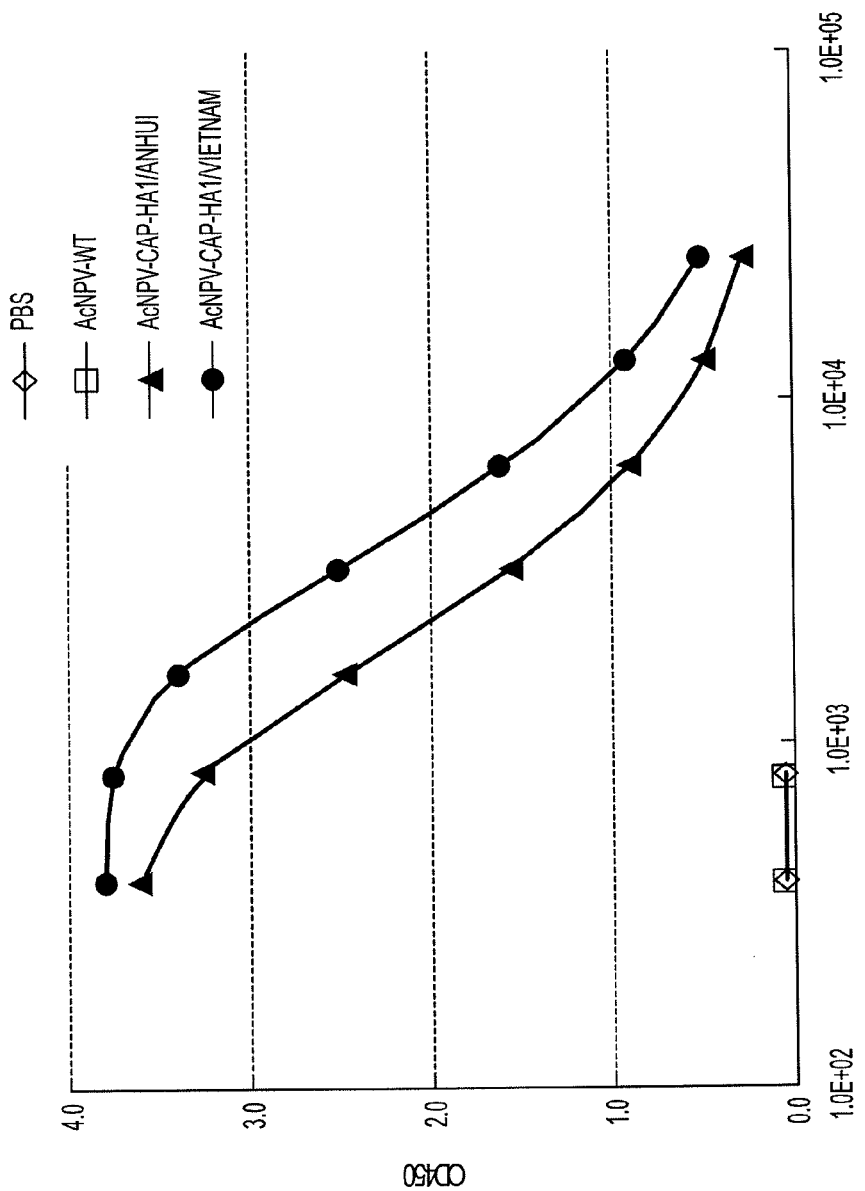

In FIG. 10, intrapulmonary virus amounts 6 days after the infection with influenza virus in the PBS group, the AcNPV-Dual-M2e inoculation group and the AcNPV-Dual-H1N1/HA1 inoculation group are shown.

Example 11

Study for Identifying Preventive Effect of Pharmaceutical Containing HA1/NC99 Recombinant Baculovirus as Active Component HA1/NC99 recombinant baculovirus (AcNPV-Dual-HA1/NC99) at $1.0\times10^8$ PFU per mouse was inoculated in thigh muscle twice with a two week interval. Two weeks after the final inoculation, the mouse was infected with Influenza virus A/NewCaledonia/20/99 by inoculating 0.05 mL of a solution containing the virus at $1000TCID_{50}$ in a nasal cavity. Three days after the infection, the mouse was euthanized, lung was removed and the intrapulmonary virus amount was detected using MDCK cells. As a result, no influenza virus could be detected in three of four mice inoculated with AcNPV-Dual-H1N1/NC99.

In FIG. 11, the intrapulmonary virus amounts 3 days after the infection with influenza virus in the PBS group, the wild type virus (AcNPV-WT) inoculation group, and the AcNPV-Dual-HA1/NC99 inoculation group are shown.

SEQ ID NOS: 101 and 102 represent the primers for identifying the expression of AcNPV-CP-H1N1/HA1, AcNPV-CAP-H1N1/HA1 and AcNPV-CU-H1N1/HA1.

SEQ ID NO: 103 represent a peptide known as a CD8 epitope of PbCSP.

Example 12

Study for Identifying Specific Antibody Depending on Administration Routes of Pharmaceutical Composition Containing Recombinant Baculovirus as Active Component HA1 recombinant baculovirus (AcNPV-Dual-H1N1/HA1) at $2.0\times10^7$ PFU per mouse was inoculated twice with a two week interval by inoculating 0.005 mL of the virus solution in both noses (nasal drop), inoculating 0.05 mL of the virus solution from the nose (rhinovaccination), inoculating 0.05 mL of the virus solution from a respiratory tract (through the respiratory tract) and inoculating 0.05 mL of the virus solution in thigh muscle (muscular injection). Two weeks after the final inoculation, a nasal wash, an alveolar wash and serum were collected, and the expression of the antibody specific for the influenza virus was identified. The antibody titer was measured by ELISA using a plate to which an extract of MDCK cells infected with influenza virus A/PR/8/341 had been immobilized. The ELISA was performed in accordance with standard methods. As a result, the specific IgG antibody was identified in blood from the rhinovaccination group, the intratracheal vaccination group and the intramuscular vaccination group. In particular, the antibody was identified to be strongly induced in the intratracheal vaccination group. Likewise, the antigen specific IgG antibody was also identified in the nasal wash and the alveolar wash, and in particular, the antibody was strongly induced in the intratracheal vaccination group. Furthermore, in the intratracheal vaccination group, the production of antigen specific IgA antibody was also identified in the alveolar wash.

In FIG. 12, the results of ELISA measuring the IgG antibody specific for influenza virus in the blood in the nasal drop group, the rhinovaccination group, the intratracheal vaccination group and the intramuscular vaccination group are shown.

In FIG. 13, the results of ELISA measuring the IgG and IgA antibodies specific for influenza virus in the nasal wash and the alveolar wash in the nasal drop group, the rhinovaccination group, the intratracheal vaccination group and the intramuscular vaccination group are shown.

Example 13

Study for Identifying Effects Depending on Administration Routes of Pharmaceutical Composition Containing Recombinant Baculovirus as Active Component HA1 recombinant baculovirus (AcNPV-Dual-H1N1/HA1) at $1.0\times10^7$ PFU per mouse was inoculated twice with a two week interval by the administration route of nasal drop, rhinovaccination, through the respiratory tract or muscular injection. Two weeks after the final inoculation, the mouse was infected with influenza virus A/PR/8/34 by inoculating 0.005 mL of a solution containing the virus at $1000TCID_{50}$ in the nasal cavity. Three days after the infection, the nasal wash was collected, 6 days after the infection, the lung was removed, and the intrapulmonary virus amount was detected using MDCK cells. As a result, the virus amount in the nasal cavity 3 days after the infection was remarkably reduced in the rhinovaccination group and the intratracheal vaccination group. Furthermore, in the intratracheal vaccination group, the intrapulmonary virus amount 6 days after the infection was reduced to a detection limit or lower as well as in the intramuscular vaccination group.

In FIG. 14, the virus amounts in the nasal wash 3 days after the infection with influenza virus in the nasal drop group, the rhinovaccination group, the intratracheal vaccination group and the intramuscular vaccination group are shown.

In FIG. 15, the intrapulmonary virus amounts 6 days after the infection with influenza virus in the nasal drop group, the rhinovaccination group, the intratracheal vaccination group and the intramuscular vaccination group are shown.

Example 14

Test of Expression of Vaccine Antigen from Recombinant Baculovirus of the Present Invention in Insect Cells Sf9 cells were cultured at a concentration of $1\times10^5$ cells per well in a 48-well plate (from Corning), and infected with baculoviruses AcNPV-CAP-PfCSP, AcNPV-CAP-HA1/Anhui, and AcNPV-CAP-HA1/Vietnam obtained in Example 2, or a wild-type baculovirus AcNPV-WT as a control at an infection multiplicity of about 0.1. After 5 days, the culture supernatant was removed from each well, and then Sample Buffer Solution (+2ME, ×2) (from Wako) was added in an amount of 0.05 mL per well to completely lyse the cells. The cell lysate was heated at 100° C. for 5 minutes, and electrophoresed on 7.5% SDS-PAGE. After electrophoresis, the protein was transferred to a PVDF membrane (Immobilon-P from Millipore), and blocking was performed at 4° C. overnight by immersing the membrane in 2.5% Skim Milk/SuperBlock (from Pierce). The membrane to which the protein of Sf9 cells infected with each baculovirus had been transferred was incubated with an anti-gp64 antibody (AcV5 from eBioScience) as the primary antibody, and then incubated with a HRP-labeled goat anti-mouse IgG (H+L) antibody (from BioRad) as the second antibody. Color was developed with an ECLplus Western Blotting Detection kit (from GE Healthcare) to detect the protein band. FIG. 1 shows the results.

FIG. 1 shows Western blotting analysis showing the expression of fusion antigens in insect cells from recombinant baculoviruses containing PfCSP gene of human malaria, HA1 gene of influenza virus H5N1/Anhui/1/05 strain, and HA1 gene of H5N1/Vietnam/1203/04 strain. In FIG. 1, Lane 1 shows the band of a wild-type baculovirus (AcNPV-WT); Lane 2 shows the band of a recombinant baculovirus (AcNPV-CAP-PfCSP) containing PfCSP gene and full-length gp64 gene inserted downstream of the dual promoter of the present invention; Lane 3 shows the band of a recombinant baculovirus (AcNPV-CAP-HA1/Anhui) containing HA1 gene of influenza virus H5N1/Anhui/1/05 strain and full-length gp64 gene inserted downstream of the dual promoter of the present invention; and Lane 4 shows the band of a recombinant baculovirus ((AcNPV-CAP-HA1/Vietnam) containing HA1 gene of influenza virus H5N1/Vietnam/1203/04 strain and full-length gp64 gene inserted downstream of the dual promoter of the present invention.

As shown in Lanes 2, 3 and 4 of FIG. 1, a band corresponding to the expressed fusion product of an immunogenic foreign antigen gene and gp64 gene was observed in the recombinant baculoviruses having an antigen gene and gp64 gene fused and expressed downstream of the dual promoter of the present invention.

The above results confirmed that when using the recombinant virus of the present invention, an immunogenic foreign antigen gene and gp64 gene can be fused and expressed as an expressed fusion product in insect cells.

Example 15

Test of Identification of Fusion Antigen in Vaccine Antigen Presented on Viral Particle (Virion) of Recombinant Baculovirus of the Present Invention Sf9 cells were cultured to a concentration of $1\times10^7$ cells per 150 mm cell culture plate (from Sumilon), and infected with each of the above-mentioned baculoviruses at an infection multiplicity of about 0.1. After 7 days, the medium was centrifuged at 3,000×g at 4° C. for 15 minutes twice, and the virus solution was layered over a 25% sucrose solution, and centrifuged using an ultracentrifuge at 25,000 rpm at 4° C. for 90 minutes to yield viral particles. 0.05 mL of Sample Buffer Solution (+2ME, ×2) (from Wako) was added to 0.05 mL each of the virus concentrates ($1\times10^8$ PFU/mL) of AcNPV-CAP-PfCSP, AcNPV-CAP-PfCSP/272, AcNPV-CAP-PfCSP/467, AcNPV-CAP-HA1/Vietnam, and AcNPV-WT collected by ultracentrifugation. The resulting mixtures were heated at 100° C. for 5 minutes, and electrophoresed on 7.5% SDS-PAGE. After the electrophoresis, the obtained proteins were transferred to PVDF membranes (Immobilon-P from Millipore), and immersed in 2.5% Skim Milk/SuperBlock (from Pierce) to perform blocking at 4° C. overnight. The membranes to which the virus solutions of AcNPV-CAP-PfCSP, AcNPV-CAP-PfCSP/272, and AcNPV-CAP-PfCSP/467 had been transferred were incubated with an anti-PfCSP antibody (2A10, MR-4) as the primary antibody, and then incubated with a HRP-labeled goat anti-mouse IgG (H+L) antibody (from BioRad) as the second antibody. The membrane to which the virus solution of AcNPV-CAP-HA1/Vietnam had been transferred was incubated with an anti-H5N1 antibody (IT-003-005 from Immune Technology) as the primary antibody, and then incubated with a HRP-labeled goat anti-rabbit IgG antibody (from GE Healthcare) as the second antibody. Color was developed with an ECLplus Western Blotting Detection kit (from GE Healthcare) to detect the bands of the proteins. FIG. 2 shows the results.

FIG. 2 (A) shows Western blotting analysis showing the expression of the CSP gene (PfCSP) of human malaria in viral particles of recombinant baculoviruses prepared using recombinant transfer vectors. Lane 1, the left side lane of FIG. 2 (A), shows the band of a recombinant baculovirus (AcNPV-CAP-PfCSP) containing PfCSP gene and full-length gp64 gene inserted downstream of the dual promoter of the invention; Lane 2 shows the band of a recombinant baculovirus (AcNPV-CAP-PfCSP/272) containing PfCSP gene and partial-length gp64 gene (241 amino acid residues from the C terminus) inserted downstream of the dual promoter of the invention; Lane 3 shows the band of a recombinant baculovirus (AcNPV-CAP-PfCSP/467) containing PfCSP gene and partial-length gp64 gene (46 amino acid residues from the C terminus) inserted downstream of the dual promoter of the invention. The baculoviruses were electrophoresed, and the presence of an expressed fusion product of the PfCSP gene and gp64 gene was checked. A strong band, indicating the presence of a fusion antigen of PfCSP gene and gp64 gene in the recombinant viral particles, was detected in all the lanes of FIG. 2 (A).

FIG. 2 (B) shows Western blotting analysis showing the expression of H5N1/HA1 gene in viral particles of recombinant baculoviruses prepared using recombinant transfer vectors. Lane 1, left side lane of FIG. 2 (B), shows the results obtained using the infected AcNPV-WT cell lysate prepared in Example 3; Lane 2 shows the results obtained using the AcNPV-CAP-HA1/Anhui-infected cell lysate prepared in Example 3; Lane 3 shows the results obtained using the AcNPV-CAP-HA1/Vietnam-infected cell lysate prepared in Example 3; and Lane 4 shows the results of viral particles of a wild-type baculovirus (AcNPV-WT); Lane 5 shows the results of viral particles of a recombinant baculovirus (AcNPV-CAP-HA1/Vietnam) containing the HA1 gene of influenza virus H5N1/Vietnam/1203/04 strain and full-length gp64 gene inserted downstream of the dual promoter of the present invention; and Lane 6 shows the results of purified HA antigen of H5N1 (IT-003-0053p from Immune Technology). The baculoviruses were electrophoresed, and the presence of an expressed fusion product of the PfCSP gene and gp64 gene was checked. A strong band, indicating the presence of a fusion antigen of HA1 gene of H5N1/Vietnam/1203/04 and gp64 gene in the recombinant viral particles, was detected in Lane 5 of FIG. 2(B).

The above results of Example 4 show that a foreign gene having the desired immunogenicity and gp64 gene can be fused and expressed in recombinant viral particles of the recombinant baculovirus of the present invention produced by using the recombinant transfer vector of the present invention.

Example 16

Test of Expression of Vaccine Antigen from Recombinant Baculovirus of the Present Invention in Mammals HepG2 cells were infected with AcNPV-Dual-PfMSP1-PfCSP at an infection multiplicity of 1. After 48 hours, the culture supernatant was removed, and the plate was rinsed with PBS three times. An acetone/ethanol solution (a mixed ratio of 7:3) cooled to −20° C. was added to immobilize the cells at −20° C. for 5 minutes. A 5% normal goat serum (from Sigma) was added to perform blocking at room temperature for 1 hour. To detect the expression of PfCSP, an anti-PfCSP antibody (2A10, MR-4) labeled with Alexa Flour 594 was added; and to detect the expression of PfMSP-$1_{19}$, an anti-PfMSP-$1_{19}$ antibody (5.2, MR-4) and then an anti-mouse antibody labeled with FITC were added. After incubation, the reacted cells were detected under a fluorescence microscope.

FIG. 3 shows the results.

FIG. 3 shows HepG2 cells stained with a fluorescence-labeled antibody, which indicates that an antigen is expressed from a recombinant baculovirus containing a fusion gene of the PfMSP1 gene and PfCSP gene in the HepG2 cells. The results of FIG. 3 (A) confirmed that a PfCSP antigen was expressed. The results of FIG. 3 (B) confirmed that a PfMSP-$1_{19}$ antigen was expressed. It was thus confirmed that fusion antigens can be expressed in mammalian cells. The results of FIG. 3 (A) and (B) clearly show that the recombinant baculovirus produced by using the transfer vector containing the dual promoter of the present invention can express the desired antigen in mammalian cells.

This suggests that when the recombinant baculovirus produced using the recombinant transfer vector of the present invention is administered to humans and other mammals, the virus particles enter the mammalian cells, and a mammalian promoter operates to produce a fusion product of the desired foreign antigen gene and gp64 gene in the mammalian cells, thus inducing the acquired immunity.

Example 17

Induction of Antibody by PfCSP Antigen Recombinant Virus and H5N1/HA1 Antigen Recombinant Virus 1. Inoculation of Virus Solution Virus solutions of AcNPV-WT, AcNPV-CAP-PfCSP, AcNPV-CAP-PfCSP/467, AcNPV-CAP-HA1/Anhui, and AcNPV-CAP-HA1/Vietnam concentrated by ultracentrifugation were inoculated into the thigh muscles of BALB/c female mice in an amount of $1 \times 10^8$ PUF twice at two week-intervals.

2. Measurement of Antibody Titers

The mice were euthanized two weeks after the final immunization, and sera were collected from the mice and used for measuring antigen-specific antibody titers. Induction of PfCSP antigen-specific antibody titers by AcNPV-CAP-PfCSP and AcNPV-CAP-PfCSP/467 was measured by ELISA using a plate on which (NANP)$_4$NVDPC peptide (from Sigma), i.e., B-cell epitope of PfCSP, had been immobilized. Induction of H5N1/HA antigen-specific antibody titers by AcNPV-CAP-HA1/Anhui and AcNPV-CAP-HA1/Vietnam was measured by ELISA using a plate on which purified HA antigen of H5N1 virus (IT-003-005p from Immune Technology) had been immobilized. The absorbance at OD450 nm was measured using MaxiSorp (from NUNC) as the ELISA plate, HRP-labeled goat anti-mouse IgG (H&L) antibody (from American Qualex) as the secondary antibody, and TMB (from Calbiochem) for the color reaction.

FIG. 4 shows the results.

FIG. 4 (A) is a graph plotting the average absorbance of each group at OD450 nm obtained when the mouse sera were subjected to two-fold serial dilution from 800-fold to 102, 400-fold dilutions. In the groups inoculated with PBS and AcNPV-WT, whose sera contained no antibody to the antigen, absorbance of even the 800-fold dilutions was 0.1 or less, indicating low reactivity. In contrast, in the groups inoculated with AcNPV-CAP-PfCSP and AcNPV-CAP-PfCSP/467, absorbance of the 800-fold dilutions was 1.138 and 1.878, respectively, indicating strong reactivity and clearly showing that antigen-specific antibodies were induced. FIG. 4 (B) is a graph plotting the average absorbance of each group at OD450 nm obtained when the mouse sera were subjected to two-fold serial dilution from 400-fold to 25,600-fold dilutions. In the groups inoculated with PBS and AcNPV-WT, whose sera contained no antibody to the antigen, absorbance of the 800-fold dilutions was 0.1 or less, indicating low reactivity. In contrast, in the group inoculated with AcNPV-CAP-HA1/Anhui and AcNPV-CAP-HA1/Vietnam, absorbance of the 3,200-fold dilution was 1.551 and 2.503, respectively, indicating strong reactivity and clearly showing that antigen-specific antibodies were induced. FIG. 4 clearly shows that the recombinant baculovirus produced using a transfer vector containing the dual promoter of the present invention can induce an antibody to the desired antigen in mammals.

3. Measurement of Neutralization Value

A hemagglutination inhibition (HI) test was performed using a mouse serum inoculated with AcNPV-CAP-HA1/Anhui. More specifically, the test was performed according to the method described in the instructions packaged with an influenza HI reagent "Seiken" (from Denka Seiken Co., Ltd.), using purified HA antigen of H5N1 virus (IT-003-0053p from Immune Technology). Absorption of non-specific agglutinins was performed using erythrocyte, and removal of non-specific agglutination inhibitors was performed using RDE (II) of "Seiken" (from Denka Seiken Co., Ltd.). The HI test was performed in the following manner. 0.025 mL of 10-fold diluted antiserum in a 96-well plate was subjected to 2-fold serial dilution using a diluent. To each well of the 96-well plate containing the diluted antiserum, 0.025 mL of HA antigen of H5N1 virus diluted to obtain an HA titer of 4 per 0.025 mL thereof was added. The plate was allowed to stand at room temperature for 30 minutes. 0.05 mL of an erythrocyte suspension for the reaction was added and stirred well. The mixture was allowed to stand at room temperature for 60 minutes. The final dilution of the test sample at which hemagglutination was completely inhibited was defined as the HI antibody titer.

The results show that the sera inoculated with PBS and AcNPV-WT had HI antibody titers of 10 or less, whereas the serum inoculated with AcNPV-CAP-HA1/Anhui had an HI antibody titer of 40.

The results seem to indicate that when administered to humans and other mammals, the recombinant baculovirus produced from the recombinant transfer vector of the present invention can induce an antibody effective to the desired foreign antigen gene, thus providing vaccine effects.

SEQUENCE LISTING FREE TEXT

SEQ ID NOS: 1 and 2 are the sequences of primers PbCSP-F and PbCSP-R1 for PCR of genomic DNA from *P. berghei* ANKA strain;

SEQ ID NOS: 3 and 4 are the sequences of primers phsp65-F1 and phsp65-R1 for PCR of genomic DNA from *M. tuberculosis* H37Rv;

SEQ ID NOS: 5 and 6 are the sequences of primers phsp65-F2 and phsp65-R2 for PCR with pcDNA as a template;

SEQ ID NOS: 7 and 8 are the sequences of primers pPolh-F2 and pgp64-R2 for PCR with pBACgus-1 (supplied from Novagen) as the template for obtaining a gp64 gene DNA fragment;

SEQ ID NOS: 9 and 10 are the sequences of primers HA-f and HA-r for PCR for producing an influenza virus HA gene fragment; and SEQ ID NOS: 11 and 12 are the sequences of primers pHA-F1 and pHA-R1 for PCR with pCR-Blunt-HA as the template.

SEQ ID NOS: 13 and 14 are the sequences of primers pTRAMP-F1 and pTRAMP-R1 for PCR of PbTRAMP gene.

SEQ ID NOS: 15 and 16 are the sequences of primers pAMA-F1 and pAMA-R1 for PCR of PbAMA1 gene domain 123 (D123).

SEQ ID NOS: 17 and 18 are the sequences of primers pMsp-F1 and pMsp-R1 for PCR of PbMSP119 gene.

SEQ ID NOS: 19 and 20 are the sequences of primers pPfCSP-F1 and pPfCSP-R1 for PCR of PfCSP gene.

SEQ ID NOS: 21 and 22 are the sequences of primers pPfAMA1-F1 and pPfAMA1-R1 for PCR of PfCSP gene from falciparum malaria parasite *P. falciparum* 3D7 strain.

SEQ ID NOS: 23 and 24 are the sequences of primers pPfs25-F1 and pPfs25-R1 for PCR of PfCSP gene from falciparum malaria parasite falciparum 3D7.

SEQ ID NOS: 25 and 26 are the sequences of primers Polh-f RsrII and GP64-r DraIII for PCR with pCR-Blunt-HA as the template.

SEQ ID NOS: 27 and 28 are the sequences of primers CMVenh-f FseI and CMVenh-r KpnI for PCR of CMV enhancer region.

SEQ ID NOS: 29 and 30 are the sequences of primers UBBp-f KpnI and UBBp-r RsrII for PCR of UBB promoter region.

SEQ ID NOS: 31 and 32 are the sequences of primers NP-f EcoRI and NP-r Cfr9I for RT-PCR of genomic RNA from influenza virus PR8/34 strain;

SEQ ID NOS: 33 and 34 are the sequences of primers M2-f EcoRI and M2-r Cfr9I for RT-PCR of genomic RNA from influenza virus PR8/34 strain;

SEQ ID NOS: 35 and 36 are the sequences of primers NAe-f EcoRI and NAe-r Cfr9I for RT-PCR of genomic RNA from influenza virus PR8/34 strain;

SEQ ID NOS: 37 and 38 are the sequences of primers M2-f EcoRI and M2e-r Cfr9I for PCR with pDual-H1N1/M2-gp64 as a template;

SEQ ID NOS: 39 and 40 are the sequences of primers HA1-f EcoRI and HA1-r CFr9I (NC99) for RT-PCR of genomic RNA from NewCaledonia99/20(NC99);

SEQ ID NOS: 41 and 42 are the sequences of primers HA0-f EcoRI and HA2-r Cfr9I for PCR with pCR-Blunt-HA as a template;

SEQ ID NOS: 43 and 44 are the sequences of primers HA2-f EcoRI and HA2-r Cfr9I for PCR with pCR-Blunt-HA as a template;

SEQ ID NOS: 45 and 46 are the sequences of primers vp39-f and vp39-r for PCR of vp39 gene region.

SEQ ID NOS: 47 and 48 are the sequences of primers Polh-S1 and HA1-r EcoRI for PCR of HA1 gene fragment.

SEQ ID NOS: 49 and 50 are the sequences of primers NP-f 5 EcoRI and NP-r EcoRI for PCR with pDual-H1N1/NP-gp64 as a template.

SEQ ID NOS: 3 and 4 are the sequences of primers phsp65-F1 and phsp65-R1 for PCR of genomic DNA of *M. tuberculosis* H37Rv.

SEQ ID NOS: 5 and 6 are the sequences of primers phsp65-F2 and phsp65-R2 for PCR with pcDNA-hps65 as a template.

SEQ ID NOS: 7 and 8 are the sequences of primers pPolh-F2 and pgp64-R2 for PCR with pBACsurf-1 as a template to produce a gp64 gene DNA fragment.

SEQ ID NOS: 9 and 10 are the sequences of primers HA-f and HA-r for PCR to produce an influenza virus HA gene fragment.

SEQ ID NOS: 11 and 12 are the sequences of primers pHA-F1 and pHA-R1 for PCR with pCR-Blunt-HA as a template.

SEQ ID NOS: 25 and 26 are the sequences of primers Polh-f RsrII and GP64-r DraIII for PCR with pBACsurf-HA1 as a template.

SEQ ID NOS: 31 and 32 are the sequences of primers NP-f EcoRI and NP-r Cfr9I for RT-PCR of genomic RNA of influenza virus PR/8/34 strain.

SEQ ID NOS: 51, 52, and 26 are the sequences of primers gp64 (272)-f, gp64 (467)-f, and GP64-r DraIII for PCR of pCAP-H1N1/HA1-64.

SEQ ID NOS: 53 and 54 are the sequences of primers PfCSP-f (19) and PfCSP-r (373) for PCR with *P. falciparum* genomic DNA as a template.

SEQ ID NOS: 15 and 16 are the sequences of primers pAMA-F1 and pAMA1-R1 for PCR with *P. berghei* genomic DNA as a template.

SEQ ID NOS: 19 and 20 are the sequences of primers pPfCSP-F1 and pPfCSP-R1 for PCR with *P. falciparum* genomic DNA as a template.

SEQ ID NOS: 23 and 55 are the sequences of primers pPfs25-F1 and pPfs25-R2 for PCR with *P. falciparum* genomic DNA as a template.

SEQ ID NOS: 56 and 57 are the sequences of primers pPfMSP119-F1 and pPfMSP119-R2 for PCR with *P. falciparum* genomic DNA as a template.

SEQ ID NOS: 53 and 58 are the sequences of primers PfCSP-f (19) and PfCSP-r (373 A361E) for PCR with pCAP-PfCSP as a template.

SEQ ID NOS: 59 and 58 are the sequences of primers PfCSP-f (76) and PfCSP-r (373 A361E) for PCR with pCAP-PfCSP as a template.

SEQ ID NO: 60 is the sequence of an artificial gene (PfCSP+) produced from the amino acid sequence of the PfCSP of *P. falciparum* 3D7 strain (in which, however, the A at the 361-position was replaced by E) using codons frequently used in Sf9 and human cells.

SEQ ID NOS: 61 and 62 are the sequences of primers PfCSP-f (+209) and PfCSP-r (+A361E) for PCR with PfCSP+ as a template.

SEQ ID NOS: 63, 64, 65 and 64 are the sequences of primers PfCSP-f (+76), PfCSP-r (+128), PfCSP-f (+209) BamHI, and PfCSP-r (+A361E) for PCR with PfCSP+ as a template.

SEQ ID NO: 66 is the sequence of an artificial gene produced from the amino acid sequence of the HA1 region of the hemagglutinin of influenza virus H5N1/Anhui/1/05 using codons frequently used in Sf9 and human cells.

SEQ ID NOS: 67 and 68 are the sequences of primers AH-F1 (5'-CAGT<u>CTGCAG</u>GACCAGATTTGCATC-3': (SEQ ID NO: 67); the PstI site is underlined) and AH-R4 (5'-CAGT<u>CCCGGG</u>CTCTCTTGCGCCTGC-3': (SEQ ID NO: 68); the XmaI site is underlined) for PCR with the artificial gene sequence of SEQ ID NO: 66 as a template.

SEQ ID NO: 69 is the sequence of an artificial gene produced from the amino acid sequence of the HA1 region of the hemagglutinin of influenza virus H5N1/Vietnam/1203/04 using codons frequently used in Sf9 and human cells.

SEQ ID NOS: 70 and 71 are the sequences of primers VN-F1 (5'-CAGT<u>CTGCAG</u>GACCAGATCTGTATC-3':

(SEQ ID NO: 70); the PstI site is underlined), and VN-R4 (5'-CAGT<u>CCCGGG</u>CTCTCTTCTTCCTGC-3': (SEQ ID NO: 71); the XmaI site is underlined) for PCR with the artificial gene sequence of SEQ ID NO: 69 as a template.

SEQ ID NOS: 72, 73, 74, 75, and 26 are the sequences of primers gp64(51)-f (5'-GACTC<u>CCCGGG</u>TGGAAATCACCATCGTGGAGACG-3': (SEQ ID NO: 72); the XmaI site is underlined), gp64(101)-f (5'-GACTC<u>CCCGGG</u>ATTTGCTTATGTGGAGCATCAGG-3': (SEQ ID NO: 73); the XmaI site is underlined), gp64(154)-f (5'-GACTC<u>CCCGGG</u>CGCACCACACGTGCAACAAATCG-3': (SEQ ID NO: 74); the XmaI site is underlined), gp64(201)-f (5'-GACTC<u>CCCGGG</u>ACACTGTGCTTCATCGAGACGGC-3': (SEQ ID NO: 75); the XmaI site is underlined), and GP64-r DraIII (5'-GGG CAC<u>TTAGTGA</u>TATTGTCTATTACGGTTTCTAATC-3' (SEQ ID NO: 26); the DraIII site is underlined).

SEQ ID NO: 76 is the sequence of an artificial gene produced from the amino acid sequence of the HA1 region of the hemagglutinin of influenza virus H5N1/Anhui/1/05 by codon optimization using Gene Designer available from DNA2.0, Inc.

SEQ ID NOS: 77, 78, 79, 80, and 81 are the sequences of AH17-F (5'-GACT<u>CTGCAG</u>GATCAGATCTGTATTGGGTACC-3': (SEQ ID NO: 77); the PstI site is underlined, and AH345-R (5'-CGAT<u>CCCGGG</u>CTCTCTTTCTCCTCCGCTCGC-3': (SEQ ID NO: 78); the XmaI site is underlined), AH410-R (5'-CGAT<u>CCCGGG</u>CGGCCTCGAACTGGGTGTTCATT-3': (SEQ ID NO: 79); the XmaI site is underlined), AH473-R (5'-CGAT<u>CCCGGG</u>CGTCTCTGAGTTGAAGGCGCAC-3': (SEQ ID NO: 80); the XmaI site is underlined, and AH520-R (5'-CGAT<u>CCCGGG</u>CACCACTAATTTCCTCTCGCTTC-3': (SEQ ID NO: 81); the XmaI site is underlined) for PCR with the artificial gene sequence of SEQ ID NO: 76 as a template.

SEQ ID NO: 82 is the sequence of an artificial gene produced from the amino acid sequence of the HA1 region of the hemagglutinin of influenza virus H5N1/Vietnam/1203/04 by codon optimization using Gene Designer available from DNA2.0, Inc.

SEQ ID NOS: 83, 84, 85, 85, and 87 are the sequences of primers VN17-F (5'-GACT<u>CTGCAG</u>GATCAGATCTGTATCGGATATC-3': (SEQ ID NO: 83); the PstI site is underlined), and VN346-R (5'-CGAT<u>CCCGGG</u>CCCGCTTTTTCCTCCTCCGTTCG-3': (SEQ ID NO: 84); the XmaI site is underlined), VN410-R (5'-CGAT<u>CCCGGG</u>CCTCAAACTGCGTATTCATTTTG-3': (SEQ ID NO: 85); the XmaI site is underlined), VN473-R (5'-CGAT<u>CCCGGG</u>CTCTAAGCTGGAGCCTGACTTTGTC-3': (SEQ ID NO: 86); the XmaI site is underlined), and VN520-R (5'-CGAT<u>CCCGGG</u>CACTAATCTCCTCTCTTTTAAGTC-3': (SEQ ID NO: 87); the XmaI site is underlined) for PCR with the artificial gene sequence of SEQ ID NO: 82 as a template.

SEQ ID NO: 88 is the sequence of an artificial gene produced from the amino acid sequence of the CSP of *Plasmodium falciparum* 3D7 strain by codon optimization using Gene Designer available from DNA2.0, Inc.

SEQ ID NOS: 89, 90, 91, 92, and 93 are the sequences of primers PfCSP_opt-f (5'-GACT<u>CTGCAG</u>ATGATGCGAAAATTGGCCATACTG-3': (SEQ ID NO: 89); the PstI site is underlined), PfCSP_opt-r (397) (5'-CGAT<u>CCCGGG</u>CATTGAGGAACAGAAAGGAAAGAACCATG-3': (SEQ ID NO: 90); the XmaI site is underlined), PfCSP_opt-f (19) (5'-GACT<u>CTGCAG</u>CTGTTTCAGGAATACCAGTGCTATGG-3': (SEQ ID NO: 91); (the PstI site is underlined), PfCSP_opt-1 (373) (5'-CGAT<u>CCCGGG</u>CCTTCT- CCATCTTA-CAAATTTTCTTTTCAATATCATTAGC-3': (SEQ ID NO: 92); (the XmaI site is underlined), PfCSP_opt-f (76) (5'-GACT<u>CTGCAG</u>GACGACGGAAATAATGAGGACAACG-3': (SEQ ID NO: 93); the PstI site is underlined), and PfCSP_opt-f (205) (5'-GACT<u>CTGCAG</u>AATGCAAACCCAAATGCCAATCCAAACGC-3': (SEQ ID NO: 94); the PstI site is underlined) for PCR with the artificial gene sequence of SEQ ID NO: 88 as a template.

SEQ ID NOS: 95, 96, 97, and 98 are the sequences of primers gp64-p-f (5'-GACT<u>CGGACCG</u>GCCAGATAAAAATAATCTTATCAATTAAG-3': (SEQ ID NO: 95); the RsrII site is underlined), gp64-p-r (5'-CGAT<u>ACTAGT</u>AGCACTGAGGCTTCTTATATACCCG-3': (SEQ ID NO: 96); the SpeI site is underlined), and vp39-p-f (5'-GACT<u>CGGACCG</u>CGTCGTACAAATCGAAATATTGTTGTG-3': (SEQ ID NO: 97); the RsrII site is underlined), and vp39-p-r (5'-CGAT<u>ACTAGT</u>GTGATTGAGAAAGAAATCTCTTATTC-3': (SEQ ID NO: 98); the SpeI site is underlined) for PCR with Baculovirus genomic DNA as a template.

SEQ ID NOS: 99 and 100 are the sequences of primers VSV-G-f (5'-GACT<u>CCCCGGG</u>CGTTCGAACATCCTCACATTCAAG-3' (SEQ ID NO: 99); the XmaI site is underlined), and VSV-G-r (5'-GACT<u>CACTTAGT</u>GCTTTCCAAGTCGGTTCATCTC-3': (SEQ ID NO: 100); the DraIII site is underlined) for PCR with pVSV-G as a template.

SEQ ID NOS: 101 and 102 are the sequences of primers for detecting expression of AcNPV-CP-H1N1/HA1, AcNPV-CAP-H1N1/HA1 and AcNPV-CU-H1N1/HA1.

SEQ ID NOS: 103 is a polypeptide which is known as CD8 epitope of PbCSP.

SEQ ID NOS: 104 is the amino acid sequence of PfCSP protein. (GENBANK Accession number XP_001351122)

SEQ ID NOS: 105 is the amino acid sequence of HA/A/Anhui/1/2005 protein. (GENBANK Accession number ABD28180)

SEQ ID NOS: 106 is the amino acid sequence of HA/A/Vietnam/1203/2004 protein. (GENBANK Accession number AAW80717)

SEQ ID NOS: 107 is the amino acid sequence of PfMSP1 protein. (GENBANK Accession number XP_001352170)

SEQ ID NOS: 108 is the amino acid sequence of Pfs25 protein. (GENBANK Accession number XP_001347587)

SEQ ID NOS: 109 is the polynucleotide sequence of PfCSP gene. (GENBANK Accession number XM_001351086)

SEQ ID NOS: 110 is the polynucleotide sequence of HA/A/Anhui/1/2005 gene. (GENBANK Accession number DQ371928)

SEQ ID NOS: 111 is the polynucleotide sequence of HA/A/Vietnam/1203/2004 gene. (GENBANK Accession number AY818135)

SEQ ID NOS: 112 is the polynucleotide sequence of PfMSP1 gene. (GENBANK Accession number XM_001352134)

SEQ ID NOS: 113 is the polynucleotide sequence of Pfs25 gene. (GENBANK Accession number XM_001347551)

SEQ ID NO 114 is the amino acid sequence consisting of 21-512 amino acid residues of GenBank Accession No. L22858

The invention claimed is:

1. A pharmaceutical composition comprising a recombinant *Autographa californica* nucleopolyhedrosis virus (AcNPV) as an active agent and, optionally, a pharmaceutically acceptable carrier,
   wherein the recombinant AcNPV contains a gene structure having a fusion gene of
   (A) a gene encoding a partial amino acid sequence of SEQ ID NO:104 (*Plasmodium falciparum* CircumSporozoite Protein; PfCSP), and
   (B) a gene encoding a partial amino acid sequence of SEQ ID NO: 114 under the control of a dual promoter comprising a Polyhedrin promoter and a CAG promoter linked to each other (CAP); and
   wherein the recombinant AcNPV is selected from the group consisting of:
   (1) a recombinant AcNPV which contains a gene encoding an amino acid sequence consisting of 19-373 amino acid residues of SEQ ID NO:104 as a gene of (A), and a gene encoding an amino acid sequence of SEQ ID NO: 114 as a gene of (B) (AcNPV-CAP-PfCSP),
   (2) a recombinant AcNPV which contains a gene encoding an amino acid sequence consisting of 19-373 amino acid residues of SEQ ID NO:104 as a gene of (A), and a gene encoding an amino acid sequence consisting of 447-492 amino acid residues of SEQ ID NO: 114 as a gene of (B) (AcNPV-CAP-PfCSP/467),
   (3) a recombinant AcNPV which contains a gene encoding an amino acid sequence consisting of 205-373 amino acid residues of SEQ ID NO:104 as a gene of (A), and a gene encoding an amino acid sequence of SEQ ID NO: 114 as a gene of (B.) (AcNPV-CAP-CO/205),
   (4) a recombinant AcNPV which contains a gene encoding an amino acid sequence consisting of 76-373 amino acid residues of SEQ ID NO:104 as a gene of (A), and a gene encoding an amino acid sequence consisting of 447-492 amino acid residues of SEQ ID NO: 114 as a gene of (B) (AcNPV-CAP-CO/76/467),
   (5) a recombinant AcNPV which contains a gene encoding an amino acid sequence consisting of 76-373 amino acid residues of SEQ ID NO:104 as a gene of (A), and a gene encoding an amino acid sequence of SEQ ID NO: 114 as a gene of (B) (AcNPV-CAP-CO/76),
   (6) a recombinant AcNPV which contains a gene encoding an amino acid sequence consisting of 1-397 amino acid residues of SEQ ID NO:104 as a gene of (A), and a gene encoding an amino acid sequence of SEQ ID NO: 114 as a gene of (B) (AcNPV-CAP-CO/full).

2. A pharmaceutical composition of claim 1, which is a malaria vaccine.

3. A vaccine comprising a recombinant *Autographa californica* nucleopolyhedrosis virus (AcNPV) as an active agent in an amount from 0.0002% (w/v) to about 0.2% (w/v) and, optionally, a pharmaceutically acceptable carrier,
   wherein the recombinant AcNPV contains a gene structure having a fusion gene of
   (A) a gene encoding a partial amino acid sequence of SEQ ID NO:104 (Plasmodium falciparum CircumSporozoite Protein; PfCSP), and
   (B) a gene encoding a partial amino acid sequence of SEQ ID NO: 114under the control of a dual promoter comprising a Polyhedrin promoter and a CAG promoter linked to each other (CAP) ; and wherein the recombinant AcNPV is selected from the group consisting of:

(1) a recombinant AcNPV which contains a gene encoding an amino acid sequence consisting of 19-373 amino acid residues of SEQ ID NO:104 as a gene of (A), and a gene encoding an amino acid sequence of SEQ ID NO: 114 as a gene of (B) (AcNPV-CAP-PfCSP), (2) a recombinant AcNPV which contains a gene encoding an amino acid sequence consisting of 19-373 amino acid residues of SEQ ID NO:104 as a gene of (A), and a gene encoding an amino acid sequence consisting of 447-492 amino acid residues of SEQ ID NO: 114 as a gene of (B) (AcNPV-CAP-PfCSP/467) , (3) a recombinant AcNPV which contains a gene encoding an amino acid sequence consisting of 205-373 amino acid residues of SEQ ID NO:104 as a gene of (A), and a gene encoding an amino acid sequence of SEQ ID NO: 114 as a gene of (B.) (AcNPV-CAP-CO/205), (4) a recombinant AcNPV which contains a gene encoding an amino acid sequence consisting of 76-373 amino acid residues of SEQ ID NO:104 as a gene of (A), and a gene encoding an amino acid sequence consisting of 447-492 amino acid residues of SEQ ID NO: 114as a gene of (B) (AcNPV-CAP-CO/76/467), (5) a recombinant AcNPV which contains a gene encoding an amino acid sequence consisting of 76-373 amino acid residues of SEQ ID NO:104 as a gene of (A), and a gene encoding an amino acid sequence of SEQ ID NO: 114 as a gene of (B) (AcNPV-CAP-CO/76), (6) a recombinant AcNPV which contains a gene encoding an amino acid sequence consisting of 1-397 amino acid residues of SEQ ID NO:104 as a gene of (A), and a gene encoding an amino acid sequence of SEQ ID NO: 114 as a gene of (B) (AcNPV-CAP-CO/full).

4. The vaccine of claim 3, wherein the vaccine is in a dosage form suitable for intramuscular, respiratory, or nasal administration.

* * * * *

SEQUENCE LISTING

<160> NUMBER OF SEQ ID NOS: 114

<210> SEQ ID NO 1
<211> LENGTH: 140
<212> TYPE: DNA
<213> ORGANISM: Artificial Sequence
<220> FEATURE:
<223> OTHER INFORMATION: primer PbCSP-1

<400> SEQUENCE: 1

```
ggagggctag catggagaca gacacactcc tgctatgggt actgctgctc tgggttccag      60
gttccactgg tgacgcggat ccactgcagg actacaagga cgtagacaag ggatatggac    120
aaaataaagc atccaagccc                                                140
```

<210> SEQ ID NO 2
<211> LENGTH: 67
<212> TYPE: DNA
<213> ORGANISM: Artificial Sequence
<220> FEATURE:
<223> OTHER INFORMATION: primer PbCSP-R1

<400> SEQUENCE: 2

```
ggagggcggc cgcatcccgg gttttcttat ttgaaccttt tcgttttcta actcttatac      60
cagaacc                                                               67
```

<210> SEQ ID NO 3
<211> LENGTH: 42
<212> TYPE: DNA
<213> ORGANISM: Artificial Sequence
<220> FEATURE:
<223> OTHER INFORMATION: primer phsp65-F1

<400> SEQUENCE: 3

```
aataatagat ctaatggcca agacaattgc gtacgacgaa ga                        42
```

<210> SEQ ID NO 4
<211> LENGTH: 63
<212> TYPE: DNA
<213> ORGANISM: Artificial Sequence
<220> FEATURE:
<223> OTHER INFORMATION: primer phsp65-R1

<400> SEQUENCE: 4

```
aatccaatgc ggccgcggga attcgattcc tgcaggtcag aaatccatgc cacccatgtc      60
gcc                                                                   63
```

<210> SEQ ID NO 5
<211> LENGTH: 74
<212> TYPE: DNA
<213> ORGANISM: Artificial Sequence
<220> FEATURE:
<223> OTHER INFORMATION: primer phsp65-F2

<400> SEQUENCE: 5

```
cacccctgca ggactacaag gacgacgatg acaaggaatt catggccaag acaattgcgt      60
acgacgaaga ggcc                                                       74
```

<210> SEQ ID NO 6

```
<211> LENGTH: 37
<212> TYPE: DNA
<213> ORGANISM: Artificial Sequence
<220> FEATURE:
<223> OTHER INFORMATION: primer phsp65-R2

<400> SEQUENCE: 6
cccgggcgaa atccatgcca cccatgtcgc cgccacc                                37

<210> SEQ ID NO 7
<211> LENGTH: 48
<212> TYPE: DNA
<213> ORGANISM: Artificial Sequence
<220> FEATURE:
<223> OTHER INFORMATION: primer pPolh-F2

<400> SEQUENCE: 7
cacccggacc ggataattaa aatgataacc atctcgcaaa taaataag                    48

<210> SEQ ID NO 8
<211> LENGTH: 35
<212> TYPE: DNA
<213> ORGANISM: Artificial Sequence
<220> FEATURE:
<223> OTHER INFORMATION: primer pgp64-R2

<400> SEQUENCE: 8
ggtaccatat tgtctattac ggtttctaat catac                                  35

<210> SEQ ID NO 9
<211> LENGTH: 30
<212> TYPE: DNA
<213> ORGANISM: Artificial Sequence
<220> FEATURE:
<223> OTHER INFORMATION: primer HA-f

<400> SEQUENCE: 9
cctgcaggta tgaaggcaaa cctactggtc                                        30

<210> SEQ ID NO 10
<211> LENGTH: 23
<212> TYPE: DNA
<213> ORGANISM: Artificial Sequence
<220> FEATURE:
<223> OTHER INFORMATION: primer HA-r

<400> SEQUENCE: 10
gcccgggcga tgcatattct gca                                               23

<210> SEQ ID NO 11
<211> LENGTH: 37
<212> TYPE: DNA
<213> ORGANISM: Artificial Sequence
<220> FEATURE:
<223> OTHER INFORMATION: primer pHA-F1

<400> SEQUENCE: 11
caccgaattc gacacaatat gtataggcta ccatgcg                                37

<210> SEQ ID NO 12
<211> LENGTH: 32
<212> TYPE: DNA
<213> ORGANISM: Artificial Sequence
<220> FEATURE:
<223> OTHER INFORMATION: primer pHA-R1

<400> SEQUENCE: 12
```

```
cccgggcacc tctggattgg atggacggaa tg                                    32
```

<210> SEQ ID NO 13
<211> LENGTH: 35
<212> TYPE: DNA
<213> ORGANISM: Artificial Sequence
<220> FEATURE:
<223> OTHER INFORMATION: primer pTRAMP-F1

<400> SEQUENCE: 13

```
caccgaattc aaaattgata cgaaaaaaaa tgaag                                 35
```

<210> SEQ ID NO 14
<211> LENGTH: 34
<212> TYPE: DNA
<213> ORGANISM: Artificial Sequence
<220> FEATURE:
<223> OTHER INFORMATION: primer pTRAMP-R1

<400> SEQUENCE: 14

```
cccgggcttt taattttgag gagtctttat tttc                                  34
```

<210> SEQ ID NO 15
<211> LENGTH: 40
<212> TYPE: DNA
<213> ORGANISM: Artificial Sequence
<220> FEATURE:
<223> OTHER INFORMATION: primer pAMA-F1

<400> SEQUENCE: 15

```
caccgaattc aatccatggg aaaagtatac ggaaaaatat                            40
```

<210> SEQ ID NO 16
<211> LENGTH: 37
<212> TYPE: DNA
<213> ORGANISM: Artificial Sequence
<220> FEATURE:
<223> OTHER INFORMATION: primer pAMA-R1

<400> SEQUENCE: 16

```
cccgggcttc tctggtttga tgggctttca tatgcac                               37
```

<210> SEQ ID NO 17
<211> LENGTH: 75
<212> TYPE: DNA
<213> ORGANISM: Artificial Sequence
<220> FEATURE:
<223> OTHER INFORMATION: primer pMsp1-F1

<400> SEQUENCE: 17

```
caccctgcag gactacaagg acgacgatga caagcacata gcctcaatag ctttaaataa      60
cttaaataaa tctgg                                                       75
```

<210> SEQ ID NO 18
<211> LENGTH: 40
<212> TYPE: DNA
<213> ORGANISM: Artificial Sequence
<220> FEATURE:
<223> OTHER INFORMATION: primer pMsp1-R1

<400> SEQUENCE: 18

```
cccgggttcc cataaagctg gaagagctac agaatacacc                            40
```

<210> SEQ ID NO 19

-continued

<210> SEQ ID NO 19
<211> LENGTH: 40
<212> TYPE: DNA
<213> ORGANISM: Artificial Sequence
<220> FEATURE:
<223> OTHER INFORMATION: primer pPfCSP-F1

<400> SEQUENCE: 19
caccgaattc ttattccagg aataccagtg ctatggaagt                          40

<210> SEQ ID NO 20
<211> LENGTH: 34
<212> TYPE: DNA
<213> ORGANISM: Artificial Sequence
<220> FEATURE:
<223> OTHER INFORMATION: primer pPfCSP-R1

<400> SEQUENCE: 20
cccgggcttt ttccatttta caaattttt tttc                                34

<210> SEQ ID NO 21
<211> LENGTH: 73
<212> TYPE: DNA
<213> ORGANISM: Artificial Sequence
<220> FEATURE:
<223> OTHER INFORMATION: primer pPfAMA1-F1

<400> SEQUENCE: 21
caccctgcag gactacaagg acgacgatga caagcagaat tattgggaac atccatatca    60
aaatagtgat gtg                                                      73

<210> SEQ ID NO 22
<211> LENGTH: 34
<212> TYPE: DNA
<213> ORGANISM: Artificial Sequence
<220> FEATURE:
<223> OTHER INFORMATION: primer pPfAMA1-R1

<400> SEQUENCE: 22
cccgggcttt cattttatca taagttggtt tatg                               34

<210> SEQ ID NO 23
<211> LENGTH: 43
<212> TYPE: DNA
<213> ORGANISM: Artificial Sequence
<220> FEATURE:
<223> OTHER INFORMATION: primer pPfs25-F1

<400> SEQUENCE: 23
caccgaattc aaagttaccg tggatactgt atgcaaaaga gga                     43

<210> SEQ ID NO 24
<211> LENGTH: 34
<212> TYPE: DNA
<213> ORGANISM: Artificial Sequence
<220> FEATURE:
<223> OTHER INFORMATION: primer pPfs25-R1

<400> SEQUENCE: 24
cccgggcagt acatatagag ctttcattat ctat                               34

<210> SEQ ID NO 25
<211> LENGTH: 35
<212> TYPE: DNA
<213> ORGANISM: Artificial Sequence
<220> FEATURE:
<223> OTHER INFORMATION: primer Polh-f RsrII

<400> SEQUENCE: 25
gggcggaccg gataattaaa atgataacca tctcg                      35

<210> SEQ ID NO 26
<211> LENGTH: 37
<212> TYPE: DNA
<213> ORGANISM: Artificial Sequence
<220> FEATURE:
<223> OTHER INFORMATION: primer GP64-r DraIII

<400> SEQUENCE: 26
gggcacttag tgatattgtc tattacggtt tctaatc                    37

<210> SEQ ID NO 27
<211> LENGTH: 36
<212> TYPE: DNA
<213> ORGANISM: Artificial Sequence
<220> FEATURE:
<223> OTHER INFORMATION: primer CMVenh-f FseI

<400> SEQUENCE: 27
gggggccggc cctagttatt aatagtaatc aattac                     36

<210> SEQ ID NO 28
<211> LENGTH: 34
<212> TYPE: DNA
<213> ORGANISM: Artificial Sequence
<220> FEATURE:
<223> OTHER INFORMATION: primer CMVenh-r KpnI

<400> SEQUENCE: 28
gggggtaccc atggtaatag cgatgactaa tacg                       34

<210> SEQ ID NO 29
<211> LENGTH: 31
<212> TYPE: DNA
<213> ORGANISM: Artificial Sequence
<220> FEATURE:
<223> OTHER INFORMATION: primers UBBp-f KpnI

<400> SEQUENCE: 29 ggggtacct cgaggaaggt ttcttcaact c                           31

<210> SEQ ID NO 30
<211> LENGTH: 36
<212> TYPE: DNA
<213> ORGANISM: Artificial Sequence
<220> FEATURE:
<223> OTHER INFORMATION: primer UBBp-r RsrII

<400> SEQUENCE: 30
gggcggtccg gacctagttt aaaagtaaaa cataag                     36

<210> SEQ ID NO 31
<211> LENGTH: 27
<212> TYPE: DNA
<213> ORGANISM: Artificial Sequence
<220> FEATURE:
<223> OTHER INFORMATION: primer NP-f EcoRI

<400> SEQUENCE: 31
acggaattcc attcaattca aactgga                               27

<210> SEQ ID NO 32

```
<211> LENGTH: 31
<212> TYPE: DNA
<213> ORGANISM: Artificial Sequence
<220> FEATURE:
<223> OTHER INFORMATION: primer NP-r Cfr9I

<400> SEQUENCE: 32
gatcccgggc cttgtcaatg ctgaatggca a                              31

<210> SEQ ID NO 33
<211> LENGTH: 27
<212> TYPE: DNA
<213> ORGANISM: Artificial Sequence
<220> FEATURE:
<223> OTHER INFORMATION: primer M2-f EcoRI

<400> SEQUENCE: 33
cggaattcat gagtcttcta accgagg                                   27

<210> SEQ ID NO 34
<211> LENGTH: 28
<212> TYPE: DNA
<213> ORGANISM: Artificial Sequence
<220> FEATURE:
<223> OTHER INFORMATION: primer M2-r Cfr9I

<400> SEQUENCE: 34
gatcccgggc ctccagctct atgctgac                                  28

<210> SEQ ID NO 35
<211> LENGTH: 27
<212> TYPE: DNA
<213> ORGANISM: Artificial Sequence
<220> FEATURE:
<223> OTHER INFORMATION: primer NAe-f EcoRI

<400> SEQUENCE: 35
acggaattcc attcaattca aactgga                                   27

<210> SEQ ID NO 36
<211> LENGTH: 31
<212> TYPE: DNA
<213> ORGANISM: Artificial Sequence
<220> FEATURE:
<223> OTHER INFORMATION: primer NAe-r Cfr9I

<400> SEQUENCE: 36
gatcccgggc cttgtcaatg ctgaatggca a                              31

<210> SEQ ID NO 37
<211> LENGTH: 27
<212> TYPE: DNA
<213> ORGANISM: Artificial Sequence
<220> FEATURE:
<223> OTHER INFORMATION: primer M2-f EcoRI

<400> SEQUENCE: 37
cggaattcat gagtcttcta accgagg                                   27

<210> SEQ ID NO 38
<211> LENGTH: 28
<212> TYPE: DNA
<213> ORGANISM: Artificial Sequence
<220> FEATURE:
<223> OTHER INFORMATION: primer M2e-r Cfr9I

<400> SEQUENCE: 38
```

-continued gatcccgggc atcacttgaa ccgttgca                                              28

<210> SEQ ID NO 39
<211> LENGTH: 31
<212> TYPE: DNA
<213> ORGANISM: Artificial Sequence
<220> FEATURE:
<223> OTHER INFORMATION: primer HA1-f EcoRI

<400> SEQUENCE: 39
gatgaattcg acacaatatg tataggctac c                                          31

<210> SEQ ID NO 40
<211> LENGTH: 32
<212> TYPE: DNA
<213> ORGANISM: Artificial Sequence
<220> FEATURE:
<223> OTHER INFORMATION: primer HA1-r CFr9I

<400> SEQUENCE: 40
gatcccgggc tctggattga atggatggga tg                                         32

<210> SEQ ID NO 41
<211> LENGTH: 28
<212> TYPE: DNA
<213> ORGANISM: Artificial Sequence
<220> FEATURE:
<223> OTHER INFORMATION: primers HA0-f EcoRI

<400> SEQUENCE: 41
ggggaattca tgaaggcaaa cctactgg                                              28

<210> SEQ ID NO 42
<211> LENGTH: 25
<212> TYPE: DNA
<213> ORGANISM: Artificial Sequence
<220> FEATURE:
<223> OTHER INFORMATION: primer HA2-r Cfr9I

<400> SEQUENCE: 42
gatcccgggc gatgcatatt ctgca                                                 25

<210> SEQ ID NO 43
<211> LENGTH: 28
<212> TYPE: DNA
<213> ORGANISM: Artificial Sequence
<220> FEATURE:
<223> OTHER INFORMATION: primer HA2-f EcoRI

<400> SEQUENCE: 43
gatgaattca tatttggagc cattgccg                                              28

<210> SEQ ID NO 44
<211> LENGTH: 25
<212> TYPE: DNA
<213> ORGANISM: Artificial Sequence
<220> FEATURE:
<223> OTHER INFORMATION: primer HA2-r Cfr9I

<400> SEQUENCE: 44
gatcccgggc gatgcatatt ctgca                                                 25

<210> SEQ ID NO 45
<211> LENGTH: 75
<212> TYPE: DNA

```
<213> ORGANISM: Artificial Sequence
<220> FEATURE:
<223> OTHER INFORMATION: primer vp39-f

<400> SEQUENCE: 45
cttactagta tggactacaa ggacgacgat gacaaggaat cggcggcgg cggctcggcg      60 ctagtgcccg tgggt                                                     75

<210> SEQ ID NO 46
<211> LENGTH: 66
<212> TYPE: DNA
<213> ORGANISM: Artificial Sequence
<220> FEATURE:
<223> OTHER INFORMATION: primer vp39-r

<400> SEQUENCE: 46
cttcacttag tgatggtgat gatggtggtg cccggggctt taaagcttga cggctattcc    60
tccacc                                                                66

<210> SEQ ID NO 47
<211> LENGTH: 18
<212> TYPE: DNA
<213> ORGANISM: Artificial Sequence
<220> FEATURE:
<223> OTHER INFORMATION: primers Polh-S1

<400> SEQUENCE: 47
gctaaccatg ttcatgcc                                                  18

<210> SEQ ID NO 48
<211> LENGTH: 28
<212> TYPE: DNA
<213> ORGANISM: Artificial Sequence
<220> FEATURE:
<223> OTHER INFORMATION: primer HA1-r EcoRI

<400> SEQUENCE: 48
ggggaattca cctctggatt ggatggac                                       28

<210> SEQ ID NO 49
<211> LENGTH: 27
<212> TYPE: DNA
<213> ORGANISM: Artificial Sequence
<220> FEATURE:
<223> OTHER INFORMATION: primers NP-f 5 EcoRI

<400> SEQUENCE: 49
acggaattca tggcgtccca aggcacc                                        27

<210> SEQ ID NO 50
<211> LENGTH: 31
<212> TYPE: DNA
<213> ORGANISM: Artificial Sequence
<220> FEATURE:
<223> OTHER INFORMATION: primer NP-r EcoRI

<400> SEQUENCE: 50
acggaattca ttgtcgtact cctctgcatt g                                   31

<210> SEQ ID NO 51
<211> LENGTH: 31
<212> TYPE: DNA
<213> ORGANISM: Artificial Sequence
<220> FEATURE:
<223> OTHER INFORMATION: primer gp64(272)-f
```

```
<400> SEQUENCE: 51
gactccccgg gtcgagcacc gagtcaagaa g                                    31

<210> SEQ ID NO 52
<211> LENGTH: 31
<212> TYPE: DNA
<213> ORGANISM: Artificial Sequence
<220> FEATURE:
<223> OTHER INFORMATION: primer gp64(467)-f

<400> SEQUENCE: 52
gactccccgg gacatcactt ccatggctga a                                    31

<210> SEQ ID NO 53
<211> LENGTH: 39
<212> TYPE: DNA
<213> ORGANISM: Artificial Sequence
<220> FEATURE:
<223> OTHER INFORMATION: primer PfCSP-f(19)

<400> SEQUENCE: 53
gactctgcag ttattccagg aataccagtg ctatggaag                            39

<210> SEQ ID NO 54
<211> LENGTH: 44
<212> TYPE: DNA
<213> ORGANISM: Artificial Sequence
<220> FEATURE:
<223> OTHER INFORMATION: PfCSP-r(373)

<400> SEQUENCE: 54
cgatcccggg cttttttccat ttacaaatt ttttttttcaa tatc                     44

<210> SEQ ID NO 55
<211> LENGTH: 66
<212> TYPE: DNA
<213> ORGANISM: Artificial Sequence
<220> FEATURE:
<223> OTHER INFORMATION: primer pPfs25-R2

<400> SEQUENCE: 55
caattgagat ccgccgccac cgccaccagt acatatagag ctttcattat ctattataaa     60
tccatc                                                                66

<210> SEQ ID NO 56
<211> LENGTH: 41
<212> TYPE: DNA
<213> ORGANISM: Artificial Sequence
<220> FEATURE:
<223> OTHER INFORMATION: primer pPfMSP119-F1

<400> SEQUENCE: 56
caccgaattc aacatttcac aacaccaatg cgtaaaaaaa c                         41

<210> SEQ ID NO 57
<211> LENGTH: 64
<212> TYPE: DNA
<213> ORGANISM: Artificial Sequence
<220> FEATURE:
<223> OTHER INFORMATION: primer pPfMSP119-R2

<400> SEQUENCE: 57
caattgagat ccgccgccac cgccaccgtt agaggaactg cagaaaatac catcgaaaag     60
```

```
                                                                  tgga                                                    64

<210> SEQ ID NO 58
<211> LENGTH: 50
<212> TYPE: DNA
<213> ORGANISM: Artificial Sequence
<220> FEATURE:
<223> OTHER INFORMATION: primer PfCSP-r(373 A361E)

<400> SEQUENCE: 58
cgatcccggg cttttttccat tttacaaatt ttttttttcaa tatcattttc                  50

<210> SEQ ID NO 59
<211> LENGTH: 35
<212> TYPE: DNA
<213> ORGANISM: Artificial Sequence
<220> FEATURE:
<223> OTHER INFORMATION: primer PfCSP-f(76)

<400> SEQUENCE: 59
gactctgcag gatgatggaa ataacgaaga caacg                                    35

<210> SEQ ID NO 60
<211> LENGTH: 1194
<212> TYPE: DNA
<213> ORGANISM: Plasmodium falciparum

<400> SEQUENCE: 60
atgatgcgca aactggccat tctgagcgtg agcagctttc tgtttgtgga agccctgttt         60
caggaatacc agtgctacgg cagcagcagc aacacccgcg tgctgaacga actgaactac        120
gacaacgccg gcaccaacct gtacaacgaa ctggaaatga actactacgg caaacaggaa        180
aactggtaca gcctgaaaaa aaacagccgc agcctgggcg aaaacgacga cggcaacaac        240
gaagacaacg aaaaactgcg caaacccaaa cacaaaaaac tgaaacagcc cgccgacggc        300
aaccccgacc ccaacgccaa ccccaacgtg accccaatgc caacccaaa tgtggaccca        360 aatgccaacc caaatgtgga tcctaacgcc aacccaaacg caaatcccaa tgccaaccct        420
aacgctaatc caaacgccaa ccccaacgct aaccctaatg ctaacccaaa cgctaaccct        480
aacgctaacc ctaacgccaa tcccaatgcc aaccccaacg ccaacccaaa cgctaaccca        540
aacgctaacc ctaacgccaa cccaaacgcc aatcccaacg ctaaccctaa cgtggacccc        600
aatgcaaatc ccaacgccaa tccaaacgct aatccaaacg ctaatcccaa cgctaatccc        660
aatgccaacc caaacgcaaa tccaaatgcc aaccccaacg ccaaccctaa cgccaaccct        720
aacgcaaacc caaacgccaa ccccaatgcc aaccctaacg ctaacccaaa cgccaatccc        780
aatgccaacc caaacgctaa ccctaacgcc aatcccaaca gaacaaccca gggcaatggc        840
cagggccaca atatgccaaa tgaccccaac cgcaacgtgg acgaaaacgc caacgccaac        900
agcgccgtga aaacaacaa caacgaagaa cccagcgaca acacattaa agaatacctg         960 aacaaaattc agaacagcct gagcaccgaa tggagcccct gcagcgtgac ctgcggcaac       1020
ggcattcagg tgcgcattaa acccggcagc gccaacaaac ccaaagacga actggactac       1080
gaaaacgaca ttgaaaaaaa aatttgcaaa atggaaaaat gcagcagcgt gtttaacgtg       1140
gtgaacagca gcattggcct gattatggtg ctgagctttc tgtttctgaa ctag              1194

<210> SEQ ID NO 61
<211> LENGTH: 52
<212> TYPE: DNA
<213> ORGANISM: Artificial Sequence
```

<220> FEATURE:
<223> OTHER INFORMATION: primer PfCSP-f(+209)

<400> SEQUENCE: 61
gactctgcag aacgctaatc caaacgctaa tcccaacgct aatcccaatg cc        52

<210> SEQ ID NO 62
<211> LENGTH: 35
<212> TYPE: DNA
<213> ORGANISM: Artificial Sequence
<220> FEATURE:
<223> OTHER INFORMATION: primer PfCSP-r(+ A361E)

<400> SEQUENCE: 62
cgatcccggg cttttttccat tttgcaaatt ttttt        35

<210> SEQ ID NO 63
<211> LENGTH: 35
<212> TYPE: DNA
<213> ORGANISM: Artificial Sequence
<220> FEATURE:
<223> OTHER INFORMATION: primer PfCSP-f(+76)

<400> SEQUENCE: 63
gactctgcag gacgacggca acaacgaaga caacg        35

<210> SEQ ID NO 64
<211> LENGTH: 32
<212> TYPE: DNA
<213> ORGANISM: Artificial Sequence
<220> FEATURE:
<223> OTHER INFORMATION: primer PfCSP-r(+128)

<400> SEQUENCE: 64
cgttaggatc cacatttggg ttggcatttg gg        32

<210> SEQ ID NO 65
<211> LENGTH: 35
<212> TYPE: DNA
<213> ORGANISM: Artificial Sequence
<220> FEATURE:
<223> OTHER INFORMATION: primer PfCSP-f(+209)

<400> SEQUENCE: 65
gactggatcc taacgctaat ccaaacgcta atccc        35

<210> SEQ ID NO 66
<211> LENGTH: 987
<212> TYPE: DNA
<213> ORGANISM: Influenza virus

<400> SEQUENCE: 66
gaccagattt gcatcggata ccacgccaac aacagcaccg agcaggtcga taccatcatg    60
gagaaaaacg tgaccgtcac ccacgctcag gacatcctgg agaagactca caatggaaag   120
ctctgcgacc tggacggcgt gaaacccctc atcctgagag attgttctgt ggccggatgg   180
ctgctgggaa accccatgtg cgatgaattt atcaacgtcc agagtggag ttacatcgtg    240 gagaaggcca accctgccaa cgacctgtgt taccccggca acttcaacga ctacgaggag   300
ctgaagcacc tgctctcacg catcaaccac ttcgagaaga tccagattat ccctaagtct   360
agttggagtg accacgaggc cagttccggc gtgtcctctg cctgtccata ccagggcaca   420
cccagtttct tcagaaacgt cgtctggctg atcaagaaga caacacata ccccaccatc   480

```
aagcgaagtt acaacaacac caaccaggag gacctcctca tcctgtgggg aatccaccac    540
tctaacgacg ctgccgaaca gacaaagctg taccagaatc ccaccaccta catctccgtg    600
ggaacaagca ccctcaacca gcgcctggtg cccaagatcg ctacacgatc aaaggtgaat    660
ggccagtccg gcaggatgga cttttttctgg accatcctca aacccaacga cgccatcaat    720
tttgagtcta atggcaactt catcgccccc gagtacgctt acaagatcgt caagaaagga    780
gactccgcca tcgtgaagtc cgaggtggag tacggcaact gcaacaccaa gtgccagacc    840
ccaattggag ccattaactc cagtatgccc ttccacaata tccacccact gacaattggc    900
gaatgcccca aatacgtgaa aagcaacaaa ctggtcctgg ctaccggact gcgcaacagc    960
cccctgcgcg agcgcaggcg caagaga                                        987
```

```
<210> SEQ ID NO 67
<211> LENGTH: 25
<212> TYPE: DNA
<213> ORGANISM: Artificial Sequence
<220> FEATURE:
<223> OTHER INFORMATION: primer AH-F1

<400> SEQUENCE: 67
cagtctgcag gaccagattt gcatc                                          25

<210> SEQ ID NO 68
<211> LENGTH: 25
<212> TYPE: DNA
<213> ORGANISM: Artificial Sequence
<220> FEATURE:
<223> OTHER INFORMATION: primer AH-R4

<400> SEQUENCE: 68
cagtcccggg ctctcttgcg cctgc                                          25

<210> SEQ ID NO 69
<211> LENGTH: 990
<212> TYPE: DNA
<213> ORGANISM: influenza virus

<400> SEQUENCE: 69
```

```
gaccagatct gtatcggata ccacgccaac aacagtaccg aacaggtgga caccattatg     60
gagaagaatg tgaccgtgac ccacgcccag gatatcctgg agaagaagca caacggcaaa    120
ctgtgcgatc tggacggcgt gaagcccctg atcctgcgcg attgctccgt ggccggatgg    180
ctgctgggca accctatgtg cgacgaattt atcaacgtgc ccgaatggag ttacattgtg    240
gagaaggcta accccgtgaa tgacctgtgc taccccggag acttcaacga ctacgaagag    300
ctgaagcatc tgctgtcaag gattaaccac ttcgagaaga tccagattat tcccaagtct    360
agctggagct cccacgaggc ctcactggga gtgtccagcg cctgccccta ccagggcaag    420
tcaagcttct ttcgcaacgt ggtgtggctg atcaagaaga atagtaccta ccccacaatc    480
aagaggtcct acaacaacac caaccaggaa gacctgctgg tgctgtgggg aatccatcac    540
cccaatgacg ctgccgaaca gaccaagctg taccagaacc caactaccta catcagcgtg    600
ggcaccagca cactgaacca gcgcctggtg cctagaatcg ccaccagatc caaagtgaac    660
ggccagtccg gccgcatgga attttttctgg acaatcctga agcccaatga tgccatcaac    720
ttcgagagca atggaaactt catcgccccc gaatacgcct acaagattgt gaaaaaggc    780
gattccacca tcatgaagtc agaactggag tacggcaact gtaacaccaa gtgccagact    840
cccatgggcg ccatcaactc cagcatgcca ttccacaaca tccatccact gaccatcggc    900
```

```
gagtgcccca agtacgtgaa gtccaacaga ctggtgctgg ctaccggact gcgcaattcc        960
ccacagaggg agagacgcag gaagaagaga                                        990
```

<210> SEQ ID NO 70
<211> LENGTH: 25
<212> TYPE: DNA
<213> ORGANISM: Artificial Sequence
<220> FEATURE:
<223> OTHER INFORMATION: primer VN-F1

<400> SEQUENCE: 70

```
cagtctgcag gaccagatct gtatc                                             25
```

<210> SEQ ID NO 71
<211> LENGTH: 25
<212> TYPE: DNA
<213> ORGANISM: Artificial Sequence
<220> FEATURE:
<223> OTHER INFORMATION: primer VN-R4

<400> SEQUENCE: 71

```
cagtcccggg ctctcttctt cctgc                                             25
```

<210> SEQ ID NO 72
<211> LENGTH: 34
<212> TYPE: DNA
<213> ORGANISM: Artificial Sequence
<220> FEATURE:
<223> OTHER INFORMATION: primer gp64(51)-f

<400> SEQUENCE: 72

```
gactccccgg gtggaaatca ccatcgtgga gacg                                   34
```

<210> SEQ ID NO 73
<211> LENGTH: 34
<212> TYPE: DNA
<213> ORGANISM: Artificial Sequence
<220> FEATURE:
<223> OTHER INFORMATION: primer gp64(101)-f

<400> SEQUENCE: 73

```
gactccccgg gatttgctta tgtggagcat cagg                                   34
```

<210> SEQ ID NO 74
<211> LENGTH: 34
<212> TYPE: DNA
<213> ORGANISM: Artificial Sequence
<220> FEATURE:
<223> OTHER INFORMATION: primer gp64(154)-f

<400> SEQUENCE: 74

```
gactccccgg gcgcaccaca cgtgcaacaa atcg                                   34
```

<210> SEQ ID NO 75
<211> LENGTH: 34
<212> TYPE: DNA
<213> ORGANISM: Artificial Sequence
<220> FEATURE:
<223> OTHER INFORMATION: primer gp64(201)-f

<400> SEQUENCE: 75

```
gactccccgg gacactgtgc ttcatcgaga cggc                                   34
```

<210> SEQ ID NO 76

<211> LENGTH: 1701
<212> TYPE: DNA
<213> ORGANISM: influenza virus

<400> SEQUENCE: 76

```
atggagaaga tcgtgctgtt gctggcaata gttagtttgg tcaagtcaga tcagatctgt      60
attgggtacc ac

```
<212> TYPE: DNA
<213> ORGANISM: Artificial Sequence
<220> FEATURE:
<223> OTHER INFORMATION: primer AH345-R

<400> SEQUENCE: 78
cgatcccggg ctctctttct cctccgctcg c                                     31

<210> SEQ ID NO 79
<211> LENGTH: 33
<212> TYPE: DNA
<213> ORGANISM: Artificial Sequence
<220> FEATURE:
<223> OTHER INFORMATION: primer AH410-R

<400> SEQUENCE: 79
cgatcccggg cggcctcgaa ctgggtgttc att                                   33

<210> SEQ ID NO 80
<211> LENGTH: 32
<212> TYPE: DNA
<213> ORGANISM: Artificial Sequence
<220> FEATURE:
<223> OTHER INFORMATION: primer AH473-R

<400> SEQUENCE: 80
cgatcccggg cgtctctgag ttgaaggcgc ac                                    32

<210> SEQ ID NO 81
<211> LENGTH: 33
<212> TYPE: DNA
<213> ORGANISM: Artificial Sequence
<220> FEATURE:
<223> OTHER INFORMATION: primer AH520-R

<400> SEQUENCE: 81
cgatcccggg caccactaat ttcctctcgc ttc                                   33

<210> SEQ ID NO 82
<211> LENGTH: 1704
<212> TYPE: DNA
<213> ORGANISM: influenza virus

<400> SEQUENCE: 82
atggagaaaa ttgtcctgct gttcgctatt gtttccctgg ttaaatccga tcagatctgt      60
atcggatatc acgcgaataa tagcacagag caagtggata ccattatgga aaagaatgtg     120
actgtgaccc acgctcagga cattctggag aaaaagcaca acggaaaatt gtgcgacctt     180 gatgggtga agccattgat tctgagagac tgctctgtgg ctggatggct gctggggaac     240
cctatgtgcg atgagttcat taatgttccc gagtggtcct acatagtcga aaaggctaat     300
cctgtcaatg atctttgcta ccctgggggat tttaatgact atgaggagct gaaacatttg     360
ttgagtagaa tcaaccactt tgagaaaatc cagatcatcc caagagttc ctggtcatct     420 catgaagcaa gccttggtgt gagctcagcc tgcccttatc aaggcaaatc cagcttcttt     480
cggaacgtgg tctggctcat caagaaaaat tcaacctatc cgactatcaa gagatcctat     540
aacaacacaa tcaggagga tctgttggta ctgtggggca tccaccatcc taacgatgca     600
gcagagcaga ccaagctcta ccagaaccca actacctaca tctccgttgg aactagcaca     660
ctgaaccaga gattggtacc tagaattgct acccgatcca aagtcaatgg ccagtccgga     720
agaatggaat tcttctggac aattctgaaa cccaatgacg ccattaattt cgagtcaaac     780
```

```
ggcaatttca ttgctccaga gtatgcttac aagatcgtga aaaagggtga tagtacaatt      840
atgaagagtg agttggagta cggcaactgc aatacaaaat gtcaaacacc catgggcgct      900
atcaattcat ccatgccttt ccacaatatc cacccccttc ctatcggaga gtgcccgaag      960
tatgtcaagt ccaacaggct ggtcctggca actggactgc ggaatagccc gcaacgcgaa     1020
cggaggagga aaaagcgggg actgtttgga gctattgcag gcttcatcga aggtggttgg     1080
cagggcatgg tggacggttg gtatgggtat catcactcca acgaacaggg gagcggttat     1140
gccgcagaca aagagtcaac tcagaaggca attgatggag ttacaaacaa agtgaatagc     1200
attatcgaca aaatgaatac gcagtttgag gctgtcggcc gcgagttcaa taatctggag     1260
cggagaatcg aaaacctgaa caaaaagatg gaggacggct tcctggacgt gtggacatat     1320
aacgcagaac tgctcgtgct tatggagaat aacggaccc tcgattttca cgactccaac      1380
gtaaagaatc tgtatgacaa agtcaggctc cagcttagag ataacgccaa ggaattgggg     1440
aatggatgtt ttgaattcta ccataagtgc gacaacgagt gcatggagtc cgtaagaaac     1500
ggaacctatg actatcccca gtactcagag gaggcaagac ttaaaagaga ggagattagt     1560
ggtgtgaaac tcgagtccat aggcatctat cagatcctga gtatctactc tacggtggcg     1620
tcatccctgg ccctggccat catggttgct ggcttgtcac tctggatgtg tagtaacggg     1680
agtctgcaat gcagaatatg tatt                                            1704

<210> SEQ ID NO 83
<211> LENGTH: 32
<212> TYPE: DNA
<213> ORGANISM: Artificial Sequence
<220> FEATURE:
<223> OTHER INFORMATION: primer VN17-F

<400> SEQUENCE: 83
gactctgcag gatcagatct gtatcggata tc                                     32

<210> SEQ ID NO 84
<211> LENGTH: 33
<212> TYPE: DNA
<213> ORGANISM: Artificial Sequence
<220> FEATURE:
<223> OTHER INFORMATION: primer VN346-R

<400> SEQUENCE: 84
cgatcccggg cccgcttttt cctcctccgt tcg                                    33

<210> SEQ ID NO 85
<211> LENGTH: 33
<212> TYPE: DNA
<213> ORGANISM: Artificial Sequence
<220> FEATURE:
<223> OTHER INFORMATION: primer VN410-R

<400> SEQUENCE: 85
cgatcccggg cctcaaactg cgtattcatt ttg                                    33

<210> SEQ ID NO 86
<211> LENGTH: 35
<212> TYPE: DNA
<213> ORGANISM: Artificial Sequence
<220> FEATURE:
<223> OTHER INFORMATION: primer VN473-R

<400> SEQUENCE: 86
cgatcccggg ctctaagctg gagcctgact ttgtc                                  35
```

```
<210> SEQ ID NO 87
<211> LENGTH: 34
<212> TYPE: DNA
<213> ORGANISM: Artificial Sequence
<220> FEATURE:
<223> OTHER INFORMATION: primer VN520-R

<400> SEQUENCE: 87
cgatcccggg cactaatctc ctctcttta agtc                                  34

<210> SEQ ID NO 88
<211> LENGTH: 1191
<212> TYPE: DNA
<213> ORGANISM: Plasmodium falciparum

<400> SEQUENCE: 88
atgatgcgaa aattggccat actgtcagtc agcagcttct tgttcgtgga ggccctgttt     60
caggaatacc agtgctatgg ttccagctct aatacgcgag ttctgaacga gctgaactac    120
gataacgccg gcaccaacct ctacaatgag ctggagatga attactacgg caagcaggag    180
aattggtact cactcaagaa gaactccaga agtctcgggg agaacgacga cggaaataat    240
gaggacaacg aaaaacttag aaacccaaa cacaagaaac tgaaacaacc tgccgatggt    300
aatcctgatc ctaatgcaaa cccaaatgtg accccaatg ctaacccaa cgtcgatccg    360 aacgcgaacc taatgtgga tcctaacgcc aatccaaacg cgaatccgaa tgccaaccca    420
aacgccaacc caaacgctaa ccccaacgcg aaccccaacg ctaatccgaa cgccaatccc    480
aatgctaatc ccaatgcgaa ccctaacgct aatcccaacg caaatccgaa cgcaaaccct    540
aacgcaaacc ccaatgccaa ccctaacgcc aacccgaatg ccaatcctaa tgtggacccg    600
aacgccaatc cgaatgcaaa cccaaatgcc aatccaaacg ctaatcctaa cgccaaccccc    660 aacgccaacc ctaatgctaa tccgaatgcg aatccaaatg ctaacccgaa cgctaatcca    720
aatgcaaatc ccaatgcaaa tccaaatgcg aacccgaatg ctaaccctaa tgcaaatcct    780
aatgcaaacc ctaatgcgaa tcccaatgca aaccccaata gaataatca gggaaatggc    840 cagggacata atatgcctaa tgaccctaac aggaacgttg atgagaacgc gaatgcgaac    900
tctgctgtaa agaacaacaa caatgaagag ccctccgata acatattaa ggagtatctg    960 aataagatcc agaactcctt gtctaccgaa tggtccccct gttctgtgac gtgtggtaac   1020
ggaatccagg taaggatcaa acccggcagt gccaacaagc caaggacga gctcgattac   1080 gctaatgata ttgaaaagaa aattgtaag atggagaagt gcagctccgt attcaatgtg   1140
gtcaacagct caattggcct catcatggtt ctttccttc tgttcctcaa t             1191

<210> SEQ ID NO 89
<211> LENGTH: 34
<212> TYPE: DNA
<213> ORGANISM: Artificial Sequence
<220> FEATURE:
<223> OTHER INFORMATION: primer PfCSP_opt-f

<400> SEQUENCE: 89
gactctgcag atgatgcgaa aattggccat actg                                 34

<210> SEQ ID NO 90
<211> LENGTH: 39
<212> TYPE: DNA
<213> ORGANISM: Artificial Sequence
<220> FEATURE:
```

<223> OTHER INFORMATION: primer PfCSP_opt-r(397)

<400> SEQUENCE: 90
cgatcccggg cattgaggaa cagaaaggaa agaaccatg                                   39

<210> SEQ ID NO 91
<211> LENGTH: 36
<212> TYPE: DNA
<213> ORGANISM: Artificial Sequence
<220> FEATURE:
<223> OTHER INFORMATION: primer PfCSP_opt-f(19)

<400> SEQUENCE: 91
gactctgcag ctgtttcagg aataccagtg ctatgg                                     36

<210> SEQ ID NO 92
<211> LENGTH: 50
<212> TYPE: DNA
<213> ORGANISM: Artificial Sequence
<220> FEATURE:
<223> OTHER INFORMATION: primer PfCSP_opt-r(373)

<400> SEQUENCE: 92
cgatcccggg ccttctccat cttacaaatt ttcttttcaa tatcattagc                      50

<210> SEQ ID NO 93
<211> LENGTH: 35
<212> TYPE: DNA
<213> ORGANISM: Artificial Sequence
<220> FEATURE:
<223> OTHER INFORMATION: primer PfCSP_opt-f(76)

<400> SEQUENCE: 93
gactctgcag gacgacggaa ataatgagga caacg                                      35

<210> SEQ ID NO 94
<211> LENGTH: 39
<212> TYPE: DNA
<213> ORGANISM: Artificial Sequence
<220> FEATURE:
<223> OTHER INFORMATION: primer PfCSP_opt-f(205)

<400> SEQUENCE: 94
gactctgcag aatgcaaacc caaatgccaa tccaaacgc                                  39

<210> SEQ ID NO 95
<211> LENGTH: 40
<212> TYPE: DNA
<213> ORGANISM: Artificial Sequence
<220> FEATURE:
<223> OTHER INFORMATION: primer gp64-p-f

<400> SEQUENCE: 95
gactcggacc ggccagataa aaataatctt atcaattaag                                 40

<210> SEQ ID NO 96
<211> LENGTH: 35
<212> TYPE: DNA
<213> ORGANISM: Artificial Sequence
<220> FEATURE:
<223> OTHER INFORMATION: primer gp64-p-r

<400> SEQUENCE: 96
cgatactagt agcactgagg cttcttatat acccg                                      35

```
<210> SEQ ID NO 97
<211> LENGTH: 38
<212> TYPE: DNA
<213> ORGANISM: Artificial Sequence
<220> FEATURE:
<223> OTHER INFORMATION: primer vp39-p-f

<400> SEQUENCE: 97
gactcggacc gcgtcgtaca aatcgaaata ttgttgtg                              38

<210> SEQ ID NO 98
<211> LENGTH: 36
<212> TYPE: DNA
<213> ORGANISM: Artificial Sequence
<220> FEATURE:
<223> OTHER INFORMATION: primer gp64-p-r

<400> SEQUENCE: 98
cgatactagt gtgattgaga aagaaatctc ttattc                                36

<210> SEQ ID NO 99
<211> LENGTH: 35
<212> TYPE: DNA
<213> ORGANISM: Artificial Sequence
<220> FEATURE:
<223> OTHER INFORMATION: primer VSV-G-f

<400> SEQUENCE: 99
gactccccgg gcgttcgaac atcctcacat tcaag                                 35

<210> SEQ ID NO 100
<211> LENGTH: 34
<212> TYPE: DNA
<213> ORGANISM: Artificial Sequence
<220> FEATURE:
<223> OTHER INFORMATION: primer VSV-G-r

<400> SEQUENCE: 100
gactcactta gtgctttcca agtcggttca tctc                                  34

<210> SEQ ID NO 101
<211> LENGTH: 20
<212> TYPE: DNA
<213> ORGANISM: Artificial Sequence
<220> FEATURE:
<223> OTHER INFORMATION: primer HA1_F01

<400> SEQUENCE: 101
gagctgaggg agcaattgag                                                  20

<210> SEQ ID NO 102
<211> LENGTH: 20
<212> TYPE: DNA
<213> ORGANISM: Artificial Sequence
<220> FEATURE:
<223> OTHER INFORMATION: primer HA1_R01

<400> SEQUENCE: 102
gggtgatgaa taccccacag                                                  20

<210> SEQ ID NO 103
<211> LENGTH: 9
<212> TYPE: PRT
<213> ORGANISM: Artificial Sequence
<220> FEATURE:
<223> OTHER INFORMATION: A peptide of CD 8 epitope of PbCSP
```

-continued

<400> SEQUENCE: 103

Ser Tyr Ile Pro Ser Ala Glu Lys Ile
1               5

<210> SEQ ID NO 104
<211> LENGTH: 397
<212> TYPE: PRT
<213> ORGANISM: Plasmodium falciparum
<220> FEATURE:
<223> OTHER INFORMATION: PfCSP protein XP_001351122

<400> SEQUENCE: 104

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
            100                 105                 110

Asn Ala Asn Pro Asn Val Asp Pro Asn Ala Asn Pro Asn Val Asp Pro
        115                 120                 125

Asn Ala Asn Pro Asn Ala Asn Pro Asn Ala Asn Pro Asn Ala Asn Pro
    130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190

Asn Ala Asn Pro Asn Val Asp Pro Asn Ala Asn Pro Asn Ala Asn Pro
        195                 200                 205

Asn Ala Asn Pro Asn Ala Asn Pro Asn Ala Asn Pro Asn Ala Asn Pro
    210                 215                 220

Asn Ala Asn Pro Asn Ala Asn Pro Asn Ala Asn Pro Asn Ala Asn Pro
225                 230                 235                 240

Asn Ala Asn Pro Asn Ala Asn Pro Asn Ala Asn Pro Asn Ala Asn Pro
                245                 250                 255

Asn Ala Asn Pro Asn Ala Asn Pro Asn Ala Asn Pro Asn Ala Asn Pro
            260                 265                 270

Asn Lys Asn Asn Gln Gly Asn Gly Gln Gly His Asn Met Pro Asn Asp
        275                 280                 285

Pro Asn Arg Asn Val Asp Glu Asn Ala Asn Ala Asn Ser Ala Val Lys
    290                 295                 300

Asn Asn Asn Asn Glu Glu Pro Ser Asp Lys His Ile Lys Glu Tyr Leu
305                 310                 315                 320

Asn Lys Ile Gln Asn Ser Leu Ser Thr Glu Trp Ser Pro Cys Ser Val
                325                 330                 335

Thr Cys Gly Asn Gly Ile Gln Val Arg Ile Lys Pro Gly Ser Ala Asn

```
            340             345             350
Lys Pro Lys Asp Glu Leu Asp Tyr Ala Asn Asp Ile Glu Lys Lys Ile
            355             360             365
Cys Lys Met Glu Lys Cys Ser Ser Val Phe Asn Val Asn Ser Ser
        370             375             380
Ile Gly Leu Ile Met Val Leu Ser Phe Leu Phe Leu Asn
385             390             395

<210> SEQ ID NO 105
<211> LENGTH: 567
<212> TYPE: PRT
<213> ORGANISM: influenza virus
<220> FEATURE:
<223> OTHER INFORMATION: HA/A/Anhui/1/2005 protein ABD28180

<400> SEQUENCE: 105

Met Glu Lys Ile Val Leu Leu Leu Ala Ile Val Ser Leu Val Lys Ser
1               5                   10                  15
Asp Gln Ile Cys Ile Gly Tyr His Ala Asn Asn Ser Thr Glu Gln Val
            20                  25                  30
Asp Thr Ile Met Glu Lys Asn Val Thr Val Thr His Ala Gln Asp Ile
        35                  40                  45
Leu Glu Lys Thr His Asn Gly Lys Leu Cys Asp Leu Asp Gly Val Lys
    50                  55                  60
Pro Leu Ile Leu Arg Asp Cys Ser Val Ala Gly Trp Leu Leu Gly Asn
65                  70                  75                  80
Pro Met Cys Asp Glu Phe Ile Asn Val Pro Glu Trp Ser Tyr Ile Val
                85                  90                  95
Glu Lys Ala Asn Pro Ala Asn Asp Leu Cys Tyr Pro Gly Asn Phe Asn
            100                 105                 110
Asp Tyr Glu Glu Leu Lys His Leu Leu Ser Arg Ile Asn His Phe Glu
        115                 120                 125
Lys Ile Gln Ile Ile Pro Lys Ser Ser Trp Ser Asp His Glu Ala Ser
    130                 135                 140
Ser Gly Val Ser Ser Ala Cys Pro Tyr Gln Gly Thr Pro Ser Phe Phe
145                 150                 155                 160
Arg Asn Val Val Trp Leu Ile Lys Lys Asn Asn Thr Tyr Pro Thr Ile
                165                 170                 175
Lys Arg Ser Tyr Asn Asn Thr Asn Gln Glu Asp Leu Leu Ile Leu Trp
            180                 185                 190
Gly Ile His His Ser Asn Asp Ala Ala Glu Gln Thr Lys Leu Tyr Gln
        195                 200                 205
Asn Pro Thr Thr Tyr Ile Ser Val Gly Thr Ser Thr Leu Asn Gln Arg
    210                 215                 220
Leu Val Pro Lys Ile Ala Thr Arg Ser Lys Val Asn Gly Gln Ser Gly
225                 230                 235                 240
Arg Met Asp Phe Phe Trp Thr Ile Leu Lys Pro Asn Asp Ala Ile Asn
                245                 250                 255
Phe Glu Ser Asn Gly Asn Phe Ile Ala Pro Glu Tyr Ala Tyr Lys Ile
            260                 265                 270
Val Lys Lys Gly Asp Ser Ala Ile Val Lys Ser Glu Val Glu Tyr Gly
        275                 280                 285
Asn Cys Asn Thr Lys Cys Gln Thr Pro Ile Gly Ala Ile Asn Ser Ser
    290                 295                 300
Met Pro Phe His Asn Ile His Pro Leu Thr Ile Gly Glu Cys Pro Lys
```

```
            305                 310                 315                 320

Tyr Val Lys Ser Asn Lys Leu Val Leu Ala Thr Gly Leu Arg Asn Ser
                325                 330                 335

Pro Leu Arg Glu Arg Arg Lys Arg Gly Leu Phe Gly Ala Ile Ala
                340                 345                 350

Gly Phe Ile Glu Gly Gly Trp Gln Gly Met Val Asp Gly Trp Tyr Gly
                355                 360                 365

Tyr His His Ser Asn Glu Gln Gly Ser Gly Tyr Ala Ala Asp Lys Glu
                370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
                420                 425                 430

Phe Leu Asp Val Trp Thr Tyr Asn Ala Glu Leu Leu Val Leu Met Glu
                435                 440                 445

Asn Glu Arg Thr Leu Asp Phe His Asp Ser Asn Val Lys Asn Leu Tyr
                450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Arg
                500                 505                 510

Leu Lys Arg Glu Glu Ile Ser Gly Val Lys Leu Glu Ser Ile Gly Thr
                515                 520                 525

Tyr Gln Ile Leu Ser Ile Tyr Ser Thr Val Ala Ser Ser Leu Ala Leu
                530                 535                 540

Ala Ile Met Val Ala Gly Leu Ser Leu Trp Met Cys Ser Asn Gly Ser
545                 550                 555                 560

Leu Gln Cys Arg Ile Cys Ile
                565

<210> SEQ ID NO 106
<211> LENGTH: 568
<212> TYPE: PRT
<213> ORGANISM: influenza virus
<220> FEATURE:
<223> OTHER INFORMATION: HA/A/Vietnam/1203/2004 protein  AAW80717

<400> SEQUENCE: 106

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asp Ile
                35                  40                  45

Leu Glu Lys Lys His Asn Gly Lys Leu Cys Asp Leu Asp Gly Val Lys
                50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
```

-continued

```
            100                 105                 110
Asp Tyr Glu Glu Leu Lys His Leu Leu Ser Arg Ile Asn His Phe Glu
            115                 120                 125

Lys Ile Gln Ile Ile Pro Lys Ser Ser Trp Ser Ser His Glu Ala Ser
            130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
                180                 185                 190

Gly Ile His His Pro Asn Asp Ala Ala Glu Gln Thr Lys Leu Tyr Gln
                195                 200                 205

Asn Pro Thr Thr Tyr Ile Ser Val Gly Thr Ser Thr Leu Asn Gln Arg
            210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
                260                 265                 270

Val Lys Lys Gly Asp Ser Thr Ile Met Lys Ser Glu Leu Glu Tyr Gly
            275                 280                 285

Asn Cys Asn Thr Lys Cys Gln Thr Pro Met Gly Ala Ile Asn Ser Ser
            290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Arg Lys Lys Arg Gly Leu Phe Gly Ala Ile
                340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
            370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
                420                 425                 430

Gly Phe Leu Asp Val Trp Thr Tyr Asn Ala Glu Leu Leu Val Leu Met
                435                 440                 445

Glu Asn Glu Arg Thr Leu Asp Phe His Asp Ser Asn Val Lys Asn Leu
            450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
                500                 505                 510

Arg Leu Lys Arg Glu Glu Ile Ser Gly Val Lys Leu Glu Ser Ile Gly
                515                 520                 525
```

```
Ile Tyr Gln Ile Leu Ser Ile Tyr Ser Thr Val Ala Ser Ser Leu Ala
            530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 107
<211> LENGTH: 1720
<212> TYPE: PRT
<213> ORGANISM: Plasmodium falciparum
<220> FEATURE:
<223> OTHER INFORMATION: PfMSP1 protein  XP_001352170

<400> SEQUENCE: 107

Met Lys Ile Ile Phe Phe Leu Cys Ser Phe Leu Phe Phe Ile Ile Asn
1               5                   10                  15

Thr Gln Cys Val Thr His Glu Ser Tyr Gln Glu Leu Val Lys Lys Leu
            20                  25                  30

Glu Ala Leu Glu Asp Ala Val Leu Thr Gly Tyr Ser Leu Phe Gln Lys
        35                  40                  45

Glu Lys Met Val Leu Asn Glu Glu Ile Thr Thr Lys Gly Ala Ser
    50                  55                  60

Ala Gln Ser Gly Ala Ser Ala Gln Ser Gly Ala Ser Ala Gln Ser Gly
65                  70                  75                  80

Ala Ser Ala Gln Ser Gly Ala Ser Ala Gln Ser Gly Ala Ser Ala Gln
                85                  90                  95

Ser Gly Thr Ser Gly Pro Ser Gly Pro Ser Gly Thr Ser Pro Ser Ser
            100                 105                 110

Arg Ser Asn Thr Leu Pro Arg Ser Asn Thr Ser Ser Gly Ala Ser Pro
        115                 120                 125

Pro Ala Asp Ala Ser Asp Ser Asp Ala Lys Ser Tyr Ala Asp Leu Lys
130                 135                 140

His Arg Val Arg Asn Tyr Leu Phe Thr Ile Lys Glu Leu Lys Tyr Pro
145                 150                 155                 160

Glu Leu Phe Asp Leu Thr Asn His Met Leu Thr Leu Cys Asp Asn Ile
                165                 170                 175

His Gly Phe Lys Tyr Leu Ile Asp Gly Tyr Glu Glu Ile Asn Glu Leu
            180                 185                 190

Leu Tyr Lys Leu Asn Phe Tyr Phe Asp Leu Leu Arg Ala Lys Leu Asn
        195                 200                 205

Asp Val Cys Ala Asn Asp Tyr Cys Gln Ile Pro Phe Asn Leu Lys Ile
210                 215                 220

Arg Ala Asn Glu Leu Asp Val Leu Lys Lys Leu Val Phe Gly Tyr Arg
225                 230                 235                 240

Lys Pro Leu Asp Asn Ile Lys Asp Asn Val Gly Lys Met Glu Asp Tyr
                245                 250                 255

Ile Lys Lys Asn Lys Thr Thr Ile Ala Asn Ile Asn Glu Leu Ile Glu
            260                 265                 270

Gly Ser Lys Lys Thr Ile Asp Gln Asn Lys Asn Ala Asp Asn Glu Glu
        275                 280                 285

Gly Lys Lys Lys Leu Tyr Gln Ala Gln Tyr Asp Leu Ser Ile Tyr Asn
290                 295                 300

Lys Gln Leu Glu Glu Ala His Asn Leu Ile Ser Val Leu Glu Lys Arg
305                 310                 315                 320
```

```
Ile Asp Thr Leu Lys Lys Asn Glu Asn Ile Lys Lys Leu Leu Asp Lys
            325                 330                 335

Ile Asn Glu Ile Lys Asn Pro Pro Ala Asn Ser Gly Asn Thr Pro
            340                 345                 350

Asn Thr Leu Leu Asp Lys Asn Lys Lys Ile Glu Glu His Glu Glu Lys
            355                 360                 365

Ile Lys Glu Ile Ala Lys Thr Ile Lys Phe Asn Ile Asp Ser Leu Phe
        370                 375                 380

Thr Asp Pro Leu Glu Leu Glu Tyr Tyr Leu Arg Glu Lys Asn Lys Lys
385                 390                 395                 400

Val Asp Val Thr Pro Lys Ser Gln Asp Pro Thr Lys Ser Val Gln Ile
                405                 410                 415

Pro Lys Val Pro Tyr Pro Asn Gly Ile Val Tyr Pro Leu Pro Leu Thr
                420                 425                 430

Asp Ile His Asn Ser Leu Ala Ala Asp Asn Asp Lys Asn Ser Tyr Gly
            435                 440                 445

Asp Leu Met Asn Pro His Thr Lys Glu Lys Ile Asn Glu Lys Ile Ile
        450                 455                 460

Thr Asp Asn Lys Glu Arg Lys Ile Phe Ile Asn Asn Ile Lys Lys Lys
465                 470                 475                 480

Ile Asp Leu Glu Glu Lys Asn Ile Asn His Thr Lys Glu Gln Asn Lys
                485                 490                 495

Lys Leu Leu Glu Asp Tyr Glu Lys Ser Lys Lys Asp Tyr Glu Glu Leu
            500                 505                 510

Leu Glu Lys Phe Tyr Glu Met Lys Phe Asn Asn Asn Phe Asn Lys Asp
            515                 520                 525

Val Val Asp Lys Ile Phe Ser Ala Arg Tyr Thr Tyr Asn Val Glu Lys
        530                 535                 540

Gln Arg Tyr Asn Asn Lys Phe Ser Ser Ser Asn Asn Ser Val Tyr Asn
545                 550                 555                 560

Val Gln Lys Leu Lys Lys Ala Leu Ser Tyr Leu Glu Asp Tyr Ser Leu
                565                 570                 575

Arg Lys Gly Ile Ser Glu Lys Asp Phe Asn His Tyr Tyr Thr Leu Lys
            580                 585                 590

Thr Gly Leu Glu Ala Asp Ile Lys Lys Leu Thr Glu Glu Ile Lys Ser
        595                 600                 605

Ser Glu Asn Lys Ile Leu Glu Lys Asn Phe Lys Gly Leu Thr His Ser
            610                 615                 620

Ala Asn Gly Ser Leu Glu Val Ser Asp Ile Val Lys Leu Gln Val Gln
625                 630                 635                 640

Lys Val Leu Leu Ile Lys Lys Ile Glu Asp Leu Arg Lys Ile Glu Leu
                645                 650                 655

Phe Leu Lys Asn Ala Gln Leu Lys Asp Ser Ile His Val Pro Asn Ile
            660                 665                 670

Tyr Lys Pro Gln Asn Lys Pro Glu Pro Tyr Tyr Leu Ile Val Leu Lys
        675                 680                 685

Lys Glu Val Asp Lys Leu Lys Glu Phe Ile Pro Lys Val Lys Asp Met
        690                 695                 700

Leu Lys Lys Glu Gln Ala Val Leu Ser Ser Ile Thr Gln Pro Leu Val
705                 710                 715                 720

Ala Ala Ser Glu Thr Thr Glu Asp Gly Gly His Ser Thr His Thr Leu
                725                 730                 735
```

```
Ser Gln Ser Gly Glu Thr Glu Val Thr Glu Thr Glu Thr Glu
            740                 745                 750

Glu Thr Val Gly His Thr Thr Val Thr Ile Thr Leu Pro Pro Thr
            755                 760                 765

Gln Pro Ser Pro Pro Lys Glu Val Lys Val Val Glu Asn Ser Ile Glu
            770                 775                 780

His Lys Ser Asn Asp Asn Ser Gln Ala Leu Thr Lys Thr Val Tyr Leu
785             790                 795                 800

Lys Lys Leu Asp Glu Phe Leu Thr Lys Ser Tyr Ile Cys His Lys Tyr
                805                 810                 815

Ile Leu Val Ser Asn Ser Ser Met Asp Gln Lys Leu Leu Glu Val Tyr
            820                 825                 830

Asn Leu Thr Pro Glu Glu Asn Glu Leu Lys Ser Cys Asp Pro Leu
            835                 840                 845

Asp Leu Leu Phe Asn Ile Gln Asn Asn Ile Pro Ala Met Tyr Ser Leu
            850                 855                 860

Tyr Asp Ser Met Asn Asn Asp Leu Gln His Leu Phe Phe Glu Leu Tyr
865             870                 875                 880

Gln Lys Glu Met Ile Tyr Tyr Leu His Lys Leu Lys Glu Glu Asn His
                885                 890                 895

Ile Lys Lys Leu Leu Glu Glu Gln Lys Gln Ile Thr Gly Thr Ser Ser
            900                 905                 910

Thr Ser Ser Pro Gly Asn Thr Thr Val Asn Thr Ala Gln Ser Ala Thr
            915                 920                 925

His Ser Asn Ser Gln Asn Gln Gln Ser Asn Ala Ser Ser Thr Asn Thr
            930                 935                 940

Gln Asn Gly Val Ala Val Ser Ser Gly Pro Ala Val Val Glu Glu Ser
945             950                 955                 960

His Asp Pro Leu Thr Val Leu Ser Ile Ser Asn Asp Leu Lys Gly Ile
                965                 970                 975

Val Ser Leu Leu Asn Leu Gly Asn Lys Thr Lys Val Pro Asn Pro Leu
            980                 985                 990

Thr Ile Ser Thr Thr Glu Met Glu Lys Phe Tyr Glu Asn Ile Leu Lys
            995                 1000                1005

Asn Asn Asp Thr Tyr Phe Asp Asp Ile Lys Gln Phe Val Lys
1010                1015                1020

Ser Asn Ser Lys Val Ile Thr Gly Leu Thr Glu Thr Gln Lys Asn
1025                1030                1035

Ala Leu Asn Asp Glu Ile Lys Lys Leu Lys Asp Thr Leu Gln Leu
1040                1045                1050

Ser Phe Asp Leu Tyr Asn Lys Tyr Lys Leu Lys Leu Asp Arg Leu
1055                1060                1065

Phe Asn Lys Lys Lys Glu Leu Gly Gln Asp Lys Met Gln Ile Lys
1070                1075                1080

Lys Leu Thr Leu Leu Lys Glu Gln Leu Glu Ser Lys Leu Asn Ser
1085                1090                1095

Leu Asn Asn Pro His Asn Val Leu Gln Asn Phe Ser Val Phe Phe
1100                1105                1110

Asn Lys Lys Lys Glu Ala Glu Ile Ala Glu Thr Glu Asn Thr Leu
1115                1120                1125

Glu Asn Thr Lys Ile Leu Leu Lys His Tyr Lys Gly Leu Val Lys
1130                1135                1140

Tyr Tyr Asn Gly Glu Ser Ser Pro Leu Lys Thr Leu Ser Glu Val
```

-continued

```
                1145                1150                1155

Ser Ile Gln Thr Glu Asp Asn Tyr Ala Asn Leu Glu Lys Phe Arg
                1160                1165                1170

Val Leu Ser Lys Ile Asp Gly Lys Leu Asn Asp Asn Leu His Leu
                1175                1180                1185

Gly Lys Lys Lys Leu Ser Phe Leu Ser Ser Gly Leu His His Leu
                1190                1195                1200

Ile Thr Glu Leu Lys Glu Val Ile Lys Asn Lys Asn Tyr Thr Gly
                1205                1210                1215

Asn Ser Pro Ser Glu Asn Asn Lys Lys Val Asn Glu Ala Leu Lys
                1220                1225                1230

Ser Tyr Glu Asn Phe Leu Pro Glu Ala Lys Val Thr Thr Val Val
                1235                1240                1245

Thr Pro Pro Gln Pro Asp Val Thr Pro Ser Pro Leu Ser Val Arg
                1250                1255                1260

Val Ser Gly Ser Ser Gly Ser Thr Lys Glu Glu Thr Gln Ile Pro
                1265                1270                1275

Thr Ser Gly Ser Leu Leu Thr Glu Leu Gln Gln Val Val Gln Leu
                1280                1285                1290

Gln Asn Tyr Asp Glu Glu Asp Ser Leu Val Val Leu Pro Ile
                1295                1300                1305

Phe Gly Glu Ser Glu Asp Asn Asp Glu Tyr Leu Asp Gln Val Val
                1310                1315                1320

Thr Gly Glu Ala Ile Ser Val Thr Met Asp Asn Ile Leu Ser Gly
                1325                1330                1335

Phe Glu Asn Glu Tyr Asp Val Ile Tyr Leu Lys Pro Leu Ala Gly
                1340                1345                1350

Val Tyr Arg Ser Leu Lys Lys Gln Ile Glu Lys Asn Ile Phe Thr
                1355                1360                1365

Phe Asn Leu Asn Leu Asn Asp Ile Leu Asn Ser Arg Leu Lys Lys
                1370                1375                1380

Arg Lys Tyr Phe Leu Asp Val Leu Glu Ser Asp Leu Met Gln Phe
                1385                1390                1395

Lys His Ile Ser Ser Asn Glu Tyr Ile Ile Glu Asp Ser Phe Lys
                1400                1405                1410

Leu Leu Asn Ser Glu Gln Lys Asn Thr Leu Leu Lys Ser Tyr Lys
                1415                1420                1425

Tyr Ile Lys Glu Ser Val Glu Asn Asp Ile Lys Phe Ala Gln Glu
                1430                1435                1440

Gly Ile Ser Tyr Tyr Glu Lys Val Leu Ala Lys Tyr Lys Asp Asp
                1445                1450                1455

Leu Glu Ser Ile Lys Lys Val Ile Lys Glu Glu Lys Glu Lys Phe
                1460                1465                1470

Pro Ser Ser Pro Pro Thr Thr Pro Pro Ser Pro Ala Lys Thr Asp
                1475                1480                1485

Glu Gln Lys Lys Glu Ser Lys Phe Leu Pro Phe Leu Thr Asn Ile
                1490                1495                1500

Glu Thr Leu Tyr Asn Asn Leu Val Asn Lys Ile Asp Asp Tyr Leu
                1505                1510                1515

Ile Asn Leu Lys Ala Lys Ile Asn Asp Cys Asn Val Glu Lys Asp
                1520                1525                1530

Glu Ala His Val Lys Ile Thr Lys Leu Ser Asp Leu Lys Ala Ile
                1535                1540                1545
```

```
Asp Asp Lys Ile Asp Leu Phe Lys Asn Pro Tyr Asp Phe Glu Ala
    1550                1555                1560

Ile Lys Lys Leu Ile Asn Asp Asp Thr Lys Lys Asp Met Leu Gly
    1565                1570                1575

Lys Leu Leu Ser Thr Gly Leu Val Gln Asn Phe Pro Asn Thr Ile
    1580                1585                1590

Ile Ser Lys Leu Ile Glu Gly Lys Phe Gln Asp Met Leu Asn Ile
    1595                1600                1605

Ser Gln His Gln Cys Val Lys Lys Gln Cys Pro Glu Asn Ser Gly
    1610                1615                1620

Cys Phe Arg His Leu Asp Glu Arg Glu Cys Lys Cys Leu Leu
    1625                1630                1635

Asn Tyr Lys Gln Glu Gly Asp Lys Cys Val Glu Asn Pro Asn Pro
    1640                1645                1650

Thr Cys Asn Glu Asn Asn Gly Gly Cys Asp Ala Asp Ala Thr Cys
    1655                1660                1665

Thr Glu Glu Asp Ser Gly Ser Ser Arg Lys Lys Ile Thr Cys Glu
    1670                1675                1680

Cys Thr Lys Pro Asp Ser Tyr Pro Leu Phe Asp Gly Ile Phe Cys
    1685                1690                1695

Ser Ser Ser Asn Phe Leu Gly Ile Ser Phe Leu Leu Ile Leu Met
    1700                1705                1710

Leu Ile Leu Tyr Ser Phe Ile
    1715                1720

<210> SEQ ID NO 108
<211> LENGTH: 217
<212> TYPE: PRT
<213> ORGANISM: Plasmodium falciparum
<220> FEATURE:
<223> OTHER INFORMATION: Pfs25 protein  XP_001347587

<400> SEQUENCE: 108

Met Asn Lys Leu Tyr Ser Leu Phe Leu Phe Leu Phe Ile Gln Leu Ser
1               5                   10                  15

Ile Lys Tyr Asn Asn Ala Lys Val Thr Val Asp Thr Val Cys Lys Arg
                20                  25                  30

Gly Phe Leu Ile Gln Met Ser Gly His Leu Glu Cys Cys Glu Asn
                35                  40                  45

Asp Leu Val Leu Val Asn Glu Glu Thr Cys Glu Glu Lys Val Leu Lys
        50                  55                  60

Cys Asp Glu Lys Thr Val Asn Lys Pro Cys Gly Asp Phe Ser Lys Cys
65                  70                  75                  80

Ile Lys Ile Asp Gly Asn Pro Val Ser Tyr Ala Cys Lys Cys Asn Leu
                85                  90                  95

Gly Tyr Asp Met Val Asn Asn Val Cys Ile Pro Asn Glu Cys Lys Asn
                100                 105                 110

Val Thr Cys Gly Asn Gly Lys Cys Ile Leu Asp Thr Ser Asn Pro Val
        115                 120                 125

Lys Thr Gly Val Cys Ser Cys Asn Ile Gly Lys Val Pro Asn Val Gln
        130                 135                 140

Asp Gln Asn Lys Cys Ser Lys Asp Gly Glu Thr Lys Cys Ser Leu Lys
145                 150                 155                 160

Cys Leu Lys Glu Asn Glu Thr Cys Lys Ala Val Asp Gly Ile Tyr Lys
                165                 170                 175
```

Cys Asp Cys Lys Asp Gly Phe Ile Ile Asp Asn Glu Ser Ser Ile Cys
            180                 185                 190

Thr Ala Phe Ser Ala Tyr Asn Ile Leu Asn Leu Ser Ile Met Phe Ile
        195                 200                 205

Leu Phe Ser Val Cys Phe Phe Ile Met
        210                 215

<210> SEQ ID NO 109
<211> LENGTH: 1194
<212> TYPE: DNA
<213> ORGANISM: Plasmodium falciparum
<220> FEATURE:
<223> OTHER INFORMATION: PfCSP gene XM_001351086

<400> SEQUENCE: 109

```
atgatgagaa aattagctat tttatctgtt tcttcctttt tatttgttga ggccttattc      60
caggaatacc agtgctatgg aagttcgtca aacacaaggg ttctaaatga attaaattat     120
gataatgcag gcactaattt atataatgaa ttagaaatga attattatgg gaaacaggaa     180
aattggtata gtcttaaaaa aaatagtaga tcacttggag aaaatgatga tggaaataac     240
gaagacaacg agaaattaag gaaaccaaaa cataaaaaat aaagcaacc agcggatggt      300
aatcctgatc caaatgcaaa cccaaatgta gatcccaatg ccaacccaaa tgtagatcca     360
aatgcaaacc caaatgtaga tccaaatgca acccaaatg caaacccaaa tgcaaaccca     420
aatgcaaacc caaatgcaaa cccaaatgca acccaaatg caaacccaaa tgcaaaccca     480
aatgcaaacc caaatgcaaa cccaaatgca acccaaatg caaacccaaa tgcaaaccca     540
aatgcaaacc ccaatgcaaa tcctaatgca acccaaatg caaacccaaa cgtagatcct     600
aatgcaaatc caaatgcaaa cccaaacgca accccaatg caaatcctaa tgcaaacccc     660
aatgcaaatc ctaatgcaaa tcctaatgcc aatccaaatg caaatccaaa tgcaaaccca     720
aacgcaaacc ccaatgcaaa tcctaatgcc aatccaaatg caaatccaaa tgcaaaccca     780
aatgcaaacc caaatgcaaa ccccaatgca atcctaata aaaacaatca aggtaatgga     840
caaggtcaca atatgccaaa tgacccaaac cgaaatgtag atgaaaatgc taatgccaac     900
agtgctgtaa aaataataa taacgaagaa ccaagtgata agcacataaa agaatattta     960
aacaaaatac aaaattctct ttcaactgaa tggtccccat gtagtgtaac ttgtggaaat    1020
ggtattcaag ttagaataaa gcctggctct gctaataaac ctaaagacga attagattat    1080
gcaaatgata ttgaaaaaaa aatttgtaaa atggaaaaat gttccagtgt gtttaatgtc    1140
gtaaatagtt caataggatt aataatggta ttatccttct tgttccttaa ttag          1194
```

<210> SEQ ID NO 110
<211> LENGTH: 1704
<212> TYPE: DNA
<213> ORGANISM: influenza virus
<220> FEATURE:
<223> OTHER INFORMATION: HA/A/Anhui/1/2005 gene DQ371928

<400> SEQUENCE: 110

```
atggagaaaa tagtgcttct tcttgcaata gtcagccttg ttaaaagtga tcagatttgc      60
attggttacc atgcaaacaa ctcgacagag caggttgaca caataatgga aaagaacgtt     120
actgttacac atgcccaaga catactggaa aagacacaca cgggaagct ctgcgatcta     180
gatggagtga agcctctgat tttaagagat tgtagtgtag ctggatggct cctcggaaac     240
ccaatgtgtg acgaattcat caatgtgccg gaatggtctt acatagtgga aaggccaac     300
```

```
ccagccaatg acctctgtta cccagggaat ttcaacgact atgaagaact gaaacaccta      360
ttgagcagaa taaccatttt tgagaaaatt cagatcatcc ccaaaagttc ttggtccgat      420
catgaagcct catcagggt  gagctcagca tgtccatacc agggaacgcc ctccttttc       480
agaaatgtgg tatggcttat caaaaagaac aatacatacc caacaataaa gagaagctac     540
aataatacca accaggaaga tcttttgata ctgtgggga  ttcatcattc taatgatgcg      600
gcagagcaga caaagctcta tcaaaaccca accacctata tttccgttgg gacatcaaca     660
ctaaaccaga gattggtacc aaaaatagct actagatcca agtaaacgg  gcaaagtgga     720
aggatggatt tcttctggac aatttttaaaa ccgaatgatg caatcaactt cgagagtaat    780
ggaaatttca ttgctccaga atatgcatac aaaattgtca agaaggggga ctcagcaatt    840
gttaaaagtg aagtggaata tggtaactgc aacacaaagt gtcaaactcc aatagggcg     900
ataaactcta gtatgccatt ccacaacata cccctctca  ccatcgggga atgccccaaa    960
tatgtgaaat caaacaaatt agtccttgcg actgggctca gaaatagtcc tctaagagaa   1020
agaagaagaa aaagaggact atttggagct atagcagggt ttatagaggg aggatggcag   1080
ggaatggtag atggttggta tgggtaccac catagcaatg agcaggggag tgggtacgct   1140
gcagacaaag aatccactca aaaggcaata gatggagtca ccaataaggt caactcgatc   1200
attgacaaaa tgaacactca gtttgaggcc gttggaaggg aatttaataa cttagaaagg   1260
agaatagaga tttaaacaa  gaaaatggaa gacggattcc tagatgtctg gacttataat   1320
gctgaacttc tggttctcat ggaaaatgag agaactctag acttccatga ttcaaatgtc   1380
aagaaccttt acgacaaggt ccgactacag cttagggata atgcaaagga gctgggtaac   1440
ggttgtttcg agttctatca caatgtgat  aatgaatgta tggaaagtgt aagaaacgga   1500
acgtatgact acccgcagta ttcagaagaa gcaagattaa aaagagagga ataagtgga    1560
gtaaaattgg aatcaatagg aacttaccaa atactgtcaa tttattcaac agttgcgagt   1620
tctctagcac tggcaatcat ggtggctggt ctatctttgt ggatgtgctc caatgggtcg   1680
ttacaatgca gaatttgcat ttaa                                            1704
```

<210> SEQ ID NO 111
<211> LENGTH: 1707
<212> TYPE: DNA
<213> ORGANISM: influenza virus
<220> FEATURE:
<223> OTHER INFORMATION: HA/A/Vietnam/1203/2004 gene AY818135

<400> SEQUENCE: 111

```
atggagaaaa tagtgcttct ttttgcaata gtcagtcttg ttaaaagtga tcagatttgc       60
attggttacc atgcaaacaa ctcgacagag caggttgaca caataatgga aaagaacgtt     120
actgttacac atgcccaaga catactggaa aagaaacaca acgggaagct ctgcgatcta     180
gatgagtga  agcctctaat tttgagagat tgtagcgtag ctggatggct cctcggaaac     240
ccaatgtgtg acgaattcat caatgtgccg gaatggtctt acatagtgga aaggccaat     300
ccagtcaatg acctctgtta cccaggggat ttcaatgact atgaagaatt gaaacaccta     360
ttgagcagaa taaccatttt tgagaaaatt cagatcatcc ccaaaagttc ttggtccagt     420
catgaagcct cattagggt  gagctcagca tgtccatacc agggaaagtc ctccttttc      480
agaaatgtgg tatggcttat caaaaagaac agtacatacc caacaataaa gaggagctac    540
aataatacca accaagaaga tcttttggta ctgtggggga ttcaccatcc taatgatgcg    600
```

| | |
|---|---|
| gcagagcaga caaagctcta tcaaaaccca accacctata tttccgttgg gacatcaaca | 660 |
| ctaaaccaga gattggtacc aagaatagct actagatcca aagtaaacgg gcaaagtgga | 720 |
| aggatggagt tcttctggac aattttaaag ccgaatgatg caatcaactt cgagagtaat | 780 |
| ggaaatttca ttgctccaga atatgcatac aaaattgtca agaaagggga ctcaacaatt | 840 |
| atgaaaagtg aattggaata tggtaactgc aacaccaagt gtcaaactcc aatggggcg | 900 |
| ataaactcta gcatgccatt ccacaatata caccctctca ccattgggga atgcccaaa | 960 |
| tatgtgaaat caaacagatt agtccttgcg actgggctca gaaatagccc tcaagagag | 1020 |
| agaagaagaa aaaagagagg attatttgga gctatagcag gttttataga gggaggatgg | 1080 |
| cagggaatgg tagatggttg gtatgggtac caccatagca atgagcaggg gagtgggtac | 1140 |
| gctgcagaca agaatccac tcaaaaggca atagatggag tcaccaataa ggtcaactcg | 1200 |
| atcattgaca aaatgaacac tcagtttgag gccgttggaa gggaatttaa caacttagaa | 1260 |
| aggagaatag agaatttaaa caagaagatg gaagacgggt tcctagatgt ctggacttat | 1320 |
| aatgctgaac ttctggttct catggaaaat gagagaactc tagactttca tgactcaaat | 1380 |
| gtcaagaacc tttacgacaa ggtccgacta cagcttaggg ataatgcaaa ggagctgggt | 1440 |
| aacggttgtt tcgagttcta tcataaatgt gataatgaat gtatggaaag tgtaagaaat | 1500 |
| ggaacgtatg actacccgca gtattcagaa gaagcgagac taaaaagaga ggaaataagt | 1560 |
| ggagtaaaat tggaatcaat aggaatttac caaatactgt caatttattc tacagtggcg | 1620 |
| agttccctag cactggcaat catggtagct ggtctatcct tatggatgtg ctccaatgga | 1680 |
| tcgttacaat gcagaatttg catttaa | 1707 |

<210> SEQ ID NO 112
<211> LENGTH: 5163
<212> TYPE: DNA
<213> ORGANISM: Plasmodium falciparum
<220> FEATURE:
<223> OTHER INFORMATION: PfMSP1 gene XM_001352134

<400> SEQUENCE: 112

| | |
|---|---|
| atgaagatca tattcttttt atgttcattt ctttttttta ttataaatac acaatgtgta | 60 |
| acacatgaaa gttatcaaga acttgtcaaa aaactagaag ctttagaaga tgcagtattg | 120 |
| acaggttata gttatttca aaaggaaaaa atggtattaa atgaagaaga attactaca | 180 |
| aaaggtgcaa gtgctcaaag tggtgcaagt gctcaaagtg gtgcaagtgc tcaaagtggt | 240 |
| gcaagtgctc aaagtggtgc aagtgctcaa agtggtgcaa gtgctcaaag tggtacaagt | 300 |
| ggtccaagtg gtccaagtgg tacaagtcca tcatctcgtt caaacacttt acctcgttca | 360 |
| aatacttcat ctggtgcaag ccctccagct gatgcaagcg attcagatgc taaatcttac | 420 |
| gctgatttaa aacacagagt acgaaattac ttgttcacta ttaaagaact caaatatccc | 480 |
| gaactctttg atttaaccaa tcatatgtta actttgtgtg ataatattca tggtttcaaa | 540 |
| tatttaattg atggatatga agaaattaat gaattattat ataaattaaa cttttatttt | 600 |
| gatttattaa gagcaaaatt aaatgatgta tgtgctaatg attattgtca ataccttc | 660 |
| aatcttaaaa ttcgtgcaaa tgaattagac gtacttaaaa acttgtgtt cggatataga | 720 |
| aaccattag acaatattaa agataatgta ggaaaaatgg aagattacat taaaaaaat | 780 |
| aaaacaacca tagcaaatat aaatgaatta ttgaaggaa gtaagaaaac aattgatcaa | 840 |
| aataagaatg cagataatga agaagggaaa aaaaaattat accaagctca atatgatctt | 900 |
| tctatttaca ataaacaatt agaagaagca cataatttaa taagcgtttt agaaaaacgt | 960 |

```
attgcacactt taaaaaaaaa tgaaaacata agaaaattac ttgataagat aaatgaaatt    1020 aaaaatccc caccggccaa ttctggaaat acaccaaata ctctccttga taagaacaaa     1080
aaaatcgagg aacacgaaga aaaaataaaa gaaattgcca aaactattaa atttaacatt    1140
gatagtttat ttactgatcc acttgaatta gaatattatt taagagaaaa aaataaaaaa    1200
gttgatgtaa cacctaaatc acaagatcct acgaaatctg ttcaaatacc aaaagttcct    1260
tatccaaatg gtattgtata tcctttacca ctcactgata ttcataattc attagctgca    1320
gataatgata aaaattcata tggtgattta atgaatcctc atactaaaga aaaaattaat    1380
gaaaaaatta ttacagataa taaggaaaga aaaatattca ttaataacat taaaaaaaaa    1440
attgatttag aagaaaaaaa cattaatcac acaaaagaac aaaataaaaa attacttgaa    1500
gattatgaaa agtcaaaaaa ggattatgaa gaattacttg aaaaattta tgaaatgaaa     1560 tttaataata attttaacaa agatgtcgta gataaaatat tcagtgcaag atatacatat    1620
aatgttgaaa aacaaagata taataataaa ttttcatcct ctaataattc tgtatataat    1680
gttcaaaaat taaaaaaggc tctttcatat cttgaagatt attctttaag aaaaggaatt    1740
tctgaaaaag attttaatca ttattatact ttgaaaactg gcctcgaagc tgatataaaa    1800
aaattaacag aagaaataaa gagtagtgaa acaaaattc tagaaaaaaa ttttaaagga    1860
ctaacacatt cagcaaatgg ttccttagaa gtatctgata ttgtaaaatt acaagtacaa    1920
aaagttttat taattaaaaa aatagaagac ttaagaaaga tagaattatt tttaaaaaat    1980
gcacaactaa aagatagtat tcatgtacca aatatttata aaccacaaaa taaaccagaa    2040
ccatattatt taattgtatt aaaaaaagaa gtagataaat taaagaatt tataccaaaa     2100 gtaaaagaca tgttaaagaa agaacaagct gtcttatcaa gtattacaca acctttagtt    2160
gcagcaagcg aaacaactga agatgggggt cactccacac acacattatc ccaatcagga    2220
gaaacagaag taacagaaga aacagaagaa acagaagaaa cagtaggaca cacaacaacg    2280
gtaacaataa cattaccacc aacacaacca tcaccaccaa aagaagtaaa agttgttgaa    2340
aattcaatag aacataagag taatgacaat tcacaagcct tgacaaaaac agtttatcta    2400
aagaaattag atgaattttt aactaaatca tatatatgtc ataaatatat tttagtatca    2460
aactctagta tggaccaaaa attattagag gtatataatc ttactccaga agaagaaat     2520 gaattaaaat catgtgatcc attagattta ttattaata ttcaaaataa catacctgct    2580
atgtattcat tatatgatag tatgaacaat gatttacaac atctcttttt tgaattatat    2640
caaaaggaaa tgatttatta tttacataaa ctaaagagg aaaatcacat caaaaaatta    2700
ttagaggagc aaaaacaaat aactggaaca tcatctacat ccagtcctgg aaatacaacc    2760
gtaaatactg ctcaatccgc aactcacagt aattcccaaa accaacaatc aaatgcatcc    2820
tctaccaata cccaaaatgg tgtagctgta tcatctggtc ctgctgtagt tgaagaaagt    2880
catgatccct taacagtatt gtctattagt aacgatttga aaggtattgt tagtctctta    2940
aatcttggaa ataaaactaa agtacctaat ccattaacca tttctacaac agagatggaa    3000
aaattttatg agaatatttt aaaaaataat gataccatatt ttaatgatga tatcaaacaa    3060
ttcgtaaaat ctaattcaaa agtaattaca ggtttgaccg aaacacaaaa aaatgcatta    3120
aatgatgaaa ttaaaaaatt aaagatact ttacagttat catttgattt atataataaa    3180
tataaattaa aattagatag attatttaat aagaaaaaag aacttggcca agacaaaatg    3240
caaattaaaa aacttacttt attaaaagaa caattagaat caaaattgaa ttcacttaat    3300
```

| | |
|---|---|
| aacccacata atgtattaca aaacttttct gttttcttta acaaaaaaaa agaagctgaa | 3360 |
| atagcagaaa ctgaaaacac attagaaaac acaaaaatat tattgaaaca ttataaagga | 3420 |
| cttgttaaat attataatgg tgaatcatct ccattaaaaa ctttaagtga agtatcaatt | 3480 |
| caaacagaag ataattatgc caatttagaa aaatttagag tattaagtaa aatagatgga | 3540 |
| aaactcaatg ataatttaca tttaggaaag aaaaaattat ctttcttatc aagtggatta | 3600 |
| catcatttaa ttactgaatt aaaagaagta ataaaaaata aaattatac aggtaattct | 3660 |
| ccaagtgaaa ataataagaa agttaacgaa gctttaaaat cttacgaaaa ttttctccca | 3720 |
| gaagcaaaag ttcaacagt tgtaactcca cctcaaccag atgtaactcc atctccatta | 3780 |
| tctgtaaggg taagtggtag ttcaggatcc acaaagaag aaacacaaat accaacttca | 3840 |
| ggctctttat aacagaatt acaacaagta gtacaattac aaaattatga cgaagaagat | 3900 |
| gattccttag ttgtattacc cattttttgga gaatccgaag ataatgacga atatttagat | 3960 |
| caagtagtaa ctggagaagc aatatctgtc acaatggata atatcctctc aggatttgaa | 4020 |
| aatgaatatg atgttatata tttaaaacct ttagctggag tatatagaag cttaaaaaaa | 4080 |
| caaattgaaa aaaacatttt tacatttaat ttaaatttga acgatatctt aaattcacgt | 4140 |
| cttaagaaac gaaaatattt cttagatgta ttagaatctg atttaatgca atttaaacat | 4200 |
| atatcctcaa atgaatacat tattgaagat tcatttaaat tattgaattc agaacaaaaa | 4260 |
| aacacacttt taaaagtta caaatatata aagaatcag tagaaaatga tattaaattt | 4320 |
| gcacaggaag gtataagtta ttatgaaaag gttttagcga aatataagga tgatttagaa | 4380 |
| tcaattaaaa aagttatcaa agaagaaaag gagaagttcc catcatcacc accaacaaca | 4440 |
| cctccgtcac cagcaaaaac agacgaacaa aagaaggaaa gtaagttcct tccatttta | 4500 |
| acaaacattg agaccttata caataactta gttaataaaa ttgacgatta cttaattaac | 4560 |
| ttaaaggcaa agattaacga ttgtaatgtt gaaaagatg aagcacatgt taaaataact | 4620 |
| aaacttagtg atttaaaagc aattgatgac aaaatagatc ttttttaaaaa cccttacgac | 4680 |
| ttcgaagcaa ttaaaaaatt gataaatgat gatacgaaaa aagatatgct tggcaaatta | 4740 |
| cttagtacag gattagttca aaattttcct aatacaataa tatcaaaatt aattgaagga | 4800 |
| aaattccaag atatgttaaa catttcacaa caccaatgcg taaaaaaaca atgtccagaa | 4860 |
| aattctggat gtttcagaca tttagatgaa agagaagaat gtaaatgttt attaaattac | 4920 |
| aaacaagaag gtgataaatg tgttgaaaat ccaaatccta cttgtaacga aataatggt | 4980 |
| ggatgtgatg cagatgccac atgtaccgaa gaagattcag gtagcagcag aaagaaaatc | 5040 |
| acatgtgaat gtactaaacc tgattcttat ccacttttcg atggtatttt ctgcagttcc | 5100 |
| tctaacttct taggaatatc attcttatta atactcatgt taatattata cagtttcatt | 5160 |
| taa | 5163 |

```
<210> SEQ ID NO 113
<211> LENGTH: 654
<212> TYPE: DNA
<213> ORGANISM: Plasmodium falciparum
<220> FEATURE:
<223> OTHER INFORMATION: Pfs25 gene XM_001347551

<400> SEQUENCE: 113
```

| | |
|---|---|
| atgaataaac tttacagttt gtttcttttc cttttcattc aacttagcat aaaatataat | 60 |
| aatgcgaaag ttaccgtgga tactgtatgc aaaagaggat ttttaattca gatgagtggt | 120 |
| catttggaat gtaaatgtga aaatgatttg gtgttagtaa atgaagaaac atgtgaagaa | 180 |

```
aaagttctga aatgtgacga aaagactgta aataaaccat gtggagattt ttccaaatgt      240
attaaaatag atggaaatcc cgtttcatac gcttgtaaat gtaatcttgg atatgatatg      300
gtaaataatg tttgtatacc aaatgaatgt aagaatgtaa cttgtggtaa cggtaaatgt      360
atattagata caagcaatcc tgttaaaact ggagtttgct catgtaatat aggcaaagtt      420
cccaatgtac aagatcaaaa taaatgttca aaagatggag aaaccaaatg ctcattaaaa      480
tgcttaaaag aaaatgaaac ctgtaaagct gttgatggaa tttataaatg tgattgtaaa      540
gatggattta taatagataa tgaaagctct atatgtactg cttttcagc atataatatt      600 ttaaatctaa gcattatgtt tatactattt tcagtatgct tttttataat gtaa            654

<210> SEQ ID NO 114
<211> LENGTH: 492
<212> TYPE: PRT
<213> ORGANISM: Artificial Sequence
<220> FEATURE:
<223> OTHER INFORMATION: baculovirus gp64 protein

<400> SEQUENCE: 114

Ala Glu His Cys Asn Ala Gln Met Lys Thr Gly Pro Tyr Lys Ile Lys
1               5                   10                  15

Asn Leu Asp Ile Thr Pro Pro Lys Glu Thr Leu Gln Lys Asp Val Glu
            20                  25                  30

Ile Thr Ile Val Glu Thr Asp Tyr Asn Glu Asn Val Ile Ile Gly Tyr
        35                  40                  45

Lys Gly Tyr Tyr Gln Ala Tyr Ala Tyr Asn Gly Gly Ser Leu Asp Pro
    50                  55                  60

Asn Thr Arg Val Glu Glu Thr Met Lys Thr Leu Asn Val Gly Lys Glu
65                  70                  75                  80

Asp Leu Leu Met Trp Ser Ile Arg Gln Gln Cys Glu Val Gly Glu Glu
                85                  90                  95

Leu Ile Asp Arg Trp Gly Ser Asp Ser Asp Cys Phe Arg Asp Asn
            100                 105                 110

Glu Gly Arg Gly Gln Trp Val Lys Gly Lys Glu Leu Val Lys Arg Gln
        115                 120                 125

Asn Asn Asn His Phe Ala His Thr Cys Asn Lys Ser Trp Arg Cys
    130                 135                 140

Gly Ile Ser Thr Ser Lys Met Tyr Ser Arg Leu Glu Cys Gln Asp Asp
145                 150                 155                 160

Thr Asp Glu Cys Gln Val Tyr Ile Leu Asp Ala Glu Gly Asn Pro Ile
                165                 170                 175

Asn Val Thr Val Asp Thr Val Leu His Arg Asp Gly Val Ser Met Ile
            180                 185                 190

Leu Lys Gln Lys Ser Thr Phe Thr Thr Arg Gln Ile Lys Ala Ala Cys
        195                 200                 205

Leu Leu Ile Lys Asp Asp Lys Asn Asn Pro Glu Ser Val Thr Arg Glu
    210                 215                 220

His Cys Leu Ile Asp Asn Asp Ile Tyr Asp Leu Ser Lys Asn Thr Trp
225                 230                 235                 240

Asn Cys Lys Phe Asn Arg Cys Ile Lys Arg Lys Val Glu His Arg Val
                245                 250                 255

Lys Lys Arg Pro Pro Thr Trp Arg His Asn Val Arg Ala Lys Tyr Thr
            260                 265                 270

Glu Gly Asp Thr Ala Thr Lys Gly Asp Leu Met His Ile Gln Glu Glu
```

-continued

```
                275                 280                 285
Leu Met Tyr Glu Asn Asp Leu Leu Lys Met Asn Ile Glu Leu Met His
        290                 295                 300

Ala His Ile Asn Lys Leu Asn Asn Met Leu His Asp Leu Ile Val Ser
305                 310                 315                 320

Val Ala Lys Val Asp Glu Arg Leu Ile Gly Asn Leu Met Asn Asn Ser
                325                 330                 335

Val Ser Ser Thr Phe Leu Ser Asp Asp Thr Phe Leu Leu Met Pro Cys
            340                 345                 350

Thr Asn Pro Pro Ala His Thr Ser Asn Cys Tyr Asn Asn Ser Ile Tyr
        355                 360                 365

Lys Glu Gly Arg Trp Val Ala Asn Thr Asp Ser Ser Gln Cys Ile Asp
        370                 375                 380

Phe Ser Asn Tyr Lys Glu Leu Ala Ile Asp Asp Asp Val Glu Phe Trp
385                 390                 395                 400

Ile Pro Thr Ile Gly Asn Thr Thr Tyr His Asp Ser Trp Lys Asp Ala
                405                 410                 415

Ser Gly Trp Ser Phe Ile Ala Gln Gln Lys Ser Asn Leu Ile Thr Thr
            420                 425                 430

Met Glu Asn Thr Lys Phe Gly Gly Val Gly Thr Ser Leu Ser Asp Ile
        435                 440                 445

Thr Ser Met Ala Glu Gly Glu Leu Ala Ala Lys Leu Thr Ser Phe Met
    450                 455                 460

Phe Gly His Val Val Asn Phe Val Ile Ile Leu Ile Val Ile Leu Phe
465                 470                 475                 480

Leu Tyr Cys Met Ile Arg Asn Arg Asn Arg Gln Tyr
                485                 490
```